(12) United States Patent
Zhou et al.

(10) Patent No.: US 7,071,173 B2
(45) Date of Patent: Jul. 4, 2006

(54) ANTIVIRAL METHODS EMPLOYING DOUBLE ESTERS OF 2', 3'-DIDEOXY-3'-FLUOROGUANOSINE

(75) Inventors: Xiao-Xiong Zhou, Huddinge (SE); Horst Wahling, Skarholmen (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 11/202,682

(22) Filed: Aug. 12, 2005

(65) Prior Publication Data

US 2006/0058259 A1 Mar. 16, 2006

Related U.S. Application Data

(62) Division of application No. 10/015,184, filed on Nov. 16, 2001, now Pat. No. 6,974,802, which is a division of application No. 09/249,317, filed on Feb. 12, 1999, now Pat. No. 6,458,772.

(30) Foreign Application Priority Data

| Feb. 16, 1998 | (SE) | 9800469 |
| Feb. 19, 1998 | (SE) | 9800452 |
| Apr. 3, 1998 | (SE) | 9801216 |
| Aug. 13, 1998 | (ZA) | 98/7267 |
| Aug. 14, 1998 | (WO) | PCT/SE98/01467 |
| Oct. 7, 1998 | (SE) | 9803438 |

(51) Int. Cl.
*A01N 43/04* (2006.01)
*A61K 31/70* (2006.01)
*C07H 149/00* (2006.01)
*C07H 19/22* (2006.01)

(52) U.S. Cl. ................ 514/45; 514/48; 536/22.1; 536/27.1; 536/27.13; 536/27.14; 536/27.2

(58) Field of Classification Search .......... 536/22.1, 536/27.1, 27.13, 27.14, 27.2; 514/45
See application file for complete search history.

(56) References Cited

U.S. PATENT DOCUMENTS

| 3,705,191 A | 12/1972 | Kerst |
| 4,168,267 A | 9/1979 | Petrillo, Jr. |
| 4,309,364 A | 1/1982 | Bentzen et al. |
| 4,337,201 A | 6/1982 | Petrillo, Jr. |
| 4,486,425 A | 12/1984 | Nakao |
| 4,594,199 A | 6/1986 | Thottathil |
| 4,760,057 A | 7/1988 | Alexander |
| 4,942,157 A | 7/1990 | Gall et al. |
| 4,957,924 A | 9/1990 | Beauchamp |
| 4,963,662 A | 10/1990 | Matthes et al. |
| 5,001,115 A | 3/1991 | Sloan |
| 5,073,641 A | 12/1991 | Bundgaard et al. |
| 5,198,539 A | 3/1993 | Rahim et al. |
| 5,227,506 A | 7/1993 | Saari et al. |
| 5,376,649 A | 12/1994 | Pohjala et al. |
| 5,441,942 A | 8/1995 | Goodman et al. |
| 5,466,811 A | 11/1995 | Alexander |
| 5,484,911 A | 1/1996 | Hong et al. |
| 5,543,414 A | 8/1996 | Nestor et al. |
| 5,618,804 A | 4/1997 | Kawabe et al. |
| 5,624,897 A | 4/1997 | Jeschke et al. |
| 5,624,917 A | 4/1997 | Kitano et al. |
| 5,717,095 A | 2/1998 | Arimilli et al. |
| 6,458,772 B1 | 10/2002 | Zhou et al. |
| 2002/0142969 A1 | 10/2002 | Jeschke et al. |
| 2003/0139369 A1* | 7/2003 | Yeadon .................. 514/46 |

FOREIGN PATENT DOCUMENTS

| DE | 2112057 | 9/1971 |
| DE | 195 29 604 A1 | 8/1995 |
| EP | 176 217 | 4/1986 |
| EP | 372 268 | 6/1990 |
| EP | 0375329 A2 | 6/1990 |
| EP | 658 551 | 6/1995 |
| EP | 0694547 A2 | 1/1996 |
| JP | 05-229997 | 9/1993 |
| WO | WO8800050 | 1/1988 |
| WO | WO8903837 | 5/1989 |
| WO | WO9008128 | 7/1990 |
| WO | WO9008155 | 7/1990 |
| WO | WO 91/06554 | 5/1991 |
| WO | WO9119721 | 12/1991 |
| WO | WO9200988 | 1/1992 |
| WO | WO9213561 | 8/1992 |
| WO | WO9413324 | 6/1994 |
| WO | WO9424134 | 10/1994 |
| WO | WO9501363 | 1/1995 |

(Continued)

OTHER PUBLICATIONS

Tetrehedron Letters, 30 (51) 1989, 7141-44, Iyer, R et al "Synthesis of Acyloxyalkyl Acylphosphonates . . . "

(Continued)

*Primary Examiner*—James O. Wilson
*Assistant Examiner*—Traviss C. McIntosh, III
(74) *Attorney, Agent, or Firm*—Birch, Stewart, Kolasch & Birch, LLP

(57) ABSTRACT

A method for treatment of HBV and HIV infections comprising administering the compound or salt of formula Ig

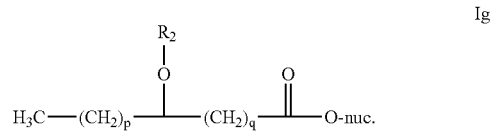

8 Claims, 2 Drawing Sheets

FOREIGN PATENT DOCUMENTS

| | | |
|---|---|---|
| WO | WO9512604 | 5/1995 |
| WO | WO9512605 | 5/1995 |
| WO | WO9514016 | 5/1995 |
| WO | WO9532984 | 12/1995 |
| WO | WO9615132 | 5/1996 |
| WO | WO9621440 | 7/1996 |
| WO | WO9622303 | 7/1996 |
| WO | WO9631227 | 10/1996 |
| WO | WO9633201 | 10/1996 |
| WO | WO9705154 | 2/1997 |
| WO | WO9727194 | 7/1997 |
| WO | WO9730051 | 8/1997 |
| WO | WO9821223 | 5/1998 |
| WO | WO9846576 | 10/1998 |
| WO | WO9851692 | 11/1998 |

OTHER PUBLICATIONS

J Med Chem 39 (1) 1996, 10-18, Robinson, R et al "Discovery of the Hemifumarate and . . . "

International J of Pharmaceutics 104 (1994) 157-67, Walker, I et al. "Drug delivery via active transport at the blood-brain barrier: affinity . . . "

Abstract of WO 98/11126, Sep. 9, 1997, Larsen, B et al. "Peptide prodrugs containing an alpha-hydroxyacid linker".

Meziane-Cherif, D. et al., "Purification and characterization of the VanB . . . ," FEBS Letters 354 (1994) pp. 141-142.

Ohyama, M. et al., "Total Synthesis of the Anthelmintic . . . ," Biosci. Biotech. Biochem. (1994), 58 (6), pp. 1193-1194.

Wu, Z. et al., "Overexperssion, Purification, and Characterization . . . ," Biochemistry (1995), 34, pp. 2455-2463.

Nyeki, O. et al., "Synthesis of Angiotensin II . . . ," J. Med. Chem. (1987), 30, pp. 1719-1724.

Kigasawa, K. et al., "Decomposition and Stabilization of Drugs . . . ," Yakugaku Zasshi (1979), 99, pp. 402-412.

Schacht, E. et al., "Biomedical Applications of Degradable . . . ," Biotechnology and Bioengineering (1996), 52, pp. 102-108.

* cited by examiner

ANTIVIRAL METHODS EMPLOYING DOUBLE ESTERS OF 2', 3'-DIDEOXY-3'-FLUOROGUANOSINE

This application is a Divisional of application Ser. No. 10/015,184, filed on Nov. 16, 2001, now U.S. Pat. No. 6,974,802, which is a divisional of application Ser. No. 09/249,317, filed on Feb. 12, 1999 now U.S. Pat. No. 6,458,772, the entire contents of which are hereby incorporated by reference and for which priority is claimed under 35 U.S.C. § 120; and this application claims priority of Application No. 9803438.2 filed in SWEDEN on Oct. 7, 1998; Application No. 9800452-6 filed in SWEDEN on Feb. 13, 1998; Application No. 9801216-4 filed in SWEDEN on Apr. 3, 1998; Application No. 9800469-0 filed in SWEDEN on Feb. 16, 1998; Application PCT/SE98/01467 filed in SWEDEN on Aug. 14, 1998; and Application No. 98/7267 filed in South Africa on Aug. 13, 1998 under 35 U.S.C. § 119.

TECHNICAL FIELD

This invention relates to the field of prodrugs, that is novel derivatives of otherwise known and proven drugs which release that drug in active or pro-active form in vivo. The enzymatic and/or chemical cleavage of the compounds of the present invention occurs in such a manner that the parent drug is released and the moiety or moieties split off remain non-toxic or are metabolized so that non-toxic or acceptable amounts of metabolic products are produced. The present compounds thus modify the in vivo availability of the parent compound compared to what would be the case if the parent compound was to be administered itself. For instance the prodrugs of the invention may give higher bioavailabities, varied bioavailability kinetics or bioavailabilities with a decreased interpersonal spread.

A first aspect of the invention relates to the field of nucleoside analogues, such as antivirals including inhibitors of retroviral reverse transcriptase and the DNA polymerase of Hepatitis B Virus (HBV). The invention provides novel compounds with favourable pharmaceutical parameters, methods for their preparation, pharmaceutical compositions comprising these compounds and methods employing then for the inhibition of viral and neoplastic diseases including HBV and HIV.

BACKGROUND TO THE INVENTION

International patent application no. WO 88/00050 describes the antiretroviral and anti-HBV activity of a series of 3'-fluorinated nucleosides, including the compounds 2',3'-dideoxy, 3'-fluoroguanosine (FLG) and 3'-fluorothymidine (FLT). The latter compound underwent clinical evaluation as an anti-HIV agent and although its antiviral activity and pharmacokinetics were good, it showed unexpected toxicity (Flexner et al, J Inf Dis 170(6) 1394–403 (1994)). The former compound FLG is very active in vitro however the present inventors have detected that its bioavailability is so poor—around 4%—that the in vivo utility of the compound has thus far been limited to intraperitoneally or subcutaneously administered animal models.

U.S. Pat. No. 4,963,662 discloses generically a series of 3'-fluorinated nucleosides and corresponding triphosphates and specifically describes the preparation of the 5'-Opalmitoyl derivative of FLT, without reporting any improvement in bioavailability. International patent application WO 93 13778 describes FLG derivatives modified at the 6-position of the base, in particular with n-propoxy, cyclobutoxy, cyclopropanylamino, piperidino or pyrrolidino. International patent application no. 93 14103 describes FLG derivatives where the oxygen at the guanine 6-position is replaced with amino, ether, halo or sulphonate.

BRIEF DESCRIPTION OF THE INVENTION

In accordance with one aspect of the invention there are provided compounds of the formula I:

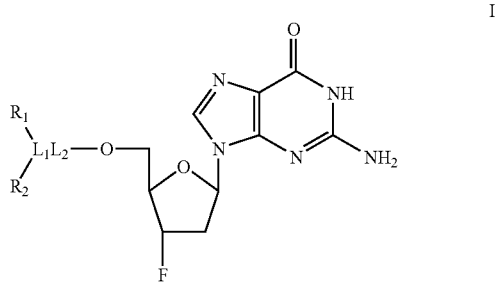

wherein:

$R_1$ is selected from
  hydroxy, amino or carboxy; optionally having esterified/amide bonded thereon a $C_4$–$C_{22}$ saturated or unsaturated, optionally substituted fatty acid or alcohol, or an aliphatic L-amino acid;

$R_2$ is the residue of an aliphatic L-amino acid;

$L_1$ is a trifunctional linker group;

$L_2$ is absent or a difunctional linker group;

and pharmaceutically acceptable salts thereof.

The invention further provides pharmaceutical compositions comprising the compounds and salts of formula I and pharmaceutically acceptable carriers or diluents therefor. Additional aspects of the invention provide methods for the inhibition of HBV and retroviruses such as HIV, comprising bringing a compound or salt of the formula I into contact with a retrovirus or HBV, for example by administering an effective amount of the compound or salt to an individual afflicted with a retrovirus or HBV. The invention also extends to the use of the compounds or salts of formula I in therapy, for example in the preparation of a medicament for the treatment of retroviral or HBV infections.

In treating conditions caused by retroviruses such as HIV, or HBV, the compounds or salts of formula I are preferably administered in an amount of 50 to 1 500 mg once, twice or three times per day, especially 100 to 700 mg twice or thrice daily. It is desirable to achieve serum levels of the active metabolite of 0.01 to 100 μg/ml, especially 0.1 to 5 μg/ml.

Where $R_1$ is a fatty acid residue, it preferably has in total an even number of carbon atoms, advantageously decanoyl ($C_{10}$), lauryl ($C_{12}$), myristoyl ($C_{14}$), palmitoyl ($C_{16}$), stearoyl ($C_{18}$), eicosanoyl ($C_{20}$) or behenoyl ($C_{22}$). The fatty acid preferably has in total 10 to 22, and more preferably 16 to 20 carbon atoms, especially 18. The fatty acid may be unsaturated and have one to three double bonds, especially one double bond. Unsaturated fatty acids preferably belong to the n-3 or n-6 series. Convenient unsaturated $R_1$ groups include those derived from the monounsaturated acids myristoleic, myristelaidic, palmitoleic, palmitelaidic, n6-octadecenoic, oleic, elaidic, gandoic, erucic, brassidic acids or multiply unsaturated fatty acids such as linoleic, ylinolenic, arachidonic acid and α-linolenic acid. Preferably, however, $R_1$ as a fatty acid is saturated as these compounds tend to have superior stability and shelf life.

$R_1$ as fatty alcohol residue preferably corresponds to one of the above described fatty acids. Alternatively the fatty alcohol may comprise residues of shorter alcohols, such as methanol, ethanol or propanol.

$R_1$ as a saturated or unsaturated fatty acid or alcohol may optionally be substituted with up to five similar or different substituents independently selected from the group consisting of hydroxy, $C_1-C_6$ alkyl, $C_1-C_6$ alkoxy, $C_1-C_6$ alkoxy $C_1-C_6$ alkyl, $C_1-C_6$ alkanoyl, amino, halo, cyano, azido, oxo, mercapto and nitro, and the like.

Suitable aliphatic amino acids for $R_2$ and, if present $R_1$, include L-alanine, L-leucine, L-isoleucine and most preferably L-valine. For ease of synthesis it is preferred that both $R_2$ and $R_1$ are residues of aliphatic amino acids, preferably the same residue.

The expression trifunctional in the context of the first linker group $L_1$ means that the linker has at least three functional groups, including at least two functional groups derived from respective hydroxy, amine or carboxyl groups, the amine and hydroxy function(s) being available for esterification/amide bonding with the carboxy functions of $R_1$ and $R_2$ whereas a carboxy function(s) on the linker is available for amide bonding with the free α-amine function of $R_2$, or $R_1$ as the case may be, or esterification with $R_1$ as a fatty alcohol. Where $R_1$ itself defines an hydroxy, amine or carboxy group, the hydroxy group being presently favoured of the three, one of said functions on the trifunctional linker simply comprises this hydroxy, amine or carboxy group.

The trifunctional linker further comprises a third functional group for linkage with either the optional second linker group $L_2$ illustrated in more detail below, or the hydroxy group at the 5' position of the mother nucleoside, such as 2',3'-dideoxy-3'-fluoroguanosine. Appropriate third functional groups will depend on the nature of the cooperating function on optional linker group $L_2$, if present, and may include amino, hydoxy, carbonyl, sulfonyl, phosphoryl, phosphonyl, carbamoyl and the like. If $L_2$ is absent, this third functional group on first linker $L_1$ will typically comprise a carboxyl function which can esterify with the 5'-O group of the nucleoside analogue.

Preferably the functional groups on the trifunctional linker which cooperate with $R_1$ and $R_2$ are hydroxyl functions and the linkage is an ester linkage with the carboxyl functions of an $R_1$ fatty acid, if present, and $R_2$. A further preferred embodiment comprises a free hydroxy group as $R_1$ and an hydroxyl function on the linker esterified to the carboxy function of $R_2$. An alternative embodiment comprises an (optionally protected) carboxyl group as $R_1$ and an hydroxyl function on the linker esterifed to a carboxy function on $R_2$.

Useful trifunctional $L_1$ group, especially for esterifying directly to the nucleoside include linkers of the formula IIa or IIb:

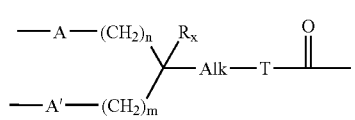
IIa where A and A' define a respective ester linkage between an hydroxy on the linker and the carboxy on $R_1$ or $R_2$ or an ester linkage between a carboxy on the linker and the hydroxy on $R_1$ as a fatty alcohol, or an amide linkage between an amine on the linker and a carboxy on $R_1$ or $R_2$, or an amide linkage between a carboxy on the linker and an amine on $R_1$ or $R_2$, or one of A and A' is as defined and the other is hydroxy, amino or carboxy in the event that $R_1$ itself is a free hydroxy, amino or carboxy group.

Rx is H or $C_1-C_3$ alkyl,

T is a bond, —O— or —NH—;

Alk is absent, $C_1-C_4$ alkyl or $C_2-C_4$ alkenyl, optionally substituted as described above; and m and n are independently 0, 1 or 2.

In a preferred embodiment of this aspect of the invention, the $R_1$ or $R_2$ groups are each esterified to a respective one of the leftmost functional hydroxy groups (viz A and A') of Formula IIa, while the carbonyl moiety to the right is esterified, optionally via a second linker group $L_2$, to the 5'-O-group of the nucleoside.

Alternatively the $L_1$ group may comprise a linker of the formula IIb:

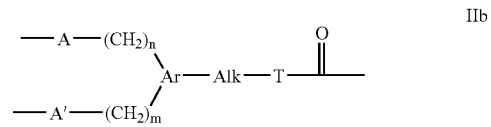
IIb where

Ar is a saturated or unsaturated, preferably monocyclic carbo- or heterocycle with 5 or 6 ring atoms; and A, A'', T, Alk, m and n are as defined above.

In Formula IIb, Ar is preferably an aromatic group such as pyridine or especially phenyl, such as aromatic moieties wherein the arms bearing the $R_1$ and $R_2$ groups are respectively para and ortho, meta and ortho, both ortho, or preferably para and meta, both para or both meta to the remainder of the linker.

In formulae IIa and IIb, the following combinations of m, n and Alk are presently favoured:

| m | n | Alk |
|---|---|---|
| 1 | 0 | absent |
| 1 | 0 | methylene |
| 1 | 0 | ethylene |
| 1 | 1 | absent |
| 1 | 1 | methylene |
| 1 | 1 | ethylene |
| 1 | 1 | propylene |
| 1 | 2 | absent |
| 1 | 2 | methylene |
| 1 | 1 | ethenylene |
| 1 | 1 | propenylene |

As $R_1$ and $R_2$ may have different structures, it will be apparent that many $L_1$ groups, particularly those of formula ila, will define chiral structures and the invention includes all enantiomers thereof, as racemates or as preparations of >80%, preferably >95% enantiomerically pure compound.

A favoured structure within formula IIa has the formula:

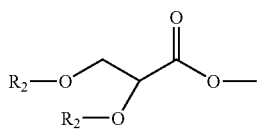

which breaks down in vivo to the nature identical glyceric acid. Particularly preferred are compounds derived from D-glyceric acid.

Thus preferred compounds of formula I include:
5'-O-[(S,R) 2,3-bis-(L-valyloxy)-propionyl]-2',3'-dideoxy-3'-fluoroguanosine,
5'-O-[(S,R) 2,3-bis-(L-isoleucyloxy)-propionyl]-2',3'-dideoxy-3'-fluoroguanosine, and most preferably
5'-O-[(R) 2,3-bis-(L-valyloxy)-propionyl]-2',3'-dideoxy-3'-fluoroguanosine,
5'-O-[(R) 2,3-bis-(L-isoleucyloxy)-propionyl]-2',3'-dideoxy-3'-fluoroguanosine; and their pharmaceutically acceptable salts.

A particularly preferred group of trifunctional linkers comprise glycerol derivatives of the formula IIc

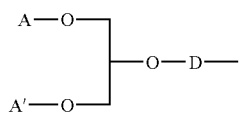

where A is hydrogen, the acyl residue of an aliphatic L-amino acid ester or the acyl residue of a fatty acid ester, A' is the acyl residue of an aliphatic amino acid residue and D is a $C_2$–$C_6$ saturated or unsaturated dicarboxylic acid residue. Trifunctional linkers of the formula IIc are hydrolysed or otherwise break down in vivo to release the nature identical compounds glycerol, the L-amino acid, the fatty acid (if present) and the dicarboxylic acid, each of which are generally safely metabolised and/or excreted by the body. Preferably A and A' are both residues of an aliphatic amino acid, most preferably the same residue, particularly residues of L-valine or L-isoleucine.

In the event that the dicarboxylic acid moiety in the derivative of formula IIc is esterified directly to the 5' hydroxy function (or equivalent) on the nucleoside, an alternative analysis would be to define the glycerol moiety as trifunctional linker $L_1$ and the dicarboxylic acid moiety as difunctional linker $L_2$.

Particularly preferred dicarboxylic acid residues include those derived from oxalic, malonic, tartronic, succinic, maleic, fumaric, malic, tartaric, glutaric, glutaconic, citraconic, itaconic, ethidine-malonic, mesaconic, adipic, allylmalonic, propylidenemalonic, hydromuconic, pyrocinchonic and muconic acids and the like. The dicarboxylic acid residue may be optionally substituted, for example with the substituents listed above in respect of $R_1$ as a fatty acid. Hydroxy substituents can in turn be esterified with a further L-amino acid or fatty acid residue.

Several of the abovementioned dicarboxylic acids can themselves define a trifunctional linker. For instance hydroxy-substituted dicarboxylic acids such as tartaric acid or malic acid offer a number of configurations within the scope of the invention. Taking tartaric acid as an example a carboxyl function is available for esterification with the 5'-hydroxyl function of a nucleoside (optionally via difunctional linker $L_2$). The hydroxy functions are available for esterification with the respective carboxyl functions of $R_2$ and an $R_1$ fatty acid or amino acid while the remaining carboxy group can be free, or optionally protected, for instance with a conventional pharmaceutically acceptable ester such as the methyl or ethyl ester. Alternatively the optional protection of the free carboxy function can itself comprise an ester with an $R_1$ fatty alcohol, with one or both hydroxyl functions being esterified to $R_2$:

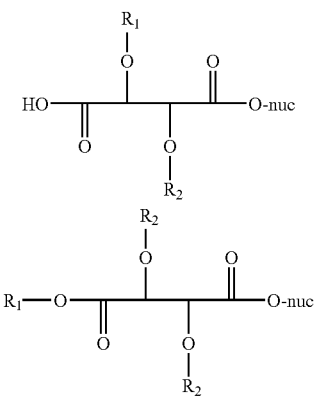

Favoured linkers of the tartaric acid series above can be generically depicted as Formula IIe:

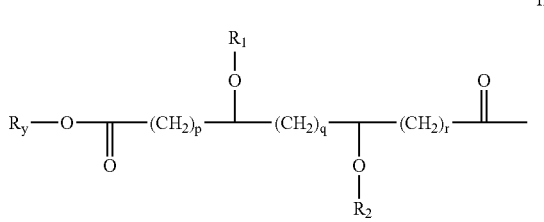

and isomers where $R_1$ and $R_2$ are reversed, where $R_1$ and $R_2$ are as shown above, p, q and r are each independently 0 to 5, preferably 0 or 1 and $R_y$ is the free acid, an $R_1$ ester or a conventional pharmaceutically acceptable carboxy protecting group, such as the methyl, benzyl or especially the ethyl ester.

Favoured linkers of the malic series have the formula IIf:

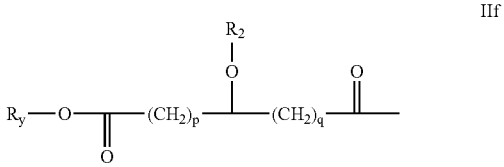

where Ry, p,q and $R_2$ are as defined above, preferably those where p and q are zero.

Preferred compounds of this aspect of the invention thus include:
5'-O-[3-methoxycarbonyl-2-valyloxy-propionyl]-2',3'-dideoxy-3'-fluoroguanosine, 5'-O-[3-benzyloxycarbonyl-2-valyloxy-propionyl]-2',3'-dideoxy-3'-fluoroguanosine,
5'-O-[3-methoxycarbonyl-2-isoleucloxy-propionyl]-2',3'-dideoxy-3'-fluoroguanosine,
5'-O-[3-benzyloxycarbonyl-2-isoleucyloxy-propionyl]-2',3'-dideoxy-3'-fluoroguanosine,
5'-O-[4-methoxycarbonyl-2,3-bis-valyloxy-butyryl]-2',3'-dideoxy-3'-fluoroguanosine,
5'-O-[4-benzyloxycarbonyl-2,3-bis-valyloxy-butyryl]-2',3'-dideoxy-3'-fluoroguanosine,
5'-O-[4-methoxycarbonyl-2,3-bis-isoleucyloxy-butyryl]-2',3'-dideoxy-3'-fluoroguanosine,
5'-O-[4-benzyloxycarbonyl-2,3-bis-isoleucyloxy-butyryl]-2',3'-dideoxy-3'-fluoroguanosine;

particularly those derived from L-malic acid and L-tartaric acid; and corresponding derivatives employing conventional pharmaceutically acceptable esters on the terminal carboxy function.

Particularly favoured compounds include:
5'-O-[3-ethoxycarbonyl-2-valyloxy-propionyl]-2',3'-dideoxy-3'-fluoroguanosine,
5'-O-[3-ethoxycarbonyl-2-isoleucyloxy-propionyl]-2',3'-dideoxy-3'-fluoroguanosine,
5'-O-[4-ethoxycarbonyl-2,3-bis-valyloxy-butyryl]-2',3'-dideoxy-3'-fluoroguanosine,
5'-O-[4-ethoxycarbonyl-2,3-bis-isoleucyloxy-butyryl]-2',3'-dideoxy-3'-fluoroguanosine, expecially the isomers derived from L-malic and L-tartaric acid.

In a related alternative aspect of the invention one of $R_1$ and $R_2$ is omitted. Representative compounds of this aspect of the invention include those of the formual Ia:

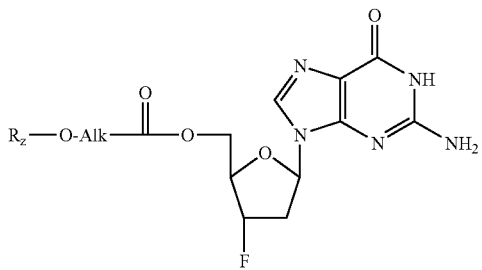

where Alk is optionally substituted $C_1$–$C_4$ alkyl or $C_2$–$C_4$ alkenyl and $R_z$ is the ester residue of an aliphatic L-amino acid or a fatty acid as defined for $R_1$ and $R_2$ above. Linkers of this aspect of the invention are conveniently prepared from α-hydroxy cocarboxylic acids such as carbonic acid, glycollic acid, hydroxypropanoic acid, hydroxybutyric acid, hydroxyvaleric acid or hydroxycaproic acid.

Representative compounds of Formula Ia include:
2',3'-dideoxy-3'-fluoro-5-O-[3-(L-valyloxy)-propionyl]guanosine
2',3'-dideoxy-3'-fluoro-5'-O-[5-(L-valyloxy)-pentanoyl]guanosine,
2',3'-dideoxy-3'-fluoro-5-O-[6-(L-valyloxy)-hexanoyl]guanosine,
2',3'-dideoxy-3'-fluoro-5-O-[3-(L-isoleuclyoxy)-propionyl]guanosine
2',3'-dideoxy-3'-fluoro-5'-O-[5-(L-isoleucyloxy)-pentanoyl]guanosine,
2',3'-dideoxy-3'-fluoro-5'-O-[6-(L-isoleucyloxy)-hexanoyl]guanosine, and pharmaceutically acceptable salts thereof.

Particularly favoured compounds of formula Ia include:
2',3'-dideoxy-3'-fluoro-5'-O-[4-(L-valyloxy)-butyryl]guanosine; and
2',3'-dideoxy-3'-fluoro-5'-O-[4-(L-isoleucyloxy)-butyryl]guanosine and pharmaceutically acceptable salts thereof.

In these compounds hydrolysis and removal of the $R_2$ group in vivo leaves a reactive terminal radical which will tend to cyclize and prompt the effective release of the mother nucleoside.

In a related alternative aspect of the invention, $R_1$ as a fatty acid residue is itself used as the linker, with the aliphatic L-amino acid residue of $R_2$ being esterified/amide bonded to an amino, hydroxy or carboxy function on the fatty acid alkyl chain, for example on the β-carbon. In this embodiment the fatty acid of $R_1$ is esterified directly on the 5'-hydroxy (or equivalent) function of the nucleoside, generally with the $R_2$ group already esterified/amide bonded thereon. Alternatively, the functionalised fatty acid (the carboxy/hydroxy/amino function being appropriately protected) can be first esterified to the nucleoside and deprotected prior to coupling with $R_2$. Linkers in accordance with a preferred embodiment of this aspect have the formula IId:

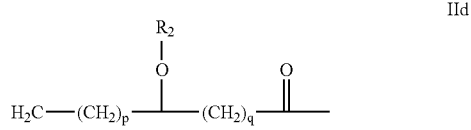

where $R_2$ is the residue of an aliphatic L-amino acid and, p is 0, 1 or 2–20 (optionally including a double bond) and q is 0–5, preferably 0. Representative compounds include:
2',3'-dideoxy-3'-fluoro-5-O-[2-(L-valyloxy)-butyryl]guanosine,
2',3'-dideoxy-3'-fluoro-5-O-[2-(L-valyloxy)-hexanoyl]guanosine,
2',3'-dideoxy-3'-fluoro-5-O-[2-(L-valyloxy)-octanoyl]guanosine,
2',3'-dideoxy-3'-fluoro-5-O-[2-(L-valyloxy)-decanoyl]guanosine,
2',3'-dideoxy-3'-fluoro-5-O-[2-(L-valyloxy)-dodecanoyl]guanosine,
2',3'-dideoxy-3'-fluoro-5-O-[2-(L-valyloxy)-myristoyl]guanosine,
2',3'-dideoxy-3'-fluoro-5-O-[2-(L-valyloxy)-palmitoyl]guanosine,
2',3'-dideoxy-3'-fluoro-5-O-[2-(L-valyloxy)-stearoyl]guanosine,
2',3'-dideoxy-3'-fluoro-5-O-[2-(L-valyloxy)-docosanoyl]guanosine,
2',3'-dideoxy-3'-fluoro-5-O-[2-(L-valyloxy)-eicosanoyl]guanosine
2',3'-dideoxy-3'-fluoro-5-O-[2-(L-isoleucyloxy)-butyryl]guanosine,
2',3'-dideoxy-3'-fluoro-5-O-[2-(L-isoleucyloxy)-hexanoyl]guanosine,
2',3'-dideoxy-3'-fluoro-5-O-[2-(L-isoleucyloxy)-octanoyl]guanosine,
2',3'-dideoxy-3'-fluoro-5-O-[2-(L-isoleucyloxy)-decanoyl]guanosine,
2',3'-dideoxy-3'-fluoro-5-O-[2-(L-isoleucyloxy)-dodecanoyl]guanosine,
2',3'-dideoxy-3'-fluoro-5-O-[2-(L-isoleucyloxy)-myristoyl]guanosine, 2',3'-dideoxy-3'-fluoro-5-O-[2-(L-isoleucyloxy)-palmitoyl] guanosine,
2',3'-dideoxy-3'-fluoro-5-O-[2-(L-isoleucyloxy)-stearoyl] guanosine,
2',3'-dideoxy-3'-fluoro-5-O-[2-(L-isoleucyloxy)-docosanoyl]guanosine,
2',3'-dideoxy-3'-fluoro-5-O-[2-(L-isoleucyloxy)-eicosanoyl] guanosine,
and the corresponding n-3 and n-6 monounsaturated analogues, such as 6 or 9 octadecenoyl derivatives.

In formula IId, p and q are preferably 0, thus defining lactic acid derivatives, preferably L-lactic acid derivatives, such as
2',3'-dideoxy-3'-fluoro-5-O-[2-(L-valyloxy)-propionyl]guanosine; and
2',3'-dideoxy-3'-fluoro-5-O-[2-(L-isoleucyloxy)-propionyl] guanosine and pharmaceutically acceptable salts thereof, as the breakdown products, lactic acid and the amino aicd are both well accepted physiologically.

The expression bifunctional in the context of second linker group $L_2$ means that the the linker has two functions enabling it to act a spacer or bridge between the first linker group $L_1$ and the 5'-O group of the nucleoside. For instance the optional group $L_2$ may comprise a linker of the formula IIIa:

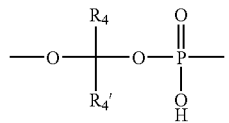

where $R_4$ and $R_4'$ are hydrogen or $C_1$–$C_4$ alkyl. In formula IIIa, $R_4$ is preferably hydrogen, methyl, ethyl or isopropyl and $R_4'$ is hydrogen. Linkers of formula IIIa are convenient as many nucleosides such as the FLG mother compound must first be phosphorylated by cellular enzymes before it can inhibit the viral polymerase. An initial or sequential hydrolysis of compounds of the invention can release a monophosphorylated nucleoside in vivo which is available for immediate conversion to the di- and triphosphate.

Alternatively the optional bifunctional linker group $L_2$ may comprise a structure of the formula IIIb:

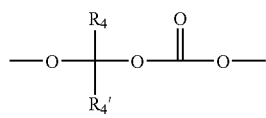

where $R_4$ and $R_4'$ are independently H or $C_1$–$C_4$ alkyl.

A still further group of bifunctional linkers have the formula IIIc:

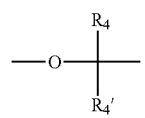

As described above, a preferred group of bifunctional linkers comprises α,ω-dicarboxylic $C_2$–$C_6$ alkyl derivatives, such as succinic acid, which are optionally substituted (for instance with the substituents defined above for $R_1$ as a fatty acid) and/or optionally mono or polyunsaturated, such as n-3 or n-6 monounsaturated. Preferred moieties within this class are listed above.

Although the disclosure above has concentrated on glycerol $L_1$ groups in conjunction with dicarboxylic $L_2$ groups, it will be appreciated that a wide variety of trifunctional linkers are appropriate with dicarboxylic $L_2$ groups, for instance structures of the formula IIa and IIb above lacking the rightmost carbonyl.

The invention further includes double prodrugs comprising $R_1(R_2)$ $LIL_2$-derivatives of conventional FLG prodrugs, which conventional prodrugs release FLG in vivo, such as prodrug derivatives at the 2 and 6 positions of the FLG guanine base. Examples of such conventional FLG-prodrugs include compounds of the formula IV:

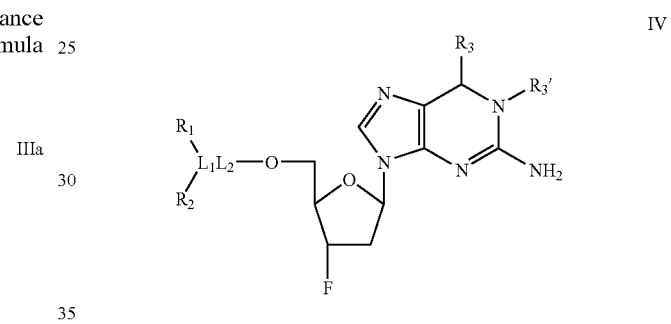

where
  $R_1$, $R_2$, $L_1$ and $L_2$ are as defined above; and
  $R_3$ is H, $N_3$, $NH_2$, or OH or a pharmaceutically acceptable ether or ester thereof; and
  $R_3'$ is an aromatic bond or hydrogen;

Potential pharmaceutically acceptable esters for $R_3$ include the fatty acids described in relation to $R_1$ above, such as stearolyl, oleoyl etc or shorter esters such as acetyl or butyryl. Other potential esters include the amino acid derivatives of $R_2$ or esters of phosphoric acid, such as monophosphate. Alternative esters include the corresponding fatty acid or alkylaryl carbonate, carbamate or sulphonic esters.

Suitable pharmaceutically acceptable ethers for $R_3$ include $C_1$–$C_6$ alkyl, cycloalkyl, $C_6$–$C_{12}$ alkaryl such as benzyl or methylpyridyl, any of which may be optionally substituted as for $R_1$ above. Convenient ethers include those described in the abovementioned WO 93 13778 such as n-propoxy, cyclobutoxy, cyclopropanylamino, piperidino or pyrrolidino and the like.

The invention has thus far been described with reference to the monohydroxylated nucleoside FLG, however it will be apparent that corresponding derivatives can be prepared of other monohydroxylated nucleoside analogues, particularly those where the monohydroxy group corresponds to the 5' hydroxy function of a nucleoside. Thus an additional aspect of the invention provides compounds of the formula Ic:

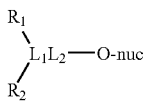

where $R_1$, $R_2$, $L_1$ and $L_2$ are as defined above and -O-nuc is the residue of a monohydroxyl bearing D- or L-nucleoside analogue. Representative nucleosides in accordance with this aspect of the invention include acyclic nucleoside analogues such as acyclovir and cyclic nucleoside analogues such as ddI (didanosine), ddC (zalcitabine), d4T (stavudine), FTC, lamivudine (3TC), 1592U89 (4-[2-amino-6-(cyclopropylamino)-9H-purin-9-yl]-2-cyclopentene-1-methanol), AZT (zidovudine), DAPD (D-2,6-diaminopurine dioxolane), F-ddA and the like, each of which are well known in the nucleoside art. A number of monohydric L-nucleosides are under development and the invention will also find utility on this compounds. Compounds within this aspect of the invention will find utility in the corresponding indications to the mother compounds, for instance herpesvirus infections for acyclovir derivatives, HIV for ddI, stavudine, ddC, lamivudine, AZT & 1592U89, HBV for lamivudine, FTC etc.

A favoured subgroup within Formula Ic comprises derivatives of monohydric nucleosides of the formula Ic':

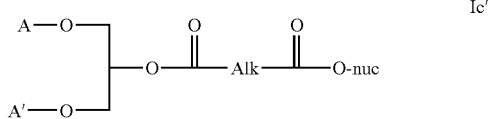

where A, A', Alk and O-nuc are as defined above. Formula Ic' above depicts compounds wherein A and A' depend from the 1 and 3 positions of the glycereol moiety and $L_2$ depends from the glycerol 2 position. In alternative isomers A and A' depend 1 and 2 or 2 and 3 and $L_2$ from 3 or 2 respectively.

Representative compounds within this aspect of the invention include:
4'-O-[3-((2,3-bis-L-valyloxy)-1-propyloxycarbonyl)propionyl]acyclovir,
4'-O-[3-((2-hydroxy-3-L-valyloxy)-1-propyloxycarbonyl)propionyl]acyclovir,
4'-O-[3-((2,3-bis-L-isoleucyloxy)-1-propyloxycarbonyl)propionyl]acyclovir,
4'-O-[3-((2-hydroxy-3-L-isoleucyloxy)-1-propyloxycarbonyl)propionyl]acyclovir,
4'-O-[3-((1,3-bis-L-valyloxy)-2-propyloxycarbonyl)propionyl]acyclovir,
4'-O-[3-((1-hydroxy-3-L-valyloxy)-2-propyloxycarbonyl)propionyl]acyclovir,
4'-O-[3-((1,3-bis-L-isoleucyloxy)-2-propyloxycarbonyl)propionyl]acyclovir,
4'-O-[3-((1-hydroxy-3-L-isoleucyloxy)-2-propyloxycarbonyl)propionyl]acyclovir,
5'-O-[3-((2,3-bis-L-valyloxy)-1-propyloxycarbonyl)propionyl]lamivudine,
5'-O-[3-((2-hydroxy-3-L-valyloxy)-1-propyloxycarbonyl)propionyl]lamivudine,
5'-O-[3-((2,3-bis-L-isoleucyloxy)-1-propyloxycarbonyl)propionyl]lamivudine,
5'-O-[3-((2-hydroxy-3-L-isoleucyloxy)-1-propyloxycarbonyl)propionyl]lamivudine,
5'-O-[3-((1,3-bis-L-valyloxy)-2-propyloxycarbonyl)propionyl]lamivudine,
5'-O-[3-((1-hydroxy-3-L-valyloxy)-2-propyloxycarbonyl)propionyl]lamivudine,
5'-O-[3-((1,3-bis-L-isoleucyloxy)-2-propyloxycarbonyl)propionyl]lamivudine,
5'-O-[3-((1-hydroxy-3-L-isoleucyloxy)-2-propyloxycarbonyl)propionyl]lamivudine,
5'-O-[3-((2,3-bis-L-valyloxy)-1-propyloxycarbonyl)propionyl]DAPD,
5'-O-[3-((2-hydroxy-3-L-valyloxy)-1-propyloxycarbonyl)propionyl]DAPD,
5'-O-[3-((2,3-bis-L-isoleucyloxy)-1-propyloxycarbonyl)propionyl]DAPD,
5'-O-[3-((2-hydroxy-3-L-isoleucyloxy)-1-propyloxycarbonyl)propionyl]DAPD,
5'-O-[3-((1,3-bis-L-valyloxy)-2-propyloxycarbonyl)propionyl]DAPD,
5'-O-[3-((1-hydroxy-3-L-valyloxy)-2-propyloxycarbonyl)propionyl]DAPD,
5'-O-[3-((1,3-bis-L-isoleucyloxy)-2-propyloxycarbonyl)propionyl]DAPD,
5'-O-[3-((1-hydroxy-3-L-isoleucyloxy)-2-propyloxycarbonyl)propionyl]DAPD,
5'-O-[3-((2,3-bis-L-valyloxy)-1-propyloxycarbonyl)propionyl]-2',3'-dideoxyinosine
5-O-[3-((2-hydroxy-3-L-valyloxy)-1-propyloxycarbonyl)propionyl]-2',3'-dideoxyinosine,
5'-O-[3-((2,3-bis-L-isoleucyloxy)-1-propyloxycarbonyl)propionyl]-2',3'-dideoxyinosine,
5'-O-[3-((2-hydroxy-3-L-isoleucyloxy)-1-propyloxycarbonyl)propionyl]-2',3'-dideoxyinosine,
5'-O-[3-((1,3-bis-L-valyloxy)-2-propyloxycarbonyl)propionyl]-2',3'-dideoxyinosine,
5'-O-[3-((1-hydroxy-3-L-valyloxy)-2-propyloxycarbonyl)propionyl]-2',3'-dideoxyinosine,
5'-O-[3-((1,3-bis-L-isoleucyloxy)-2-propyloxycarbonyl)propionyl]-2',3'-dideoxyinosine,
5'-O-[3-((1-hydroxy-3-L-isoleucyloxy)-2-propyloxycarbonyl)propionyl]-2',3'-dideoxyinosine,
5'-O-[3-((2,3-bis-L-valyloxy)-1-propyloxycarbonyl)propionyl]stavudine,
5'-O-[3-((2-hydroxy-3-L-valyloxy)-1-propyloxycarbonyl)propionyl]stavudine,
5'-O-[3-((2,3-bis-L-isoleucyloxy)-1-propyloxycarbonyl)propionyl]stavudine,
5'-O-[3-((2-hydroxy-3-L-isoleucyloxy)-1-propyloxycarbonyl)propionyl]stavudine,
5'-O-[3-((1,3-bis-L-valyloxy)-2-propyloxycarbonyl)propionyl]stavudine,
5'-O-[3-((1-hydroxy-3-L-valyloxy)-2-propyloxycarbonyl)propionyl]stavudine,
5'-O-[3-((1,3-bis-L-isoleucyloxy)-2-propyloxycarbonyl)propionyl]stavudine,
5'-O-[3-((1-hydroxy-3-L-isoleucyloxy)-2-propyloxycarbonyl)propionyl]stavudine, the corresponding derivatives of 4-[2-amino-6(cyclopropylamino)-9H-purin-9-yl]-2-cyclopentene-1-methanol, and pharmaceutically acceptable salts thereof.

A preferred group of compound sis based on glyceric acid, including
5'-O-[(S) 2,3-bis-(L-valyloxy)-propionyl]-stavudine
5'-O-[(S) 2,3-bis-(L-isoleucyloxy)-propionyl]-stavudine;
5'-O-[(S) 2,3-bis-(L-valyloxy)-propionyl]-dideoxyinosine 5'-O-[(S) 2,3-bis-(L-isoleucyloxy)-propionyl]-dideoxyinosine
5'-O-[(S) 2,3-bis-(L-valyloxy)-propionyl]-DAPD
5'-O-[(S) 2,3-bis-(L-isoleucyloxy)-propionyl]-DAPD
5'-O-[(S) 2,3-bis-(L-valyloxy)-propionyl]-lamivudine
5'-O-[(S) 2,3-bis-(L-isoleucyloxy)-propionyl]-lamivudine
5'-O-[(S) 2,3-bis-(L-valyloxy)-propionyl]-acyclovir
5'-O-[(S) 2,3-bis-(L-isoleucyloxy)-propionyl]-acyclovir and pharmaceutically acceptable salts thereof.

An alternative subset of compounds within this aspect of the invention comprise those of the formula Id:

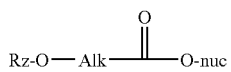

where Rz and Alk are as defined for formula Ia and O-nuc is as defined above.

Representative compounds of formula Id include
4'-O-[4-(L-valyloxy)-propionyl]acyclovir,
4'-O-[5-(L-valyloxy)-pentanoyl]acyclovir,
4'-O-[6-(L-valyloxy)-hexanoyl]acyclovir,
4'-O-[4-(L-isoleucyloxy)-propionyl]acyclovir,
4'-O-[5-(L-isoleucyloxy)-pentanoyl]acyclovir,
4'-O-[6-(L-isoleucyloxy)-hexanoyl]acyclovir,
5'-O-[4-(L-valyloxy)-propionyl]ddI,
5'-O-[5-(L-valyloxy)-pentanoyl]ddI,
5'-O-[6-(L-valyloxy)-hexanoyl]ddI,
5'-O-[4-(L-isoleucyloxy)-propionyl]ddI,
5'-O-[5-(L-isoleucyloxy)-pentanoyl]ddI,
5'-O-[6-(L-isoleucyloxy)-hexanoyl]ddI,
5'-O-[4-(L-valyloxy)-propionyl] stavudine,
5'-O-[5-(L-valyloxy)-pentanoyl] stavudine,
5'-O-[6-(L-valyloxy)-hexanoyl] stavudine,
5'-O-[4-(L-isoleucyloxy)-propionyl] stavudine,
5'-O-[5-(L-isoleucyloxy)-pentanoyl] stavudine,
5'-O-[6-(L-isoleucyloxy)-hexanoyl] stavudine,
5'-O-[4-(L-valyloxy)-propionyl] DAPD,
5'-O-[5-(L-valyloxy)-pentanoyl] DAPD,
5'-O-[6-(L-valyloxy)-hexanoyl] DAPD,
5'-O-[4-(L-isoleucyloxy)-propionyl] DAPD,
5'-O-[5-(L-isoleucyloxy)-pentanoyl] DAPD,
5'-O-[6-(L-isoleucyloxy)-hexanoyl] DAPD,
5'-O-[4-(L-valyloxy)-propionyl] lamivudine,
5'-O-[5-(L-valyloxy)-pentanoyl] lamivudine,
5'-O-[6-(L-valyloxy)-hexanoyl] lamivudine,
5'-O-[4-(L-isoleucyloxy)-propionyl] lamivudine,
5'-O-[5-(L-isoleucyloxy)-pentanoyl] lamivudine,
5'-O-[6-(L-isoleucyloxy)-hexanoyl] lamivudine, and the corresponding derivatives of 4-[2-amino-6(cyclopropylamino)-9H-purin-9-yl]-2-cyclopentene-1-methanol.

Particularly preferred compounds within Formula Id include:
4'-O-[4-(L-valyloxy)-butyryl]acyclovir,
4'-O-[3-(L-isoleucyloxy)-butyryl]acyclovir,
5'-O-[4-(L-valyloxy)-butyryl]ddI,
5'-O-[3-(L-isoleucyloxy)-butyryl] ddI,
5'-O-[4-(L-valyloxy)-butyryl]stavudine,
5'-O-[3-(L-isoleucyloxy)-butyryl] stavudine,
5'-O-[4-(L-valyloxy)-butyryl] DAPD,
5'-O-[3-(L-isoleucyloxy)-butyryl] DAPD,
5'-O-[4-(L-valyloxy)-butyryl]lamivudine,
5'-O-[3-(L-isoleucyloxy)-butyrylyl] lamivudine, and the corresponding derivatives of 4-[2-amino-6(cyclopropylamino)-9H-purin-9-yl]-2-cyclopentene-1-methanol; and pharmaceutically acceptable salts thereof, In these compounds hydrolysis and removal of the $R_2$ group in vivo leaves a reactive terminal radical which will tend to cyclize and prompt the effective release of the mother nucleoside.

Similarly the invention extends to compounds of the formula If:

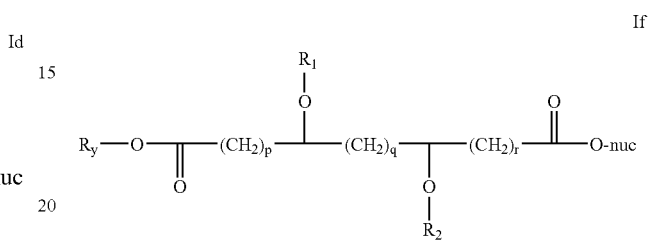

where $R_1$, $R_2$, $R_y$, p, q, r and o-nuc are as defined above.

Favoured compounds of this aspect of the invention include:
5'-O-[3-ethoxycarbonyl-2-valyloxy-propionyl]-ddI,
5'-O-[3-ethoxycarbonyl-2-isoleucyloxy-propionyl]-ddI
5'-O-[4-ethoxycarbonyl-2,3-bis-valyloxy-butyryl]-ddI,
5'-O-[4-ethoxycarbonyl-2,3-bis-isoleucyloxy-butyryl]-ddI,
4'-O-[3-ethoxycarbonyl-2-valyloxy-propionyl]-acyclovir,
4'-O-[3-ethoxycarbonyl-2-isoleucyloxy-propionyl]-acyclovir
4'-O-[4-ethoxycarbonyl-2,3-bis-valyloxy-butyryl]-aciclovir,
4'-O-[4-ethoxycarbonyl-2,3-bis-isoleucyloxy-butyryl]-aciclovir,
5'-O-[3-ethoxycarbonyl-2-valyloxy-propionyl]-DAPD,
5'-O-[3-ethoxycarbonyl-2-isoleucyloxy-propionyl]-DAPD
5'-O-[4-ethoxycarbonyl-2,3-bis-valyloxy-butyryl]-DAPD,
5'-O-[4-ethoxycarbonyl-2,3-bis-isoleucyloxy-butyryl]-DAPD,
5'-O-[3-ethoxycarbonyl-2-valyloxy-propionyl]-stavudine,
5'-O-[3-ethoxycarbonyl-2-isoleucyloxy-propionyl]-stavudine
5'-O-[4-ethoxycarbonyl-2,3-bis-valyloxy-butyryl]-stavudine,
5'-O-[3-ethoxycarbonyl-2-valyloxy-propionyl]-lamivudine,
5'-O-[3-ethoxycarbonyl-2-isoleucyloxy-propionyl]-lamivudine
5'-O-[4-ethoxycarbonyl-2,3-bis-valyloxy-butyryl]-lamivudine,
5'-O-[4-ethoxycarbonyl-2,3-bis-isoleucyloxy-butyryl]-lamivudine, and the corrresponding malic and tartric derivatives of 4-[2-amino-6(cyclopropylamino)-9H-purin-9-yl]-2-cyclopentene-1-methanol and pharpamceutically acceptable salts thereof; in each case the isomers derived from Ltartrate and L-malate derivatives being preferred.

The invention also extends to compounds of the formula Ig

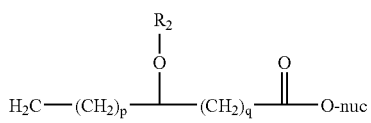

where R$_2$, p, q and O-nuc are as defined above.

Preferred compounds of formula Ig include:
4'-O-[2-(L-valyloxy)-propionyl] acyclovir,
4'-O-[2-(L-isoleucyloxy)-propionyl] acyclovir
5'-O-[2-(L-valyloxy)-propionyl] ddI,
5'-O-[2-(L-isoleucyloxy)-propionyl] ddI,
5'-O-[2-(L-valyloxy)-propionyl] stavudine,
5'-O-[2-(L-isoleucyloxy)-propionyl] stavudine
5'-O-[2-(L-valyloxy)-propionyl] lamivudine,
5'-O-[2-(L-isoleucyloxy)-propionyl] lamivudine,
5'-O-[2-(L-valyloxy)-propionyl] DAPD,
5'-O-[2-(L-isoleucyloxy)-propionyl] DAPD
and the corresponding derivatives of 4-[2-amino-6(cyclopropylamino)-9H-purin-9-yl]-2-cyclopentene-1-methanol; and pharmaceutically acceptable salts thereof.

The breakdown products of such compounds, lactic acid and the amino acid, are both well accepted physiologically.

The compounds of the invention can form salts which form an additional aspect of the invention. Appropriate pharmaceutically acceptable salts of the compounds of Formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

The compounds of Formula I may in some cases be isolated as the hydrate. The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, tbutylacetyl, 2-chloroacetyl, 2-bromoacetyl, trifluoracetyl, trichloroacetyl, phthalyl, onitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, ptoluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, allyl, F-moc, benzoyl, pivaloyl, t-butylacetyl, phenylsulfonyl, benzyl, t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), tbutyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

In keeping with the usual practice with retroviral and HBV inhibitors it is advantageous to co-administer one to three or more additional antivirals, such as AZT, ddI, ddC, d4T, 3TC, H2G, foscamet, ritonavir, indinavir, saquinavir, nevirapine, delaviridine, Vertex VX 478 or Agouron AG1343 and the like in the case of UV or lamivudine, interferon, famciclovir etc in the case of HBV. Such additional antivirals will normally be administered at dosages relative to each other which broadly reflect their respective therapeutic values. Molar ratios of 100:1 to 1:100, especially 25:1 to 1:25, relative to the compound or salt of formula I will often be convenient. Administration of additional antivirals is generally less common with those antiviral nucleosides intended for treating herpes infections.

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

A still further aspect of the invention provides a method for the preparation of a compound of Formula I or Ic comprising the acylation of the nucleoside, represented here by FLG, Formula V, typically at the 5' hydroxy group:

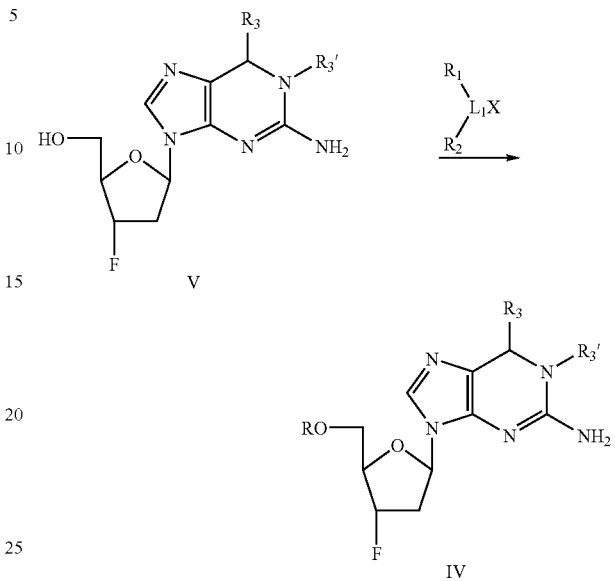

in which $R_1(R_2)L_1X$ represents an activated acid, such as the carboxylic derivatives of Formula IIa or IIb, where $R_1$, $R_2$, and $L_1$ are as defined above or protected derivatives thereof. Alternatively the activated acid may comprise a compound of the formula $R_1(R_2)$glycerol-D-X, where $R_1$, $R_2$ and D are as defined in formula IIc or an activated Rz-O-Alk-C(=O)X derivative in the case of compounds of formula Ia. In the latter cases the linkers may be built up sequentially by first esterifying a suitably protected D or ω-hydroxy carboxylic acid to the nucleoside, deprotecting the terminal carboxy or hydroxy function and esterifying the suitably protected glycerol or Rz moiety thereon.

The activated derivative used in the acylation may comprise e.g. the acid halide, acid anhydride, activated acid ester or the acid in the presence of coupling reagent, for example dicyclohexylcarbodiimide. Representative activated acid derivatives include the acid chloride, anhydrides derived from alkoxycarbonyl halides such as isobutyloxycarbonylchloride and the like, N-hydroxysuccinamide derived esters, N-hydroxyphthalimide derived esters, N-hydroxy-5-norbornene-2,3-dicarboxamide derived esters, 2,4,5-trichlorophenol derived esters and the like. Further activated acids include those where X in the formula RX represents an OR'moiety where R is $R_2$ as defined herein, and R' is, for example $COCH_3$, $COCH_2CH_3$ or $COCF_3$ or where X is benzotriazole.

Corresponding methodology will be applicable when the invention is applied to other monohydroxylated nucleosides, that is the activated derivative is correspondingly esterified to the free 5' hydroxy (or equivalent) of monohydric nucleosides such as acyclovir, ddI, FTC, lamivudine, 1592U89, DAPD, F-ddA and the like.

The intermediates used in the above methods themselves define novel compounds, especially those of the formula: IIc'

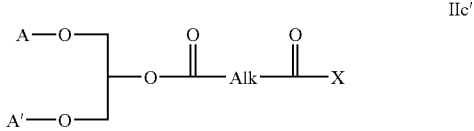

where A, A' and Alk are as defined above (A and A' being optionally protected with conventional protecting groups) and X represents the free acid or an activated acid as illustrated above.

Corresponding compounds to those of formula IIc' include:
malonic acid 2,3-bis-(L-valyloxy)-propyl ester,
malonic acid 2,3-bis-(N-CBZ-L-valyloxy)-propyl ester,
malonic acid 2,3-bis-(N-Fmoc-L-valyloxy)-propyl ester,
malonic acid 2,3-bis-(N-Boc-L-valyloxy)-propyl ester,
malonic acid 2,3-bis-(L-isoleucyloxy)-propyl ester,
malonic acid 2,3-bis-(N-CBZ-L-isoleucyloxy)-propyl ester,
malonic acid 2,3-bis-(N-Fmoc-L-isoleucyloxy)-propyl ester,
malonic acid 2,3-bis-(N-Boc-L-isoleucyloxy)-propyl ester,
succinic acid 2,3-bis-(L-valyloxy)-propyl ester,
succinic acid 2,3-bis-(N-CBZ-L-valyloxy)-propyl ester,
succinic acid 2,3-bis-(N-Fmoc-L-valyloxy)-propyl ester,
succinic acid 2,3-bis-(N-Boc-L-valyloxy)-propyl ester,
succinic acid 2,3-bis-(L-isoleucyloxy)-propyl ester,
succinic acid 2,3-bis-(N-CBZ-L-isoleucyloxy)-propyl ester,
succinic acid 2,3-bis-(N-Fmoc-L-isoleucyloxy)-propyl ester,
succinic acid 2,3-bis-(N-Boc-L-isoleucyloxy)-propyl ester,
glutaric acid 2,3-bis-(L-valyloxy)-propyl ester,
glutaric acid 2,3-bis-(N-CBZ-L-valyloxy)-propyl ester,
glutaric acid 2,3-bis-(N-Fmoc-L-valyloxy)-propyl ester,
glutaric acid 2,3-bis-(N-Boc-L-valyloxy)-propyl ester,
glutaric acid 2,3-bis-(L-isoleucyloxy)-propyl ester,
glutaric acid 2,3-bis-(N-CBZ-L-isoleucyloxy)-propyl ester,
glutaric acid 2,3-bis-(N-Fmoc-L-isoleucyloxy)-propyl ester,
glutaric acid 2,3-bis-(N-Boc-L-isoleucyloxy)-propyl ester, and the corresponding acid halides, in particular the chloride, acid anhydrides and diesters of each of the above, for instance
succinic acid 2,3-bis-(N-CBZ-L-valyloxy)-propyl ester,4-methoxybenzyl ester
succinic acid 2,3-bis-(N-CBZ-L-valyloxy)-propyl ester, 1,1-dimethylethyl ester, etc.

A preferred group of compounds in Formula IIc' include
malonic acid 1,3-bis-(L-valyloxy)-propyl ester,
malonic acid 1,3-bis-(N-CBZ-L-valyloxy)-propyl ester,
malonic acid 1,3-bis-(N-Fmoc-L-valyloxy)-propyl ester,
malonic acid 1,3-bis-(N-Boc-L-valyloxy)-propyl ester,
malonic acid 1,3-bis-(L-isoleucyloxy)-propyl ester,
malonic acid 1,3-bis-(N-CBZ-L-isoleucyloxy)-propyl ester,
malonic acid 1,3-bis-(N-Fmoc-L-isoleucyloxy)-propyl ester,
malonic acid 1,3-bis-(N-Boc-L-isoleucyloxy)-propyl ester,
succinic acid 1,3-bis-(L-valyloxy)-propyl ester,
succinic acid 1,3-bis-(N-CBZ-L-valyloxy)-propyl ester,
succinic acid 1,3-bis-(N-Fmoc-L-valyloxy)-propyl ester,
succinic acid 1,3-bis-(N-Boc-L-valyloxy)-propyl ester,
succinic acid 1,3-bis-(L-isoleucyloxy)-propyl ester,
succinic acid 1,3-bis-(N-CBZ-L-isoleucyloxy)-propyl ester,
succinic acid 1,3-bis-(N-Fmoc-L-isoleucyloxy)-propyl ester,
succinic acid 1,3-bis-(N-Boc-L-isoleucyloxy)-propyl ester,
glutaric acid 1,3-bis-(L-valyloxy)-propyl ester,
glutaric acid 1,3-bis-(N-CBZ-L-valyloxy)-propyl ester,
glutaric acid 1,3-bis-(N-Fmoc-L-valyloxy)-propyl ester,
glutaric acid 1,3-bis-(N-Boc-L-valyloxy)-propyl ester,
glutaric acid 1,3-bis-(L-isoleucyloxy)-propyl ester,
glutaric acid 1,3-bis-(N-CBZ-L-isoleucyloxy)-propyl ester,
glutaric acid 1,3-bis-(N-Fmoc-L-isoleucyloxy)-propyl ester,
glutaric acid 1,3-bis-(N-Boc-L-isoleucyloxy)-propyl ester, and the corresponding acid halides, in particular the chloride, acid anhydrides and diesters of each of the above, for instance
succinic acid 1,3-bis-(N-CBZ-L-valyloxy)-propyl ester,4-methoxybenzyl ester
succinic acid 13-bis-(N-CBZ-L-valyloxy)-propyl ester, 1,1-dimethylethyl ester, etc.

A further preferred group of intermediates comprise those of the formula IIa':

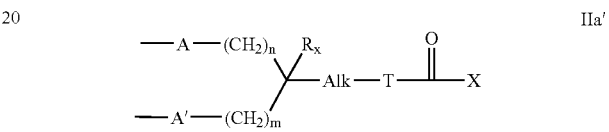

where $R_x$, Alk, m, n and T are as described above, A and A' represent acyl residues of L'-aliphatic amino acids (N-protected as necessary) esterified to hydroxy functions on the linker or one of A and A' is the acyl residue and the other is a free hydroxy group, and X represents the free acid or an activated acid as illustrated above. Preferably A and A' are the same amino acid residue.

Other novel intermediates include the free or activated acid precursors of compounds of the formula Ia such as:
3-N-Boc-L-valyloxypropanoic acid, 3-N-Fmoc-L-valyloxypropanoic acid, 3-NCBZ-L-valyloxypropanoic acid, 3-N-Boc-L-isoleucyloxypropanoic acid, 3-NFmoc-L-isoleucyloxypropanoic acid, 3-N-CBZ-L-isoleucyloxypropanoic acid,
4-N-Boc-L-valyloxybutyric acid, 4-N-Fmoc-L-valyloxybutyric acid, 4-N-CBZL-valyloxybutyric acid, 4-N-Boc-L-isoleucyloxybutyric acid, 4-N-Fmoc-Lisoleucyloxybutyric acid, 4-N-CBZ-L-isoleucyloxybutyric acid and the like;

and the activated derivatives, such as the acid halides
Further novel intermediates include precursors of compounds of the formula IIe and IIf above, especially those derived from "natural" configurations such as L-malic and L-tartaric acid; for instance:
3-ethoxycarbonyl-2-valyloxy-propionic acid
3-ethoxycarbonyl-2-isoleucyloxy-propionic acid
4-ethoxycarbonyl-2,3-bis-valyloxy-butyric acid
4-ethoxycarbonyl-2,3-bis-isoleucyloxy-butyric acid
3-t-butoxycarbonyl-2-valyloxy-propionic acid
3-t-butoxycarbonyl-2-isoleucyloxy-propionic acid
4-t-butoxycarbonyl-2,3-bis-valyloxy-butyric acid
4-t-butoxycarbonyl-2,3-bis-isoleucyloxy-butyric acid
3-benzyloxycarbonyl-2-valyloxy-propionic acid 3-benzyloxycarbonyl-2-isoleucyloxy-propionic acid 4-benzyloxycarbonyl-2,3-bis-valyloxy-butyric acid 4-benzyloxycarbonyl-2,3-bis-isoleucyloxy-butyric acid, and the like;

the corresponding compounds wherein the amino acid is N-protected, particularly with a protecting group allowing selective deprotection of the N-protective group without removal of the carboxy protecting group; and the corresponding activated derivatives such as the acid halides.

Still further novel intermediates include precursors corresponding to structure IId, such as;

2-(L-valyloxy)propanoic acid, 2-(N-Boc-L-valyloxy)propanoic acid, 2-(N-Fmoc-L-valyloxy)propanoic acid, 2-(N-CBZ-L-valyloxy)propanoic acid, 2-(L-isoleucyloxy)propanoic acid, 2-(N-Boc-L-isoleucyloxy)propanoic acid, N-(Fmoc-L-isoleucyloxy)propanoic acid, N-(CBZ-L-isoleucyloxy)propanoic acid, 2-(L-valyloxy)butyric acid, 2-(N-Boc-L-valyloxy)butyric acid, 2-(N-Fmoc-L-valyloxy)butyric acid, 2-(N-CBZ-L-valyloxy)butyric acid, 2-(L-isoleucyloxy)butyric acid, 2-(N-Boc-L-isoleucyloxy)butyric acid, N-(Fmoc-L-isoleucyloxy)butyric acid, N-(CBZ-L-isoleucyloxy)butyric acid, and the like;

and activated derivatives therof, such as the acid halides.

Preparation of 3' fluoronucleosides such as those of formula V has been extensively reviewed by Herdiwijn et al. in Nucleosides and Nucleotides 8 (1) 65–96 (1989), which is hereby incorporated by reference. The preparation of other monohydric nucleosides such as acyclovir, ddI (didanosine), ddC (zalcitabine), d4T (stavudine), FTC, lamivudine (3TC), 1592U89 (4-[2-amino-6-(cyclopropylamino)-9H-purin-9-yl]-2-cyclopentene-1-methanol), AZT (zidovudine), DAPD (D-2,6-diaminopurine dioxolane), F-ddA and the like are well known and extensively described in the literature.

The reactive derivatives of the $R_1(R_2)L_1L_2X$ group may be pre-formed or generated in situ by the use of reagents such as dicyclohexylcarbodiimide (DCC) or O-(1H-benzotriazol-1-yl) N,N,N',N'-tetramethyluronium tetrafluoroborate (TBTU). When an acid halide, such as the acid chloride is used, a tertiary amine catalyst, such as triethylamine, N,N'-dimethylaniline, pyridine or dimethylaminopyridine may be added to the reaction mixture to bind the liberated hydrohalic acid.

The reactions are preferably carried out in an unreactive solvent such as N,N'-dimethylformamide, tetrahydrofuran, dioxane, acetonitrile or a halogenatated hydrocarbon, such as dichloromethane. If desired, any of the above mentioned tertiary amine catalysts may be used as solvent, taking care that a suitable excess is present. The reaction temperature can typically be varied between 0° C. and 60° C., but will preferably be kept between 5° and 50° C. After a period of 1 to 60 hours the reaction will usually be essentially complete. The progress of the reaction can be followed using thin layer chromatography (TLC) and appropriate solvent systems. In general, when the reaction is completed as determined by TLC, the product is extracted with an organic solvent and purified by chromatography and/or recrystallisation from an appropriate solvent system.

By-products where acylation has taken place on the nucleoside base can be separated by chromatography, but such misacylation can be minimized by controlled reaction conditions. These controlled conditions can be achieved, for example, by manipulating the reagent concentrations or rate of addition, especially of the acylating agent, by lowering the temperature or by the choice of solvent. The reaction can be followed by TLC to monitor the controlled conditions. It may be convenient to protect the 6-oxo group on the base and especially the 2 amino with conventional protecting groups to forestall misacylation.

Compounds of Formula IV in which $R_3$ is hydrogen may be prepared by 6-activating the correponding guanine compound of Formula I (wherein the exposed amino function of the amino acid residue of $R_2$ is optionally protected with conventional N-protecting groups) with an activating group such as halo. The thus activated 6-purine is subsequently reduced to purine, for instance with a palladium or nickel catalyst and deprotected to the desired compound of Formula IV or Formula V.

Compounds wherein $R_3$ is an $R_1$ or other ester may be prepared by conventional esterification (analogous to the esterification described above) of the corresponding hydroxy compound of Formula I or Formula V, optionally after conventional N-protecting the exposed amine function of the amino acid residue of $R_2$ and/or $R_3$. Compounds wherein $R_3$ is an ether may be prepared analogously to the process disclosed in the abovementioned WO 93 13778, again in conjunction with optional N-protection of exposed amine groups. Compounds wherein $R_3$ is an azide can be prepared as described in WO 97 09052.

Intermediates of the formula IId are conveniently prepared by acylation of a carboxy-protected hydroxy alkanoic acid, typically a 2-hydroxy-1-alkanoic acid, with the appropriate activated and N-protected $R_2$ derivative, such as NCBZ valyl or isoleucyl in conjunction with a conventional coupling reagent such as DMAP/DCC or with the amino acid halide. The carboxy protecting group is then removed, for instance by acid hydrolysis and the resulting intermediate is activated as described above or the free acid is unsed in conjunction with a coupling reagent to esterify the the nucleoside under conventional esterification conditions.

Compounds within the scope of the invention are also conveniently prepared by the methodology in the immediately preceding paragraph, namely esterification of a carboxy protected α-hydroxy, ω-carboxy acid, such as glycollic acid, lactic acid, hydroxybutyric acid etc with the appropriate N-protected $R_2$ derivative, either as the free acid in conjunction with a coupling agent or activated, for instance to the corresponding acid halide. The carboxy protecting group is removed and the resulting intermediate esterified with the nucleoside with the methodology described above.

Compounds comprising a structure of the formula IIe or IIf are prepared by carboxy protecting the terminal carboxy groups of the respective dicarboxylic acid, such as L-tartaric acid or L-malic acid, with conventional carboxy protecting groups such as benzyl. The free hydroxy group (s) are then esterified with conventional esterification techniques, such as DMAP & DCC in DMF with the appropriate N-protected $R_2$ amino acid, such asN-Boc-L-valyl or NBoc-L-isoleucyl. The benzyl carboxy protecting groups are removed and the resulting product is esterified to the 5'-hydroxy function of a monohydric nucleoside, using conventional conditions, such as those in the accompanying Examples. Finally, the free carboxy function is esterified with an $R_1$ group or, more preferrably a conventional pharmaceutically acceptable ester, such as the ethyl ester.

Compounds comprising a phosphorylated moiety III may be prepared by reacting 2',3'-dideoxy-3'-fluoroguanine-5-monophosphate with a compound of Formula VIa

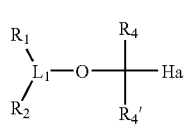

where Ha is halo, such as chloro, iodo or bromo, in analagous conditions to those described in U.S. Pat. No. 4,337, 201, U.S. Pat. No. 5,227,506, WO 94/13682 & WO 94/13324, Starret et al J Med Chem 37 1857–1864 (1994) and Iyer et al Tetrahedron Lett 30 7141–7144 (1989) which are incorporated herein by reference. The monophosphate can be prepared by conventional phosphorylation of FLG, as described, for instance, in Herdwyn et al ibid. Corresponding methodology will apply to the monophosphates of other monohydric nucleosides.

Compounds comprising an optional linker $L_2$ may also be prepared by a two stage process. In particular a compound of the formula $ClC(=O)OC(R_4)(R_4')Cl$ can be reacted with the 5'-hydroxy of FLG (optionally protected on the base with conventional protecting groups) as is known in the cephalosporin art. The resulting FLG-5'-O—C(=O)OC($R_4$)($R_4'$) chloride is then reacted with an $R_1$ and $R_2$ bearing trifunctional linker wherein the third function comprises a carboxyl function, such as the potassium salt.

It will be appreciated that trifunctional $L_1$ groups of formula IIa wherein and n and m are 1 and Alk is absent can be prepared from glycerol by regioselective esterification as depicted below in scheme 1 by reference to a stearoyl/L-valyl combination. In short $R_1$ and $R_2$ are regioselectively esterified to positions 1 and 3 of the glycerol and position 2 is then converted to the appropriate -T-C(=O)— group, which is then esterified to the 5'-position of the fluoronucleoside or to a cooperating function on $L_2$ (not depicted). Alternatively the hydroxy at position 2 of the glycerol derivative can be esterified with an $L_2$ group containing a cooperating carbonyl function on its left hand end.

$L_1$ groups of formula IIa wherein m is 1, n is 0 and Alk is methylene can also be prepared from glycerol by regioselectively esterifying $R_1$ and $R_2$ to positions 1 and 2 of the glycerol, as also depicted below in scheme 1, followed by conversion of the hydroxy at position 3 to the appropriate -T-C(=O)-group. The leftmost series of reactions on Scheme 1 shows the situation where $R_1$ is esterified to position 1 of the glycerol and $R_2$ is esterified to position 2. The corresponding arrangement where $R_1$ is esterified to position 2 and $R_2$ to position 1 can be achieved by first treating the glycerol with CBz-L-valine/DCC/DMAP/DMF and then protecting the 3 position with pixyl chloride prior to esterifying the fatty acid of $R_1$ to position 2 of the glycerol, deprotecting and converting the 3 position as necessary.

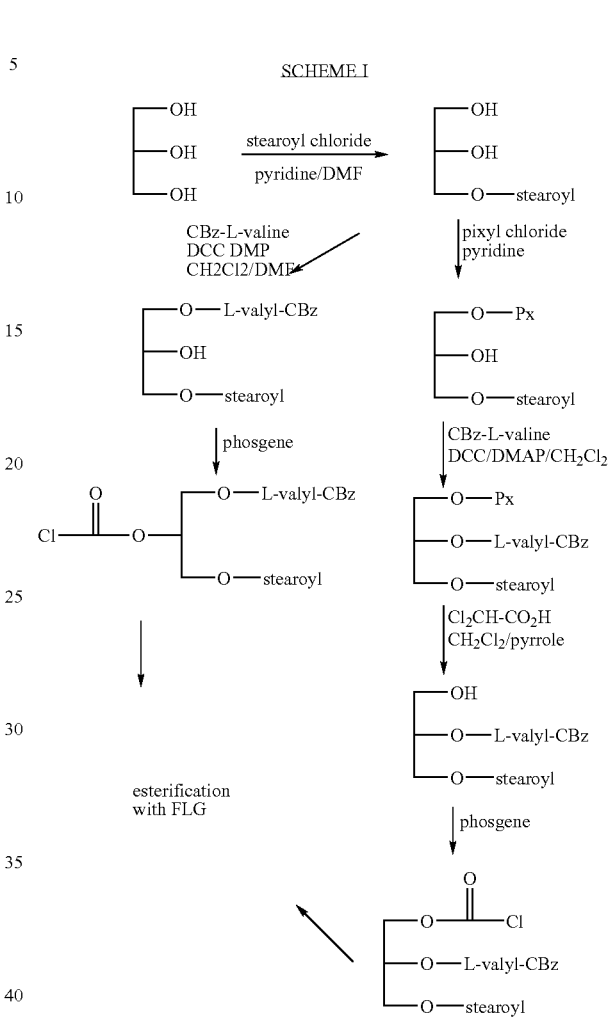

Although Scheme 1 has been illustrated by reference to a combination wherein $R_1$ is stearoyl and $R_2$ is L-valyl, it will be appreciated that this basic scheme will also be applicable to other amino acids, where present other fatty acids, or using conventional protection groups, to combinations of $R_2$ as an amino acid derivative and $R_1$ as hydroxy. Linkers where T comprises an —NH— group can be prepared by analogous regioselective esterification followed by conversion of the free hydroxyl to amine, reduction to azide and reaction with phosgene to form the corresponding chlorocarbamate.

A variation of scheme I allowing the preparation of linkers of the formula IIc. In this variation, the phosgene step shown above is replaced by reaction with an activated dicarboxylic acid, such as succinic anhydride. This results in a glycerol triester (comprising the (optionally protected) $R_1$ ester, the protected $R_2$ ester and the ester of the dicarboxylic acid) and the free carboxy on the dicarboxylic acid is then activated and esterified to the nucleoside in a conventional fashion. Alternatively linkers of formula IIc can be built up in situ on the nucleoside. In this variant, the dicarboxylic acid is esterified to a suitably protected glycerol derivative. This succinyl monoester is then esterified to the 5'-hydroxy function of the nucleoside in a conventional manner. Finally one or both of the protecting groups on the glycerol moiety is replaced with the L-amino acid ester, and, if present, the remaining protecting group is replaced with a fatty acid ester or removed to leave a free hydroxy group This is depicted in Scheme IA which illustrates an example wherein the nucleoside in acyclovir (FLG shown in shadow), the dicarboxylic acid is succinyl and $R_1$ and $R_2$ are both CBZ-protected valyl, but will, of course be applicable to other variations of Formula Ic. In each case coupling conditions means standard esterification conditions such as coupling reagents DMAP, DCC etc or alternatively conversion of the relevant carboxy function to an activated derivative such as the acid chloride or the activated succinic moiety can also comprise the anhydride.

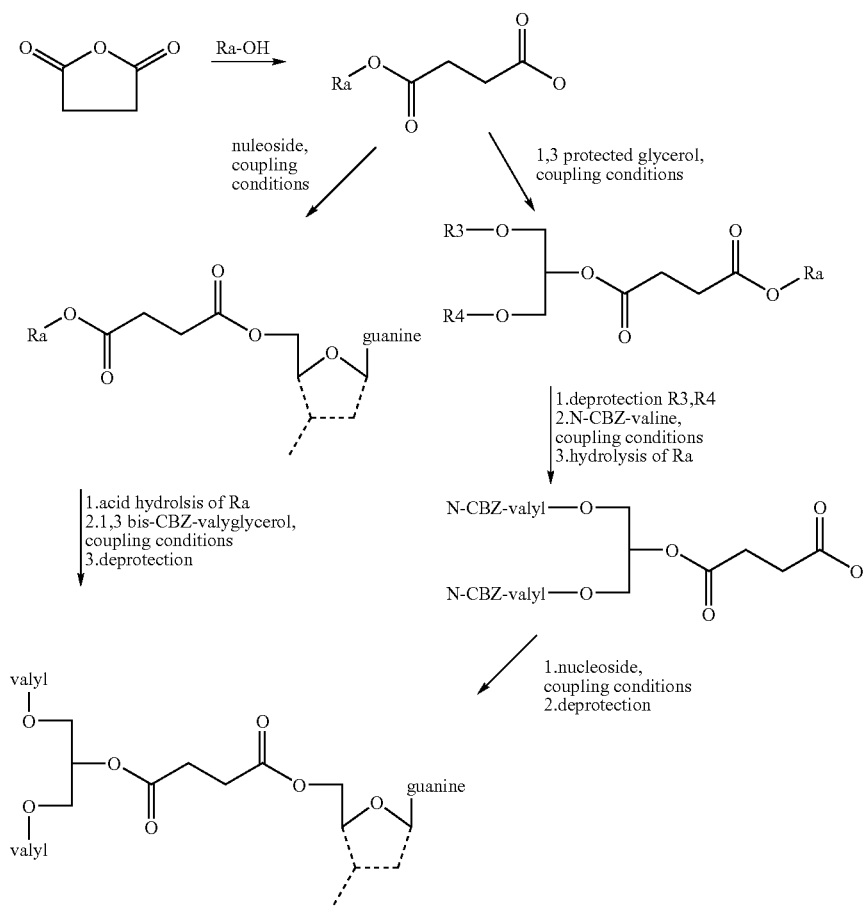

In a variation of Scheme IA, the succinic anhydride is reacted directly with the nucleoside, thus avoiding the first protection and deprotection steps. A further alternative is to regioselectively esterify the glycerol moiety with the N-protected amino acid moiety(ies), generally in conjunction with protection of the hydroxy function intended for coupling to the nucleoside, followed by deprotection of that hydroxy and coupling to the nucleoside.

SCHEME II

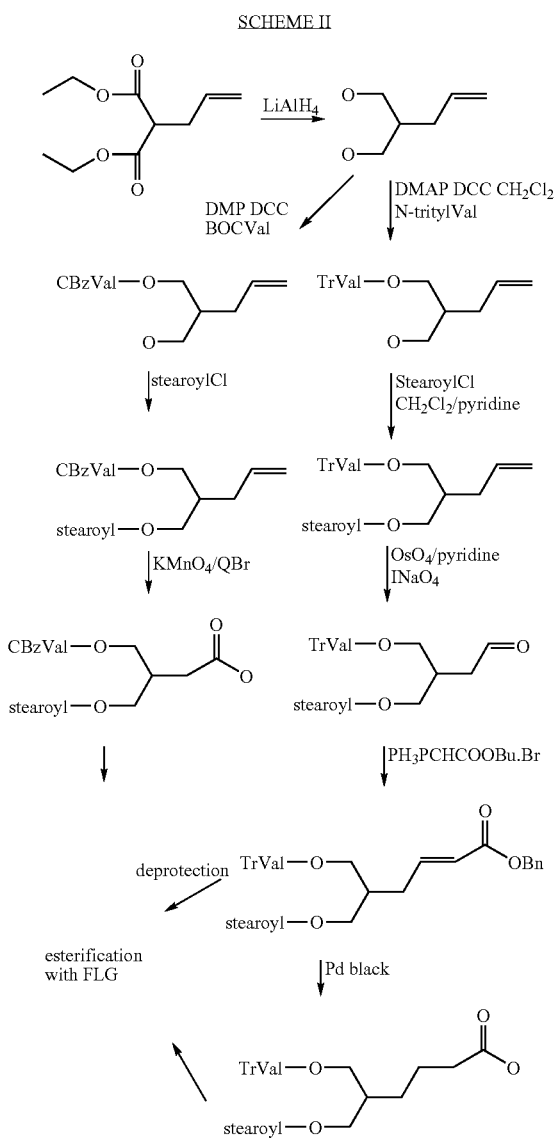

Linkers where m and n are 1, Alk is alkylene or alkenylene and T is a bond can be prepared as shown in Scheme II above. Other permutations of m, n, Alk and the various functions in the trifunctional linker group $L_1$ of formula IIa can be prepared analagously to the above with the corresponding starter materials, such as 1,2,4-trihydroxybutane (CA registry number 3968-00-6), 3,4-dihydroxybutanoic acid (1518-61-2 & 22329-74-4), (S)-3,4-dihydroxybutanoic acid (51267-44-8), (R)-3,4-dihydroxybutanoic acid (158800-76-1), 1,2,5-pentanetriol (51064-73-4 & 14697-46-2), (S)-1,2,5-pentanetriol (13942-73-9), (R)-1,2,5-pentanetriol (171335-70-9), 4,5-dihydroxypentanoic acid (66679-29-6 & 12972514-0), 1,3,5-pentanetriol (4328-94-3) and 3-(2-hydroxyethyl)-1,5-pentanediol (53378-75-9). The preparation of each of these starting materials is described in the references to the respective registry number. Ohsawa et al in Chem Pharm Bull 41 (11) 1906–1909 (1993) and Terao et al Chem. Pharm. Bull. 39(3) 823–825 (1991) describe the control of the sterochemistry of trifunctional linker groups with lipase P.

The amino acid derivative of $R_2$ and, if present, $R_1$ can alternatively be esterified to the linker group with the 2-oxa-4-aza-cycloalkane-1,3-dione methodology described in international patent application no. WO 94/29311, the contents of which are hereby incorporated by reference.

Linking of the carboxy function of $R_1$ and/or $R_2$ to an amine group on the linker derivative proceeds by conventional peptide chemistry, generally in conjunction with protection of the α-amine with conventional N-protecting groups. Formation of an amide bond between a carboxyl function on the linker and the α-amine group of $R_2$ also proceeds by conventional peptide chemistry, generally in conjunction with protection of the α-carboxy function. Esterification of $R_1$ as a fatty alcohol to a carboxy function on the linker proceeds analogously, but conversely, to the above esterifiation of $R_1$ as a fatty acid.

The above description has centred around monohydric nucleosides derivatised with a linker group which in turn is derivatised with an ester residue of an aliphatic amino acid, and, optionally, the acyl residue of a fatty acid.

In a further aspect of the invention, however, said linker group and derivatised aliphatic amino acid ester, but this time without the optional fatty ester, can be applied to a broader range of drugs. Thus the invention further provides compounds of the formula D-L*-$R_2$ where $R_2$ is the amide or ester residue of an aliphatic amino acid, D is a drug residue bearing an accesible function such as an amine, hydroxy, carboxy, phosphonate, phosphinate or phosphoryl function and L is an at least bifunctional linker comprising a first function bound to said accessible function spaced from a second function forming an amide or acyl bond with the aliphatic amino acid.

The prodrugs of this aspect of the invention are distinct from those described in WO98/21233 in that the latter comprise an obligatory fatty acid ester.

Drug residue as used in its conventional significance, that is implying that during linkage a hydrogen or hydroxy has been eliminated from an accessible amino, phosphoryl, phosphinyl, phosphonyl, carboxy or hydroxy function on the Drug. The amine function on the Drug can be a primary amine (—$NH_2$) or a secondary amine (—NH—). The amino acid of $R_2$ may be optionally N-protected in those configurations where it possesses a free amine function.

The expression difunctional in the context of the linker group L means that the linker has at least one hydroxy or amine function available for esterification or amide bonding with $R_2$, or a carboxyl function available for amide bonding with the free α-camine function of $R_2$. Spaced therefrom on the difunctional linker is a further functional group for linkage to a cooperating function on the Drug such as hydroxy, carboxy, phosphonyl, phosphoryl, phosphinyl and the like.

The linker may in fact be trifunctional, that is the linker has at least three functions including two independently selected from hydroxy, amine or carboxy, the amine and hydroxy function(s) being available for esterification/amide bonding with the carboxyl functions of a pair of $R_2$, or the carboxy function(s) on the linker being available for amide bonding with the free α-amine function of $R_2$. These hydroxy/amine/carboxy functions are spaced from a further functional group for linkage with a cooperating function on the drug, such as hydroxy, carboxy, phosphonyl, phosphoryl, phosphinyl, amine etc. Other trifunctional linker groups may comprise a first hydroxy, amine or carboxy function cooperating with $R_2$, a function cooperating with the drug and a further functional group either underivatised such as hydroxy, carboxy, amine etc or alternatively protected with conventional pharmaceutically acceptable protecting groups.

The invention further provides pharmaceutical compositions comprising the compounds of the present broader aspect of the invention and pharmaceutically acceptable carriers or diluents therefor. Additional aspects of the invention provide methods of medical treatment or prophylaxis comprising the administration of a compound of the invention to a human or animal suffering from or prone to the ailment to which the respective Drug is applicable.

By the use of the invention the pharmacokinetics of a broad range of orally administered drugs are enhanced, for instance by improving absolute bioavailability or by providing a more even release of the mother compound or by providing for a reduced interpersonal spread in pharmacokinetic performance. However the compounds of the invention are not limited to those based on orally administered drugs as the prodrugs of the invention, when parenterally administered, provide enhanced pharmacokinetic performance, for instance by improving solubility, while still allowing for efficient release of the mother compound.

Linker as used in this second aspect of the invention specifically embraces each and every linker described above in relation to the monohydric nucleoside aspect of the invention (to the extent that these omit a fatty acid ester), including the structures >$L_1L_2$ and structures of the formulae IIa, IIb, IIc, IId, IIe, IIf, IIIa, IIIb, IIIc, (optionally protected) tartaric and malic acid linkers, and linkers depicted in formulae I, Ia, Ic, Ic', Id, If and Ig. However it will be apparent that these linker structures are of wider applicability than the monohydric nucleosides there described.

Convenient linker groups, for instance when the Drug comprises an amine or hydroxy function, include those of the Formulae IIaa or II'aa

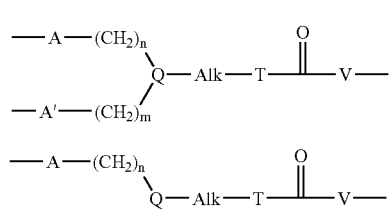

where A and A' are independently an ester linkage between an hydroxy on the linker and the carboxy on $R_2$ (or a pair of $R_2$), or an amide linkage between an amine on the linker and a carboxy on $R_2$, or a pair of $R_2$;

Q is a structure:

or

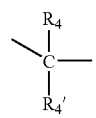

or Q is a monocyclic, saturated or unsaturated carbo- or heterocycle
with 4, 5 or 6 ring atoms;
Alk is absent, $C_1$–$C_4$ alkylene or $C_2$–$C_4$ alkenylene;
T is a bond, —O— or —N($R_4$)—,
V is a bond or a structure of the formula IIbb or IIcc:

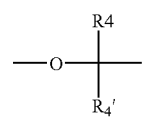

or

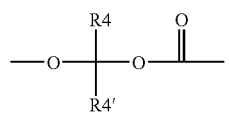

$R_4$ and $R_4'$ are independently hydrogen or $C_1$–$C_3$ alkyl; and
m and n are independently 0, 1 or 2;

In Formulae IIa–IIe, Q as a ring is preferably an aromatic group such as pyridine, furyl, imidazol etc or especially phenyl, such as aromatic moieties wherein the arm(s) bearing the or each $R_2$ group are respectively para and meta or both meta to the remainder of the linker.

Particularly convenient structures when the drug comprises an hydroxy function include the corresponding structures to: formulae IIc*, that is

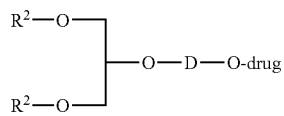

formula II e*, that is

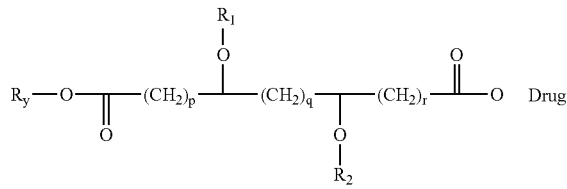
IIe* formula II f*, that is

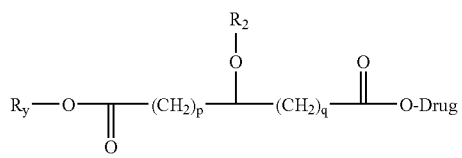
IIf*

Formula Id*, that is

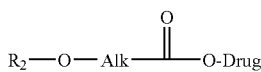
Id*

Where the Drug comprises a carboxyl function, the linker may comprise a structure of the formulae VIII or VIII':

where A, A', Q, Alk, m, and n are as defined for Formula IIaa & II'aa.

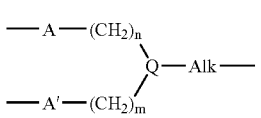
VIII

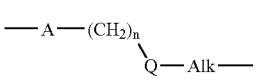
VIII'

Preferably, however, when the Drug comprises a carboxy function, the di- or trifunctional linker group L is a structure of Formulae IIdd or II'dd (that is a compound of Formulae IIaa or II'aa, wherein T is 0 and V is a structure of the formula IIbb):

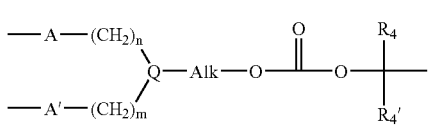
IIdd

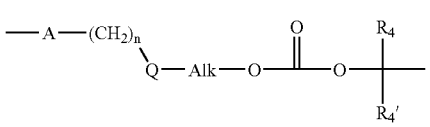
II'dd

In structure IIdd, $R_4'$ is preferably hydrogen and $R_4$ is ethyl, phenyl, and especially methyl or hydrogen or $R_4$ and $R_4'$ together define isopropyl Where the Drug comprises a phosphoryl, phosphinyl or phosphonyl function, the di or trifunctional linker group L may comprise a structure of the formula IIaa or II'aa, especially those of the formula IIee or II'ee:

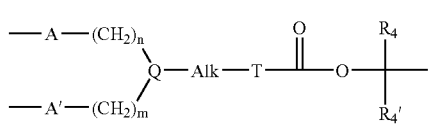
IIee

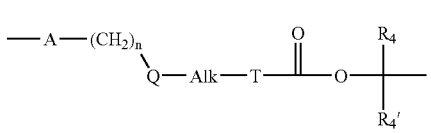
II'ee where T is a bond, —NH— or —O— and Q and A are as defined above including the cyclic Q structures such as cycloalkyl, phenyl and heterocycles such as furyl, pyridyl etc. In structures IIee and II'ee, $R_4'$ is preferably hydrogen and $R_4$ is methyl, ethyl, phenyl and especially hydrogen or $R_4$ and $R_4$ define isopropyl.

Preferably, however, where the Drug comprises a phosphonyl, phosphinyl or phosphoryl function, the difunctional linker comprises a structure of the formula II''b:

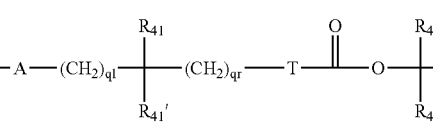
II'b where T is a bond, —O— or —NH—, $R_{41}$ $R_{4r'}$ and $R_{4r}'$ and $R_{4r'}$ are independently H or $CC_3$ alkyl and A is as defined above (or wherein A is a further difunctional linker to which one or more $R_2$ depends as described above). Examples of structures belonging to the latter possibility for A include those of Formula Va and Vb:

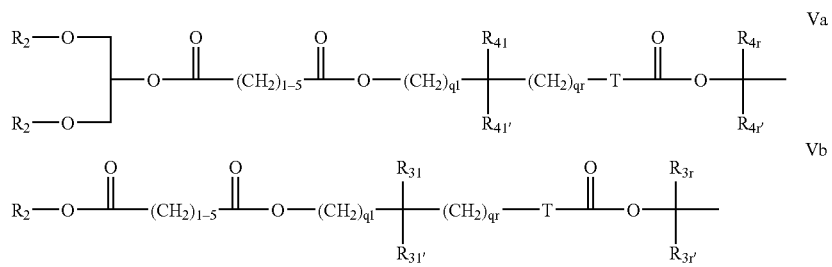

where T, q, $R_2$, $R_{4l}$ $R_{4l}'$ $R_{4r}$ and $R_{4r}'$ are as defined above. Although formulae Va and Vb depict the dicarboxylate moiety as unbranched, it will be apparent that a wide variety of dicarboxylates will be suitable here, including branched and/or unsaturated and/or substituted dicarboxylic acid derivatives or various lengths, as described in more detail above.

Amongst the preferred configurations for formulae II″b, Va and Vb, are those wherein T is absent.

Convenient values for the rightmost $R_4$ and $R_4$ are hydrogen and for the left most $R_4$ and $R_4$ both methyl. Other preferred embodiments comprise structures of the formulae II″b, Va or Vb wherein the rightmost $R_4$ is H and the rightmost $R_4$ is isopropyl, cyclo$C_{1-6}$alkyl, phenyl or benzyl.

Convenient values of the rightmost q and leftmost q are as follows:

zero: 1 zero:2, zero:3

1:1

1: zero

2:2

3:zero

3:1.

Still further preferred embodiments comprise structures of the formula II″b, Va or Vb wherein T is —NH— or —O—.

In drugs comprising multiple phosphoryl/phosphonate/phosphinate functions, it is generally advantageous that an hydroxy group on each phosphorous moiety is esterified with a structure of Formula II'e or II″b etc. Regioselective protecting groups which bridge the phosphate groups of bis phosphonates and thus assist mono and diacylation include Si compounds such as dichlorotetraisopropyldisosiloxane.

Methodology for the derivatisation of phosphorous containing compounds with acyloxyalkyl groups and which can be used analogously for the coupling of the difunctional and trifunctional linkers of the invention is described in U.S. Pat. No. 5,227,506, WO 94/13682, WO 94/13324, WO 98/04569 Starret et al J Med Chem 37 1857–1864 (1994) and Iyer et al Tetrahedron Lett 30 7141–7144 (1989).

A further aspect of the invention comprises novel intermediates useful in applying structures of the formulae II″b to a drug and having the formula N–1:

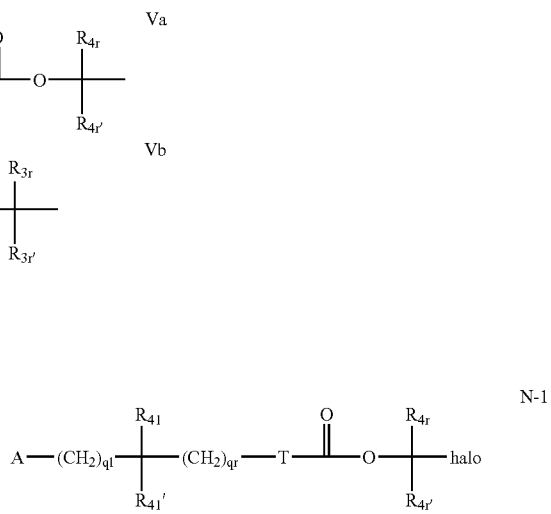

where A, q, $R_4$, $R_4'$ and T are as defined for formula II″b.

A particularly preferred group of compounds substantially within formula N–1 are those of the formula N-2

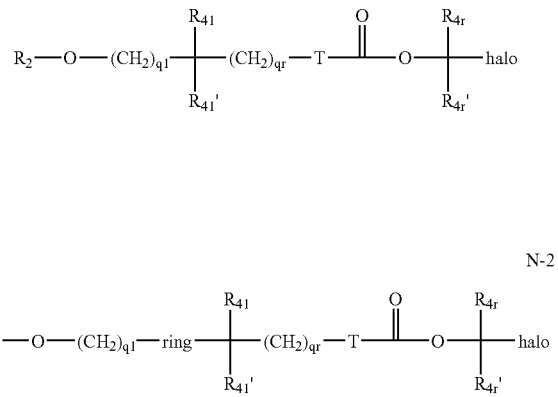

where $R_2$ is the acyl residue of an aliphatic amino acid, $R_{3L}$ and $R_{3L}'$ are independently H, $C_{1-3}$ alkyl, $C_{3-6}$cycloalkyl, $C_{1-3}$alkyl-$C_1$-$C_6$-cycloalkyl phenyl or benzyl, $R_{3R}$ and $R_{3R}'$ are independently H or $C_{1-3}$ alkyl q1 is 0–3, qr is 0–3, T is a bond, —$NR_3$— or —O—

$R_3$ is H or $C_{1-3}$alkyl;

"ring" is an optionally substituted aromatic or non-aromatic, hetero-or carbocycle; and halo is bromo, chloro or iodo.

Representative compounds within formula N-2 include:

2,2-dimethyl-3-(N-Boc-L-valyloxy)propionic acid iodomethyl ester 3,3-bis (N-CBz-L-valyloxymethyl)-propionic acid iodomethyl ester, 2-(N-CBz-L-valyloxy)ethoxycarbonyloxymethyl iodide Iodomethyl 1,3-bis(N-benzyloxycarbonyl-L-valyloxy)-2-propyl carbonate, Iodomethyl 2-methyl-2-(N-benzyloxycarbonyl-L-valyloxymethyl) propionate,
Iodomethyl 2-(N-benzyloxycarbonyl-L-valyloxy)-DL-propionate.
Iodomethyl 2-(N-benzyloxycarbonyl-L-valyloxy)isobutyrate.
Iodomethyl 2-(N-benzyloxycarbonyl-L-valyloxy)-3-methyl-(S)-(+)-butyrate.
Iodomethyl 2-O-(N-benzyloxycarbonyl-L-valyloxy)-2-phenyl-DL-acetate
Iodomethyl 4-(N-benzyloxycarbonyl-L-valyloxy) benzoate.
Iodomethyl 5-(N-CBz-L-valyloxy)-2,2-dimethylvalerate
2-(N-CBz-L-valyloxy)-ethyl iodomethyl carbonate
4-(N-CBz-L-valyloxy) butyric acid iodomethyl ester
Iodomethyl-3-(N-benzyloxycarbonyl-L-valyloxy)-benzoate
Iodomethyl-3-(N-benzyloxycarbonyl-L-valyloxy)-propionate
1,3-bis(N-tert-butoxycarbonyl-L-valyloxy)-2-propyl 1-iodoethyl carbonate
3-(N-benzyloxycarbonyl-L-valyloxy)-2,2-dimethylpropyl iodomethyl carbonate
Iodomethyl 3,4-di-(N-CBZ-L-valyloxy)hydrocinnamate
3-(N-CBZ-L-valyloxy)phenyl iodomethyl carbonate
Iodomethyl 2-(N-CBZ-L-valyloxy)phenylacetate
Iodomethyl 4-(N-CBZ-L-valyloxyxy)phenylacetate
Iodomethyl 4-(2-N-benzyloxycarbonyl-L-valyloxyethyl) benzoate
Iodomethyl 4-(N-benzyloxycarbonyl-L-valyloxy)cyclohexanoate.
Iodomethyl 2-(N-benzyloxycarbonyl-L-valyloxymethyl)-2-ethyl butyrate
2-(N-(iodomethoxycarbonyl)-amino)-2-methyl-1-(N-benzyloxycarbonyl-L-valyloxy)-propane
1-(2-N-CBz-L-valyloxyethyl)-6-oxo-1,6-dihydro-pyridine-3-carboxylic acid iodomethyl ester
Iodomethyl 5-[(N-benzyloxycarbonyl-L-valyloxy)methyl]-2-furoate
Iodomethyl 4-(2-N-benzyloxycarbonyl-L-valyloxyethoxy)-benzoic acid
2,2-dimethyl-3-(N-Boc-L-isoleucyloxy)propionic acid iodomethyl ester
3,3-bis (N-CBz-L-isoleucyloxymethyl)-propionic acid iodomethyl ester,
2-(N-CBz-L-isoleucyloxy)ethoxycarbonyloxymethyl iodide
Iodomethyl 1,3-bis(N-benzyloxycarbonyl-L-isoleucyloxy)-2-propyl carbonate,
Iodomethyl 2-methyl-2-(N-benzyloxycarbonyl-L-isoleucyloxymethyl) propionate,
Iodomethyl 2-(N-benzyloxycarbonyl-L-isoleucyloxy)-DL-propionate.
Iodomethyl 2-(N-benzyloxycarbonyl-L-isoleucyloxy)isobutyrate.
Iodomethyl 2-(N-benzyloxycarbonyl-L-isoleucyloxy)-3-methyl-(S)-(+)-butyrate.
Iodomethyl 2-(N-benzyloxycarbonyl-L-isoleucyloxy)-2-phenyl-DL-acetate
Iodomethyl 4-(N-benzyloxycarbonyl-L-isoleucyloxy) benzoate.
Iodomethyl 5-(N-CBz-L-isoleucyloxy)-2,2-dimethylvalerate
2-(N-CBz-L-isoleucyloxy)-ethyl iodomethyl carbonate
4-(N-CBz-L-isoleucyloxy) butyric acid iodomethyl ester
Iodomethyl-3-(N-benzyloxycarbonyl-L-isoleuclyoxy)-benzoate
Iodomethyl-3-(N-benzyloxycarbonyl-L-isoleucyloxy)-propionate
1,3-bis(N-tert-butoxycarbonyl-L-isoleucyloxy)-2-propyl 1-iodoethyl carbonate
3-(N-benzyloxycarbonyl-L-isoleucyloxy)-2,2-dimethylpropyl iodomethyl carbonate
Iodomethyl 3,4-di-(N-CBz-L-isoleucyloxy)hydrocinnamate
3-(N-CBz-L-isoleucyloxy)phenyl iodomethyl carbonate
Iodomethyl 2-(N-CBz-L-isoleucyloxy)phenylacetate
Iodomethyl 4-(N-CBz-L-isoleucyloxy)phenylacetate
Iodomethyl 4-(2-N-benzyloxycarbonyl-L-isoleucyloxyethyl) benzoate
Iodomethyl 4-(N-benzyloxycarbonyl-L-isoleucyloxy)cyclohexanoate,
Iodomethyl 2-(N-benzyloxycarbonyl-L-isoleucyloxymethyl)-2-ethyl butyrate,
2-(N-(iodomethoxycarbonyl)-amino)-2-methyl-1-(N-benzyloxycarbonylL-isoleucyloxy)-propane,
1-(2-N-CBz-L-isoleucyloxyethyl)-6-oxo-1,6-dihydro-pyridine-3-carboxylic acid iodomethyl ester
iodomethyl 5-[(N-benzyloxycarbonyl-L-isoleucyloxy)methyl]-2-furoate
iodomethyl 4-(2-N-benzyloxycarbonyl-L-isoleucyloxyethoxy)-benzoic acid and the corresponding chloro analogues.

Further aspects of the invention include the use of intermediate compounds, such as those of the formula N-1, N-2, IIc', IIa' VII, the free or activated acid precursors of formula Ia, IIe, IId, IIf etc in the preparation of a pharmaceutical prodrug.

The invention further provides pharmaceutical compositions comprising the compounds of the invention and pharmaceutically acceptable carriers or diluents therefor. Additional aspects of the invention provide methods of medical treatment or prophylaxis comprising the administration of a compound of the invention to a human or animal suffering from or prone to the ailment to which the respective Drug is applicable.

Representative drugs having carboxyl functional groups include;

angiotensin-converting enzyme inhibitors such as alecapril, captopril, 1-[4-carboxy-2-methyl-2R,4R-pentanoyl]-2,3-duhydro-2S-indole-2-carboxylic acid, enalprilic acid, lisinopril, N-cyclopentyl-N-[3-[(2,2-dimethyl-1-oxopropyl)thio]-2-methyl-1-oxopropyl]glycine, pivopril, (2R, 4R)-2-hydroxyphenyl)-3-(3-mercaptopropionyl)-4-thiazolidinecarboxylic acid, (S) benzamido-4-oxo-6-phenylhexenoyl-2-carboxypyrrolidine, [2S-1[R*(R*))]] 2α, 3αβ, 7αβ]-1[2-[[1-carboxy-3-phenylpropyl]-amino]-1-oxopropyl]octahydro-1H-indole-2-carboxylic acid, [3S-1 [R*(R*))]], 3R*]-2-[2-[[1-carboxy-3-phenylpropyl]-amino]-1-oxopropyl]-1,2,3,4-tetrahydro-3-isoquinolone carboxylic acid and tiopronin;

cephalosporin antibiotics such as cefaclor, cefadroxil, cefamandole, cefatrizine, cefazedone, cefazuflur, cefazolin, cefbuperazone, cefinenoxime, cefinetazole, cefodizime, cefonicid, cefoperazone, ceforamide, cefotaxime, cefotefan, cefotiam, cefoxitin, cefpimizole, cefpirome, cefroxadine, cefsulodin, cefpiramide, ceftazidime, ceftezole, ceftizoxime, ceftriaxone, cefuroxime, cephacetrile, cephalexin, cephaloglycin, cephaloridine, cephalosporin, cephanone, cephradine and latamoxef; penicillins such as amoxycillin, ampicillin, apalcillin, azidocillin, azlocillin, benzylpencillin, carbenicillin, carfecillin, carindacillin, cloxacillin, cyclacillin, dicloxacillin, epicillin, flucloxacillin, hetacillin, methicillin, mezlocillin, nafcillin, oxacillin, phenethicillin, piperazillin, sulbenicllin, temocillin and ticarcillin;

non-steroidal antiinflammatory agents such as acametacin, alclofenac, alminoprofen, aspirin (acetylsalicylic acid), 4-biphenylacetic acid, bucloxic acid, carprofen, cinchofen, cinmetacin, clometacin, clonixin, diclofenac, diflunisal, etodolac, fenbufen, fenclofenac, fenclosic acid, fenoprofen, ferobufen, flufenamic acid, flufenisal, flurbiprofin, fluprofen, flutiazin, ibufenac, ibuprofen, indomethacin, indoprofen, ketoprofen, ketorolac, lonazolac, loxoprofen, meclofenamic acid, mefenamic acid, 2-(8-methyl-10,11-dihydro-11-oxodibenz[b,f]oxepin-2-yl)propionic acid, naproxen, nifluminic acid, O-(carbamoylphenoxy)acetic acid, oxoprozin, pirprofen, prodolic acid, salicylic acid, salicylsalicylic acid, sulindac, suprofen, tiaprofenic acid, tolfenamic acid, tolmetin and zopemirac;

prostaglandins such as ciprostene, 16-deoxy-16-hydroxy-16-vinyl prostaglandin $E_2$, 16, 16-dimethylprostaglandin $E_2$, epoprostostenol, meteneprost, nileprost, prostacyclin, prostaglandins $E_1$, $E_2$, or $F_{2\alpha}$ and thromboxane $A_2$;

quinolone antibiotics such as acrosoxacin, cinoxacin, ciprofloxacin, enoxacin, flumequine, naladixic acid, norfloxacin, ofloxacin, oxolinic acid, pefloxacin, pipemidic acid and piromidic acid.

Representative drugs containing amine groups include:

acebutalol, albuterol, alprenolol, atenolol, bunolol, butopamine, butoxamine, carbuterol, cartelolol, colterol, deterenol, dexpropanolol, diacetolol, dobutamine, exaprolol, exprenolol, fenoterol, fenyripol, labotolol, levobunolol, metolol, metaproterenol, metoprolol, nadolol, pamatolol, penbutalol, pindolol, pirbuterol, practolol, prenalterol, primidolol, prizidilol, procaterol, propanolol, quinterenol, rimiterol, ritodrine, solotol, soterenol, sulfiniolol, sulfinterol, sulictidil, tazaolol, terbutaline, timolol, tiprenolol, tipridil, tolamolol, thiabendazole, albendazole, albutoin, alinidine, alizapride, amiloride, a minorex, aprinocid, cambendazole, cimetidine, clonidine, cyclobenzadole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, dimethoxyphenethylamine, N-[3(R)-[2-piperidin-4-yl) ethyl]-2-piperidone-1-yl]acetyl-3(R)-methyl-α-alanine adrenolone, aletamine, amidephrine, amphetamine, aspartame, bamethan, betahistine, clorprenaline, chlortermine, dopamine, ephrinephrine etryptamine, fenfluramine, methyldopamine, norepinephrine, tocainide enviroxime, nifedipine, nimodipine, triamterene, norfloxacin and similar compounds such as pipedemic acid, 1-ethyl-6-fluoro-1,4-dihydro-4-oxo-7-(1-piperazinyl)-1,8-napthyridine-3-carbokylic acid, 1-cyclopropyl-6-fluoro-1,4-dihydro-4-oxo-7-(piperazinyl)-3-quinolinecarboxylic acid.

A favoured amine drug, [[3(R)-2-piperidin-4-ylethyl)-2-oxopiperidinyl]acetyl]-3(R)-methyl-β-alanine (also known as L-734,217) has the formula:

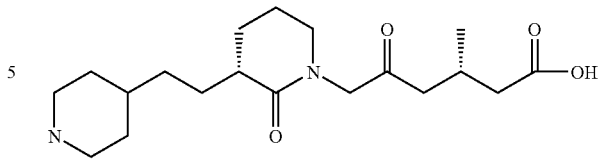

A further preferred amino drug are the bicyclam anti HIV agents, such as AMD 3100:

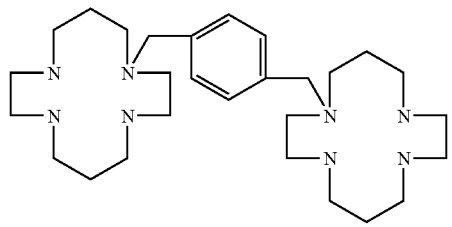

Representative drugs containing hydroxy groups include:

steroidal hormones such as allylestrenol, cingestol, dehydroepiandrosteron, dienostrol, diethylstilbestrol, dimethisteron, ethyneron, ethynodiol, estradiol, estron, ethinyl estradiol, ethisteron, lynestrenol, mestranol, methyl testosterone, norethindron, norgestrel, norvinsteron, oxogeston, quinestrol, testosteron and tigestol;

tranquilizers such as dofexazepam, hydroxyzin, lorazepam and oxazepam; neuroleptics such as acetophenazine, carphenazine, fluphenazine, perphenyzine and piperaetazine;

cytostatics such as aclarubicin, daunorubicin, dihydro-5-azacytidine, doxorubicin, epirubicin, estramustin, etoposide, 7-hydroxychlorpromazin, neplanocin A, pentostatin, podophyllotoxin, vinblastin, vincristin, vindesin;

hormones and hormone antagonists such as buserilin, gonadoliberin, icatibrant and leuprorelin acetate;

antihistamines such as terphenadine;

analgesics such as diflunisal, naproxol, paracetamol, salicylamide and salicyclic acid; antibiotics such as azidamphenicol, cefamandol, chloramphenicol, clavulanic acid, clindamycin, comptothecin, demeclocyclin, doxycyclin, imipenem, latamoxef, novobiocin, oleandomycin, oxytetracyclin, tetracyclin and thiamenicol;

prostaglandins such as arbaprostil, carboprost and prostacydin;

antidepressives such as 8-hydroxychlorimipramine and 2-hydroxyimipramine;

antihypertonics such as sotarol and fenoldopam;

anticholinerogenics such as piperidine, carbidopa, procyclidin and trihexyphenidal;

antiallergenics such as cromolyn;

glucocorticoids such as betamethasone, budenosid, chlorprednison, clobetasol, clobetasone, corticosteron, cortisone, cortodexon, dexamethason, flucortolon, fludrocortisone, flumethasone, flunisolid, fluprednisolon, flurandrenolide, flurandrenolon acetonide, hydrocortisone, meprednisone, methylpresnisolon, paramethasone, prednisolon, prednisol, triamcinolon and triamcinolon acetonide;

narcotic agonists and antagonists such as apomorphine, buprenorphine, butorphanol, codein, cyclazocin, hydromorphon, ketobemidon, levallorphan, levorphanol, metazocin, morphine, nalbuphin, nalmefen, naloxon, nalorphine, naltrexon, oxycodon, oxymorphon and pentazocin; stimulants such asmazindol and pseudoephidrine;

anaesthetics such as hydroxydion and propofol;

β-receptor blockers such as acebutolol, albuterol, alprenolol, atenolol, betazolol, bucindolol, cartelolol, celiprolol, cetamolol, labetalol, levobunelol, metoprolol, metipranolol, nadolol, oxyprenolol, pindolol, propanolol and timolol;

α-sympathomimetics such as adrenalin, metaraminol, midodrin, norfenefrin, octapamine, oxedrin, oxilofrin, oximetazolin and phenylefrin;

β-sympathomimetics such as bamethan, clenbuterol, fenoterol, hexoprenalin, isoprenalin, isoxsuprin, orciprenalin, reproterol, salbutamol and terbutalin; bronchodilators such as carbuterol, dyphillin, etophyllin, fenoterol, pirbuterol, rimiterol and terbutalin;

cardiotonics such as digitoxin, dobutamin, etilefrin and prenalterol; antimycotics such as amphotericin B, chlorphenesin, nystatin and perimycin; anticoagulants such as acenocoumarol, dicoumarol, phenprocoumon and warfarin; vasodilators such as bamethan, dipyrimadol, diprophyllin, isoxsuprin, vincamin and xantinol nicotinate;

antihypocholesteremics such as compactin, eptastatin, mevinolin and simvastatin; miscellaneous drugs such as bromperidol (antipsychotic), dithranol (psoriasis) ergotamine (migraine) ivermectin (antihelminthic), metronidazole and secnizadole (antiprotozoals), nandrolon (anabolic), propafenon and quinadine (antiarythmics), srotonin (neurotransmitter) and silybin (hepatic disturbance).

The above mentioned monohydric nucleosides are an example of the prodrugs of the invention applied to chain hydroxy functions, typically the 5' hydroxy function of the (pseudo)saccharide moiety of the nucleoside. However, the fatty acid free aspect of the invention is not limited to the monohydric nucleosides disclosed above, but is also applicable to L and D-nucleosides bearing di, tri and tetrahyric (pseudo)saccharides, such as those of the formula N-3:

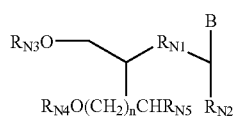

where
B is a natural or unnatural nucleotide base,
$R_{N1}$ is 0 or —$CH_2$—, S
$R_{N2}$ and $R_{N3}$ are each H or $R_{N2}$ is methylene or —CH(OH)— and $R_{N5}$ is a bond thereto, or $R_{N2}$ and $R_{N5}$ together are a bond;
n is 0 or 1;
one of $R_{N3}$ and $R_{N4}$ comprises a linker-$R_2$ structure such as those of formulae IIaa, II'aa, IIc', IIe', IIf*, id' and the other is hydrogen or a further linker-$R_2$ structure.

An alternative group drugs to which the invention is applicable includes those of formula N-3a:

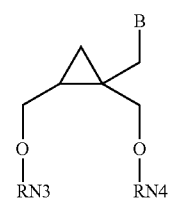

where B, $NR_3$ and $NR_4$ are as defined above.

An alternative group of drugs within the scope of the invention has the formula N-3b:

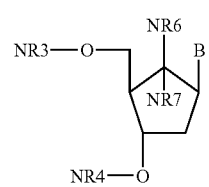

where B, $R_{N3}$ and $R_{N4}$ are as defined above and $R_{N6}$ is fluoro and $R_{N7}$ is hydrogen or $R_{N6}$ and $R_{N7}$ are both fluoro or $R_{N6}$ and $R_{N7}$ together define an exo-methenyl group. The preferred base is guanine in this alternative.

A further group of nucleosides within the scope of the invention has the formula N-3c

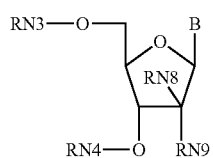

where B, RN3 and RN4 are as defined above, RN8 and RN9 are fluoro (or one of them is fluoro and the other is hydrogen) or RN8 and RN9 together define exomethenyl or exomethenyl mono or di-subsituted with fluoro. These nucleosides have anticancer activity.

The invention is also applicable to other nucleosides having at least two hydroxy groups, but outside the scope of formula N-3a–c, for instance, 9-[3,3-dihydroxymethyl-4-hydroxy-but-1-yl]guanine as described in WO 95/22330 and 9-[4-hydroxy-(2-hydroxymethyl)butyl]guanine as described in EP 343 133. The invention is applicable to both L and D stereo forms of the various nucleoside analogues The compounds of the invention, especially cytosine or guanine derivatives where $NR_1$ is oxygen, n is 1 and $NR_2$ and $NR_5$ define a ring are also active against certain retroviral infections, notably SIV, HIV-1 and HIV-2, and Hepatitis B virus. The compounds of the invention, especially cytosine, guanosine or 6-methoxyguanosine derivatives wherein NR1 is oxygen, n is O and NR2 and NR5 define an arabinose ring are potent anticancer compounds.

The compounds of the invention, especially derivatives comprising a 1,2,4-triazole-3-carboxamide base, where $NR_1$ is O, NR$_2$ is —CH(OH)—, NR$_3$ is a bond thereto and n is 0 (ribavirin) are expected to be active against hepatitis C virus (HCV). Compounds comprising a substituted benzimidazole base, where NR1 is O, NR2 is —CH(OH)—, NR$_5$ is a bond thereto and n is 0 (for instance Glaxo Wellcome's 1263W94 where the base is 2-isopropylamin-5,6-dichloro-benzimidazol-3-yl) are expected to be active against CMV. Compounds comprising an adenine base, where NR1 is O, NR2 is —CH(OH)—, NR5 is a bond thereto and n is 0 (vidarabine) are expected to be active against HSV encephalitis. Compounds comprising a 2-chloroadenine base with a 2'-deoxyribose sugar are expected to have anticancer activity.

The nucleoside derivatives of the invention are particularly useful for guanine nucleoside and analogues which tend to have poorer uptake than pyrimidine nucleosides. Accordingly B is preferably guanine or a guanine derivative.

A group of hydroxy bearing drugs which are particularly amenable to the prodrugs of the invention are the ring hydroxy compounds. By ring hydroxy is meant that the hydroxy function to which the prodrug of the invention is bound is bonded directly onto an aromatic or non-aromatic, heterocyclic or carbocyclic ring structure.

Examples of ring hydroxy compounds include the cyclic urea HIV protease inhibitors, such as those described in WO 9843969, WO9820008, and WO 9419329. Representative protease inhibitors include:

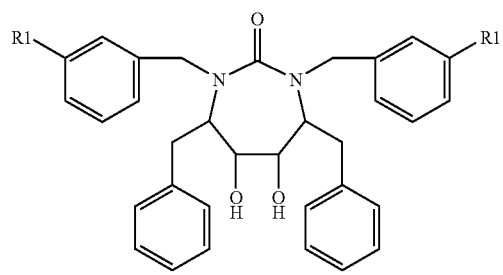

where R1 is NH$_2$ (DMP 450) or

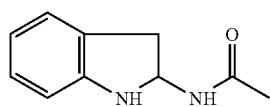
(SD 146)

Some examples of phenolic ring hydroxy compounds include the PETT NNRTI discussed below or the compound described in J Med Chem 35 3467 (1992):

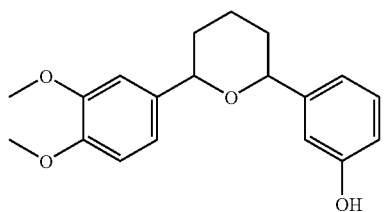

Pancratistatin described in Anticancer Drug Design 10: 243 & 299 (1995) and Bioorg Med Chem Lett 6 157 1996:

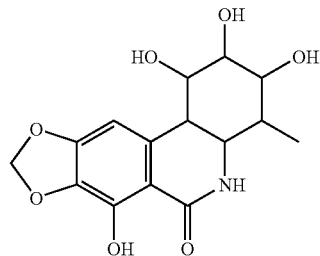

has both phenolic and carbocyclic ring hydroxy functions. A further useful drug with a combination of phenolic and carbocyclic hydroxy functions is etoposide:

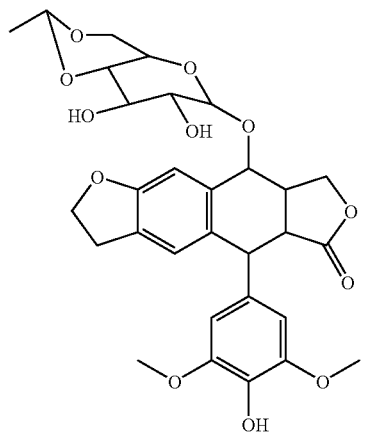

as described in Bioorg Med Chem Lett 4 2567 (1994) and Clinical Cancer Res 1 105 1995.

Representative phosphorous containing drugs include phosfestrol, (E)-(α,β-diethyl-4,4'-stilbenylen)bis(dihydrogenphosphate) and cytostatic metabolites such as phosphorylated cytarabin or gemcitabin, Other phosphonates include antiviral nucleoside or nucleotide analogues such as PMEA, HPMPC, PMPA and the like or phosphates such as the monophosphates of those nucleoside analogues which require phosphorylation for activity, such as ACV AZT, ddI, ddC, PCV, GCV, BVDU, FMAU, 3TC, FTC etc. As described above, certain mixed amino acid/fatty acid acyloxyalkylphosphonates are described in our copending application PCT SE97 001903 and it should be thus appreciated that the prodrugs of the present invention are fatty acyl-free and/or apply the novel linkers defined herein in the phosphonate nucleotide field.

Taking the phosphonate antivirals adefovir and cidovir as examples, prodrugs of the invention can be applied as shown in Formula PF2:

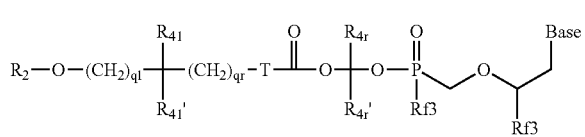

or

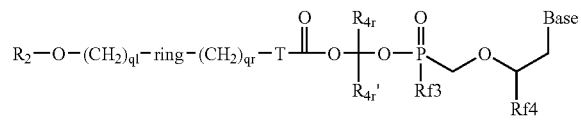

where

R$_2$ is the acyl residue of an aliphatic amino acid,

R$_{4L}$ and R$_{4R}$' are independently H, C$_{1-3}$ alkyl, C$_{3-6}$cycloalkyl, C$_{1-3}$alkyl-C$_1$C$_6$cycloalkyl phenyl or benzyl, R$_{4R}$ and R$_{4R}$' are independently H, C$_{1-3}$ alkyl or phenyl ql is 0–3, qr is 0–3, T is a bond, —NR$_4$— or —OR—

R$_4$ is H or C$_{1-3}$ alkyl;

ring is an optionally substituted aromatic or non-aromatic, hetero-or carbocycle; base is a natural or unnatural nucleotide base, especially guanine, adenine or cytosine, Rf3 is H or a further structure of the formula II"b and Rf4 is H or CH$_2$OH.

Currently favoured values in formula PF2 include: R$_{3R}$ and R$_{3R}$' are preferably H and/or R$_{3L}$ and R$_{3L}$' are preferably ethyl or especially methyl. T is preferably —O— or more preferably a bond. Preferably qr is 1 or more preferably 0.

Thus a preferred group of phosphonate antivirals within the scope of the invention include:

9-[2-phosphonomethoxy)ethyl]adenine, mono(2-methyl-2-(L-valyloxymethyl) propionyloxymethyl) ester, 9-[2-phosphonomethoxy)ethyl]adenine, mono(2-methyl-2-(L-valyloxy) propionyloxymethyl) ester, 9-[2-phosphonomethoxy)ethyl]adenine, mono(2-(L-valyloxy)-3-methyl-(S)-(+)-butyryloxymethyl) ester, 9-[2-phosphonomethoxy)ethyl]adenine, mono(2-(-L-valyloxy)-2-phenyl-DL-acetyloxymethyl) ester, 9-[2-phosphonomethoxy)ethyl]adenine, mono((1,3-di-valyloxy)propyl-2-oxycarbonyloxy methyl) ester, 9-[2-phosphonomethoxy)ethyl]adenine, mono(2-L-valyloxy)-DL-propionyloxymethyl) ester, 9-[2-phosphonomethoxy)ethyl]adenine, mono-(5-(L-valyloxy)-2,2-dimethylvaleryloxymethyl) ester, 9-[2-phosphonomethoxy)ethyl]adenine, mono-((2-(L-valyloxy)-ethoxycarbonyloxy) methyl) ester, 9-[2-phosphonomethoxy)ethyl]adenine, mono [4-(L-valyloxy)-butanoyloxymethyl] ester, 9-[2-phosphonomethoxy)ethyl]adenine, mono-(4-(L-valyloxy) benzoyloxymethyl) ester, 9-[2-phosphonomethoxy)ethyl]adenine, mono-(3-(3,4-di-(L-valyloxy) phenyl) propionyloxymethyl) ester, 9-[2-phosphonomethoxy)ethyl]adenine, mono-(2-methyl-1-(L-valyloxy)-2-propoxycarbonyloxymethyl) ester, 9-[2-phosphonomethoxy)ethyl]adenine, mono-(4-N-valyloxy)-cyclohexanoyloxymethyl) ester 9-[2-phosphonomethoxy)ethyl]adenine, mono-(1-valyloxy-2-methylpropane-2-aminocarbonyloxymethyl) ester 9-[2-phosphonomethoxy)ethyl]adenine, mono-(1-(2-L-valyloxyethyl)-6-oxo-1,6-dihydro-pyridine-3-carbonyloxymethyl) ester 9-[2-phosphonomethoxy)ethyl]adenine, mono(2-methyl-2-(L-isoleucyloxymethyl) propionyloxymethyl) ester, 9-[2-phosphonomethoxy)ethyl]adenine, mono(2-methyl-2-(L-isoleucyloxy) propionyloxymethyl) ester, 9-[2-phosphonomethoxy)ethyl]adenine, mono(2-(L-isoleucyloxy)-3-methyl-(S)-(+)-butyryloxymethyl) ester, 9-[2-phosphonomethoxy)ethyl]adenine, mono(2-(-L-isoleucyloxy)-2-phenyl-DL-acetyloxymethyl) ester, 9-[2-phosphonomethoxy)ethyl]adenine, mono((1,3-di-isoleucyloxy)propyl-2-oxycarbonyloxy methyl) ester, 9-[2-phosphonomethoxy)ethyl]adenine, mono(2-L-isoleucyloxy)-DL-propionyloxymethyl) ester, 9-[2-phosphonomethoxy)ethyl]adenine, mono-(5-(L-isoleucyloxy)-2,2-dimethylvaleryloxymethyl) ester, 9-[2-phosphonomethoxy)ethyl]adenine, mono-((2-(L-isoleucyloxy)-ethoxycarbonyloxy) methyl) ester, 9-[2-phosphonomethoxy)ethyl]adenine, mono [4-(L-isoleucyloxy)-butanoyloxymethyl] ester, 9-[2-phosphonomethoxy)ethyl]adenine, mono-(4-(L-isoleucyloxy) benzoyloxymethyl) ester, 9-[2-phosphonomethoxy)ethyl]adenine, mono-(3-(3,4-di-(L-isoleucyloxy) phenyl) propionyloxymethyl) ester, 9-[2-phosphonomethoxy)ethyl]adenine, mono-(2-methyl-1-(L-isoleucyloxy)-2-propoxycarbonyloxymethyl) ester, 9-[2-phosphonomethoxy)ethyl]adenine, mono-(4-N-isoleucyloxy)cyclohexanoyloxymethyl) ester 9-[2-phosphonomethoxy)ethyl]adenine, mono-(1-isoleucyloxy-2-methylpropane-2-aminocarbonyloxymethyl) ester 9-[2-phosphonomethoxy)ethyl]adenine, mono-(1-(2-L-isoleucyloxyethyl)-6-oxo-1,6-dihydro-pyridine-3-carbonyloxymethyl) ester the corresponding bis esters and pharmaceutically acceptable salts thereof. A further preferred group comprises the corresponding derivatives of PMPA and HPMPC.

A further group of phosphorous containing antivirals amenable to the invention include foscarnet (phosphonoformate) and PAA (phosphonoacetate). Taking foscarnet as an example:

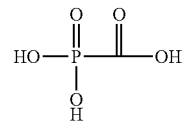

it will be apparent that linkers such as those of formula IId or II'd can be applied to the carboxy function. Preferably, however, or additionally, one or two linkers of formula IIb, II'b, II'e, II"e or especially II"b can be applied to the phosphonate hydroxy functions to define compounds such as:

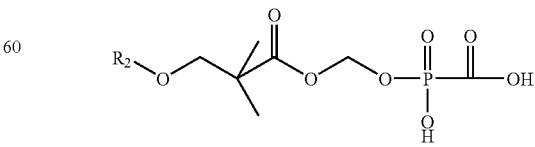

Thus a preferred group of compounds comprises foscarnet derivatives of the formula PF1:

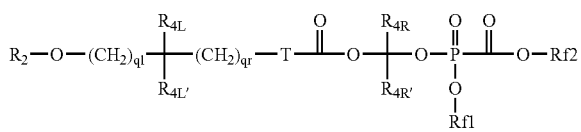

or

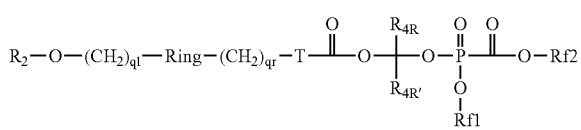

where

R₂ is the acyl residue of an aliphatic amino acid, $R_{4L}$ and $R_{4R'}$ are independently H, $C_{1-3}$ alkyl, $C_{3-6}$ cycloalkyl, $C_{1-3}$alkyl-$C_1$–$C_6$-cycloalkyl phenyl or benzyl, $R_{4R}$ and $R_{4R}'$ are independently H, $C_{1-3}$ alkyl or phenyl q1 is 0–3, qr is 0–3, T is a bond, —NR₄— or —O—

R₄ is H or $C_{1-3}$alkyl;

ring is an optionally substituted aromatic or non-aromatic, hetero-or carbocycle; and Rf1 is H or a further ester of formula I″b and Rf2 is H or a conventional pharmaceutically acceptable ester.

Currently favoured values in Formula PF1 include: $R_4R$ and $R_4R'$ are preferably H and/or $R_{4L}$ and $R_{4L}'$ are preferably ethyl or especially methyl. T is preferably —O— or more preferably a bond. Preferably qr is 1 or more preferably 0. If Rf1 is a further ester it is convenient if it is identical to other linker-R₂ moiety. Conventional pharmaceutically acceptable esters for Rf2 include the methyl, ethyl and isopropyl esters.

A favoured group of compounds within formula PF1 include:

phosphonoformic acid, mono(2-methyl-2-(L-valyloxymethyl) propionyloxymethyl) ester, phosphonoformic acid, mono(2-methyl-2-(L-valyloxy) propionyloxymethyl) ester, phosphonoformic acid, mono(2-(L-valyloxy)-3-methyl-(S)-(+)-butyryloxymethyl) ester, phosphonoformic acid, mono(2-(-L-valyloxy)-2-phenyl-DL-acetyloxymethyl) ester, phosphonoformic acid, mono((1,3-di-valyloxy)propyl-2-oxycarbonyloxy methyl) ester, phosphonoformic acid, mono(2-L-valyloxy)-DL-propionyloxymethyl) ester, phosphonoformic acid, mono-(5-(L-valyloxy)-2,2-dimethylvaleryloxymethyl) ester, phosphonoformic acid, mono-((2-(L-valyloxy)-ethoxycarbonyloxy) methyl) ester, phosphonoformic acid, mono [4-(L-valyloxy)-butanoyloxymethyl] ester, phosphonoformic acid, mono-(4-(L-valyloxy) benzoyloxymethyl) ester, phosphonoformic acid, mono-(3-(3,4-di-(L-valyloxy) phenyl) propionyloxymethyl) ester, phosphonoformic acid, mono-(2-methyl-1-(L-valyloxy)-2-propoxycarbonyloxymethyl) ester, phosphonoformic acid, mono-(4-N-valyloxy)cyclohexanoyloxymethyl) ester phosphonoformic acid, mono-(1-valyloxy-2-methylpropane-2-aminocarbonyloxymethyl) ester phosphonoformic acid, mono-(1-(2-L-valyloxyethyl)-6-oxo-1,6-dihydro-pyridine-3 carbonyloxymethyl) ester phosphonoformic acid, mono(2-methyl-2-(L-isoleucyloxymethyl) propionyloxymethyl) ester, phosphonoformic acid, mono(2-methyl-2-(L-isoleucyloxy) propionyloxymethyl) ester, phosphonoformic acid, mono(2-(L-isoleucyloxy)-3-methyl-(S)-(+)butyryloxymethyl) ester, phosphonoformic acid, mono(2-(-L-isoleucyloxy)-2-phenyl-DL-acetyloxymethyl) ester, phosphonoformic acid, mono((1,3-di-isoleucyloxy)propyl-2-oxycarbonyloxy methyl) ester, phosphonoformic acid, mono(2-L-isoleucyloxy)-DL-propionyloxymethyl) ester, phosphonoformic acid, mono-(5-(L-isoleucyloxy)-2,2-dimethylvaleryloxymethyl) ester, phosphonoformic acid, mono-((2-(L-isoleucyloxy)-ethoxycarbonyloxy) methyl) ester, phosphonoformic acid, mono [4-(L-isoleucyloxy)-butanoyloxymethyl] ester, phosphonoformic acid, mono-(4-(L-isoleucyloxy) benzoyloxymethyl) ester, phosphonoformic acid, mono-(3-(3,4-di-(L-isoleucyloxy) phenyl) propionyloxymethyl) ester, phosphonoformic acid, mono (2-methyl-1-(L-isoleucyloxy)-2-propoxycarbonyloxymethyl) ester, phosphonoformic acid, mono-(4-isoleucyloxy)cyclohexanoyloxymethyl) ester phosphonoformic acid, mono-(1-isoleucyloxy-2-methylpropane-2-aminocarbonyloxymethyl) ester phosphonoformic acid, mono-(1-(2-L-isoleucyloxyethyl)-6-oxo-1,6-dihydropyridine-3-carbonyloxymethyl) ester the corresponding bis esters, the corresponding compounds additionally bearing a C-ethyl esters, and pharmaceutically acceptable salts thereof.

A further class of phosphonates which are amenable to the invention and which share a structural similarity with phosphonoformic are the β-phosphonocarboxylic acid farnesyl protein transferase inhibitors, especially those of the of the formula PF4:

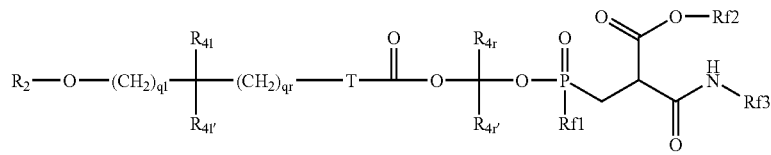

or

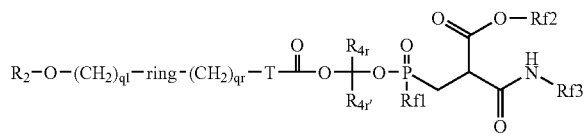

where
RF1 is H or a further structure of formula II"b
Rf2 is H or a conventional pharmaceutically acceptable ester,
Rf3 is a polyunsaturated, branched $C_{6-22}$ alkyl,
$R_2$ is the acyl residue of an aliphatic amino acid,
$R_{4L}$ and $R_{4R}'$ are independently H, $C_{1-3}$ alkyl, $C_{3-6}$cycloalkyl, $C_{1-3}$alkyl-$C_1$-$C_6$-cycloalkyl phenyl or benzyl,
$R_{R4}$ and $R_4R'$ are independently H, $C_{1-3}$ alkyl or phenyl
ql is 0–3, qr is 0–3,
T is a bond, —$NR_4$— or —O—
$R_4$ H or $C_{1-3}$alkyl;
ring is an optionally substituted aromatic or non-aromatic, hetero-or carbocycle.

Currently favoured values in Formula PF4 include: $R_{4R}$ and $R_{4R}'$ are preferably H and/or $R_{4L}$ and $R_{4L}'$ are preferably ethyl or especially methyl. T is preferably —O— or more preferably a bond. Preferably qr is 1 or more preferably 0. If Rf1 is a further ester it is convenient if it is identical to other linker-$R_2$ moiety. Conventional pharmaceutically acceptable esters for Rf2 include the methyl, ethyl and isopropyl esters. A convenient polyunsaturated alkyl Rf3 has the formula:

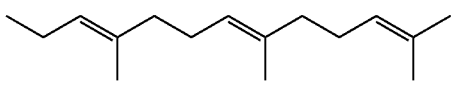

Other structurally similar phosponates include α-phosphonosulphonates such as squalene synthase inhibitors of the formula PF5:

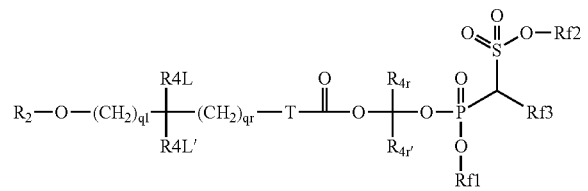

or

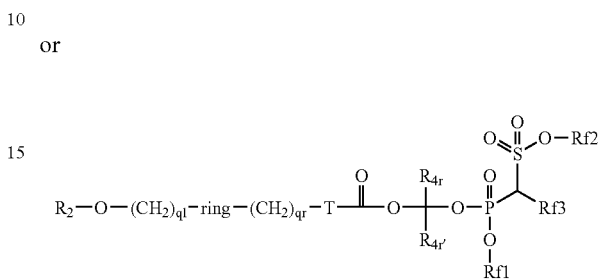

where
RF1 is H or a further structure of formula II"b
Rf2 is H or a conventional pharmaceutically acceptable ester a further structure of formula II"b
Rf3 is a polyunsaturated, branched $C_{6-22}$ alkyl,
$R_2$ is the acyl residue of an aliphatic amino acid,
$R_{4L}$ and $R_{4L}'$ are independently H, $C_{1-3}$ alkyl, $C_{3-6}$cycloalkyl, $C_{1-3}$alkyl-$C_1C_6$cycloalkyl phenyl or benzyl,
$R_4R$ and $R_4R'$ are independently H, $C_{1-3}$ alkyl or phenyl
ql is 0–3, qr is 0–3,
T is a bond, —$NR_4$— or —O—
$R_4$ is H or $C_{1-3}$alkyl;
ring is an optionally substituted aromatic or non-aromatic, hetero-or carbocycle.

Currently favoured values in Formula PF5 include: $R_4R$ and $R_4R'$ are preferably H and/or $R_{4L}$ and $R_{4R}'$ are preferably ethyl or especially methyl. T is preferably —O— or more preferably a bond. Preferably qr is 1 or more preferably 0. If Rf1 is a further ester it is convenient if it is identical to other linker-$R_2$ moiety. Conventional pharmaceutically acceptable esters for Rf2 include the methyl, ethyl and isopropyl esters. A convenient polyunsaturated alkyl Rf3 has the formula:

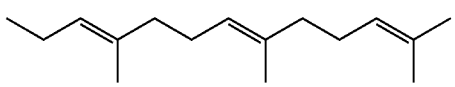

A particularly preferred group of phosphorous containing drugs are the bisphosphonates active in bone metabolism. Favoured bis-phosphonates have the formula:

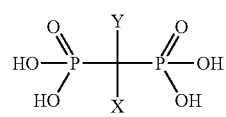

where

X is H, halo, hydroxy; and Y is a) $C_{1-10}$ alkyl, optionally substituted with
heterocycle,
—$NR_aR_b$, where $R_a$ and $R_b$ are independently hydrogen, $C_{1-6}$ alkyl or join together to form a 5 to 7 membered ring, optionally containing a further hetero atom,
OH, halo, —$S(C_{1-6}$ alkyl), phenyl, —$C_{1-7}$ cycloalkyl, (optionally substituted with —$NR_aR_b$ or OH);

b) $C_{3-7}$ cycloalkyl, optionally substituted with
—$NR_aR_b$, OH, halo, —$S(C_{1-6}$ alkyl), phenyl, morpholino or pyridyl;

c) halo;

d) piperidinyl;

e) pyrrolidinyl;

f) —$S(C_{1-6}$ alkyl), optionally substitued with
—$NR_aR_b$, OH, halo or phenyl;

g) —S-phenyl, optionally substituted with
halo, nitro, $C_{1-6}$ alkyl, $C_{1-6}$ alkoxy, trifluormethyl, -CON-$RaR_b$ or —COOH.

Preferred bis-phosphonates include alendronate (X is hydroxy, Y is $NH_2CH_2CH_2CH_2$—), clodronate (X is chloro, Y is chloro), etidronate (X is hydroxy, Y is $CH_3$—), pamidronate (X is hydroxy, Y is $NH_2CH_2CH_2$—), ibandronate (X is hydroxy, Y is $N(CH_2CH_2CH_2CH_2CH_3)(CH_3)CH_2CH_2$—), tiludronate (X is H, Y is 4-chlorophenylthio-), risedronate (X is hydroxy, Y is 3-pyridinylmethylene-) and zoledronate (X is hydroxy, Y is (2-(1H-imidazol-1-yl)methylene-)

Taking alendronate as an example:

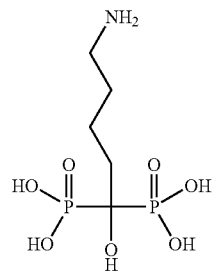

it will be apparent that the drug contains several accessible functions (viz the hydroxy group at position 1, the amino group at position 4 and two esterifiable hydroxy groups on each phosphorous. Prodrugs in accordance with the invention can thus be derivatised on one or more of these functions. For instance a linker such as those of Formula IIa above, for instance when T is a bond or —O— and V is a bond can be esterified to the 1-hydroxy position or amide-bonded to the 4-amino position. In a favoured embodiment of the invention, however, the prodrugs of the invention are derivatised to the phosphonate groups.

Thus one to three linker structures of formula IIe, II'e, Va, Vb or most preferably II"b can be esterified to one or both of the phosphonates, especially one such linker structure on each phosphonate.

Preferred compounds within this bis-phosphonate aspect of the invention thus include those of the formula A1:

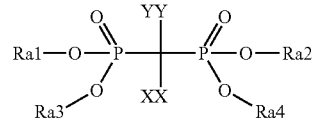

A-1 wherein YY and XX have the following values:

| YY | XX | |
|---|---|---|
| $NH_2(CH_2)_3$— | OH | (alendronate) |
| $NH_2(CH_2)_2$— | OH | (pamidronate) |
| cycloheptylamino- | H | (cimadronate) |
| chloro- | chloro | (clodronate) |
| pyrrolidin-1-yl$CH_2CH_2$— | OH | (EB 1053) |
| $CH_3$— | OH | (etidronate) |
| methylpentylamino$CH_2CH_2$— | OH | (ibandronate) |
| dimethylamino$CH_2CH_2$— | OH | (olpadronate) |
| pyridin-3-yl$CH_2$— | OH | (risedronate) |
| (4-chlorophenyl)-thio- | H | (tiludronate) |
| imidazo-(1,2-a)pyridin-3-yl$CH_2$— | OH | (YH 529) |
| 1H-imidazol-1yl$CH_2$— | OH | (zoledronate) | wherein amino groups on YY can be optionally substituted with conventional pharmaceutically acceptable amide groups such as —$C(=O)C_{1-6}$alkyl or an aminoacyl or peptidyl derivative, as described in WO 96/31227;

and wherein at least one of Ra1–Ra4 is a structure of the formula

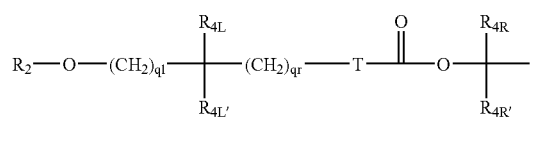

or

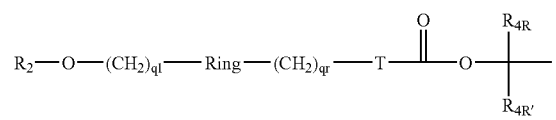

where $R_2$ is the acyl residue of an aliphatic amino acid, $R_{4R}$ and $R_{4R}'$ are independently H, $C_{1-3}$ alkyl, $C_{3-6}$cycloalkyl, $C_{1-3}$alkyl-$C_1C_6$cycloalkyl phenyl or benzyl, $R_{4R}$ and $R_{4R'}$ are independently H or $C_{1-3}$ alkyl q1 is 0–3, qr is 0–3, T is a bond, —$NR_4$— or —O—

$R_4$ is H or $C_{1-3}$alkyl;

ring is an optionally substituted aromatic or non-aromatic, hetero-or carbocycle;

and the remainder of Ra1–4 are hydrogen or conventional pharmaceutically acceptable esters.

In formula A-1, $R_{4R}$ and $R_{4R}'$ are preferably H and/or $R_{4L}$ and $R_{4R}'$ are preferably ethyl or especially methyl. T is preferably —O— or more preferably a bond. Preferably qr is 1 or more preferably 0.

Favoured compounds thus include;

(4-amino-1-hydroxybutylidine)-bisphosphonate, di(2-methyl-2-(L-valyloxymethyl) propionyloxymethyl) ester,
(4-amino-1-hydroxybutylidine)-bisphosphonate, di(2-methyl-2-(L-valyloxy) propionyloxymethyl) ester,
(4-amino-1-hydroxybutylidine)-bisphosphonate, di (2-(L-valyloxy)-3-methyl-(S)-(+)-butyryloxymethyl) ester,
(4-amino-1-hydroxybutylidine)-bisphosphonate, di (2-(-L-valyloxy)-2-phenyl-DL-acetyloxymethyl) ester,
(4-amino-1-hydroxybutylidine)-bisphosphonate, di ((1,3-di-valyloxy)propyl-2-oxycarbonyloxy methyl) ester,
(4-amino-1-hydroxybutylidine)-bisphosphonate, di (2-L-valyloxy)-DL-propionyloxymethyl) ester,
(4-amino-1-hydroxybutylidine)-bisphosphonate, di-(5-(L-valyloxy)-2,2-dimethylvaleryloxymethyl) ester,
(4-amino-1-hydroxybutylidine)-bisphosphonate, di-((2-(L-valyloxy)-ethoxycarbonyloxy) methyl) ester,
(4-amino-1-hydroxybutylidine)-bisphosphonate, bis [4-(L-valyloxy)-butanoyloxymethyl] ester,
(4-amino-1-hydroxybutylidine)-bisphosphonate, di-(4-(L-valyloxy) benzoyloxymethyl) ester,
(4-amino-1-hydroxybutylidine)-bisphosphonate, di-(3-(3,4-di-(L-valyloxy) phenyl) propionyloxymethyl) ester,
(4-amino-1-hydroxybutylidine)-bisphosphonate, di-(2-methyl-1-(L-valyloxy)-2-propoxycarbonyloxymethyl) ester,
(4-amino-1-hydroxybutylidine)-bisphosphonate, di-(4-valyloxy)cyclohexanoyloxymethyl) ester
(4-amino-1-hydroxybutylidine)-bisphosphonate, di-(1-valyloxy-2-methylpropane-2-aminocarbonyloxymethyl)
(4-amino-1-hydroxybutylidine)-bisphosphonate, di-(1-(2-L-valyloxyethyl)-6-oxo-1,6-dihydro-pyridine-3-carbonyloxymethyl)
1-hydroxy-2-(1H-imidazolyl-1-yl)ethylidene-bis phosphonate, di(2-methyl-2-(L-valyloxymethyl) propionyloxymethyl) ester,
1-hydroxy-2-(1H-imidazolyl-1-yl)ethylidene-bis phosphonate, di(2-methyl-2-(L-valyloxy) propionyloxymethyl) ester,
1-hydroxy-2-(1H-imidazolyl-1-yl)ethylidene-bis phosphonate, di (2-(L-valyloxy)-3-methyl-(S)-(+)-butyryloxymethyl) ester,
1-hydroxy-2-(1H-imidazolyl-1-yl)ethylidene-bis phosphonate, di (2-(-L-valyloxy)-2-phenyl-DL-acetyloxymethyl) ester,
1-hydroxy-2-(1H-imidazolyl-1-yl)ethylidene-bis phosphonate, di ((1,3-di-valyloxy)propyl-2-oxycarbonyloxy methyl) ester,
1-hydroxy-2-(1H-imidazolyl-1-yl)ethylidene-bis phosphonate, di (2-L-valyloxy)-DL-propionyloxymethyl) ester,
1-hydroxy-2-(1H-imidazolyl-1-yl)ethylidene-bis phosphonate, di-(5-(L-valyloxy)-2,2-dimethylvaleryloxymethyl) ester,
1-hydroxy-2-(1H-imidazolyl-1-yl)ethylidene-bis phosphonate, di-((2-(L-valyloxy)-ethoxycarbonyloxy) methyl) ester,
1-hydroxy-2-(1H-imidazolyl-1-yl)ethylidene-bis phosphonate, bis [4-(L-valyloxy)-butanoyloxymethyl] ester,
1-hydroxy-2-(1H-imidazolyl-1-yl)ethylidene-bis phosphonate, di-(4-(L-valyloxy)-benzoyloxymethyl) ester,
1-hydroxy-2-(1H-imidazolyl-1-yl)ethylidene-bis phosphonate, di-(3-(3,4-di-(L-valyloxy) phenyl) propionyloxymethyl) ester,
1-hydroxy-2-(1H-imidazolyl-1-yl)ethylidene-bis phosphonate, di(2-methyl-1-(L-valyloxy)-2-propoxycarbonyloxymethyl) ester,
1-hydroxy-2-(1H-imidazolyl-1-yl)ethylidene-bis phosphonate, di-(4-valyloxy)cyclohexanoyloxymethyl) ester
1-hydroxy-2-(1H-imidazolyl-1-yl)ethylidene-bis phosphonate, di-(1-valyloxy-2-methylpropane-2-aminocarbonyloxymethyl) ester
1-hydroxy-2-(1H-imidazolyl-1-yl)ethylidene-bis phosphonate, di-(1-(2-L-valyloxyethyl)-6-oxo-1,6-dihydro-pyridine-3-carbonyloxymethyl) ester
1-hydroxy-2-(pyrid-3-yl)ethylidene bis-phosphonate di(2-methyl-2-(L-valyloxymethyl) propionyloxymethyl) ester,
1-hydroxy-2-(pyrid-3-yl)ethylidene bis-phosphonate, di(2-methyl-2-(L-valyloxy) propionyloxymethyl) ester,
1-hydroxy-2-(pyrid-3-yl)ethylidene bis-phosphonate, di (2-(L-valyloxy)-3-methyl-(S)-(+)-butyryloxymethyl) ester,
1-hydroxy-2-(pyrid-3-yl)ethylidene bis-phosphonate, di (2-(-L-valyloxy)-2-phenyl-DL-acetyloxymethyl) ester,
1-hydroxy-2-(pyrid-3-yl)ethylidene bis-phosphonate, di ((1, 3-di-valyloxy)propyl-2-oxycarbonyloxy methyl) ester,
1-hydroxy-2-(pyrid-3-yl)ethylidene bis-phosphonate, di (2-L-valyloxy)-DL-propionyloxymethyl) ester,
1-hydroxy-2-(pyrid-3-yl)ethylidene bis-phosphonate, di-(5-(L-valyloxy)-2,2-dimethylvaleryloxymethyl) ester,
1-hydroxy-2-(pyrid-3-yl)ethylidene bis-phosphonate, di-((2-(L-valyloxy)-ethoxycarbonyloxy) methyl) ester,
1-hydroxy-2-(pyrid-3-yl)ethylidene bis-phosphonate, bis [4-(L-valyloxy)-butanoyloxymethyl) ester,
1-hydroxy-2-(pyrid-3-yl)ethylidene bis-phosphonate, di-(4-(L-valyloxy) benzoyloxymethyl) ester,
1-hydroxy-2-(pyrid-3-yl)ethylidene bis-phosphonate, di-(3-(3,4-di-(L-valyloxy) phenyl) propionyloxymethyl) ester,
1-hydroxy-2-(pyrid-3-yl)ethylidene bis-phosphonate, di-(2-methyl-1-(L-valyloxy)-2-propoxycarbonyloxymethyl) ester,
1-hydroxy-2-(pyrid-3-yl)ethylidene bis-phosphonate, di-(4-valyloxy)cyclohexanoyloxymethyl) ester
1-hydroxy-2-(pyrid-3-yl)ethylidene bis-phosphonate, di-(1-valyloxy-2-methylpropane-2-aminocarbonyloxymethyl) ester
1-hydroxy-2-(pyrid-3-yl)ethylidene bis-phosphonate, di-(1-(2-L-valyloxyethyl)-6-oxo-1,6-dihydro-pyridine-3-carbonyloxymethyl) ester and pharmaceutically acceptable salts thereof.

A further group of favoured compounds include:

(4-amino-1-hydroxybutylidine)-bisphosphonate, mono(2-methyl-2-(L-valyloxymethyl) propionyloxymethyl) ester,
(4-amino-1-hydroxybutylidine)-bisphosphonate, mono(2-methyl-2-(L-valyloxy) propionyloxymethyl) ester,
(4-amino-1-hydroxybutylidine)-bisphosphonate, mono(2-(L-valyloxy)-3-methyl-(S)-(+)-butyryloxymethyl) ester,
(4-amino-1-hydroxybutylidine)-bisphosphonate, mono(2-(-L-valyloxy)-2-phenyl-DL-acetyloxymethyl) ester,
(4-amino-1-hydroxybutylidine)-bisphosphonate, mono((1, 3-di-valyloxy)propyl-2-oxycarbonyloxy methyl) ester,
(4-amino-1-hydroxybutylidine)-bisphosphonate, mono(2-L-valyloxy)-DL-propionyloxymethyl) ester,
(4-amino-1-hydroxybutylidine)-bisphosphonate, mono-(5-(L-valyloxy)-2,2-dimethylvaleryloxymethyl) ester,
(4-amino-1-hydroxybutylidine)-bisphosphonate, mono-((2-(L-valyloxy)-ethoxycarbonyloxy) methyl) ester,
(4-amino-1-hydroxybutylidine)-bisphosphonate, mono [4-(L-valyloxy)butanoyloxymethyl] ester,
(4-amino-1-hydroxybutylidine)-bisphosphonate, mono-(4-(L-valyloxy) benzoyloxymethyl) ester, (4-amino-1-hydroxybutylidine)-bisphosphonate, mono-(3-(3,4-di-(L-valyloxy) phenyl) propionyloxymethyl) ester, (4-amino-1-hydroxybutylidine)-bisphosphonate, mono-(2-methyl-1-(L-valyloxy)-2-propoxycarbonyloxymethyl) ester, (4-amino-1-hydroxybutylidine)-bisphosphonate, mono-(4-valyloxy)cyclohexanoyloxymethyl) ester (4-amino-1-hydroxybutylidine)-bisphosphonate, mono-(1-valyloxy-2-methylpropane-2-aminocarbonyloxymethyl)

(4-amino-1-hydroxybutylidine)-bisphosphonate, mono-(1-(2-L-valyloxyethyl)-6-oxo-1,6-dihydro-pyridine-3-carbonyloxymethyl)

1-hydroxy-2-(1H-imidazolyl-1-yl)ethylidene-bis phosphonate, mono(2-methyl-2-(L-valyloxymethyl) propionyloxymethyl) ester, 1-hydroxy-2-(1H-imidazolyl-1-yl)ethylidene-bis phosphonate, mono(2-methyl-2-(L-valyloxy) propionyloxymethyl) ester, 1-hydroxy-2-(1H-imidazolyl-1-yl)ethylidene-bis phosphonate, mono (2-(L-valyloxy)-3-methyl-(S)-(+)-butyryloxymethyl) ester, 1-hydroxy-2-(1H-imidazolyl-1-yl)ethylidene-bis phosphonate, mono (2-(-L-valyloxy)-2-phenyl-DL-acetyloxymethyl) ester, 1-hydroxy-2-(1H-imidazolyl-1-yl)ethylidene-bis phosphonate, mono ((1,3-di-valyloxy)propyl-2-oxycarbonyloxy methyl) ester, 1-hydroxy-2-(1H-imidazolyl-1-yl)ethylidene-bis phosphonate, mono (2-L-valyloxy)-DL-propionyloxymethyl) ester, 1-hydroxy-2-(1H-imidazolyl-1-yl)ethylidene-bis phosphonate, mono-(5-(L-valyloxy)-2,2-dimethylvaleryloxymethyl) ester, 1-hydroxy-2-(1H-imidazolyl-1-yl)ethylidene-bis phosphonate, mono-((2-(L-valyloxy)-ethoxycarbonyloxy) methyl) ester, 1-hydroxy-2-(1H-imidazolyl-1-yl)ethylidene-bis phosphonate, mono [4-(L-valyloxy)butanoyloxymethyl] ester, 1-hydroxy-2-(1H-imidazolyl-1-yl)ethylidene-bis phosphonate, mono-(4-(L-valyloxy) benzoyloxymethyl) ester, 1-hydroxy-2-(1H-imidazolyl-1-yl)ethylidene-bis phosphonate, mono-(3-(3,4-di-(L-valyloxy) phenyl) propionyloxymethyl) ester, 1-hydroxy-2-(1H-imidazolyl-1-yl)ethylidene-bis phosphonate, mono-(2-methyl-1-(L-valyloxy)-2-propoxycarbonylmethyl) ester, 1-hydroxy-2-(1H-imidazolyl-1-yl)ethylidene-bis phosphonate, mono-(4-N-valyloxy)cyclohexanoyloxymethyl) ester, 1-hydroxy-2-(1H-imidazolyl-1-yl)ethylidene-bis phosphonate, mono-(1-valyloxy-2-methylpropane-2-aminocarbonyloxymethyl) ester, 1-hydroxy-2-(1H-imidazolyl-1-yl)ethylidene-bis phosphonate, mono-(1-(2-L-valyloxyethyl)-6-oxo-1,6-dihydro-pyridine-3-carbonyloxymethyl) ester 1-hydroxy-2-(pyrid-3-yl)ethylidene bis-phosphonate mono (2-methyl-2-(L-valyloxymethyl) propionyloxymethyl) ester, 1-hydroxy-2-(pyrid-3-yl)ethylidene bis-phosphonate, mono (2-methyl-2-(L-valyloxy) propionyloxymethyl) ester, 1-hydroxy-2-(pyrid-3-yl)ethylidene bis-phosphonate, mono (2-(L-valyloxy)-3-methyl-(S)-(+)-butyryloxymethyl) ester, 1-hydroxy-2-(pyrid-3-yl)ethylidene bis-phosphonate, mono (2-(-L-valyloxy)-2-phenyl-DL-acetyloxymethyl) ester, 1-hydroxy-2-(pyrid-3-yl)ethylidene bis-phosphonate, mono ((1,3-di-valyloxy)propyl-2-oxycarbonyloxy methyl) ester, 1-hydroxy-2-(pyrid-3-yl)ethylidene bis-phosphonate, mono (2-L-valyloxy)-DL-propionyloxymethyl) ester, 1-hydroxy-2-(pyrid-3-yl)ethylidene bis-phosphonate, mono-(5-(L-valyloxy)-2,2-dimethylvaleryloxymethyl) ester, 1-hydroxy-2-(pyrid-3-yl)ethylidene bis-phosphonate, mono-((2-(L-valyloxy)-ethoxycarbonyloxy) methyl) ester, 1-hydroxy-2-(pyrid-3-yl)ethylidene bis-phosphonate, mono [4-(L-valyloxy)-butanoyloxymethyl] ester, 1-hydroxy-2-(pyrid-3-yl)ethylidene bis-phosphonate, mono-(4-(L-valyloxy) benzoyloxymethyl) ester, 1-hydroxy-2-(pyrid-3-yl)ethylidene bis-phosphonate, mono-(3-(3,4-di-(L-valyloxy) phenyl) propionyloxymethyl) ester, 1-hydroxy-2-(pyrid-3-yl)ethylidene bis-phosphonate, mono-(2-methyl-1-(L-valyloxy)-2-propoxycarbonyloxymethyl) ester, 1-hydroxy-2-(pyrid-3-yl)ethylidene bis-phosphonate, mono-(4-valyloxy)cyclohexanoyloxymethyl) ester 1-hydroxy-2-(pyrid-3-yl)ethylidene bis-phosphonate, mono-(1-valyloxy-2-methylpropane-2-aminocarbonyloxymethyl) ester 1-hydroxy-2-(pyrid-3-yl)ethylidene bis-phosphonate, mono-(1-(2-L-valyloxyethyl)-6-oxo-1,6-dihydro-pyridine-3-carbonyloxymethyl) ester and pharmaceutically acceptable salts thereof.

A further group of favoured compound include:

(4-amino-1-hydroxybutylidine)-bisphosphonate, di(2-methyl-2-(L-isoleucyloxymethyl) propionyloxymethyl) ester, (4-amino-1-hydroxybutylidine)-bisphosphonate, di(2-methyl-2-(L-isoleucyloxy) propionyloxymethyl) ester, (4-amino-1-hydroxybutylidine)-bisphosphonate, di (2-(L-isoleucyloxy)-3-methyl-(S)-(+)-butyryloxymethyl) ester, (4-amino-1-hydroxybutylidine)-bisphosphonate, di (2-(L-isoleuclyoxy)-2-phenyl-DL-acetyloxymethyl) ester, (4-amino-1-hydroxybutylidine)-bisphosphonate, di ((1,3-di-isoleucyloxy)propyl-2-oxycarbonyloxy methyl) ester, (4-amino-1-hydroxybutylidine)-bisphosphonate, di (2-L-isoleucyloxy)-DL-propionyloxymethyl) ester, (4-amino-1-hydroxybutylidine)-bisphosphonate, di-(5-(L-isoleucyloxy)-2,2-dimethylvaleryloxymethyl) ester, (4-amino-1-hydroxybutylidine)-bisphosphonate, di-((2-(L-isoleucyloxy)-ethoxycarbonyloxy) methyl) ester, (4-amino-1-hydroxybutylidine)-bisphosphonate, bis [4-(-L-isoleucyloxy)-butanoyloxymethyl] ester, (4-amino-1-hydroxybutylidine)-bisphosphonate, di-(4-(L-isoleucyloxy) benzoyloxymethyl) ester, (4-amino-1-hydroxybutylidine)-bisphosphonate, di-(3-(3,4-di-(L-isoleucyloxy) phenyl) propionyloxymethyl) ester, (4-amino-1-hydroxybutylidine)-bisphosphonate, di-(2-methyl-1-(L-isoleucyloxy)-2-propoxycarbonyloxymethyl) ester, (4-amino-1-hydroxybutylidine)-bisphosphonate, di-(4-valyloxy)cyclohexanoyloxymethyl) ester, (4-amino-1-hydroxybutylidine)-bisphosphonate, di-(1-valyloxy-2-methylpropane-2-aminocarbonyloxymethyl) ester, (4-amino-1-hydroxybutylidine)-bisphosphonate, di-(1-(2-L-valyloxyethyl)-6-oxo-1,6-dihydro-pyridine-3-carbonyloxymethyl) ester, 1-hydroxy-2-(1H-imidazolyl-1-yl)ethylidene-bis phosphonate, di(2-methyl-2-(L-isoleucyloxymethyl) propionyloxymethyl) ester,
1-hydroxy-2-(1H-imidazolyl-1-yl)ethylidene-bis phosphonate, di(2-methyl-2-(L-isoleucyloxy) propionyloxymethyl) ester,
1-hydroxy-2-(1H-imidazolyl-1-yl)ethylidene-bis phosphonate, di (2-(L-isoleucyloxy)-3-methyl-(S)-(+)-butyryloxymethyl) ester,
1-hydroxy-2-(1H-imidazolyl-1-yl)ethylidene-bis phosphonate, di (2-(-L-isoleucyloxy)-2-phenyl-DL-acetyloxymethyl) ester,
1-hydroxy-2-(1H-imidazolyl-1-yl)ethylidene-bis phosphonate, di ((1,3-di-isoleucyloxy)propyl-2-oxycarbonyloxy methyl) ester,
1-hydroxy-2-(1H-imidazolyl-1-yl)ethylidene-bis phosphonate, di (2-L-isoleucyloxy)DL-propionyloxymethyl) ester,
1-hydroxy-2-(1H-imidazolyl-1-yl)ethylidene-bis phosphonate, di-(5-(L-isoleucyloxy)-2,2-dimethylvaleryloxymethyl) ester,
1-hydroxy-2-(1H-imidazolyl-1-yl)ethylidene-bis phosphonate, di-((2-(L-isoleucyloxy)-ethoxycarbonyloxy) methyl) ester,
1-hydroxy-2-(1H-imidazolyl-1-yl)ethylidene-bis phosphonate, bis [4-(L-isoleucyloxy)-butanoyloxymethyl] ester,
1-hydroxy-2-(1H-imidazolyl-1-yl)ethylidene-bis phosphonate, di-(4-(L-isoleucyloxy) benzoyloxymethyl) ester,
1-hydroxy-2-(1H-imidazolyl-1-yl)ethylidene-bis phosphonate, di-(3-(3,4-di-(L-isoleucyloxy) phenyl) propionyloxymethyl) ester,
1-hydroxy-2-(1H-imidazolyl-1-yl)ethylidene-bis phosphonate, di-(2-methyl-1-(L-isoleucyloxy)-2-propoxycarbonyloxymethyl) ester,
1-hydroxy-2-(1H-imidazolyl-1-yl)ethylidene-bis phosphonate, di-(4-isoleucyloxy)cyclohexanoyloxymethyl) ester
1-hydroxy-2-(1H-imidazolyl-1-yl)ethylidene-bis phosphonate, di-(1-isoleucyloxy-2-methylpropane-2-aminocarbonyloxymethyl) ester
1-hydroxy-2-(1H-imidazolyl-1-yl)ethylidene-bis phosphonate, di-(1-(2-L-isoleucyloxyethyl)-6-oxo-1,6-dihydro-pyridine-3-carbonyloxymethyl) ester
1-hydroxy-2-(pyrid-3-yl)ethylidene bis-phosphonate di(2-methyl-2-(L-isoleucyloxymethyl) propionyloxymethyl) ester,
1-hydroxy-2-(pyrid-3-yl)ethylidene bis-phosphonate, di(2-methyl-2-(L-isoleucyloxy) propionyloxymethyl) ester,
1-hydroxy-2-(pyrid-3-yl)ethylidene bis-phosphonate, di (2-(L-isoleucyloxy)-3-methyl-(S)-(+)-butyryloxymethyl) ester,
1-hydroxy-2-(pyrid-3-yl)ethylidene bis-phosphonate, di (2-(L-isoleucyloxy)-2-phenyl-DL-acetyloxymethyl) ester,
1-hydroxy-2-(pyrid-3-yl)ethylidene bis-phosphonate, di ((1,3-di-isoleucyloxy)propyl-2-oxycarbonyloxy methyl) ester,
1-hydroxy-2-(pyrid-3-yl)ethylidene bis-phosphonate, di (2-L-isoleucyloxy)-DL-propionyloxymethyl) ester,
1-hydroxy-2-(pyrid-3-yl)ethylidene bis-phosphonate, di-(5-(L-isoleucyloxy)-2,2-dimethylvaleryloxymethyl) ester,
1-hydroxy-2-(pyrid-3-yl)ethylidene bis-phosphonate, di-((2-(L-isoleucyloxy)-ethoxycarbonyloxy) methyl) ester,
1-hydroxy-2-(pyrid-3-yl)ethylidene bis-phosphonate, bis [4-(L-isoleucyloxy)-butanoyloxymethyl]ester,
1-hydroxy-2-(pyrid-3-yl)ethylidene bis-phosphonate, di-(4-(L-isoleucyloxy) benzoyloxymethyl) ester,
1-hydroxy-2-(pyrid-3-yl)ethylidene bis-phosphonate, di-(3-(3,4-di-(L-isoleucyloxy) phenyl) propionyloxymethyl) ester,
1-hydroxy-2-(pyrid-3-yl)ethylidene bis-phosphonate, di-(2-methyl-1-(L-isoleucyloxy)-2-propoxycarbonyloxymethyl) ester,
1-hydroxy-2-(pyrid-3-yl)ethylidene bis-phosphonate, di-(4-N-isoleucyloxy)cyclohexanoyloxymethyl) ester
1-hydroxy-2-(pyrid-3-yl)ethylidene bis-phosphonate, di-(1-isoleucyloxy-2-methylpropane-2-aminocarbonyloxymethyl) ester
1-hydroxy-2-(pyrid-3-yl)ethylidene bis-phosphonate, di-(1-(2-L-isoleucyloxyethyl)-6-oxo-1,6-dihydro-pyridine-3-carbonyloxymethyl) ester and pharmaceutically acceptable salts thereof.

A further group of favoured compounds include:
(4-amino-1-hydroxybutylidine)-bisphosphonate, mono(2-methyl-2-(L-isoleucyloxymethyl) propionyloxymethyl) ester,
(4-amino-1-hydroxybutylidine)-bisphosphonate, mono(2-methyl-2-(L-isoleucyloxy) propionyloxymethyl) ester,
(4-amino-1-hydroxybutylidine)-bisphosphonate, mono(2-(L-isoleucyloxy)-3-methyl-(S)-(+)-butyryloxymethyl) ester,
(4-amino-1-hydroxybutylidine)-bisphosphonate, mono(2-(-L-isoleucyloxy)-2-phenyl-DL-acetyloxymethyl) ester,
(4-amino-1-hydroxybutylidine)-bisphosphonate, mono((1,3-di-isoleucyloxy)propyl-2-oxycarbonyloxy methyl) ester,
(4-amino-1-hydroxybutylidine)-bisphosphonate, mono(2-L-isoleucyloxy)-DL-propionyloxymethyl) ester,
(4-amino-1-hydroxybutylidine)-bisphosphonate, mono-(5-(L-isoleucyloxy)-2,2-dimethylvaleryloxymethyl) ester,
(4-amino-1-hydroxybutylidine)-bisphosphonate, mono-((2-(L-isoleucyloxy)-ethoxycarbonyloxy) methyl) ester,
(4-amino-1-hydroxybutylidine)-bisphosphonate, mono [4-(L-isoleucyloxy)-butanoyloxymethyl] ester,
(4-amino-1-hydroxybutylidine)-bisphosphonate, mono-(4-(L-isoleucyloxy) benzoyloxymethyl) ester,
(4-amino-1-hydroxybutylidine)-bisphosphonate, mono-(3-(3,4-di-(L-isoleucyloxy) phenyl) propionyloxymethyl) ester,
(4-amino-1-hydroxybutylidine)-bisphosphonate, mono-(2-methyl-1-(L-isoleucyloxy)-2-propoxycarbonyloxymethyl) ester,
(4-amino-1-hydroxybutylidine)-bisphosphonate, mono-(4-isoleucyloxy)cyclohexanoyloxymethyl) ester,
(4-amino-1-hydroxybutylidine)-bisphosphonate, mono-(1-isoleucyloxy-2-methylpropane-2-aminocarbonyloxymethyl) ester
(4-amino-1-hydroxybutylidine)-bisphosphonate, mono-(1-(2-L-isoleuxyloxyethyl)-6-oxo-1,6-dihydro-pyridine-3-carbonyloxymethyl) ester
1-hydroxy-2-(1H-imidazolyl-1-yl)ethylidene-bis phosphonate, mono(2-methyl-2-(L-isoleucyloxymethyl) propionyloxymethyl) ester,
1-hydroxy-2-(1H-imidazolyl-1-yl)ethylidene-bis phosphonate, mono(2-methyl-2-(L-isoluecyloxy) propionyloxymethyl) ester,
1-hydroxy-2-(1H-imidazolyl-1-yl)ethylidene-bis phosphonate, mono (2-(L-isoleucyloxy)-3-methyl-(S)-(+)-butyryloxymethyl) ester,
1-hydroxy-2-(1H-imidazolyl-1-yl)ethylidene-bis phosphonate, mono (2-(-L-isoleucyloxy)-2-phenyl-DL-acetyloxymethyl) ester, 1-hydroxy-2-(1H-imidazolyl-1-yl)ethylidene-bis phosphonate, mono ((1,3-di-isoleucyloxy)propyl-2-oxycarbonyloxy methyl) ester,
1-hydroxy-2-(1H-imidazolyl-1-yl)ethylidene-bis phosphonate, mono (2-L-isoleucyloxy)-DL-propionyloxymethyl) ester,
1-hydroxy-2-(1H-imidazolyl-1-yl)ethylidene-bis phosphonate, mono-(5-(L-isoleuclyoxy)-2,2-dimethylvaleryloxymethyl) ester,
1-hydroxy-2-(1H-imidazolyl-1-yl)ethylidene-bis phosphonate, mono-((2-(L-isoleucyloxy)-ethoxycarbonyloxy) methyl) ester,
1-hydroxy-2-(1H-imidazolyl-1-yl)ethylidene-bis phosphonate, mono [4-(L-isoleucyloxy)-butanoyloxymethyl] ester,
1-hydroxy-2-(1H-imidazolyl-1-yl)ethylidene-bis phosphonate, mono-(4-(L-isoleucyloxy) benzoyloxymethyl) ester,
1-hydroxy-2-(1H-imidazolyl-1-yl)ethylidene-bis phosphonate, mono-(3-(3,4-di-(L-isoleucyloxy) phenyl) propionyloxymethyl) ester,
1-hydroxy-2-(1H-imidazolyl-1-yl)ethylidene-bis phosphonate, mono-(2-methyl-1-(L-isoleucyloxy)-2-propoxycarbonyloxymethyl) ester,
1-hydroxy-2-(1H-imidazolyl-1-yl)ethylidene-bis phosphonate, mono-(4-isoleucyloxy)cyclohexanoyloxymethyl) ester
1-hydroxy-2-(1H-imidazolyl-1-yl)ethylidene-bis phosphonate, mono-(1-isoleucyloxy-2-methylpropane-2-aminocarbonyloxymethyl) ester
1-hydroxy-2-(1H-imidazolyl-1-yl)ethylidene-bis phosphonate, mono-(1-(2-L-isoleucyloxyethyl)-6-oxo-1,6-dihydro-pyridine-3-carbonyloxymethyl) ester
1-hydroxy-2-(pyrid-3-yl)ethylidene bis-phosphonate mono (2-methyl-2-(L-isoleucyloxymethyl) propionyloxymethyl) ester,
1-hydroxy-2-(pyrid-3-yl)ethylidene bis-phosphonate, mono (2-methyl-2-(L-isoleucyloxy) propionyloxymethyl) ester,
1-hydroxy-2-(pyrid-3-yl)ethylidene bis-phosphonate, mono (2-(L-isoleucyloxy)-3-methyl-(S)-(+)-butyryloxymethyl) ester,
1-hydroxy-2-(pyrid-3-yl)ethylidene bis-phosphonate, mono (2-(-L-isoleucyloxy)-2-phenyl-DL-acetyloxymethyl) ester,
1-hydroxy-2-(pyrid-3-yl)ethylidene bis-phosphonate, mono ((1,3-di-isleucyloxy)propyl-2-oxycarbonyloxy methyl) ester,
1-hydroxy-2-(pyrid-3-yl)ethylidene bis-phosphonate, mono (2-L-isoleucyloxy)-DL-propionyloxymethyl) ester,
1-hydroxy-2-(pyrid-3-yl)ethylidene bis-phosphonate, mono-(5-(L-isoleucyloxy)-2,2-dimethylvaleryloxymethyl) ester,
1-hydroxy-2-(pyrid-3-yl)ethylidene bis-phosphonate, mono-((2-(L-isoleucyloxy)-ethoxycarbonyloxy) methyl) ester,
1-hydroxy-2-(pyrid-3-yl)ethylidene bis-phosphonate, mono [4-(N-CBz-L-isoleucyloxy)-butanoyloxymethyl] ester,
1-hydroxy-2-(pyrid-3-yl)ethylidene bis-phosphonate, mono-(4-(L-isoleucyloxy) benzoyloxymethyl) ester,
1-hydroxy-2-(pyrid-3-yl)ethylidene bis-phosphonate, mono-(3-(3,4-di-(L-isoleucyloxy) phenyl) propionyloxymethyl) ester,
1-hydroxy-2-(pyrid-3-yl)ethylidene bis-phosphonate, mono-(2-methyl-1-(L-isoleucyloxy)-2-propoxycarbonyloxymethyl) ester,
1-hydroxy-2-(pyrid-3-yl)ethylidene bis-phosphonate, mono-(4-isoleucyloxy)cyclohexanoyloxymethyl) ester
1-hydroxy-2-(pyrid-3-yl)ethylidene bis-phosphonate, mono-(1-isoleucyloxy-2-methylpropane-2-aminocarbonyloxymethyl) ester,
1-hydroxy-2-(pyrid-3-yl)ethylidene bis-phosphonate, mono-(1-(2-L-isoleucyloxyethyl)-6-oxo-1,6-dihydro-pyridine-3-carbonyloxymethyl) ester and pharmaceutically acceptable salts thereof.

A still further preferred group of prodrugs of the invention are those based on fosinoprilate having the formula PF3:

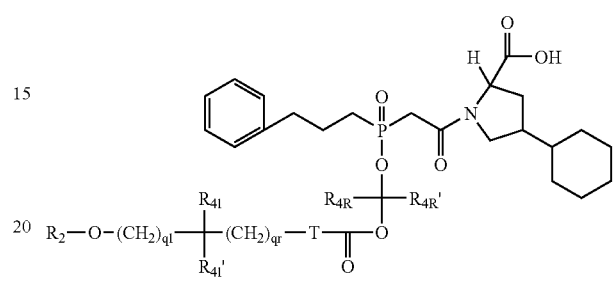

or

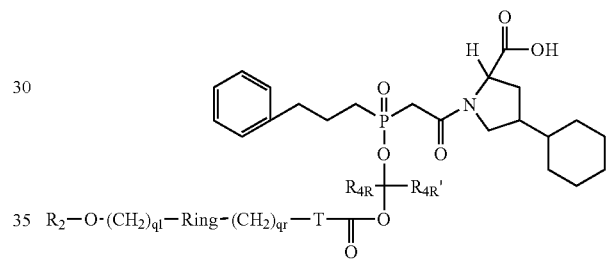

where $R_2$ is the acyl residue of an aliphatic amino acid, $R_{4L}$ and $R_{4R}'$ are independently H, $C_{1-3}$ alkyl, $C_{3-6}$cycloalkyl, $C_{1-3}$alkyl-$C_1C_6$cycloalkyl phenyl or benzyl, $R_{4R}$ and $R_{4R}'$ are independently H or $C_{1-3}$ alkyl q1 is 0–3, qr is 0–3, T is a bond, —NR$_3$— or —O—

$R_3$ is H or $C_{1-3}$alkyl;

ring is an optionally substituted aromatic or non-aromatic, hetero-or carbocycle;

and pharmaceutically acceptable salts thereof.

In formula PF3, $R_{4R}$ and $R_{4R}'$ are preferably H and/or $R_{4L}$ and $R_{4R}'$ are preferably ethyl or especially methyl. T is preferably —O— or more preferably a bond. Preferably qr is 1 or more preferably 0.

Favoured compounds within formula PF3 thus include
(4S)-4-cyclohexyl-1-[[(R)(4-phenylbutyl)phosphinyl] acetyl]-L-proline, (2-methyl-2(L-valyloxymethyl) propionyloxymethyl) ester,
(4S)-4-cyclohexyl-1-[[(R)(4-phenylbutyl)phosphinyl] acetyl]-L-proline, (2-methyl-2(L-valyloxy) propionyloxymethyl) ester,
(4S)-4-cyclohexyl-1-[[(R)(4-phenylbutyl)phosphinyl] acetyl]-L-proline, (2-(L-valyloxy)-3-methyl-(S)-(+)-butyryloxymethyl) ester, (4S)-4-cyclohexyl-1-[[(R)(4-phenylbutyl)phosphinyl] acetyl]-L-proline, (2-(-L-valyloxy)-2-phenyl-DL-acetyloxymethyl) ester,
(4S)-4-cyclohexyl-1-[[(R)(4-phenylbutyl)phosphinyl] acetyl]-L-proline, ((1,3-di-valyloxy)propyl-2-oxycarbonyloxy methyl) ester,
(4S)-4-cyclohexyl-1-[[(R)(4-phenylbutyl)phosphinyl] acetyl]-L-proline, (2-L-valyloxy)-DL-propionyloxymethyl) ester,
(4S)-4-cyclohexyl-1-[[(R)(4-phenylbutyl)phosphinyl] acetyl]-L-proline, (5-(L-valyloxy)-2,2-dimethylvaleryloxymethyl) ester,
(4S)-4-cyclohexyl-1-[[(R)(4-phenylbutyl)phosphinyl] acetyl]-L-proline, ((2-(L-valyloxy)-ethoxycarbonyloxy) methyl) ester,
(4S)-4-cyclohexyl-1-[[(R)(4-phenylbutyl)phosphinyl] acetyl]-L-proline, [4-(L-valyloxy)-butanoyloxymethyl] ester,
(4S)-4-cyclohexyl-1-[[(R)(4-phenylbutyl)phosphinyl] acetyl]-L-proline, (4-(L-valyloxy) benzoyloxymethyl) ester,
(4S)-4-cyclohexyl-1-[[(R)(4-phenylbutyl)phosphinyl] acetyl]-L-proline, (3-(3,4-di-(L-valyloxy) phenyl) propionyloxymethyl) ester,
(4S)-4-cyclohexyl-1-[[(R)(4-phenylbutyl)phosphinyl] acetyl]-L-proline, (2-methyl-1-(L-valyloxy)-2-propoxycarbonyloxymethyl) ester,
(4-N-valyloxy)cyclohexanoyloxymethyl) ester
(1-valyloxy-2-methylpropane-2-aminocarbonyloxymethyl)
(1-(2-L-valyloxyethyl)-6-oxo-1,6-dihydro-pyridine-3-carbonyloxymethyl)
(4S)-4-cyclohexyl-1-[[(R)(4-phenylbutyl)phosphinyl] acetyl]-L-proline, (2-methyl-2-(L-isoleucyloxymethyl) propionyloxymethyl) ester,
(4S)-4-cyclohexyl-1-[[(R)(4-phenylbutyl)phosphinyl] acetyl]-L-proline, (2-methyl-2-(L-isoleucyloxy) propionyloxymethyl) ester,
(4S)-4-cyclohexyl-1-[[(R)(4-phenylbutyl)phosphinyl] acetyl]-L-proline, (2-(L-isoleucyloxy)-3-methyl-(S)-(+)-butyryloxymethyl) ester,
(4S)-4-cyclohexyl-1-[[(R)(4-phenylbutyl)phosphinyl] acetyl]-L-proline, (2-(-L-isoleucyloxy)-2-phenyl-DL-acetyloxymethyl) ester,
(4S)-4-cyclohexyl-1-[[(R)(4-phenylbutyl)phosphinyl] acetyl]-L-proline, ((1,3-di-isoleucyloxy)propyl-2-oxycarbonyloxy methyl) ester,
(4S)-4-cyclohexyl-1-[[(R)(4-phenylbutyl)phosphinyl] acetyl]-L-proline, (2-L-isoleucyloxy)-DL-propionyloxymethyl) ester,
(4S)-4-cyclohexyl-1-[[(R)(4-phenylbutyl)phosphinyl] acetyl]-L-proline, (5-(L-isoleucyloxy)-2,2-dimethylvaleryloxymethyl) ester,
(4S)-4-cyclohexyl-1-[[(R)(4-phenylbutyl)phosphinyl] acetyl]-L-proline, ((2-(L-isoleucyloxy)-ethoxycarbonyloxy) methyl) ester,
(4S)-4-cyclohexyl-1-[[(R)(4-phenylbutyl)phosphinyl] acetyl]-L-proline, [4-(L-isoleucyloxy)-butanoyloxymethyl] ester,
(4S)-4-cyclohexyl-1-[[(R)(4-phenylbutyl)phosphinyl] acetyl]-L-proline, (4-(L-isoleucyloxy) benzoyloxymethyl) ester,
(4S)-4-cyclohexyl-1-[[(R)(4-phenylbutyl)phosphinyl] acetyl]-L-proline, (3-(3,4-di-(L-isoleucyloxy) phenyl) propionyloxymethyl) ester,
(4S)-4-cyclohexyl-1-[[(R)(4-phenylbutyl)phosphinyl] acetyl]-L-proline, (2-methyl-1-(L-isoleucyloxy)-2-propoxycarbonyloxymethyl) ester,
(4-N-valyloxy)cyclohexanoyloxymethyl) ester
(1-valyloxy-2-methylpropane-2-aminocarbonyloxymethyl)
(1-(2-L-valyloxyethyl)-6-oxo-1,6-dihydro-pyridine-3-carbonyloxymethyl)

and pharmaceutically acceptable salts thereof.

A further phosphonate compound amenable to the prodrugs of the invention are the neutral endopeptidase inhibitors such as CGS-24592 (Novartis), preferably those of the formula PF6:

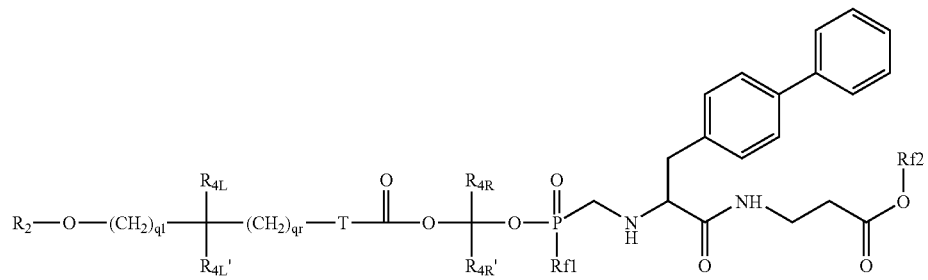

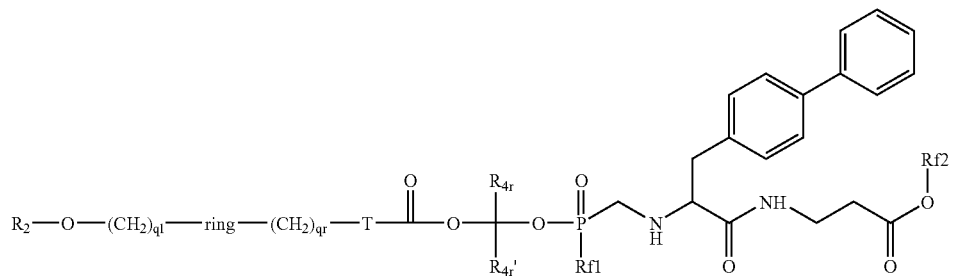

where
- RF1 is H or a further structure of formula II''b
- Rf2 is H or a conventional pharmaceutically acceptable ester,
- $R_2$ is the acyl residue of an aliphatic amino acid,
- $R_{4L}$ and $R_{4L}'$ are independently H, $C_{1-3}$ alkyl, $C_{3-6}$cycloalkyl, $C_{1-3}$alkyl-$C_1C_6$cycloalkyl phenyl or benzyl,
- $R_{4R}$ and $R_{4R}'$ are independently H or $C_{1-3}$ alkyl
- q1 is 0–3, qr is 0–3,
- T is a bond, —$NR_4$— or —O—
- $R_4$ is H or $C_{1-3}$alkyl;

ring is an optionally substituted aromatic or non-aromatic, hetero-or carbocycle.

Currently favoured values in Formula PF6 include: $R_{4R}$ and $R_{4R}'$ are preferably H and/or $R_{4L}$ and $R_{4L}'$ are preferably ethyl or especially methyl. T is preferably —O— or more preferably a bond. Preferably qr is 1 or more preferably 0. If Rf1 is a further ester it is convenient if it is identical to other linker-$R_2$ moiety. Conventional pharmaceutically acceptable esters for Rf2 include the methyl, ethyl and isopropyl esters.

A further convenient Drug for appying the prodrugs of the invention is the antiParkinsonian agent levodopa:

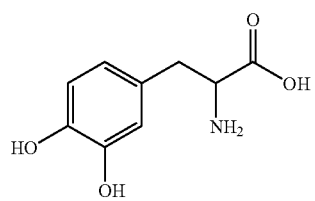

This drug has four accessible functions for applying the prodrugs of the invention, namely the 3 and 4 hydroxy groups on the phenyl and the amino and carboxy functions on the side chain.

A structure of the formula IIa or II''b be esterified to one or both of the aromatic hydroxyl functions or amide-bonded to the levodopa amino function. A trifunctional linker of Formula III or Formula IId, can be carbonyl bonded to the levodopa carboxyl function. Such "blocked" carboxyl levodopa compounds are conceivably less susceptible to in vivo peripheral decarboxylation than levodopa and may thus allow the diminution or omission of the customarily coadministered decarboxylase inhibitors such as carbidopa.

A further convenient Drug for applying the prodrugs of the invention is chromoglycate, also known as cromolyn, useful in the treatment of asthma, allergic rhinitis, mastocytosis, ulcerative colitis and inflammatory bowel disease:

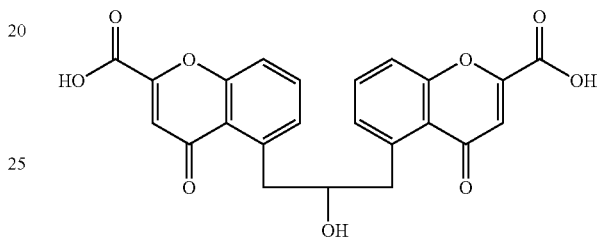

It will be apparent that cromolyn has three accessible functions suitable for applying the prodrugs of the invention. In particular, a linker of the formula IId can be carbonyl linked to either of the carboxy groups. As cromolyn is a symmetric compound it may be advantageous to bond a respective linker to each of the carboxyl groups. Alternatively or additionally, a linker of the formula IIa, II'a, IId, II'd such as those wherein T is a bond or —O— and V is a bond can be esterified to the hydroxy group depending from the propylene bridge, optionally in conjunction with conventional pharmaceutical esters on the carboxy groups.

A further group of Drugs which are amenable to the prodrugs of the invention are the pain-killer opiates such as morphine:

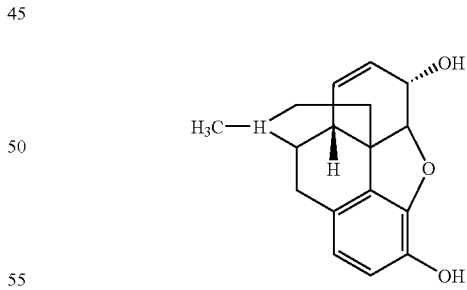

Morphine and many of its analogues have a pair of hydroxy functions accessible to the prodrug approach of the invention. For instance a structure of formula IIa wherein T is a bond or —O— and V is a bond would be convenient for esterification with the 3 and/or 6 hydroxy groups.

A further convenient group of compounds include the macrolide antibiotics such as erythromycin and roxitromycin and antibacterial glycopeptides such as vancomycin.

A further convenient group of Drugs for applying the prodrugs of the invention are the rifamycin antibiotics:

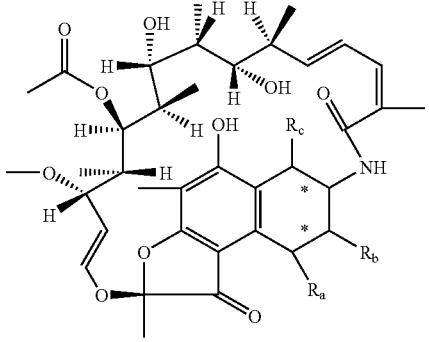

wherein the asterisks define the requisite number of aromatic bonds, including rifampicin ($R_a$ is OH, $R_b$ is —CH=N—(4-N-methylpiperazine), $R_c$ is hydroxy), rifamide ($R_a$ is $OCH_2CONH(C_2H_5)_2$, $R_b$ is hydrogen, $R_c$ is hydroxy), rifamycin B ($R_a$ is —$OCH_2COOH$, $R_b$ is hydrogen, $R_c$ is hydroxy), rifamycin O ($R_a$ is -1,3-dioxolan-4-on)-2-yl, $R_b$ is hydrogen, $R_c$ is hydroxy), rifamycin S ($R_a$ is =O, $R_b$ is hydrogen, $R_c$ is =O), rifamycin SV ($R_a$ is —OH, $R_b$ is hydrogen $R_c$ is —OH), rifaximin ($R_a$ and $R_b$ together define a structure:

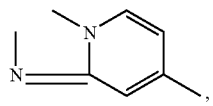

$R_c$ is hydroxy), and rifabutinum ($R_a$ and $R_b$ together define a structure:

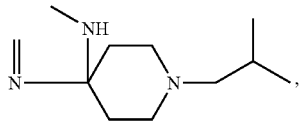

Rc is =O).

It will be apparent that the rifamycins have a number of free hydroxyls and secondary amines available for esterification or amide bonding with respective linker-$R_2$ groups in accordance with the invention such as those of Formula II'a or Formula IIa above, which linker group is bonded to one of said hydroxy or amino groups.

A further group of Drugs which are amenable to the prodrugs of the invention is the cephalosporin antibiotics:

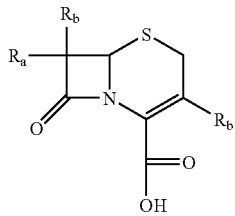

Representative cephalosporins include:

cefpodoxime ($R_a$ is [(2-amino-4-thiazolyl)(methoximino)acetyl]amino-, $R_b$ is H, $R_c$ is ethyl), cefaclor ($R_a$ is aminophenylacetylamino, $R_b$ is H, $R_c$ is chloro), cefadroxil ($R_a$ is [amino-(4-hydroxyphenyl)acetyl]amino, $R_b$ is H, $R_c$ is methyl);

cefamandole ($R_a$ is [amino-(4-hydroxyphenyl)acetyl]amino, $R_b$ is H, $R_c$ is [1-methyl-1H-tetrazol-5-yl)thio]methyl);

cefatrizine, ($R_a$ is is [amino-(4-hydroxyphenyl)acetyl]amino, $R_b$ is H, $R_c$ is [1H-1,2,3-triazol-4-ylthio]methyl);

cefazedone (Ra is [(3,5-dichloro-4-oxo-[(4H)-pyridinyl)acetyl]amino, $R_b$ is H, $R_c$ is [(5-methyl-1,3,4-thiadiazol-2-yl)thio]methyl), cefazolin (Ra is (1H-tetrazol-1-ylacetyl)-amino Rb is H, Rc is [(5-methyl-1,3,4-thiadiazol-2-yl)thio]methyl, cefbuparazone (Ra is [2-[[(4-ethyl-2,3-dioxo-1-piperazinyl)carbonyl]amino]-3-hydroxy-1-oxobutyl]amino, Rb is $OCH_3$, Rc is [(1-methyl-1H-tetrazoly-5yl)thio]methyl, cefixime (Ra is [(2-amino-4-thiozolyl)[carboxymethoxy)imino]acetyl]amino, Rb is H, Rc is —CH=$CH_2$), cefmonoxime, (Ra is [(2-amino-4-thiazolyl)(methoxyimino)acetyl]amino, Rb is h, rc is [(1-methyl-1H-tetrazol-5-yl)thio]methyl), cefmetazole ([[[(cyanomethyl)thio]acetyl]amino, Rb is H, Rc is [1-methyl-1H-tetrazol-5-yl)thio]methyl), cefminox (Ra is [[(2-amino-2-carboxyethyl)thio]acetyl]amino, Rb is $OCH_3$, Rc is is [1-methyl-1H-tetrazol-5-yl)thio]methyl), cefodoxime (Ra is [(2-amino-4-thiazolyl)(methoxyimino)acetyl]amino, Rb is H, Rc is [[5-(carboxymethyl)-4-methyl-2-thiazolyl]thio]methyl), cefonicid (Ra is (hydroxyphenylacetyl)amino, Rb is H, Rc is [[1–8sulfomethyl)-1H-tetrazol-5-yl]thio]methyl), cefoperazone (Ra is [[[(4-ethyl-2,3-dioxo-1-piperazinyl)carbonyl]amino](4-hydroxyphenyl)acetyl]amino, Rb is H, Rc is [(1-methyl-1H-tetrazol-5-yl)thio]methyl), ceforanide (Ra is [[2-(aminomethyl)phenyl]acetyl]amino, Rb is H, Rc is [[1-(carboxymethyl)-1H-tetrazol-5-yl]thio]methyl), cefotaxime (Ra is [(2-amino-4-thiazolyl)(methoxyimino)acetyl]amino, Rb is H, Rc is (acetyloxy)methyl), cefotetan (Ra is [[4-(2-amino-1-carboxy-2-oxoethylidine)-1,3-dithietan-2-yl]carbonyl]amino, Rb is $OCH_3$, Rc is [(1-methyl-1H-tetrazol-5-yl)thio]methyl, Rc is [(1-methyl-1H-tetrazol-5-yl)thio]methyl), cefotiam (Ra is [(2-amino-4-thiazolyl)acetyl]amino, Rb is H, Rc is [[1-[2-(dimethylamino)ethyl]-1H-tetrazol-5-yl]thio]methyl), cefoxitin (Ra is (2-thienylacetyl)amino, Rb is $OCH_3$, Rc is [aminocarbonyl)oxy]methyl), cefpimizole (Ra is [[[(5-carboxy-1H-imidazol-4-yl)carbonyl]amino]phenylacetyl]amino, Rb is H, Rc is (4'-(2-sulfoethyl)pyridinium) methyl hydroxide inner salt, cefpiramide (Ra is [[[(4-hydroxy-6-methyl-3-pyridinyl)carbonyl]amino](4-hydroxyphenyl)acetyl]amino, Rb is H, Rc is [(1-methyl-1H-tetrazol-5-yl)thio]methyl), cefroxadine (Ra is (amino-1,4-cyclohexadien-1-yl-acetyl) amino, Rb is H, Rc is $OCH_3$), cefsulodin (Ra is (phenylsulfoacetyl)amino, Rb is H, Rc is (4'-carbamoyl pyridinium)methyl hydroxide inner salt), ceftazidime (Ra is [(2-amino-4-thiazolyl)[(1-carboxy-1-methylethoxy)imino]acetyl]amino, Rb is H, Rc is pyridiniummethyl hydrochloride inner salt), cefteram (Ra is [(2-amino-4-thiazolyl)methoxyimino) acetyl]amino, Rb is H, Rc is (5-methyl-2H-tetrazol-2-yl) methyl), ceftezole (Ra is (1H-tetrazol-1-ylacetyl)amino, Rb is (1,3,4-thiadiazol-2-ylthio)methyl), ceftibuten (Ra is [2-(2-amino-4-thiazolyl)-4-carboxy-1-oxo-2-butenyl]amino, Rb is H, Rc is H)

ceftiofur (Ra is [(2-amino-4-thiazoyl)(methoxyimino) acetyl]amino, Rb is H, Rc is [(2-furanylcarbonyl)thio] methyl), ceftizoxime (Ra is [(2-amino-4-thiazolyl)(methoxyimino) acetyl]amino, Rb is H, Rc is H), ceftriaxone (Ra is [(2-amino-4-thiazolyl)methoxyimino) acetyl]amino, Rb is H, Rc is [1,2,5,6-tetrahydro-2-methyl-5,6-dioxo-1,2,4-triazin-3-yl)thio]methyl), cefuroxime (Ra is [2-furanyl(methoxyimino)acetyl]amino, Rb is H, Rc is [(aminocarbonyl)oxy]methyl), cefuzonam (Ra is [(2-amino-4-thiazolyl)(methoxyimino) acetyl]amino, Rb is H, Rc is (1,2,3-thiadiazol-5-ylthio) methyl), cephacetrile (Ra is (cyanocetyl)amino, Rb is H, Rc is (acetyloxy)methyl), cephalexin (Ra is (aminophenylacetyl)amino, Rb is H, Rc is methyl), cephaloglycin (Ra is (aminophenylacetyl)amino, Rb is H, Rc is (acetyloxy)methyl), cephaloridine (Ra is (2-thienylacetyl)amino, Rb is H, Rc is pyridinium methyl hydroxide inner salt), cephalosporin C (Ra is (5-amino-5-carboxy-1-oxopentyl) amino, Rb is H, Rc is (acetyloxy)methyl), cephalothin (Ra is (2-thienylacetyl)amino, Rb is H, Rc is (acetyloxy)methyl), cephamycin A (Ra is (5-amino-5-carboxy-1-oxopentyl) amino, Rb is $OCH_3$ Rc is —$CH_2OCOC(OCH_3)$=CH-(4-oxysulphyl)phenyl), cephamycin B (Ra is (5-amino-5-carboxy-1-oxopentyl) amino, Rb is $OCH_3$ Rc is —$CH_2OCOCC(OCH_3)$=CH-(4-hydroxy)phenyl), cephamycin C (Ra is (5-amino-5-carboxy-1-oxopentyl) amino, Rb is $OCH_3$ Rc is —$CH_2OCONH_2$)

cephapirin (Ra is [(4-pyridinylthio)acetyl]amino, Rb is H, Rc is (acetyloxy)methyl), cephradine (Ra is (amino-1,4-cyclohexadien-1-yl-acetyl)amino, Rb is H, Rc is $CH_3$).

Common for the above cephalosporins is the presence of a carboxy group at the 2-position which is amenable to derivation with a linker group, in particular those of Formula III & IIId and IId & IId defined above. The above listed Ra, Rb and Rc groups may also be combined in various permutations and the invention includes prodrugs of all such cephalosporins.

A further group of Drugs which are amenable to the prodrugs of the invention are the anticholinesterases such as tacrine:

where R is H or OH. It will be apparent that the tacrine itself (R=H) has a free amine group suitable for derivatisation with a linker-$R_2$ group such as those of Formula ila, for instance when T is a bond or —O— and V is a bond. The tacrine metabolite (R=OH), which is also active in vivo has an additional hydroxy function which can alternatively or additionally be derivatised with a linker such as those of Formula IIa, for instance when T is a bond or —O— and V is a bond.

A further group of Drugs which are amenable to the prodrugs of the invention are the sulphonamide diuretics such as furosemide:

It will be apparent that furosemide has a free carboxylic function, a primary amine and a secondary amine amenable to the prodrugs of the invention. In particular an $R_2$ bearing linker, such as those of Formula III, III' or Formula IId. II'd can be carbonyl linked to the free carboxy function. Alternatively or additionally, an $R_2$ bearing linker, such as those of Formula IIa or II'a, for instance where T is a bond or —O— and V is a bond can be amide bonded to the primary and/or secondary amine groups.

A further group of Drugs amenable to the prodrugs of the invention include the α-1 and β-blocker carvedilol compounds:

Carvedilol has a free hydroxy function, a secondary heterocyclic amine and a further secondary amine on the side chain, which are amenable to the prodrugs of the invention, such as those of Formula II'a, for instance where T is a bond or —O— and V is a bond which is in turn linked to the hydroxy and/or the ring amine and/or the side chain amine functions on carvedilol.

A further group of Drugs which are amenable to the prodrugs of the invention are the hypolipaemic statins, such as flustatin or compounds of the formula:

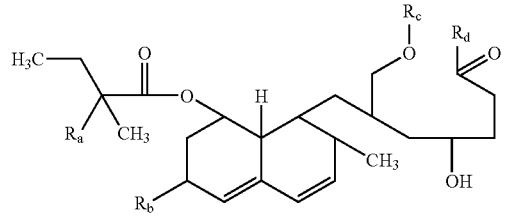

such as pravastatin (Ra=H, Rb=OH, Rc=H, Rd=OH) and simvastatin (Ra=CH₃, Rb=CH₃, Rc and Rd together define a bond).

Taking simvastatin as an example, it will be apparent that there is a free side chain hydroxyl which is available for linkage with an R₂ bearing linker, such as those of Formula IIa, for instance where T is a bond or —O— and V is a bond.

The statin pravastatin also bears a corresponding hydroxy function and can be derivatised with a linker in the same fashion. Pravastatin also bears a ring hydroxyl and a further side chain hydroxyl function which can be derivatised with a linker in a corresponding fashion. Pravastatin also bears a carboxyl function which can additionally or alternatively be derivatised with an R₂ bearing linker such as those of Formula III, III' or Formula IId, IId'.

A further group of Drugs which are amenable to the prodrugs of the invention are peptides and pseudopeptides such protease inhibitors including antifibrinolytics like aprotinin or peptidomimetic aspartyl protease inhibitors such as renin inhibitors. Other peptide Drugs include hormones such as vasopressins. Taking vasopressins as an example, peptide Drugs may be cyclic oligopeptides consisting solely of amino acids such as desmopressin or oxytocin, wherein the N and C terminals represent accessible functions for derivatisation in accordance with the invention. Additionally many peptide drugs include amino acids with side chains bearing accessible functions such as arginine, serine or aspartate. Alternatively a peptide Drug, particularly peptidomimetics can be derivatised with non-amino acid structures bearing accessible functions such as somatostatin octreotide.

Useful oligopeptides for derivisation acording to the invention include MK 383, an Arg-Gly-Asp analogue useful as an antithrombotic, DADLE (Tyr-D-Ala-Gly-Phe-DLeu), an encephalin analogue and NISIN.

An exemplary group of protease inhibitors amenable to the invention comprises the HIV protease inhibitors bearing one or more chain hydroxy functions and/or one or more ring hydroxy functions such as the indanolamine terminal group in Mercks indinavir:

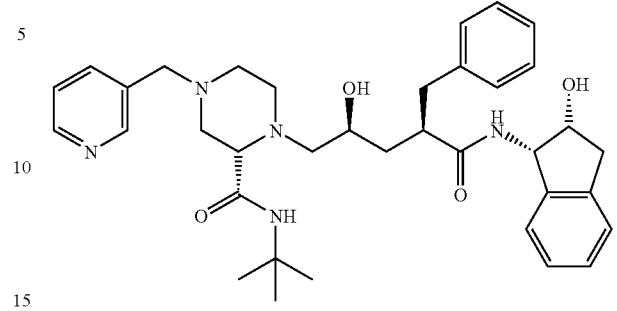

Favoured prodrugs of indinavir in accordance with the invention include [1-(1S,2R), 5(S)]-2,3,5-trideoxy-N-(2,3-dihydro-2-butyryloxy-1H-inden-1-yl)-5-[2-[[(1,1-dimethyl-ethyl)amino]carbonyl]-4-(3-pyridinylmethyl)-1-piperazi-nyl]-2-(phenylmethyl-D-erythro-pentonamide.

A further indanol based HIV protease inhibitors is Novartis/BMS SDZ PRI 053:

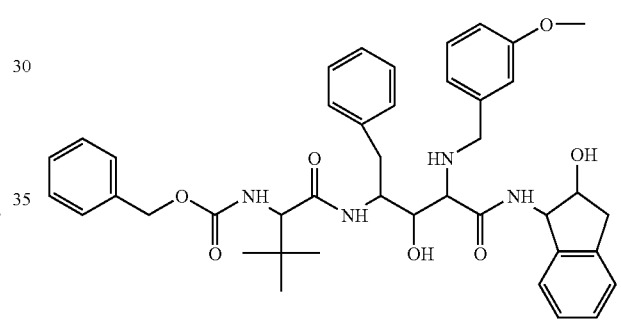

A further group of HV protease inhibitors include the hexose derived compounds described in WO 98/45330, the contents of which are hereby incorporated by reference. These compounds typically have the general formula I:

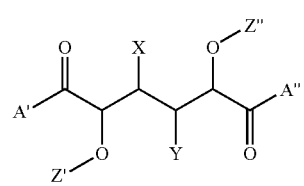

wherein:

A' and A" are independently a group of the formula II:

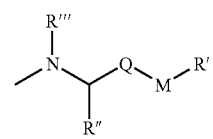

wherein:

R' is H, CH$_3$, C(CH$_3$)$_2$, —OR$^a$, —N(R$^a$)$_2$, —N(R$^a$)OR$^a$ or -DP

R''' is H, CH$_3$; R$^a$ is H, C$_1$–C$_3$ alkyl;

D is a bond, C$_{1-3}$ alkylene, —C(=O)—, —S(O)— or —S(O)$_2$—;

P is an optionally substituted, mono or bicyclic carbo- or heterocycle;

R'' is H, any of the sidechains found in the natural amino acids, carboxacetamide, or a group (CH$_2$)$_n$DP;

M is a bond or —C(=O)N(R''')—;

Q is absent, a bond, —CH(OH)— or —CH$_2$—;

or R'' together with Q, M and R' define an optionally substituted 5 or 6 membered carbo- or heterocyclic ring which is optionally fused with a further 5 or 6 membered carbo- or heterocyclic ring;

with the proviso that R' is —OR', —N(CH$_3$)$_2$, —N(R$^a$)OR$^a$ or -DP if M is a bond and Q is absent;

X is H, OH, OCH$_3$;

Y is H, OH, OCH$_3$, but X and Y are not both H;

Z' and Z'' are independently —(CH$_2$)$_m$P where P is as defined above;

and n and m are independently 0, 1 or 2, and pharmaceutically acceptable salts thereof.

Carbocyclic groups for R' as -DP and/or Z'/Z'' and/or the optional substituents thereto may be saturated, unsaturated or aromatic and include monocyclic rings such as phenyl, cyclohexenyl, cyclopentenyl, cyclohexanyl, cyclopentanyl, or bicyclic rings such as indanyl, napthyl and the like.

Heterocyclic groups for R' as -DP and/or Z'/Z'' and/or the optional substituents thereto may be saturated, unsaturated or aromatic and have 1 to 4 hetero atoms including monocyclic rings such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, and the like or bicyclic rings especially of the above fused to a phenyl ring such as indolyl, quinolinyl, isoquinolinyl, benzimidazolyl, benzothiazolyl, benzoxazolyl, benzothienyl etc. The carbo or heterocyclic ring may be bonded via a carbon or via a hetero atom, typically a nitrogen atom, such as N-piperidyl, N-morpholinyl etc.

Disclosed embodiments of Formula II for the A'/A'' groups of the compounds of formula I include those of the formula IIa:

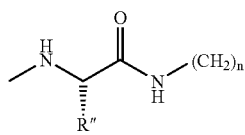

where n is 1 or 2 and R' is alkyloxy, preferably methyloxy, or those where n is 0 and R' is methyl.

Other disclosed groups of formula II include IIb below

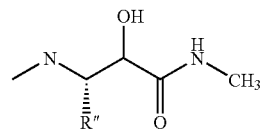

An alternative configuration for the A'/A'' groups of the compounds of the invention includes groups of the formula IIc:

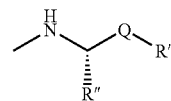

where Q is a bond, methylene or —C(OH)— and R' is —OR$^a$, —N(R$^a$)$_2$, —NR$^a$ OR$^a$, where R$^a$ is H or C$_1$–C$_3$ alkyl, or a carbo- or heterocyclic group including N-piperidine, N-morpholine, N-piperazine, pyrrolyl, imidazolyl, pyrazolyl, pyridyl, pyrimidyl, pyrazinyl etc.

A subset of compounds within formula IIc has the formula IId:

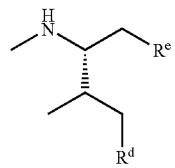

where R$^d$ is hydrogen or methyl (that is a valyl or isoleucyl side chain) and R$^e$ is

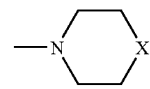

or

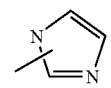

where X is methylene, O, S, S=O, S(=O)$_2$ or NH or R$^e$ is —N(CH$_3$)$_2$, —NHOH, —NHOMe, —NHOEt, —NMeOH, —NMeOMe etc.

In each of formulae IIa, IIb and IIc, R'' is hydrogen, methyl, ethyl, isopropyl, cycloalkyl such as cyclopropyl, cyclobutyl or cyclohexyl, cycloalkenyl, benzyl, carboxacetamide or 4-imidazolylmethy, any of which may be substituted as defined above. Preferred R'' groups include the side chains found in the natural amino acids, especially those of leucine, asparagine, histidine or proline. The most preferred R" groups for formula IIa, IIb, IIc and IId are the isoleucyl and especially the valyl side chain.

R' will vary depending on the nature of Q and/or M, if present, and may for instance be selected from hydrogen, methyl, ethyl, isopropyl, $R^e$ as defined above, valinol, a heterocycle such as pyridyl, thiazole, oxazole, imidazole, N-piperidine, N-morpholine, N-piperazine, pyrrolyl, imidazolyl, pyrazolyl, pyrimidyl, pyrazinyl, any of which R' groups may be substituted as defined for Z'/Z" below.

Further disclosed A'/A" groups include those of formula II where R", Q, M and R' together define an optionally substituted 5 or 6 membered carbo- or heterocyclic ring. A preferred group within this definition include groups within formula III:

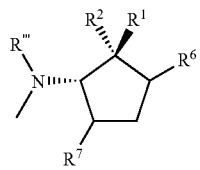

III where

R'" is as defined above, $R^1$ is H, $NR^4R^4$, $C(=O)R^3$, $CR^3R^4$ or a monocyclic, optionally substituted carbo- or heterocycle;

$R^2$ is OH, or together with $R^1$ is =O, or if $R^1$ is $NR^4R^4$, then $R^2$ may be H;

$R^3$ is H, halo, $C_1$–$C_3$ alkyl, $OR^5$, $NR^4R^4$;

$R^4$ is H, $C_1$–$C_3$ alkyl;

$R^5$ is H or a pharmaceutically acceptable ester;

$R^6$ is OH, $NH_2$, carbamoyl or carboxy;

$R^7$ is hydrogen, $C_1$–$C_4$ straight or branched alkyl or together with the adjacent carbon atoms forms a fused phenyl or heteroaromatic ring;

Preferred groups of formula III include aminoindanol and 1-amino-azaindan-2-ol, that is moieties of the formulae:

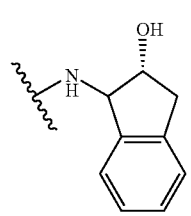

or

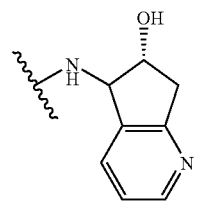

This aspect of the present invention thus provides compounds of the formula IV:

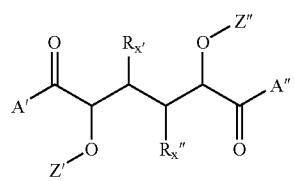

IV where A', A", Z' and Z" are as defined above, one of $R_{x'}$ and $R_{x''}$ is H, OH or $OCH_3$ and the other one of $R_{x'}$ and $R_{x''}$ is a group of the formula —O-L-$R_y$, where $R_y$ is the acyl residue of an aliphatic amino acid and L is a bifunctional linker group. With the expression "bifunctional linker group" is meant a group which bears a function amenable to an acyl bond with the carboxy funtion of the amino acid derivative $R_y$, and is also able to bond with an hydroxy function at the 3 or 4 position of the alkyl backbone of the structure of formula III. Exemplary L groups include an alkoxy moiety such as —$CH_3O$—, —$CH(CH_3)O$—, $C(CH_3)_2O$— and the like. Other exemplary L groups include an alkoxyalkoxy moiety such as —$CH_3O$-Alk-O—, —$CH(CH_3)O$-Alk-O—, $C(CH_3)_2O$-Alk-O, where Alk is a $C_1$–$C_6$ branched or straight chain saturated or unsaturated alkylene group, such as methylene, ethylene, 1,1bismethylethylene and the like. Other exemplary L groups include derivatives of hydroxyalkanoic acids, where the carboxy function is acylated to the hydroxy function at the 3 or 4 position of the backbone of the structure of formula III, while the hydroxy function is available for acylation with the carboxy function of the amino acid group $R_y$. Convenient hydroxyalkanoic acids include those derived from α-hydroxy ω-carboxylic acids such as carbonic acid, glycollic acid, hydroxypropanoic acid, hydroxybutyric acid, hydroxyvaleric acid or hydroxycaproic acid.

A number of convenient bifunctional linker groups are described in SE 9801216-4 which is hereby incorporated by reference, and also the disclosure of PCT/SE98/01467, also incorporated herein by reference.

Linkers prepared from ω-hydroxybutyric derivatives are convenient as with these compounds hydrolysis and removal of the $R_y$ group in vivo leaves a reactive terminal radical which will tend to cyclize and prompt the effective release of the mother protease inhibitor. Similarly, linkers of the formula $L_a$:

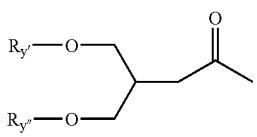

are convenient as enzymatic or spontaneous hydrolysis of a first of the $R_y$ groups will result in an active terminus able to curl back and attack the acyl linkage to the mother compound thus promoting spontaneous release of the linker fragment. Other convenient linkers along the same principle have the formula $L_b$ or $L_c$:

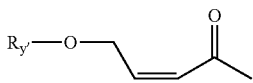

or

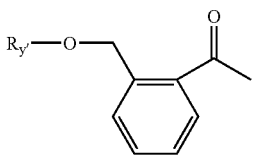

Preferred $R_y$ groups include those derived from L-alanine, L-leucine and especially L-isoleucine and L-valine.

Favoured mother compounds within Formula IV include those of the formula IVA:

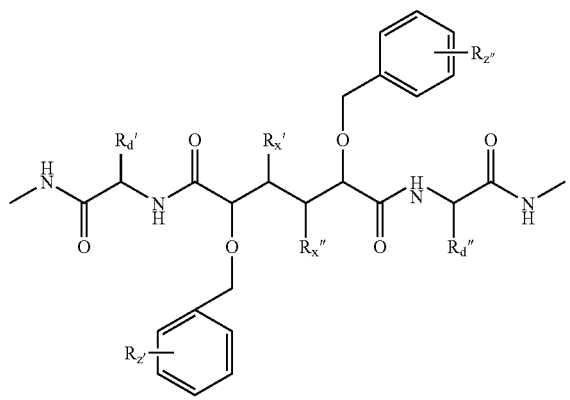

where $R_{d'}$ and $R_{d''}$ are independently the side chain of an aliphatic L-amino acid, especially those of valyl or isoleucyl, one of $R_{x'}$ and $R_{x''}$ is hydroxy or hydrogen and the other is —O-L—$R_y$, and $R_z$ and $R_{z'}$ are independently H, halo, amino, mercapto, oxo, nitro, $NHC_1$–$C_6$ alkyl, $N(C_1$–$C_6$ alkyl$)_2$, $C_1$–$C_6$ alkyl, $C_1$–$C_6$ alkenyl, $C_1$–$C_6$ alkynyl, $C_1$–$C_6$ alkanoyl, $C_1$–$C_6$ alkoxy, thio$C_1$–$C_6$ alkyl, thio$C_1$–$C_6$ alkoxy, hydroxy, hydroxy$C_1$–$C_6$ alkyl, halo$C_1$–$C_6$ alkyl, amino$C_1$–$C_6$ alkyl, cyano, carboxyl, carbalkoxy, carboxamide, carbamoyl and the like, any of which alkyl moieties being optionally fluoro substituted, or an optionally substituted 5 or 6 membered carbocyclic or heterocyclic ring structure, such as cyclohexanyl, cyclohexenyl, phenyl, furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, and the like. The ring structure may be bonded via a carbon atom or a hetero nitrogen. The ring structure may itself substituted with substituents as defined imrnediately above.

X ray crystallography indicates that there is significant scope for bulky substitution at $R_z$, and/or $R_{z'}$ with (optionally substituted) groups such as para-phenyl, para-pyrid-2-yl, para-pyrid-3yl, para-thien-2-ylyl, parathien-3yl, para-pyrimid-2-yl, para-pyrimid-3-yl, para-pyrimid-4-yl and parathiazol-2-yl.

Alternatively or additionally $R_{z'}$ and/or $R_{z''}$ can comprise a smaller substituent intended for interaction with adjacent portions of the molecule. For instance, an ortho-fluoro group can hydrogen bond with any hydroxy groups present in A'or A", thus serving to prevent hydrophobic collapse and/or functioning as a pseudoscaffold. This is best seen with the compounds of Formula IIIB below.

Exemplary compounds within Formula IVA thus include:
N1,N6-di[(1S)-2-methyl-1-(methylcarbamoyl)propyl]-(2R,3R,4R,5R)-2,5-di(benzyloxy)-3-hydroxy-4-(L-valyloxymethyloxy)hexanediamide,
N1,N6-di[(1S)-2-methyl-1-(methylcarbamoyl)propyl]-(2R,3R,4R,5R)-2,5-di(benzyloxy)-3-hydroxy-4-(L-valyloxy-(1-methyl)methyloxy)hexanediamide,
N1,N6-di[(1S)-2-methyl-1-(methylcarbamoyl)propyl]-(2R,3R,4R,5R)-2,5-di(benzyloxy)-3-hydroxy-4-O-(3-(L-valyloxy)propionyl)hexanediamide
N1,N6-di[(1S)-2-methyl-1-(methylcarbamoyl)propyl]-(2R,3R,4R,5R)-2,5-di(benzyloxy)-3-hydroxy-4-O-(4-(L-valyloxy)butyryl)hexanediamide,
N1,N6-di[(1S)-2-methyl-1-(methylcarbamoyl)propyl]-(2R,3R,4R,5R)-2,5-di(benzyloxy)-3-hydroxy-4-O-(5-(L-valyloxy)pentanoyl)hexanediamide,
N1,N6-di[(1S)-2-methyl-1-(methylcarbamoyl)propyl]-(2R,3R,4R,5R)-2,5-di(benzyloxy)-3-hydroxy-4-O-(4-(L-valyloxy)-cis-but-2-enoyl)hexanediamide,
N1,N6-di[(1S)-2-methyl-1-(methylcarbamoyl)propyl]-(2R,3R,4R,5R)-2,5-di(benzyloxy)-3-hydroxy-4-O-(2-(L-valyloxymethyl)benzoyl)hexanediamide
N1,N6-di[(1S)-2-methyl-1-(methylcarbamoyl)propyl]-(2R,3R,4R,5R)-2,5-di(4-(thien-3-yl)benzyloxy)-3-hydroxy-4-(L-valyloxymethyloxy)hexanediamide,
N1,N6-di[(1S)-2-methyl-1-(methylcarbamoyl)propyl]-(2R,3R,4R,5R)-2,5-di(4-(thien-3-yl)benzyloxy)-3-hydroxy-4-(L-valyloxy-(1-methyl)methyloxy) hexanediamide,
N1,N6-di[(1S)-2-methyl-1-(methylcarbamoyl)propyl]-(2R,3R,4R,5R)-2,5-di(4-(thien-3-yl)benzyloxy)-3-hydroxy-4-O-(3-(L-valyloxy)propionyl) hexanediamide,
N1,N6-di[(1S)-2-methyl-1-(methylcarbamoyl)propyl]-(2R,3R,4R,5R)-2,5-di(4-(thien-3-yl)fluorobenzyloxy)-3-hydroxy-4-O-(4-(L-valyloxy)butyryl) hexanediamide,
N1,N6-di[(1S)-2-methyl-1-(methylcarbamoyl)propyl]-(2R,3R,4R,5R)-2,5-di(4-(thien-3-yl)benzyloxy)-3-hydroxy-4-O-(5-(L-valyloxy)pentanoyl) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-
O-(4-(L-valyloxy)-cis-but-2-enoyl) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-
O-(2-(L-valyloxymethyl)benzoyl) hexanediamide, N1,N6-di[(1S)-2-methyl-1-(methylcarbamoyl)propyl]-(2R,
3R,4R,5R)-2,5-di(benzyloxy)-3-hydroxy-4-(L-isoleucyloxymethyloxy)hexanediamide, N1,N6-di[(1S)-2-methyl-1-(methylcarbamoyl)propyl]-(2R,
3R,4R,5R)-2,5-di(benzyloxy)-3-hydroxy-4-(L-isoleucyloxy-(1-methyl)methyloxy) hexanediamide, N1,N6-di[(1S)-2-methyl-1-(methylcarbamoyl)propyl]-(2R,
3R,4R,5R)-2,5-di(benzyloxy)-3-hydroxy-4-O-(3-(L-isoleucyloxy)propionyl)hexanediamide N1,N6-di[(1S)-2-methyl-1-(methylcarbamoyl)propyl]-(2R,
3R,4R,5R)-2,5-di(benzyloxy)-3-hydroxy-4-O-(4-(L-isoleucyloxy)butyryl)hexanediamide, N1,N6-di[(1S)-2-methyl-1-(methylcarbamoyl)propyl]-(2R,
3R,4R,5R)-2,5-di(benzyloxy)-3-hydroxy-4-O-(5-(L-isoeucyloxy)pentanoyl)hexanediamide, N1,N6-di[(1S)-2-methyl-1-(methylcarbamoyl)propyl]-(2R,
3R,4R,5R)-2,5-di(benzyloxy)-3-hydroxy-4-O-(4-(L-isoeucyloxy)-cis-but-2-enoyl) hexanediamide, N1,N6-di[(1S)-2-methyl-1-(methylcarbamoyl)propyl]-(2R,
3R,4R,5R)-2,5-di(benzyloxy)-3-hydroxy-4-O-(2-(L-isoeucyloxymethyl)benzoyl) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-(L-isoleucyloxymethyloxy) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-(L-isoelucyloxy-(1-methyl)methyloxy) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-O-(3-(L-isoleucyloxy)propionyl) hexanediamide N1,N6-di[(1S)-2-methyl-1-(methylcarbamoyl)propyl]-(2R,
3R,4R,5R)-2,5-di(4-(thien-3-yl)benzyloxy)-3-hydroxy-4-O-(4-(L-isoleucyloxy)butyryl) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-O-(5-(L-isoleuclyloxy)pentanoyl) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-O-(4-(L-isoleuclyloxy)-cis-but-2-enoyl) hexanediamide, N1,N6-di[(1S)-2-methyl-1-(methylcarbamoyl)propyl]-(2R,
3R,4R,5R)-2,5-di(4-(thien-3-yl)benzyloxy)-3-hydroxy-4-O-(2-(L-isoleuclyloxymethyl)benzoyl) hexanediamide N1,N6-di[(1S)-2-methyl-1-(methylcarbamoyl)butyl]-(2R,
3R,4R,5R)-2,5-di(benzyloxy)-3-hydroxy-4-(L-valyloxymethyloxy)hexanediamide, N1,N6-di[(1S)-2-methyl-1-(methylcarbamoyl)butyl]-(2R,
3R,4R,5R)-2,5-di(benzyloxy)-3-hydroxy-4-(L-valyloxy-(1-methyl)methyloxy)hexanediamide, N1,N6-di[(1S)-2-methyl-1-(methylcarbamoyl)butyl]-(2R,
3R,4R,5R)-2,5-di(benzyloxy)-3-hydroxy-4-O-(3-(L-valyloxy)propionyl)hexanediamide N1,N6-di[(1S)-2-methyl-1-(methylcarbamoyl)butyl]-(2R,
3R,4R,5R)-2,5-di(benzyloxy)-3-hydroxy-4-O-(4-(L-valyloxy)butyryl)hexanediamide, N1,N6-di[(1S)-2-methyl-1-(methylcarbamoyl)butyl]-(2R,
3R,4R,5R)-2,5-di(benzyloxy)-3-hydroxy-4-O-(5-(L-valyloxy)pentanoyl)hexanediamide, N1,N6-di[(1S)-2-methyl-1-(methylcarbamoyl)butyl]-(2R,
3R,4R,5R)-2,5-di(benzyloxy)-3-hydroxy-4-O-(4-(L-valyloxy)-cis-but-2-enoyl)hexanediamide, N1,N6-di[(1S)-2-methyl-1-(methylcarbamoyl)butyl]-(2R,
3R,4R,5R)-2,5-di(benzyloxy)-3-hydroxy-4-O-(2-(L-valyloxymethyl)benzoyl)hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-(L-valyloxymethyloxy)hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-(L-valyloxy-(1-methyl)methyloxy) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(3-(L-valyloxy)propionyl) hexanediamide N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(4-(L-valyloxy)butyryl)hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(5-(L-valyloxy)pentanoyl) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(4-(L-valyloxy)-cis-but-2-enoyl) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(2-(L-valyloxymethyl)benzoyl) hexanediamide, N1,N6-di[(1S)-2-methyl-1-(methylcarbamoyl)butyl]-(2R,
3R,4R,5R)-2,5-di(benzyloxy)-3-hydroxy-4-(L-isoleucyloxymethyloxy)hexanediamide, N1,N6-di[(1S)-2-methyl-1-(methylcarbamoyl)butyl]-(2R,
3R,4R,5R)-2,5-di(benzyloxy)-3-hydroxy-4-(L-isoleucyloxy-(1-methyl)methyloxy) hexanediamide, N1,N6-di[(1S)-2-methyl-1-(methylcarbamoyl)butyl]-(2R,
3R,4R,5R)-2,5-di(benzyloxy)-3-hydroxy-4-O-(3-(L-isoleucyloxy)propionyl)hexanediamide, N1,N6-di[(1S)-2-methyl-1-(methylcarbamoyl)butyl]-(2R,
3R,4R,5R)-2,5-di(benzyloxy)-3-hydroxy-4-O-(4-(L-isoleucyloxy)butyryl)hexanediamide, N1,N6-di[(1S)-2-methyl-1-(methylcarbamoyl)butyl]-(2R,
3R,4R,5R)-2,5-di(benzyloxy)-3-hydroxy-4-O-(5-(L-isoleucyloxy)pentanoyl)hexanediamide, N1,N6-di[(1S)-2-methyl-1-(methylcarbamoyl)butyl]-(2R,
3R,4R,5R)-2,5-di(benzyloxy)-3-hydroxy-4-O-(4-(L-isoleucyloxy)-cis-but-2-enoyl) hexanediamide, N1,N6-di[(1S)-2-methyl-1-(methylcarbamoyl)butyl]-(2R,
3R,4R,5R)-2,5-di(benzyloxy)-3-hydroxy-4-O-(2-(L-isoleucyloxymethyl)benzoyl) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-(L-isoleucyloxymethyloxy) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-(L-isoleucyloxy-(1-methyl)methyloxy) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(3-(L-isoleucyloxy)propionyl) hexanediamide N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(4-(L-isoleucyloxy)butyryl) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(5-(L-isoleuclyloxy)pentanoyl) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(4-(L-isoleucyloxy)-cis-but-2-enoyl) hexanediamide, N1,N6-di[(1S)-2-methyl-1-(methylcarbamoyl)butyl]-(2R,
3R,4R,5R)-2,5-di(4-(thien-3-yl)benzyloxy)-3-hydroxy-4-O-(2-(L-isoleucyloxymethyl)benzoyl) hexanediamide, A variant of this aspect of the invention provides compounds generally in accordance with Formula IVA, but wherein one or both $R_d$ comprise an isobutyl moiety. The mother compounds of this variant are prepared with the dilactone opening procedure described in PCT/SE98/00622, employing L-tert-leucine methylamide (CAS reg nr. 89226-12-0). These mother compounds are themselves novel and define a further aspect of the invention.

Preferred compounds within thus variant include:

N1,N6-di[(1 S)-2,2 dimethyl-1-(methylcarbamoyl)propyl]-(2R,3R,4R,5R)-2,5-di(benzyloxy)-3-hydroxy-4-(L-valyloxymethyloxy)hexanediamide, N1,N6-di[(1S)-2,2-dimethyl-1-(methylcarbamoyl)propyl]-(2R,3R,4R,5R)-2,5-di(benzyloxy)-3-hydroxy-4-(L-valyloxy-(1-methyl)methyloxy)hexanediamide, N1,N6-di[(1S)-2,2-dimethyl-1-(methylcarbamoyl)propyl]-(2R,3R,4R,5R)-2,5-di(benzyloxy)-3-hydroxy-4-O-(3-(L-valyloxy)propionyl)hexanediamide N1,N6-di[(1S)-2,2-dimethyl-1-(methylcarbamoyl)propyl]-(2R,3R,4R,5R)-2,5-di(benzyloxy)-3-hydroxy-4-O-(4-(L-valyloxy)butyryl)hexanediamide, N1,N6-di[(1S)-2,2-dimethyl-1-(methylcarbamoyl)propyl]-(2R,3R,4R,5R)-2,5-di(benzyloxy)-3-hydroxy-4-O-(5-(L-valyloxy)pentanoyl)hexanediamide, N1,N6-di[(1S)-2,2-dimethyl-1-(methylcarbamoyl)propyl]-(2R,3R,4R,5R)-2,5-di(benzyloxy)-3-hydroxy-4-O-(4-(L-valyloxy)-cis-but-2-enoyl)hexanediamide, N1,N6-di[(1S)-2,2-dimethyl-1-(methylcarbamoyl)propyl]-(2R,3R,4R,5R)-2,5-di(benzyloxy)-3-hydroxy-4-O-(2-(L-valyloxymethyl)benzoyl)hexanediamide N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-(L-valyloxymethyloxy) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-(L-valyloxy-(1-methyl)methyloxy) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(3-(L-valyloxy)propionyl) hexanediamide N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(4-(L-valyloxy)butyryl) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(5-(L-valyloxy)pentanoyl) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(2-(L-valyloxymethyl)benzoyl) hexanediamide, N1,N6-di[(1S)-2,2-dimethyl-1-(methylcarbamoyl)propyl]-(2R,3R,4R,5R)-2,5-di(benzyloxy)-3-hydroxy-4-(L-isoleucyloxymethyloxy)hexanediamide, N1,N6-di[(1S)-2,2-dimethyl-1-(methylcarbamoyl)propyl]-(2R,3R,4R,5R)-2,5-di(benzyloxy)-3-hydroxy-4-(L-isoleucyloxy-(1-methyl)methyloxy) hexanediamide, N1,N6-di[(1S)-2,2-dimethyl-1-(methylcarbamoyl)propyl]-(2R,3R,4R,5R)-2,5-di(benzyloxy)-3-hydroxy-4-O-(3-(L-isoleucyloxy)propionyl)hexanediamide N1,N6-di[(1S)-2,2-diethyl-1-(methylcarbamoyl)propyl]-(2R,3R,4R,5R)-2,5-di(benzyloxy)-3-hydroxy-4-O-(4-(L-isoleucyloxy)butyryl)hexanediamide, N1,N6-di[(1S)-2,2-dimethyl-1-(methylcarbamoyl)propyl]-(2R,3R,4R,5R)-2,5-di(benzyloxy)-3-hydroxy-4-O-(5-(L-isoeucyloxy)pentanoyl)hexanediamide, N1,N6-di[(1S)-2,2-dimethyl-1-(methylcarbamoyl)propyl]-(2R,3R,4R,5R)-2,5-di(benzyloxy)-3-hydroxy-4-O-(4-(L-isoeucyloxy)-cis-but-2-enoyl) hexanediamide, N1,N6-di[(1S)-2,2-dimethyl-1-(methylcarbamoyl)propyl]-(2R,3R,4R,5R)-2,5-di(benzyloxy)-3-hydroxy-4-O-(2-(L-isoeucyloxymethyl)benzoyl) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-(L-isoleucyloxymethyloxy)hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-(L-isoelucyloxy-(1-methyl)methyloxy) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(3-(L-isoleucyloxy)propionyl) hexanediamide N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(4-(L-isoleucyloxy)butyryl) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(5-(L-isoeuclyloxy)pentanoyl) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(4-(L-isoeuclyloxy)-cis-but-2-enoyl) hexanediamide, N1,N6-di[(1S)-2,2-dimethyl-1-(methylcarbamoyl)propyl]-(2R,3R,4R,5R)-2,5-di(4-(thien-3-yl)benzyloxy)-3-hydroxy-4-O-(2-(L-isoeuclyloxymethyl)benzoyl) hexanediamide.

An alternative preferred group of compounds of the invention are those of Formula IVB:

IVB where $R_{x'}$, $R_{x''}$, $R_{z'}$ and $R_{z''}$ are as defined above and wherein the ring atom adjacent one or both asterisks is optionally replaced by —N— to define a fused cyclopentanylpyridyl ring.

Currently preferred $R_{z'}$ and $R_{z''}$ groups in Formula IV include ortho halogen, or phenyl, pyridyl, pyrimidyl, thiazolyl or thienyl in the para position relative to the linkage to the benzyloxy linkage. Especially preferred is orthofluoro as this appears to allow a favourable hydrogen bonding interaction with the hydroxy group on the adjacent indanol as depicted in the representative compound denoted IVB' below:

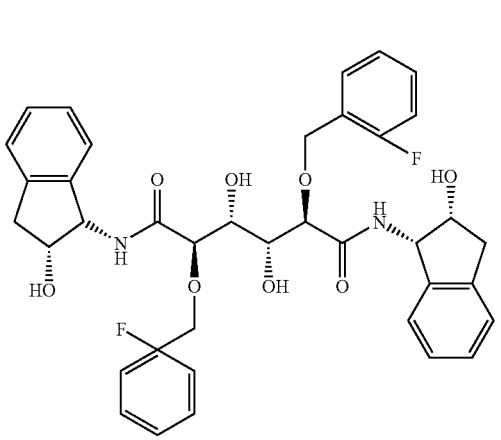

IVB'

Exemplary compounds within Formula IVB thus include:

N1,N6-di[(1S,2R)-2-hydroxy-2,3-dihydro-1H-1-indenyl]-(2R,3R,4R,5R)-2,5-di(benzyloxy)-3-hydroxy-4-(L-valyloxymethyloxy)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-(L-valyloxy-(1-methyl)-methyloxy)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(3-(L-valyloxy)propionyl)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(4-(L-valyloxy)butyryl)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(5-(L-valyloxy)pentanoyl)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(4-(L-valyloxy)-cis-but-2-enoyl)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(2-(L-valyloxymethyl)benzoyl)hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-(L-valyloxymethyloxy)hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-(L-valyloxy-(1-methyl)-methyloxy) hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(3-(L-valyloxy)propionyl) hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(4-(L-valyloxy)butyryl)hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(5-(L-valyloxy)pentanoyl) hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(4-(L-valyloxy)-cis-but-2-enoy-1) hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(2-(L-valyloxymethyl)benzoyl) hexanediamide, N1,N6-di[(1S,2R)-2-hydroxy-2,3-dihydro-1H-1-indenyl]-(2R,3R,4R,5R)-2,5-di(benzyloxy)-3-hydroxy-4-(L-isoleucyloxymethyloxy)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-(L-isoleucyloxy-(1-methyl)-methyloxy) hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(3-(L-isoleucyloxy)propionyl)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(4-(L-isoleucyloxy)butyryl)hexanediamide, N1,N6-di[(1 S,2R)-2-hydroxy-2,3-dihydro-1H-1-indenyl]-(2R,3R,4R,5R)-2,5-di(benzyloxy)-3-hydroxy-4-O-(5-(L-isoleucyloxy)pentanoyl)hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(4-(L-isoleucyloxy)-cis-but-2-enoyl) hexanediamide, N1,N6-di[(1S,2R)-2-hydroxy-2,3-dihydro-1H-1-indenyl]-(2R,3R,4R,5R)-2,5-di(benzyloxy)-3-hydroxy-4-O-(2-(L-isoleucyloxymethyl)benzoyl) hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-(L-isoleucyloxymethyloxy)hexanediamide, N1,N6-di[(1 S,2R)-2-hydroxy-2,3-dihydro-1H-1-indenyl]-(2R,3R,4R,5R)-2,5-di(2-fluorobenzyloxy)-3-hydroxy-4-(L-isoleucyloxy-(1-methyl)-methyloxy)hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(3-(L-isoleucyloxy)propionyl) hexanediamide, N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(4-(L-isoleucyloxy)butyryl) hexanediamide, N1,N6-di[(1 S,2R)-2-hydroxy-2,3-dihydro-1H-1-indenyl]-(2R,3R,4R,5R)-2,5-di(2-fluorobenzyloxy)-3-hydroxy-4-O-(5-(L-isoleucyloxy)pentanoyl) hexanediamide.

N1,N6-di[(1S,2R)-2-hydroxy-2,3-dihydro-1H-1-indenyl]-(2R,3R,4R,5R)-2,5-di(2-fluorobenzyloxy)-3-hydroxy-4-O-(4-(L-isoleucyloxy)-cis-but-2-enoyl) hexanediamide, N1,N6-di[(1 S,2R)-2-hydroxy-2,3-dihydro-1H-1-indenyl]-(2R,3R,4R,5R)-2,5-di(2-fluorobenzyloxy)-3-hydroxy-4-O-(2-(L-isoleucyloxymethyl)benzoyl) hexanediamide.

A still further aspect of the invention provides derivatives of the formula IVC, which compounds are alternative derivatives of the mother compounds of formula IVB:

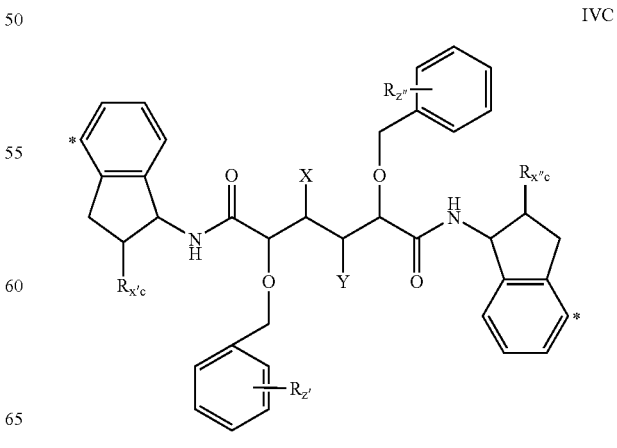

IVC where X, Y, $R_{z'}$, and $R_{z''}$ are as defined above, one of $R_{xc'}$ or $R_{xc'}$ is —O-L-$R_{d'}$ and the other is OH or —O-L-$R_{d''}$ and the position adjacent the asterisk is occupied by —CH— or —N— thereby defining a fused cyclopentanylphenyl or pyridyl ring Exemplary compounds within this aspect of the invention include:

N1,N6-di[(1S,2R)-2-(L-valyloxymethyloxy)-2,3-dihydro-1H-1-indenyl]-(2R,3R,4R,5R)-2,5-di(benzyloxy)-3,4-dihydroxy-hexanediamide, N1,N6-di[(1S,2R)-2-(L-valyloxy-(1-methyl)methyloxy)-2,3-dihydro-1H-1-indenyl]-(2R,3R,4R,5R)-2,5-di(benzyloxy)-3,4-dihydroxy-hexanediamide, N1,N6-di[(1S,2R)-2-(3-(L-valyloxy)propionyl)-2,3-dihydro-1H-1-indenyl]-(2R,3R,4R,5R)-2,5-di(benzyloxy)-3,4-dihydroxy-hexanediamide, N1,N6-di[(1S,2R)-2-(4-(L-valyloxy)butyryl)-2,3-dihydro-1H-1-indenyl]-(2R,3R,4R,5R)-2,5-di(benzyloxy)-3,4-dihydroxy-hexanediamide, N1,N6-di[(1S,2R)-2-(5-(L-valyloxy)pentanoyl)-2,3-dihydro-1H-1-indenyl]-(2R,3R,4R,5R)-2,5-di(benzyloxy)-3,4-dihydroxy-hexanediamide, N1,N6-di[(1S,2R)-2-(4-(L-valyloxy)-cis-but-2-enoyl)-2,3-dihydro-1H-1-indenyl]-(2R,3R,4R,5R)-2,5-di(benzyloxy)-3,4-dihydroxy-hexanediamide, N1,N6-di[(1S,2R)-2-(2-(L-valyloxymethyl)benzoyl)-2,3-dihydro-1H-1-indenyl]-(2R,3R,4R,5R)-2,5-di(benzyloxy)-3,4-dihydroxy-hexanediamide, N1,N6-di[(1S,2R)-2-(L-isoleucyloxymethyloxy)-2,3-dihydro-1H-1-indenyl]-(2R,3R,4R,5R)-2,5-di(benzyloxy)-3,4-dihydroxy-hexanediamide, N1,N6-di[(1S,2R)-2-(L-isoleucyloxy-(1-methyl)methyloxy)-2,3-dihydro-1-H-1 indenyl]-(2R,3R,4R,5R)-2,5-di(benzyloxy)-3,4-dihydroxy-hexanediamide, N1,N6-di[(1S,2R)-2-(3-(L-isoleucyloxy)propionyl)-2,3-dihydro-1H-1-indenyl]-(2R,3R,4R,5R)-2,5-di(benzyloxy)-3,4-dihydroxy-hexanediamide, N1,N6-di[(1S,2R)-2-(4-(L-isoleucyloxy)butyryl)-2,3-dihydro-1H-1-indenyl]-(2R,3R,4R,5R)-2,5-di(benzyloxy)-3,4-dihydroxy-hexanediamide, N1,N6-di[(1S,2R)-2-(5-(L-isoleucyloxy)pentanoyl)-2,3-dihydro-1H-1-indenyl]-(2R,3R,4R,5R)-2,5-di(benzyloxy)-3,4-dihydroxy-hexanediamide, N1,N6-di[(1S,2R)-2-(4-(L-isoleucyloxy)-cis-but-2-enoyl)-2,3-dihydro-1H-1 indenyl]-(2R,3R,4R,5R)-2,5-di(benzyloxy)-3,4-dihydroxy-hexanediamide, N1,N6-di[(1S,2R)-2-(2-(L-isoleucyloxymethyl)benzoyl)-2,3-dihydro-1H-1-indenyl]-(2R,3R,4R,5R)-2,5-di(benzyloxy)-3,4-dihydroxy-hexanediamide, N1,N6-di[(1S,2R)-2-(L-valyloxymethyloxy)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(L-valyloxy-(1-methyl)methyloxy)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(3-(L-valyloxy)propionyl)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(4-(L-valyloxy)butyryl)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(5-(L-valyloxy)pentanoyl)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(4-(L-valyloxy)-cis-but-2-enoyl)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(2-(L-valyloxymethyl)benzoyl)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(L-isoleucyloxymethyloxy)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(L-isoleucyloxy-(1-methyl)methyloxy)-2,3-dihydro-1H-1 indenyl]-(2R,3R,4R,5R)-2,5-di(2-fluorobenzyloxy)-3,4-dihydroxy-hexanediamide, N1,N6-di[(1S,2R)-2-(3-(L-isoleucyloxy)propionyl)-2,3-dihydro-1H-1-indenyl]-(2R,3R,4R,5R)-2,5-di(2-fluorobenzyloxy)-3,4-dihydroxy-hexanediamide, N1,N6-di[(1S,2R)-2-(4-(L-isoleucyloxy)butyryl)-2,3-dihydro-1H-1-indenyl]-(2R,3R,4R,5R)-2,5-di(fluorobenzyloxy)-3,4-dihydroxy-hexanediamide, N1,N6-di[(1S,2R)-2-(5-(L-isoleucyloxy)pentanoyl)-2,3-dihydro-1H-1-indenyl]-(2R,3R,4R,5R)-2,5-di(fluorobenzyloxy)-3,4-dihydroxy-hexanediamide, N1,N6-di[(1S,2R)-2-(4-(L-isoleucyloxy)-cis-but-2-enoyl)-2,3-dihydro-1H-1-indenyl]-(2R,3R,4R,5R)-2,5-di(fluorobenzyloxy)-3,4-dihydroxy-hexanediamide, N1,N6-di[(1S,2R)-2-(2-(L-isoleucyloxymethyl)benzoyl)-2,3-dihydro-1H-1-indenyl]-(2R,3R,4R,5R)-2,5-di(2-fluorobenzyloxy)-3,4-dihydroxy-hexanediamide, A further aspect of the invention provides compounds wherein A' and A" differ, preferably by including an amino terminus as depicted in Formula IVA (including the isobutyl variant) and an amino terminus as depicted in Form IVB or IVC below. Methodology for preparing such asymmetric mother compounds is disclosed in PCT/SE98/00622. Representative asymmetric compounds include those of the formula IVbb below:

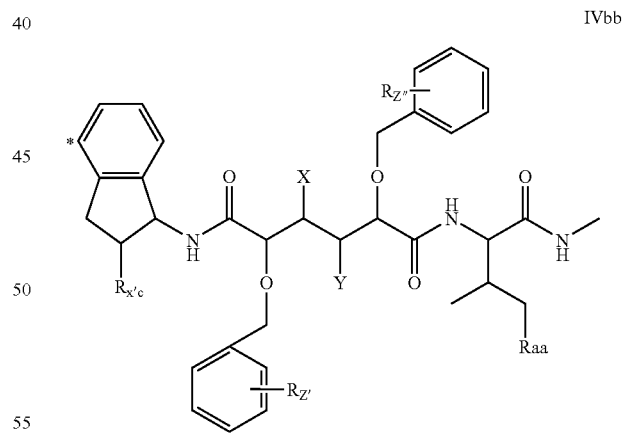

IVbb where where X, Y, $R_{z'}$, and $R_{z''}$ are as defined above, one of $R_{xc'}$ or $R_{x''c''}$ is —O-L-$R_{d'}$ and the other is OH or —O-L-Rd $R_{aa}$ is H or $CH_3$ and the position adjacent the asterisk is occupied by —CH— or —N— thereby defining a fused cyclopentanylphenyl or pyridyl ring.

Favoured mother compounds of formula UVbb include those where $R_z$ and $R_{z'}$ are a cyclic group such as phenyl, pyridyl or the thiazolyl with the formula:

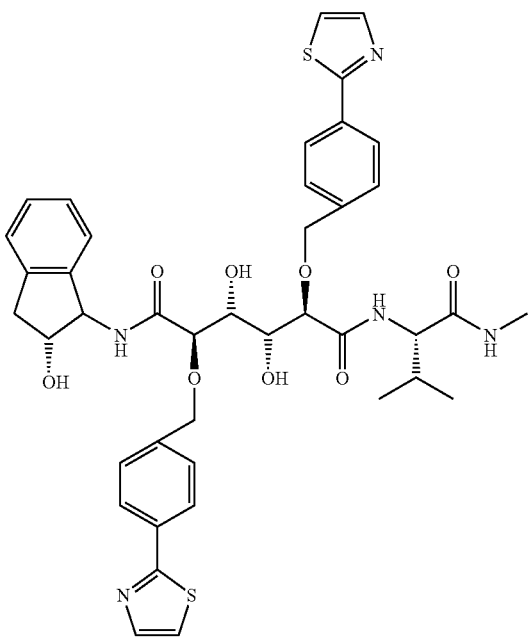

IVbb

The compounds of formula UVbb (as with indinavir above) have chain hydroxy functions amenable to the invention, but more importantly also have an easily accessible ring hydroxy function on the indanol.

In keeping with the usual practice with retroviral inhibitors it is advantageous to co-administer one to three or more additional antivirals, such as AZT, ddI, ddC, d4T, 3TC, H2G, foscarnet, ritonavir, indinavir, saquinavir, nevirapine, delaviridine, efavirenz, amprenavir, Agouron AG1343 and the like. Such additional antivirals will normally be administered at dosages relative to each other which broadly reflect their respective therapeutic values. Molar ratios of 100:1 to 1:100, especially 25:1 to 1:25, relative to the compound or salt of formula I will often be convenient.

The compounds of the aspect of the invention discussed immediately above invention are generally prepared by alkylation or acylation of the respective mother compounds, which are in turn prepared by the methodology described in PCT/SE98/00622. Alkylation or acylation generally proceeds via an activated derivative. The activated derivative used in an acylation may comprise e.g, the acid halide, acid anhydride, activated acid ester or the acid in the presence of coupling reagent, for example dicyclohexylcarbodiimide, where "acid" to a precursor group such as those of the formula PGNHC($R_d$)COO-L$\alpha$-COOH, where $R_d$ is defined above, PG is a conventional N-protecting group and $L_\alpha$ is the residue of the linker.

Activated L-$R_y$ groups wherein L is derived from an hydroxyalkanoic acid are conveniently prepared by esterification of conventionally carboxy protected hydroxyalkanoic acid, such as glycollic acid or lactic acid or more preferably an ω-hydroxyalkanoic acid such as 3-hydroxypropionic acid, 4-hydroxybutyric acid, 5-hydroxypentanoic acid etc with the appropriate N-protected $R_y$ derivative, such as N-Cbz-isoleucine, either as the free acid in conjunction with a coupling agent such as DCC, or activated, for instance to the corresponding acid halide. The carboxy protecting group is removed as is known in the art and the resulting intermediate activated and esterified with the mother compound of formula IV, such as those of formula IVA, IVB or IVC with the methodology described above. The N-protecting group on $R_y$ is then removed by conventional deprotection conditions.

Activated L-Ry groups wherein L is derived from a cis-alkenoic acid, such as 4-hydroxy-cis-but-2-en are conveniently prepared from the corresponding haloalkanoic acids, such as 4-bromo-cis-but-2-enoic acid which is carboxy protected, for instance with t-butyl prior to conventional esterification under with the appropriately N-protected $R_y$ moiety, sicha N-Cbz-valine. The carboxy protecting group is removed and the free carboxy activated and esterified with the mother compound of formula IV as described above, followed by deprotection of the N-protecting group.

Activated L-$R_y$ groups wherein L is derived from a 2-hydroxymethylbenzoic acid can be prepared from 2-methylbenzoic acid which is carboxy protected and brominated by conventional techniques. This activated intermediate is esterified with an appropriately N-protected $R_y$ moiety, such as Cbz-valine. This intermediate is carboxy deprotected and esterified with the mother compound of formula IV as described above, followed by deprotection of the $R_y$ N-protecting group.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, tbutylacetyl, 2-chloroacetyl, 2-bromoacetyl, trifluoroacetyl, trichloroacetyl, phthalyl, onitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, ptoluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl gropus such as benzyl, triphenylmethyl, benzyloxymethyl and the like; and silyl groups such as trimethylsilyl and the like. Favoured N-protecting groups include formyl, acetyl, allyl, F-moc, benzoyl, pivaloyl, t-butylacetyl, phenylsulfonyl, benzyl, t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), tbutyldimethylsilyl (TBDMS) tribenzylsilyl, triphenylsilyl, t-butyldiphenylsilyl triisopropyl silyl and the like, substituted ethyl ethers such as 1-ethoxymethyl, 1 methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

Useful intermediates for acylation with the mother compounds thus include:

3-N-Boc-L-valyloxypropanoic acid, 3-N-Fmoc-L-valyloxypropanoic acid, 3-NCBZ-L-valyloxypropanoic acid, 3-N-Boc-L-isoleucyloxypropanoic acid, 3-NFmoc-L-isoleucyloxypropanoic acid, 3-N-CBZ-L-isoleucyloxypropanoic acid, 4-N-Boc-L-valyloxybutyric acid, 3-N-Fmoc-L-valyloxybutyric acid, 4-N-CBZL-valyloxybutyric acid, 4-N-Boc-L-isoleucyloxybutyric acid, 3-N-Fmoc-L-isoleucyloxybutyric acid, 3-N-CBZ-L-isoleucyloxybutyric acid and the like;

and the activated derivatives, such as the acid halides

Still further ueful intermediates include precursors, such as;

2-(L-valyloxy)propanoic acid, 2-(N-Boc-L-valyloxy)propanoic acid, 2-(N-Fmoc-L-valyloxy)propanoic acid, 2-(N-CBZ-L-valyloxy)propanoic acid, 2-(Lisoleucyloxy)propanoic acid, 2-(N-Boc-L-isoleucyloxy)propanoic acid, N-(Fmoc-L-isoleucyloxy)propanoic acid, N-(CBZ-L-isoleucyloxy)propanoic acid, 2-(L-valyloxy)butyric acid, 2-(N-Boc-L-valyloxy)butyric acid, 2-(N-Fmoc-L-valyloxy)butyric acid, 2-(N-CBZ-L-valyloxy)butyric acid, 2-(Lisoleucyloxy)butyric acid, 2-(N-Boc-L-isoleucyloxy)butyric acid, N-(Fmoc-L-Substitute isoleucyloxy)butyric acid, N-(CBZ-L-isoleucyloxy)butyric acid, and the like; and activated derivatives therof, such as the acid halides.

Still further novel intermediates include precursors such as:
3-ethoxycarbonyl-2-valyloxy-propionic acid
3-ethoxycarbonyl-2-isoleucyloxy-propionic acid
4-ethoxycarbonyl-2,3-bis-valyloxy-butyric acid
4-ethoxycarbonyl-2,3-bis-isoleucyloxy-butyric acid
3-benzyloxycarbonyl-2-valyloxy-propionic acid
3-benzyloxycarbonyl-2-isoleucyloxy-propionic acid
4-benzyloxycarbonyl-2,3-bis-valyloxy-butyric acid
4-benzyloxycarbonyl-2,3-bis-isoleucyloxy-butyric acid, and the like;

particularly those derived from "natural" configurations such as L-malic and L-tartaric acid, and the corresponding activated derivatives such as the acid halides.

Alkylation of the mother compound of FIG. IV, for instance when group L-R$_y$ is derived from an alkoxyamino acid ester, is conveniently done with the corresponding N-protected haloalkoxyamino acid ester. Convenient alkylation intermediates thus include
iodomethyloxy-N-CBz-valyl,
iodomethyloxy-N-Boc-valyl,
iodomethyloxy-N-Fmoc-valyl
iodomethyloxy-N-CBz-isoeucyl,
iodomethyloxy-N-Boc-isoleucyl,
iodomethyloxy-N-Fmoc-isoleucyl, and corresponding derivatives bearing other N-protecting groups.

Further useful intermediates and methodology for acylation or alkylation of the mother compounds of formula IV are disclosed or suggested in (M132) SE 980216-4 filed 7 Apr. 1998, the contents of which are specifically incorporated by reference.

Preparation of compounds of the formula IVB will generally require the indanolic hydroxy groups to be protected with conventional hydroxy protecting groups prior to esterification or alkylation of the 3 and/or 4 hydroxy groups of the alkyl backbone of the mother compound. On the other hand, the differential reactivity of the indanolic hydroxy groups means that the compounds of the formula IVC can generally be prepared without corresponding protection of the 3 and 4 hydroxy groups.

Preparation of compounds of the formula IVA and IVB may require relatively stringent esterification/alkylation conditions, thus favouring, for instance, esterification with haloactivated L-Ry groups, as described above, rather than the use of a coupling agent.

A further useful group of compounds for applying the compounds of the invention are the phenolic hydroxy compounds of the PETT series of NNRTI disclosed in WO 93/03022, WO95/06034 and PCT/SE99/00053, the contents of which are incorporated by reference. Favoured ring hydroxy compounds of this class have the formula P1:

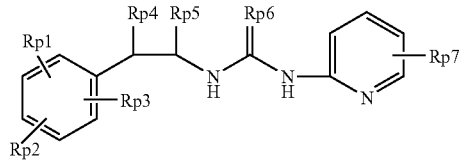

where one of Rp1–3 is hydroxy and the others are hydrogen, halo, $C_{1-6}$ alkanoyl, $C_{1-6}$ alkyl, $C_{1-6}$ alkoxy etc as defined in WO95/06034, Rp4 and Rp5 are hydrogen or join to form a cis-cyclopropyl or cyclobutyl group, Rp6 is O or S and Rp7 is halo, cyano, amino etc as defined in WO95/06034. Particularly preferred compounds of this class have the formula P2:

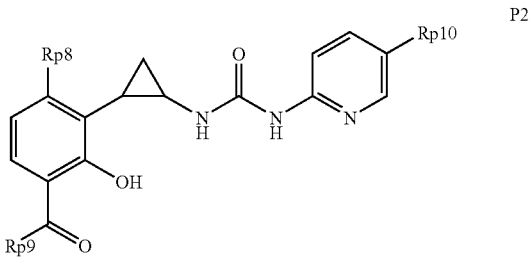

wherein

Rp8 is halo;

Rp9 is $C_1$–$C_3$ alkyl;

Rp10 is halo, especially bromo or cyano.

A preferred subset of compounds within Formula P2, particularly with regard to pharmacokinetics, has Rp10 as cyano. A further favoured subset of compounds within Formula P2, particularly with regard to ease of forming prodrugs, comprise compounds wherein Rp10 is bromo.

Preferably Rp8 is chloro and more preferably fluoro. Suitable Rp9 groups include methyl, isopropyl, n-propyl and preferably ethyl.

As depicted in Formula P2, the cyclopropyl ring is in the cis configuration, allowing two enantiomers, 1S, 2S and 1R, 2R

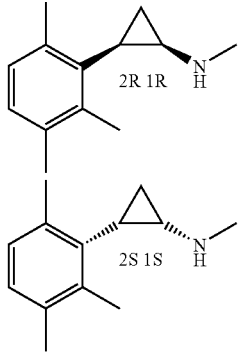

Each of these enantiomers are potent antiretrovirals, although the different enantiomers can display subtle differences in physiological properties. For instance the 1S, 2S and 1R,2R enantiomers can show a different pattern of metabolism within the P450 system. The 1S,2S enantiomer of compounds wherein Rp10 is cyano is particularly preferred as it appears unique in being able to avoid key components of the P450 system. Other retroviral agents such as the HIV protease inhibitor ritonavir interact extensively with the P450 system, leading to an array of undesirable physiological responses including extensive alteration of the metabolism of other coadministered drugs. This is of particular concern with pharmaceuticals administered for a chronic infection where patients can expect to take a number of pharmaceuticals for years, if not decades.

Preferred NNRTI mother compounds for applying the prodrugs of the invention thus include:

(1S, 2S)-N-[cis-2-(6-fluoro, 2-hydroxy, 3-propionylphenyl)-cyclopropyl]-N'-(5-cyanopyrid-2-yl)-urea, (1S, 2S)-N-[cis-2-(6-fluoro, 2-hydroxy, 3-butyrylphenyl)-cyclopropyl]-N'-(5-cyanopyrid-2-yl)-urea, (1S, 2S)-N-[cis-2-(6-fluoro, 2-hydroxy, 3-acetylphenyl)-cyclopropyl]-N'-(5-cyanopyrid-2-yl)-urea, (1S, 2S)-N-[cis-2-(6-fluoro, 2-hydroxy, 3-propionylphenyl)-cyclopropyl]-N'-(5-bromopyrid-2-yl)-urea, (1S, 2S)-N-[cis-2-(6-fluoro, 2-hydroxy, 3-butyrylphenyl)-cyclopropyl]-N'-(5-bromopyrid-2-yl)-urea, (1S, 2S)-N-[cis-2-(6-fluoro, 2-hydroxy, 3-acetylphenyl)-cyclopropyl]-N'-(5-bromopyrid-2-yl)-urea, and the corresponding R, R enantiomers.

This aspect of the invention thus provides prodrugs of NNRTI compounds of the formula P-1, especially P-2 wherein the phenolic hydroxy function is bonded to any of the generic structures above, such as those depicted in formula IIa, IIb, IIc, IId, IIe, IIf, Id, etc. These compounds are prepared by acylation of the relevant mother compound of formula P-1 or P-2 with the activated structure IIa, IIb etc, wherein the or each $R_2$ group is conventionally N-protected.

As the compounds of formula P2 include an electron withdrawing group on the phenol ring to which the prodrug moiety is attached it is generally preferred to avoid direct esters such as 4-valyloxybutyric acid derivatives which are otherwise effective on phenols and carbocyclic ring hydroxy functions.

Thus a convenient group of prodrugs within the scope of this aspect of the invention include those of the formula P3:

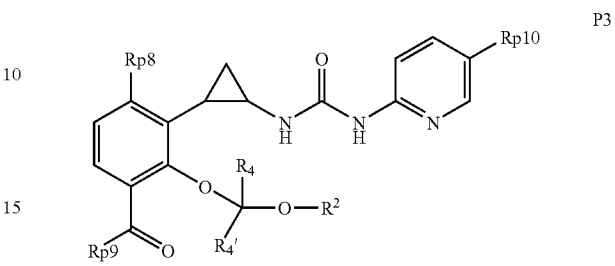

wherein
Rp8, Rp9, Rp10, $R^2$, $R_4$ and $R_{4'}$ are as defined above. Typically both of $R_4$ and $R_4$ are H.

Preferred compounds within Formula P3 include;

(1S, 2S)-N-{cis-2-[6-fluoro-2-(L-valyloxymethyloxy)-3-propionylphenyl]cyclopropyl}-N'-[2-(5-cyanopyridyl)]urea, (1S, 2S)-N-{cis-2-[6-fluoro-2-(L-isoleucyloxymethyloxy)-3-propionylphenyl]cyclopropyl}-N'-[2-(5-cyanopyridyl)]urea, (1R, 2R)-N-{cis-2-[6-fluoro-2-(L-valyloxymethyloxy)-3-propionylphenyl]cyclopropyl}-N'-[2-(5-cyanopyridyl)]urea, (1R, 2R)-N-{cis-2-[6-fluoro-2-(L-isoleucyloxymethyloxy)-3-propionylphenyl]cyclopropyl}-N'-[2-(5-cyanopyridyl)]urea, (1S, 2S)-N-{cis-2-[6-fluoro-2-(L-valyloxymethyloxy)-3-propionylphenyl]cyclopropyl}-N'-[2-(5-bromopyridyl)]urea, (1S, 2S)-N-{cis-2-[6-fluoro-2-(L-isoleucyloxymethyloxy)-3-propionylphenyl]cyclopropyl}-N'-[2-(5-bromopyridyl)]urea, (1R, 2R)-N-{cis-2-[6-fluoro-2-(L-valyloxymethyloxy)-3-propionylphenyl]cyclopropyl}-N'-[2-(5-bromopyridyl)]urea, (1R, 2R)-N-{cis-2-[6-fluoro-2-(L-isoleucyloxymethyloxy)-3-propionylphenyl]cyclopropyl}-N'-[2-(5-bromopyridyl)]urea, and pharmaceutically acceptable salts thereof.

An alternative preferred group of prodrugs of the invention have the Formula P4:

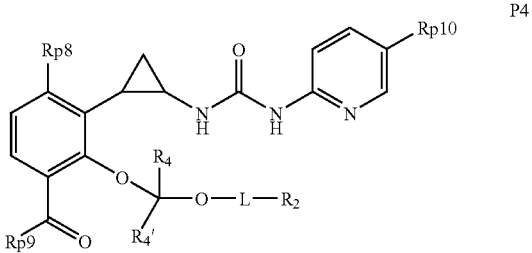

where Rp8, Rp9, Rp10, $R_4$ and $R_4'$ are as defined above. L and $R_2$ define a linker group and residue of an aliphatic amino acid, such as those of Formulae IIa, IIb, IIc, IId, IIe, IIf or those depicted in Formulae Ia and Id. Typically both of $R_4$ and $R_{4'}$ are H.

Favoured compounds within the class described in the immediately preceding paragraph include those of the formula P5:

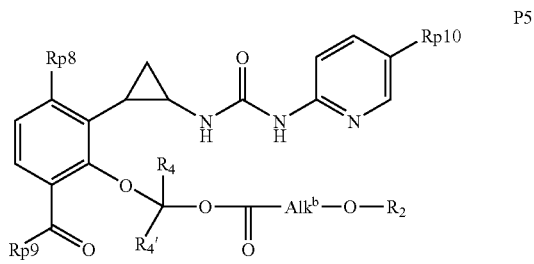

where Rp8 Rp9, $Rp_{10}$, $R_4$, $R_{4'}$ and $R_2$ are as defined above and $Alk^b$ is $C_1$–$C_6$ optionally branched, optionally monounsaturated alkyl.

Favoured compounds within Formula P5 thus include:
(1S, 2S)-N-{cis-2-[6-fluoro-2-(2,2-dimethyl-3-(L-valyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(2-methyl-3-(L-valyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(3-(L-valyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(2,2-dimethyl-3-(L-valyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(2-methyl-3-(L-valyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(3-(L-valyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(2,2-dimethyl-3-(L-isoleucyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(2-methyl-3-(L-isoleucyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(3-(L-isoleucyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(2,2-dimethyl-3-(L-isoleucyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(2-methyl-3-(L-isoleucyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(3-(L-isoleucyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(4-(L-valyloxy)-butyryl-oxymethyloxy)-3-propionylphenyl]-cyclopropyl}-N'-[2-(5-cyanopyridyl)] urea,
(1S, 2S)-N-{cis-2-[6-fluoro-2-(4-(L-isoleucyloxy)-butyryl-oxymethyloxy)-3-propionylphenyl]-cyclopropyl}-N'-[2-(5-cyanopyridyl)] urea,
(1S, 2S)-N-{cis-2-[6-fluoro-2-(4-(L-valyloxy)-butyryl-oxymethyloxy)-3-propionylphenyl]-cyclopropyl}-N'-[2-(5-bromopyridyl)] urea,
(1S, 2S)-N-{cis-2-[6-fluoro-2-(4-(L-isoleucyloxy)-butyryl-oxymethyloxy)-3-propionylphenyl]-cyclopropyl}-N'-[2-(5-bromopyridyl)] urea,
(1S, 2S)-N-{cis-2-[6-fluoro-2-(2-(L-valyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(2-(L-isoleucyloxy)-propionyl-oxymethyloxy)-3-propionylphenyl]-cyclopropyl}-N'-[2-(5-cyanopyridyl)] urea,
(1S, 2S)-N-{cis-2-[6-fluoro-2-(2-(L-valyloxy)-propionyl-oxymethyloxy)-3-propionylphenyl]-cyclopropyl}-N'-[2-(5-bromopyridyl)] urea,
(1S, 2S)-N-{cis-2-[6-fluoro-2-(2-(L-isoleucyloxy)-propionyl-oxymethyloxy)-3-propionylphenyl]-cyclopropyl}-N'-[2-(5-bromopyridyl)] urea, and the corresponding (1R, 2R) enantiomers thereof.

One variant of a branched $Alk^b$ in Formula P5 can be substituted with hydroxy which in turn is esterified with a further $R^2$, thus defining a linker of the formula IIa, as depicted in Formula P6:

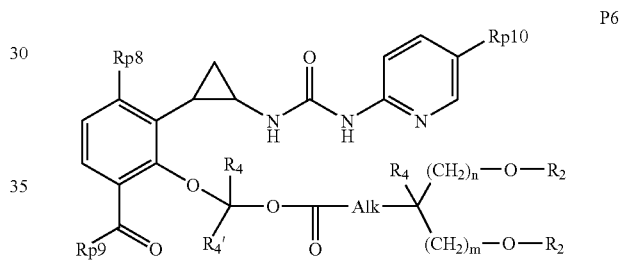

where Rp8, Rp9, Rp10, Alk, $R_4$, $R_{4'}$, m, n and $R_2$ are as defined above. Preferably each occurrence of Rx and Rx' is H. Particularly favoured values for Alk, m and n include: methylene: 1:1 and absent: 1:0 respectively.

A further favoured group of compounds has the Formula P7:

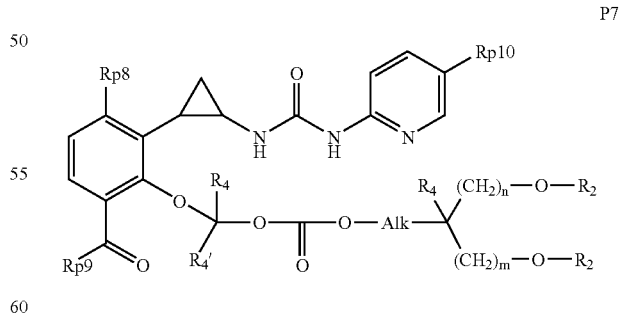

where Rp8, Rp9, Rp10, Alk, $R_4$, $R_{4'}$, m, n and $R_2$ are as defined above or wherein the -( )$_m$—O—$R_2$ arm is absent. Preferably each occurrence of Rx and Rx' is H. Particularly favoured values for Alk, m and n include: absent: 1:1, thus defining a glycerol derivative. Where the -( )$_m$—O-$R_2$ arm is absent to define a structure of the formula P7':

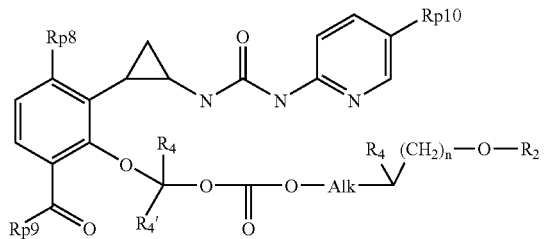

Convenient values for Alk and n include absent:1 with $R_4$, $R_4$ and $R_4'$ as H.

Favoured compounds within Formula P-7 thus include
(1S 12S)-N-[cis-2-(6-fluoro-2-(1,3-bis-L-valyloxy-2-(oxycarbonylmethoxy)propyl)-3-propionylphenyl)cyclopropyl]-N'-[2-(5-cyanopyridyl)]urea, (1S, 2S)-N-[cis-2-(6-fluoro-2-(1,3-bis-L-isoleucyloxy-2-(oxycarbonylmethoxy) propyl)-3-propionylphenyl)cyclopropyl]-N'-[2-(5-cyanopyridyl)]urea, (1S, 2S)-N-[cis-2-(6-fluoro-2-(1,3-bis-L-valyloxy-2-(oxycarbonylmethoxy)propyl)-3-propionylphenyl)cyclopropyl]-N'-[2-(5-bromopyridyl)]urea, (1S, 2S)-N-[cis-2-(6-fluoro-2-(1,3-bis-L-isoleucyloxy-2-(oxycarbonylmethoxy) propyl)-3-propionylphenyl)cyclopropyl]-N'-[2-(5-bromopyridyl)]urea, (1S, 2S)-N-{cis-2-[6-fluoro-2-(2-(L-valyloxy)-ethoxycarbonyloxymethyloxy)-3-propionylphenyl)]cyclopropyl}-N'-[2-(5-cyanopyridyl)] urea, (1S, 2S)-N-{cis-2-[6-fluoro-2-(2-(L-isoleucyloxy)-ethoxycarbonyloxymethyloxy)-3-propionylphenyl)]cyclopropyl}-N'-[2-(5-cyanopyridyl)] urea, (1S, 2S)-N-{cis-2-[6-fluoro-2-(2-(L-valyloxy)-ethoxycarbonyloxymethyloxy)-3-propionylphenyl)]cyclopropyl}-N'-[2-(5-bromopyridyl)] urea, (1S, 2S)-N-{cis-2-[6-fluoro-2-(2-(L-isoleucyloxy)-ethoxycarbonyloxymethyloxy)-3-propionylphenyl)]cyclopropyl}-N'-[2-(5-bromocyanopyridyl)] urea, and the corresponding R,R enantiomers.

A further favoured group of compounds omit the methyloxy group immediately adjacent the ring hydroxy function of the compound of formula P1 or P2. An example of such compounds has the formula P8:

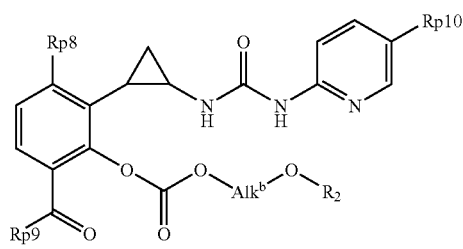

where Rp8, Rp9, Rp10, $R_2$, and $Alk^b$ are as defined above. Currently favoured values for Alk include methylene, ethylene, 1,1-dimethylethylene, propylene, butylene and, in the case of said —$OR_2$ substitution, glycerol.

Favoured compounds within formula P-8 thus include:
(1S,2S)-N-[cis-2-(6-fluoro-2-(L-valyloxymethoxycarbonyloxy)-3-propionylphenyl)cyclopropyl]-N'-[2-(5-cyanopyridyl)]urea, (1S,2S)-N-[cis-2-(6-fluoro-2-(L-isoleucyloxymethoxycarbonyloxy)-3-propionylphenyl)cyclopropyl]-N'-[2-(5-cyanopyridyl)]urea, (1S,2S)-N-[cis-2-(6-fluoro-2-(L-valyloxymethoxycarbonyloxy)-3-propionylphenyl)cyclopropyl]-N'-[2-(5-bromopyridyl)]urea, (1S,2S)-N-[cis-2-(6-fluoro-2-(L-isoleucyloxymethoxycarbonyloxy)-3-propionylphenyl)cyclopropyl]-N'-[2-(5-bromopyridyl)]urea, (1S,2S)-N-[cis-2-(6-fluoro-2-(2-(L-valyloxy)ethoxycarbonyloxy)-3-propionylphenyl)cyclopropyl]-N'-[2-(5-cyanopyridyl)]urea, (1S,2S)-N-[cis-2-(6-fluoro-2-(2-(L-isoleucyloxy)ethoxycarbonyloxy)-3-propionylphenyl)cyclopropyl]-N'-[2-(5-cyanopyridyl)]urea, (1S,2S)-N-[cis-2-(6-fluoro-2-(2-(L-valyloxy)ethoxycarbonyloxy)-3-propionylphenyl)cyclopropyl]-N'-[2-(5-bromopyridyl)]urea, (1S,2S)-N-[cis-2-(6-fluoro-2-(2-L-isoleucyloxy)ethoxycarbonyloxy)-3-propionylphenyl)cyclopropyl]-N'-[2-(5-bromopyridyl)]urea, (1S,2S)-N-[cis-2-(6-fluoro-2-(3-(L-valyloxy)propoxycarbonyloxy)-3-propionylphenyl)cyclopropyl]-N'-[2-(5-cyanopyridyl)]urea, (1S,2S)-N-[cis-2-(6-fluoro-2-(3-(L-isoleucyloxy)propoxycarbonyloxy)-3 propionylphenyl)cyclopropyl]-N'-[2-(5-cyanopyridyl)]urea, (1S,2S)-N-[cis-2-(6-fluoro-2-(3-(L-valyloxy)propoxycarbonyloxy)-3-propionylphenyl)cyclopropyl]-N'-[2-(5-bromopyridyl)]urea, (1S,2S)-N-[cis-2-(6-fluoro-2-(3-(L-isoleucyloxy)propoxycarbonyloxy)-3-propionylphenyl)cyclopropyl]-N'-[2-(5-bromopyridyl)]urea, (1S,2S)-N-[cis-2-(6-fluoro-2-(4-(L-valyloxy)butoxycarbonyloxy)-3-propionylphenyl)cyclopropyl]-N'-[2-(5-cyanopyridyl)]urea, (1S,2S)-N-[cis-2-(6-fluoro-2-(4-(L-isoleucyloxy)butoxycarbonyloxy)-3-propionylphenyl)cyclopropyl]-N'-[2-(5-cyanopyridyl)]urea, (1S,2S)-N-[cis-2-(6-fluoro-2-(4-(L-valyloxy)butoxycarbonyloxy)-3-propionylphenyl)cyclopropyl]-N'-[2-(5-bromopyridyl)]urea, (1S,2S)-N-[cis-2-(6-fluoro-2-(4-(L-isoleucyloxy)butoxycarbonyloxy)-3-propionylphenyl)cyclopropyl]-N'-[2-(5-bromopyridyl)]urea, and the corresponding R, R enantiomers As with Formula P5/P6 and P7/P7', $Alk^b$ in formula P8 can comprise an additional —O—$R_2$ substitution to define a compound of the formula P8'

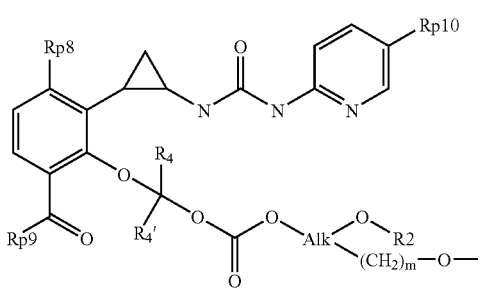

where each of the variables is as defined above.

This Formulae P aspect of the invention further provides pharmaceutical compositions comprising the compounds of formula and pharmaceutically acceptable carriers or diluents therefor. Additional aspects of the invention provide methods for the inhibition of HIV comprising administering a compound of the formula I to a subject afflicted with HIV. The invention also extends to the use of the compounds of formula I in therapy, such as in the preparation of a medicament for the treatment of HIV infections.

In treating conditions caused by HIV, the compounds of formula I are preferably administered in an amount to achieve a plasma level of the compounds of Formula P1 of around 10 to 1000 nM and more preferably 100 to 500 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500–750 mg, in one to four dosage units per day.

In keeping with the usual practice with HIV inhibitors it is advantageous to co-administer one to three additional antivirals to provide synergistic responses and to ensure complementary resistance patterns. Such additional antivirals may include AZT, ddI, ddC, D4T, 3TC, abacavir, adefovir, adefovir dipivoxil, bis-POC-PMPA, foscarnet, hydroxyurea, Hoechst-Bayer HBY 097, efavirenz, trovirdine, nevirapine, delaviridine, PFA, H2G, ABT 606, DMP-450, loviride, ritonavir, saquinavir, indinavir, amprenavir (Vertex VX 478), nelfmavir and the like, typically at molar ratios reflecting their respective activities and bioavailabilities. Generally such ratio will be of the order of 25:1 to 1:25, relative to the compound of formula I.

Compounds of this Formulae P aspect of the invention are typically prepared by alkylation of the corresponding mother compounds of Formula P1 or especially P2, which are prepared by conventional means, such as the methodology described in WO95/06034 or PCT/SE99/00053. In particular, the preparation of compounds of formula P-3 or P-4 generally proceeds by alkylation using conventional coupling conditions of a compound of the formula P-2 with the corresponding intermediate:

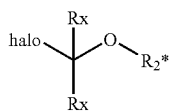

or

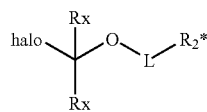

where Rx and L are as defined above and $R_2^*$ is $R_2$ as defined, but N-protected with a conventional N-protecting group. Preferably the halogen activating group is iodo, which is in turn prepared by iodination of the corresponding chloro analogue. Typical coupling conditions include treatment with a base in an organic solvent such as THF prior to addition of the halogenated intermediate followed by conventional deprotection of the $R_2$ N-protecting group.

Compounds of formula P-8 are generally prepared by esterification of a compound of the formula P-2 with an intermediate of the formula:

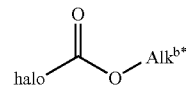

where $Alk^{b*}$ is a functionalised $Alk^b$ as described above, for example chloromethyl chloroformate, in an organic solvent, followed by iodination of the terminal chloro with NaI (or other activation of the functionalising group) and reaction with an Nprotected $R_2$.

The compounds of the invention can form salts which form an additional aspect of the invention. Appropriate pharmaceutically acceptable salts of the compounds of Formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. The compounds of the invention I may be isolated as the hydrate.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

A still further aspect of the invention provides novel $R_2$ bearing linkers suitable for derivatisation to free functions on a Drug. Preferred linkers in accordance with this aspect of the invention include compounds of the Formulae IVa:

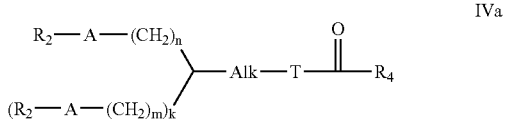

IVa where $R_2$, A, A', n, m, Q, Alk, k and T are as defined above and $R_4$ is hydroxy or an activating group such as an acid derivatives including the acid halide, such as the chloride, anhydrides derived from alkoxycarbonyl halides such as isobutyloxycarbonylchloride and the like, N-hydroxysuccinamide derived esters, N-hydroxyphthalimide derived esters, N-hydroxy-5-norbornene-2,3-dicarboxamide derived esters, 2,4,5-trichlorophenol derived esters and the like. Compounds of Formula IVa will be particularly useful for Drugs bearing hydroxy or amine functions.

Further preferred linkers in accordance with this aspect of the invention include compounds of the formulae IVe:

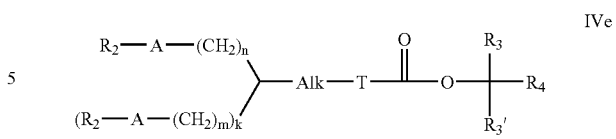

IVe where $R_2$, A, A', n, m, Q, Alk and T are as defined above, and $R_4$ an activating group such as a halide, including bromo, chloro and iodo. Compounds of Formula IVe will be especially useful for Drugs bearing carboxy functions (especially those where T is 0, $R_3$ is Me and $R_3'$ is H) or phosphonyl functions (especially those where T is a bond, $R_3$ is isopropyl and $R_3'$ is H).

Alternative preferred di- or trifunctional linker compounds of this aspect of the invention include compounds of the Formulae IIIa:

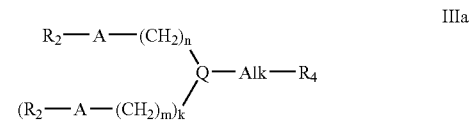

IIIa where $R_2$, A, A', n, m, Q and Alk are as defined above and $R_4$ is hydroxy or an activating moiety such as halo, including chloro, iodo and bromo.

In practice linker compounds of Formula IVa or the corresponding derivative of Formula II'a will be esterified to hydroxy-bearing Drugs using conventional acylation techniques. The activated moiety of Formula UV may be preformed or generated in situ by the use of reagents such as dicyclohexylcarbodiimide (DCC) or O-(1H-benzotriazol-1-yl) N,N,N',N'-tetramethyluronium tetrafluoroborate (TBTU). When an acid halide, such as the acid chloride is used, a tertiary amine catalyst, such as triethylamine, N,N'-dimethylaniline, pyridine or dimethylaminopyridine may be added to the reaction mixture to bind the liberated hydrohalic acid.

The reactions are preferably carried out in an unreactive solvent such as N,N'-dimethylformamide, tetrahydrofuran, dioxane, acetonitrile or a halogenated hydrocarbon, such as dichloromethane. If desired, any of the above mentioned tertiary amine catalysts may be used as solvent, taking care that a suitable excess is present. The reaction temperature can typically be varied between 20° C. and 60° C., but will preferably be kept between 5° and 50° C. After a period of 1 to 60 hours the reaction will usually be essentially complete. The progress of the reaction can be followed using thin layer chromatography (TLC) and appropriate solvent systems. In general, when the reaction is completed as determined by TLC, the product is extracted with an organic solvent and purified by chromatography and/or recrystallisation from an appropriate solvent system.

By-products where acylation has taken place on an inappropriate function can be separated by chromatography, but such misacylation can be minimized by controlled reaction conditions. These controlled conditions can be achieved, for example, by manipulating the reagent concentrations or rate of addition, especially of the acylating agent, by lowering the temperature or by the choice of solvent. The reaction can be followed by TLC to monitor the controlled conditions. It may additionally or alternatively be convenient to protect exposed hydroxy and other functions on the Drug with conventional protecting groups to forestall misacylation.

Linkers of Formula IVa or the corresponding derivatives of Formula II'a may alternatively be amide bonded to free primary or secondary amine functions on the Drug using conventional chemistry in the peptide art.

Linkers of Formula IIIa or IVd or the corresponding derivatives of Formula III' and II'd will generally be acylated to free carboxyl functions on the Drug in an analogous, but reversed fashion to the above described acylation of Drugs with hydroxy functions. U.S. Pat. No. 4,486,425 which is incorporated by reference illustrates a convenient process.

Linkers of Formula IVa wherein V comprises a structure of the formula IIc can be prepared by a by a two stage process. In particular a compound of the formula ClC(=O)OC($R_4$)($R_4$')Cl can be reacted with a suitable accessible hydroxy function on the Drug (optionally protected on other functions with conventional protecting groups) as is known in the cephalosporin art. The resulting Drug-OSubstitute C(=O)OC($R_4$)($R_4$')chloride is then reacted with an $R_2$ bearing linker wherein a free function comprises a carboxyl function, such as the potassium salt.

Linkers of Formula IVe or the corresponding derivatives of Formula IIe can be esterified to phosphonyl and phosphoryl functions of Drugs analogously to the processes shown in U.S. Pat. No. 4,337,201 and U.S. Pat. No. 5,227,506, which are incorporated by reference. Corresponding menthodology is applicable when $R_2$ is esterified to a phosphonyl or phosphoryl group via a spacer of the Formula IIb as defined above.

The preparation of further linker groups and their application to Drugs is shown in the following Examples.

As the Drugs envisaged in the use of the present invention are proven pharmaceuticals, the starting materials for preparing the prodrugs of the invention are either available in commerce or are extensively described in the medical literature, including the FDA and other registration files for the respective drugs.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, tbutylacetyl, 2-chloroacetyl, 2-bromoacetyl, trifluoroacetyl, trichloroacetyl, phthalyl, onitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, ptoluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, and the like; alkyl gropus such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), tbutyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, dipehenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

"Optional substituents" can include hydroxy, $C_1$–$C_6$ alkyl, $C_1$–$C_6$ alkoxy, $C_1$–$C_6$ alkoxy $C_1$–$C_6$ alkyl, $C_1$–$C_6$ alkanoyl, amino, halo, cyano, azido, oxo, mercapto and nitro, and the like. "Ring" as used herein includes atoms including monocyclic rings such as furyl, thienyl, pyranyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, and the like or bicyclic rings especially of the above fused to a phenyl ring such as indolyl, quinolinyl, isoquinolinyl, benzimidazolyl, benzothiazolyl, benzoxazolyl, benzothienyl etc. The carbo or heterocyclic ring may be bonded via a carbon to the remainder of the linker via a hetero atom, typically a nitrogen atom, such as N-piperidyl, N-morpholinyl etc.

DETAILED DESCRIPTION

BRIEF DESCRIPTION OF THE DRAWINGS

Various aspects of the invention will now be described by way of example only with reference to the following Examples and the accompanying drawings in which.

PREPARATION OF INTERMEDIATES

EXAMPLE P-I-1

N-BOC-L-isoleucine iodomethyl ester

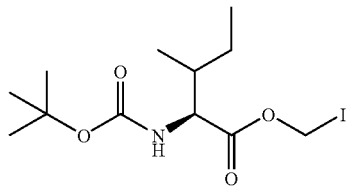

a) N-BOC-L-isoleucine chloromethyl ester

Figure 1:
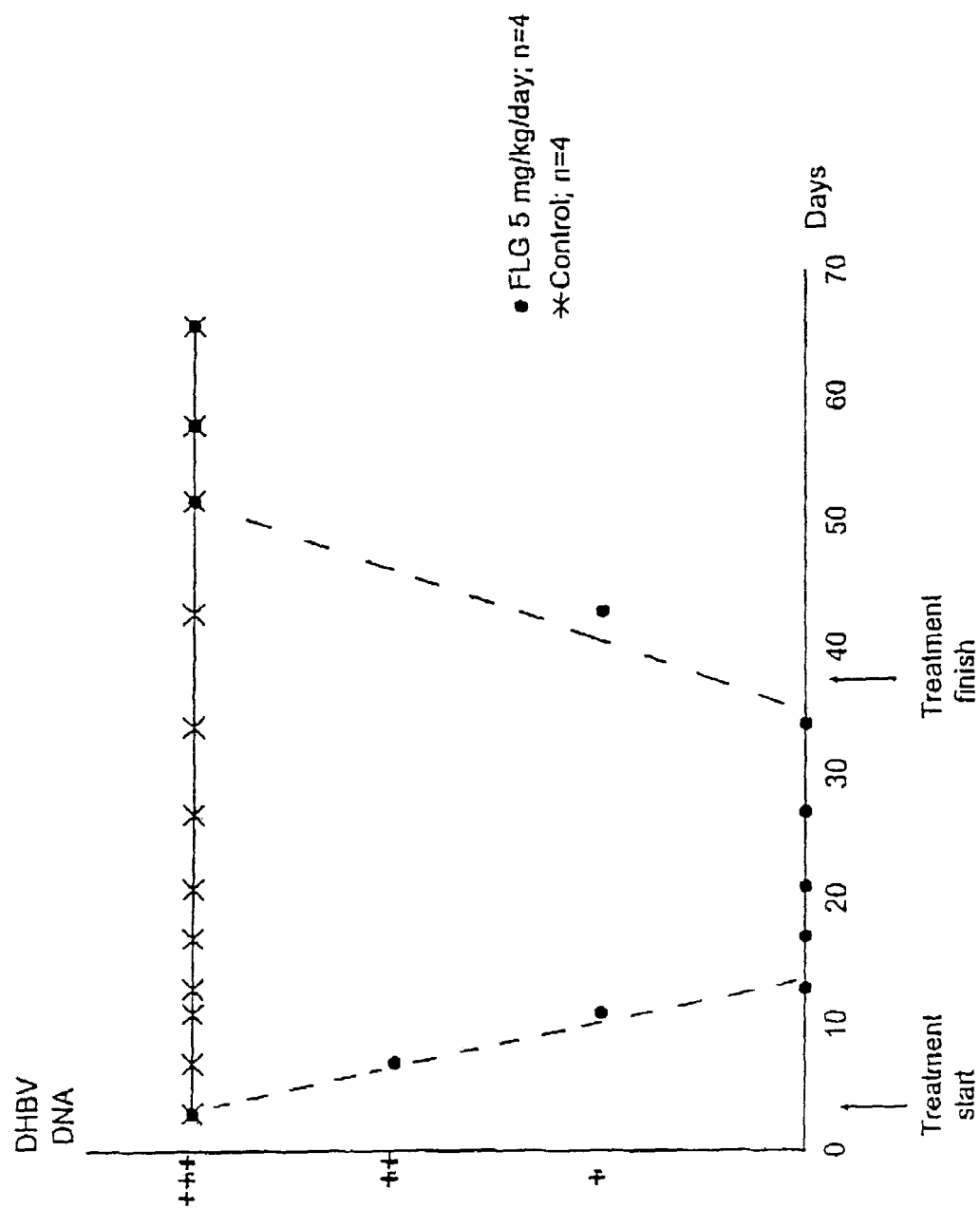
FIG. 1 depicts serum viral-DNA levels in treated and untreated, DHBV-infected ducks as a function of time, as described in Biological Example 3.

To a solution of N-BOC-L-isoleucine (23.1 g, 0.1 mol) in dioxane (500 mL), was added dropwise a 40% aqueous solution of tetrabutylammonium hydroxide (65.6 mL, 0.1 mol). After stirring for 15 min, the solution was evaporated to dryness through co-evaporation with dioxane and toluene. The residue was dissolved in dichloromethane (500 mL) and then chloroiodomethane (72.8 mL, 1 mol) was added and the solution was stirred for 6 h at room temperature. The solution was concentrated under reduced pressure and the residue was shaken with hexane/ethyl acetate (1:1 v/v, 400 mL). The yellow crystalline solid was filtered off and the filtrate was washed with aqueous solution of sodium thiosulfate (0.1 M) and then filtered through anhydrous sodium sulfate and evaporated to dryness. The residue was column chromatographed (silica gel, 1–2% MeOH in $CH_2Cl_2$), to give 20.8 g of NBOC-L-isoleucine chloromethyl ester.

$^1$H-NMR ($CDCl_3$): 5.86 (d, 1H), 5.60 (d, 1H), 5.04 (d, 1H), 4.32–4.25 (m, 1H), 2.00–1.80 (m, 1H), 1.42 (s, 9H), 1.50–1.05 (m, 2H), 0.96–0.87 (m, 6H).

b) N-BOC-L-isoleucine iodomethyl ester

To a solution of N-BOC-L-isoleucine chloromethyl ester (19.6 g, 70 mmol) in acetonitrile (300 mL), was added sodium iodide (31.5 g, 210 mmol). The solution was stirred for 4 h at 60° C. The resulting suspension was filtered and the filtrate was evaporated. The residue was dissolved in $CH_2Cl_2$ and washed with aqueous sodium thiosulfate (0.1 M). The organic phase was dried ($Na_2SO_4$) and concentrated under reduced pressure. The crude product was column chromatographed (silica gel, 2% MeOH in $CH_2Cl_2$), to give 22.6 g of N-BOC-L-isoleucine iodomethyl ester.

$^1$H-NMR ($CDCl_3$): 6.04 (d, 1H), 5.82 (d, 1H), 4.97 (d, 1H), 4.25 (dd, 1H), 1.98–1.80 (m, 1H), 1.43 (s, 9H), 1.50–1.05 (m, 2H), 0.97–0.88 (m, 6H).

EXAMPLE PI-2

2,2-dimethyl-3-(N-Boc-L-valyloxy]propionic acid iodomethyl ester

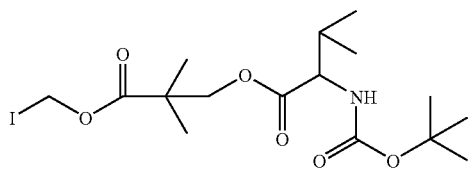

a) 2,2-dimethyl-3-(N-Boc-L-valyloxy)propionic acid

N-Boc-L-valine (10.8 g, 50 mmole), 4-dimethylaminopyridine (610 mg, 5 mmole) and DCC (6.18 g, 30 mmole) were dissolved in methylene chloride (100 ml). After stirring for 2 hour the mixture was filtered. To the filtrate were added 2,2-dimethyl-3-hydroxy-propionic acid (3.54 g, 30 mmole) and pyridine (10 ml). After 18 hr, the reaction mixture was filtered, and the filtrate was poured into sodium hydrogen carbonate aqueous solution, the organic phase was then washed with citric acid aqueous solution and water successively. After evaporation the product was isolated with silica gel column chromatography to yield 4.4 g. This compound can be activated and esterified directly to a drug or further modified as described below.

$^1$H-NMR ($CDCl_3$): 5.10 (d, 1H) 4.24 (m, 3H) 2.18 (m, 1H) 1.51 (s, 9H) 1.33 (d, 6H) 0.98 (m, 6H).

b) 2,2-dimethyl-3-(N-Boc-L-valyloxy)propionic acid chloromethyl ester 2,2-dimethyl-3-(N-Boc-L-valyloxy)propionic acid (3.9 g, 12.3 mmole) was dissolved in dioxane (60 ml). To the solution was added tetrabutylammonium hydroxide aqueous solution (40%, 7.78 ml, 12 mmole). The solution was dried in vacuo, and it was coevaporated with toluene for several times. The residue was dissolved in methylene chloride and then chloroiodomethane (18.9 ml, 260 mmole) was added to the solution. After 18 hr, the reaction solution was evaporated and the product was isolated with silica gel column chromatography to yield 3.7 g.

$^1$H-NMR ($CDCl_3$): 5.72 (s, 2H) 5.00 (d, 1H) 4.20 (m, 3H) 2.12 (m, 1H) 1.44 (s, 9H) 1.25 (d, 6H) 0.91(m, 6H)

c) 2,2-dimethyl-3-(N-Boc-L-valyloxy)propionic acid iodomethyl ester 2,2-Dimethyl-3-(N-Boc-L-valyloxy)propionic acid chloromethyl ester (3.6 g, 10 mmole) was dissolved in acetonitrile (50 ml). Sodium iodide (2.1 g, 14 mmole) was added to the solution. After reaction at 70° C. for 2 hr, the reaction mixture was filtered and the residue was dissolved in methylene chloride (20 ml) and refiltered. The solution was dried and gave 4.34 g of the titled product.

$^1$H-NMR ($CDCl_3$): 5.92 (dd, 2H) 5.10 (d, 1H) 4.24 (m, 1H) 4.15 (dd, 2H) 2.01 (m, 1H) 1.44 (s, 9H) 1.25 (d, 6H) 0.91 (m, 6H)

EXAMPLE P-I-3

3,3-bis (N-CBz-L-valyloxymethyl)-propionic acid iodomethyl ester

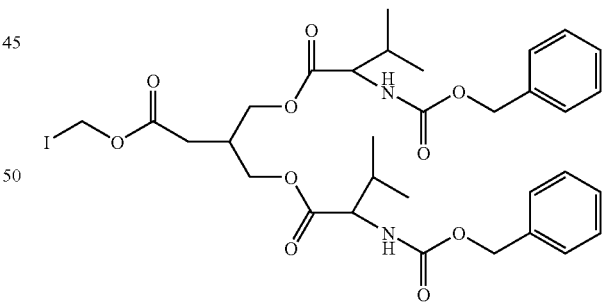

a) Preparation of 3,3-bis (N-CBz-L-valyloxymethyl)-propionic acid chloromethyl ester 3,3-bis (N-CBz-L-valyloxymethyl)-propionic acid (3 g, 5 mmole) was dissolved in dioxane (20 ml). To the solution was added tetrabutylammonium hydroxide aqueous solution (40%, 3.11 ml, 4.8 mmole). The solution was dried in vacuo, and it was coevaporated with toluene several times. The residue was dissolved in methylene chloride (15 ml) and then chloroiodomethane (7.3 ml, 100 mmole) was added to the solution. The reaction solution was refluxed for 18 hr and then evaporated and the product was isolated with silica gel column chromatography. 900 mg.

$^{1}$H-NMR (CDCl$_{3}$):7.33 (m, 10H) 5.68 (dd, 2H) 5.26 (d, 2H) 4.25 (m, 6H) 2.56 (m, 1H) 2.48 (d, 2H) 2.14 (m, 2H) 0.93 (m, 12H)

b) 3,3-bis-(N-CBz-L-valyloxymethyl)propionic acid iodomethyl ester 3,3-bis (N-CBz-L-valyloxymethyl)-propionic acid chloromethyl ester (900 mg, 1.38 mmole) was dissolved in acetonitrile (5 ml). Sodium iodide (289 mg, 1.93 mmole) was added to the solution. After reaction at 70° C. for 3 hr, the reaction mixture was filtered and the residue was dissolved in methylene chloride (5 ml) and refiltered. The solution was dried and gave the titled product. 800 mg.

$^{1}$H-NMR (CDCl$_{3}$): 7.35 (m, 10H) 5.88 (dd, 2H) 5.25 (d, 2H) 4.29 (m, 2H) 4.18 (m, 4H) 2.56 (m, 1H) 2.42 (d, 2H) 2.16 (m, 2H) 0.93 (m 12H)

EXAMPLE P-I-4

2-(N-CBz-L-valyloxy)ethoxycarbonyloxymethyl iodide

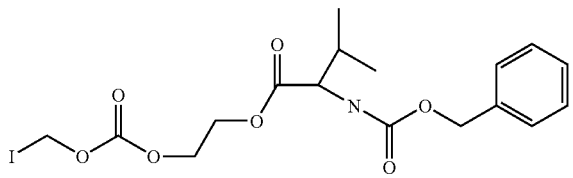

2-(N-CBz-L-valyloxy)ethoxycarbonyloxymethyl chloride (1.16 g, 3 mmole) was dissolved in acetonitrile (10 ml). Sodium iodide (630 g, 4.2 mmole) was added to the solution. After reaction at 65° C. for 2.5 hr, the reaction mixture was cooled down to room temperature and filtered and the residue was dissolved in methylene chloride (5 ml) and refiltered. The solution was dried and gave the titled product. 1.2 g.

$^{1}$H-NMR (CDCl$_{3}$): 7.35 (m, 5H) 5.93 (dd, 2H) 5.26 (d, 1H) 5.11 (s, 2H) 4.39 (m, 5H) 2.18 (m, 1H) 0.94 (m, 6H).

EXAMPLE P-I-5

1,3-bis(N-tert-butoxycarbonyl-L-valyloxy)-2-propyl iodomethyl carbonate)

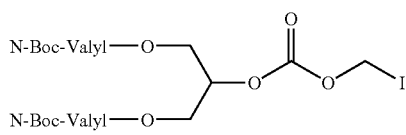

a) 1-O-(N-tert-butoxycarbonyl-L-valyl)glycerol

N-tert-Butoxycarbonyl-L-valine (32.53 g, 0.150 mol), N,N'-dicyclohexylcarbodiimide (37.85 g, 0.183 mol, and 4-dimethylaminopyridine (1.83 g, 0.015 mol) were added to glycerol (138.12 g., 1.5 mol) in 500 mL dry DMF and the mixture was stirred at rt under N$_{2}$ for 3 days. The reaction mixture was filtered, concentrated under vacuum, and then partitioned between 300 mL EtOAc and 150 mL H$_{2}$O. The aqueous phase was reextracted with 150 mL EtOAc. The organic phases were combined and washed successively with 100 mL each of saturated aqueous NaHCO$_{3}$, saturated NH$_{4}$Cl, and brine. Drying over anhydrous Na$_{2}$SO$_{4}$, and concentration under vacuum gave a viscous light yellow oil as crude product. Flash column chromatography on silica gel with 4/1 EtOAc—petroleum ether (BP 40–60° C.) gave 18.27 g (42%) of product (alternative nomenclature: 3-(N-tert-butoxycarbonyl-L-valyloxy)-1,2-propanediol). Reactions done overnight gave similar yields.

$^{1}$H NMR (250 MHz, CDCl$_{3}$) δ 0.91 (d, 3H), 0.97 (d, 3H), 1.43 (s, 9H), 2.12 (m, 1H), 3.54–3.74 (m, 2H), 3.94 (m, 1H), 4.09–4.32 (m, 3H), 5.09 (br s, 1H).

b) 1,3-di-O-(N-tert-butoxycarbonyl-L-valyl)glycerol

1-O-(N-tert-butoxycarbonyl-L-valyl)glycerol (17.95 g. 61.6 mmol), Boc-L-valine (6.69 g, 30.8 mmol), DMAP (0.38 g, 3.1 mmol), and DCC (7.10 g, 34.4 mmol) in 240 mL CH$_{2}$Cl$_{2}$ and 60 mL DMF were stirred at rt under N$_{2}$ for 18 h. The reaction mixture was filtered, concentrated under vacuum, and redissolved in 200 mL EtOAc. The organic solution was washed with 50 mL saturated NH$_{4}$Cl. The aqueous phase was reextracted with 50 mL EtOAc. The organic phases were combined, washed successively with 50 mL saturated NaHCO$_{3}$ and 50 mL brine, dried over Na$_{2}$SO$_{4}$, and concentrated under vacuum. Flash column chromatography of the crude material on silica gel (eluent 2/1 petroleum ether—EtOAc, and then EtOAc) gave 7.41 g (49%) of the title compound (alternative nomenclature: 1,3-bis(N-tert-butoxycarbonyl-L-valyloxy)-2-propanol).

$^{1}$H NMR (CDCl$_{3}$) δ 0.90 (d, 6H), 0.97 (d, 6H), 1.43 (s, 18H), 2.12 (m, 2H), 4.06–4.30 (m, 7H), 5.04 (br d, 2H).

c) 2-O-chloromethoxycarbonyl-1,3-di-O-(N-tert-butoxycarbonyl-L-valyl)glycerol

Chloromethyl chloroformate (2.70 mL, 30 mmol) was added to a solution of 1,3-di-O-(N-tert-butoxycarbonyl-L-valyl)glycerol (7.27 g, 14.8 mmol) and pyridine (7.2 mL, 89 mmol) in 60 mL dry CH$_{2}$Cl$_{2}$, in an ice bath, under N$_{2}$. After stirring for 1 h 45 min, the reaction mixture was diluted with 100 mL CH$_{2}$Cl$_{2}$ and washed with 40 mL water. The aqueous phase was reextracted with 20 mL H$_{2}$O. The organic phases were combined, washed with 40 mL saturated NaHCO$_{3}$, followed by 2×50 mL brine, dried over Na$_{2}$SO$_{4}$, and concentrated under vacuum. Flash column chromatography on silica gel with 2/1 hexane-EtOAc gave 8.03 g (93%) of the title compound (alternative nomenclature: 1,3-bis(N-tert-butoxycarbonyl-L-valyloxy)-2-propyl chloromethyl carbonate).

$^{1}$H NMR (250 MHz, CDCl$_{3}$) δ 0.84 (d, 6H), 0.92 (m, 6H), 1.39 (s, 18H), 2.08 (m, 2H), 4.15–4.50 (m, 6H), 4.99 (br d, 2H), 5.16 (m, 1H), 5.69 (s, 2H).

d) 2-O-iodomethoxycarbonyl-1,3-di-O-(N-tert-butoxycarbonyl-L-valyl)glycerol

A solution of 2-O-chloromethoxycarbonyl-1,3-di-O-(N-tert-butoxycarbonyl-L-valyl)propane-1,2,3-triol (7.86 g, 13.5 mmol) and NaI (8.09 g, 54.0 mmol) in 135 mL dry acetonitirile was refluxed at 80° C. for 4 h under N$_{2}$. The reaction mixture was concentrated under vacuum, and then partitioned between 150 mL diethyl ether and 50 mL H$_{2}$O. The aqueous layer was reextracted with 2×25 mL ether. The combined organic phases were washed successively with 25 mL aqueous Na$_{2}$S$_{2}$O$_{3}$ and 50 mL brine, dried over Na$_{2}$SO$_{4}$, and concentrated. Flash column chromatography (silica gel, 2/1 hexane-ethyl acetate gave 8.38 g (92%) title product (alternative name: 2-iodomethoxycarbonyloxy-1,3-bis-(N-tert-butoxycarbonyl-L-valyloxy)propane or 1,3-bis(N-tert-butoxycarbonyl-L-valyloxy)-2-propyl iodomethyl carbonate) as a white solid.

$^1$H NMR (250 MHz, CDCl$_3$) δ 0.81 (d, 6H), 0.88 (m, 6H), 1.36 (s, 18H), 2.06 (m, 2H), 4.11–4.46 (m, 6H), 5.0 (br d, 2H), 5.12 (m, 1H), 5.88 (s, 2H).

EXAMPLE G-I-1

2,3-Bis-(N-CBz-L-valyloxy)-propionic acid

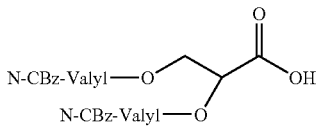

a) t-Butyl 2,3-bis (N-CBz-L-valyloxy)propionate

To a solution of t-butyl 2,3-dihydroxypropionate (2.43 g, 15 mmole), N-CBz-L-valine (7.54 g, 30 mmole) and DMAP (0.37 g, 3 mmole) in 150 ml dichloromethane was added DCC (7.2 g 35 mmole) and the mixture was stirred for two days at room temperature. The mixture was cooled to about 5° C. and the urethane was filtered. The filtrate was evaporated, ethyl acetate was added and the organic phase washed twice with 5% acetic acid, 5% sodium hydrogen carbonate and water. The organic phase was dried with sodium sulfate filtered and evaporated under reduced pressure. The product was isolated by silica gel column chromatography. Yield: 8.2 g=86%

$^1$H-NMR (DMSO d-6) 0.87 (m, 12H) 1.40 (d, 9H) 2.12 (m, 1H) 4.02–4.40 (m, 2H) 5.04 (d, 4H) 5.20 (m, 1H) 7.36 (m, 10H) 7.72 (d, 2H)

b) 2,3-Bis-(N-CBz-L-valyloxy)-propionic acid

To a solution of t-butyl -2,3-bis-(N-CBz-L-valyloxy)-propionate (7.2 g, 11.4 mmole) in dichloromethane (25 ml) was added trifluoroacetic acid (25 ml) and the solution was stirred for five hours at room temperature. The solution was evaporated under reduced pressure and coevaporated two times with toluene. The product was isolated by silica gel column chromatography. Yield: 5.9 g=90%

$^1$H-NMR (DMSO-d$_6$) 0.92 (m, 12H) 2.08 (m, 2H) 3.92–4.17 (m, 2H) 4.30–4.67 (m, 2H) 5.04 (s, 4H) 5.28 (m, 1H) 7.32 (m, 10H) 7.70 (m, 2H)

EXAMPLE G-I-2

(S)-(+)-2-(N-CBz-L-valyloxy)propionic acid

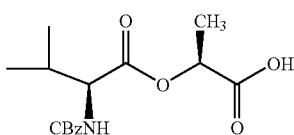

a) 4-Methoxybenzyl (S) (+)-2-hydroxypropionate

To a stirred solution of (S)(+)$_2$ hydroxypropionic acid (9.0 g, 100 mmole) in 100 ml dry DMF was added potassium tert-butoxide (12.34 g, 110 mmole) and the mixture was stirred for one hour at 25° C. 4-Methoxybenzyl chloride (18.8 g 120 mmole) was added and the mixture was stirred for six hours at 60° C. The mixture was evaporated under reduced pressure and 250 ml ethyl acatate was added. The organic phase was washed four times with water. The organic phase was dried with sodium sulfate and concentrated in vacuo. Yield: 15.6 g=74%

$^1$H-NMR (CDCl$_3$) 1.40 (d, 3H) 3.81 (s, 3H) 4.26 (m, 1H) 5.14 (s, 2H) 6.90 (d, 2H) 7.28 (d, 2H)

b) 4-Methoxybenzyl (S)-(+)-2-(N-CBz-L-valyloxy) propionate

To a solution of 4-methoxybenzyl (S)-(+)-2-hydroxypropionate (7.6 g, 36 mmole), N-CBZ-L-valine (10.05 g, 40 mmole) and DMAP (0.98 g, 8 mmole) in 150 ml dichloromethane was added a solution of DCC (8.3 g, 40 mmole) and the mixture was stirred overnight at room temperature. The mixture was cooled to about 5° C. and the urethane was filtered. The filtrate was evaporated and the product was isolated by silica gel column chromatography. Yield: 14.4 g=90%

$^1$H-NMR (CDCl$_3$) 0.94 (m, 6H) 1.50 (d, 3H) 2.26 (m, 1H) 3.81 (s, 3H) 4.34 (d, d, 1H) 5.10–5.25 (m, 6H) 6.88 (d, 2H) 7.26 (m, 7H)

c) (S)-(+)-2-(N-CBz-L-valyloxy)propionic acid

To a solution of 4-methoxybenzyl (S)-(+)-2-(N-CBz-L-valyloxy)propionate (14.0 g, 31.5 mmole) in dichloromethane (50 ml) was added trifluoroacetic acid (25 ml) and the solution was stirred for five hours at room temperature. The solution was evaporated under reduced pressure and coevaporated two times with toluene. The product was isolated by silica gel column chromatography. Yield: 9.4 g=92%

$^1$H-NMR (DMSO-d$_6$) 0.94 (m, 6H) 1.46 (d, 3H) 2.12 (m, 1H) 4.05 (m, 1H) 4.92 (m, 1H) 5.06 (s, 2H) 7.34 (m, 5H) 7.68 (d, 1H)

EXAMPLE F-I-3

3-Bis (N-CBz-L-valyloxymethyl)-propionic acid

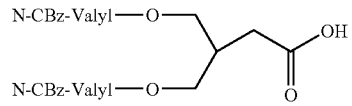

a) 4,4-bis (N-CBZ-L-valyloxymethyl)-but-1-ene

To a solution of 2-allyl-1,3-propanediol (2.32 g, 20 mmole), N-CBZ-L-valine (10.06 g, 40 mmole) and DMAP (0.488 g, 4 mmole) in 120 ml dichloromethane was added DCC (9.08 g, 44 mmole) in portions and the mixture was stirred overnight at room temperature. The mixture was cooled to 5° C. and the urethane was filtered. The filtrate was evaporated and the product was isolated by silica gel column chromatography. Yield: 9.0 g ¹H-NMR (CDCl₃) 0.89 (m, 12H) 5.11 (s, 2H) 5.73 (m, 1H)

b) 3,3-Bis (N-CBZ-L-valyloxymethyl)-propionic acid

To a cooled solution of 4,4-bis (N-CBZ-L-valyloxymethyl)-but-1-ene (14.6 g, 25 mmole) and tetrabutylammonium bromide (1.3 g, 4 mmole) in 120 ml benzene was added 100 ml water. Under strong stirring potassium permanganate (15.8 g, 100 mmole) was addded in portions and the mixture was stirred for 2 hours between 15° C. and 20° C. A sodium bisulfite aqueous solution was added to the slurry until the mixture was discolored. The mixture was acidified with 2N hydrochloric acid and extracted four times with ethyl acetate. The organic phase was washed two times with water, dried with sodium sulfate and evaporated under reduced pressure. The product was isolated by silica gel column chromatography. Yield: 7.5 g ¹H-NMR (CDCl₃) 0.89 (m, 12H) 2.05 (m, 2H) 2.46 (m, 2H) 2.62 (m, 1H) 4.20 (m, 6H) 5.11 (s, 4H) 5.30 (m, 2H) 7.35 (m, 10H)

EXAMPLE F-I-4

2-(N-CBZ-L-valyloxy)-propionic acid a) 4-methoxybenzyl 2-hydroxypropionate

To a stirred solution of DL -2 hydroxypropionic acid (9.0 g, 100 mmole) in 100 ml dry DMF was added potassium tert-butoxide (12.34 g, 110 mmole) and the mixture was stirred for one hour at 60° C. 4-methoxybenzyl chloride (18.8 g 120 mmole) was added and the mixture was stirred for eight hours at 60° C. The mixture was evaporated under reduced pressure and 250 ml ethyl acatate was added. The organic phase was washed four times with water. The organic phase was dried with sodium sulfate and concentrated in vacuo. Yield: 16.8 g ¹H-NMR (CDCl₃) 1.40 (m, 3H) 3.81 (s, 3H) 4.26 (m, 1H) 5.14 (s, 2H) 6.90 (d, 2H) 7,28 (d, 2H)

b) 4-methoxybenzyl 2-(N-CBZ-L-valyloxy)propionate

To a solution of 4-methoxybenzyl 2-hydroxypropionate (4.2 g, 20 mmole), N-CBZ-L-valine (5.02 g, 20 mmole) and DMAP (0.24 g, 2 mmole) in 100 ml dichloromethane was added a solution of DCC (4.54 g, 22 mmole) and the mixture was stirred overnight at room temperature. The mixture was cooled to 5° C. and the urethane was filtered. The filtrate was evoporated and the product was isolated by silica gel column chromatography. Yield: 7.9 g ¹H-NMR (CDCl₃) 0.88 (m, 6H) 1.50 (m, 3H) 2.26 (m, 1H) 3.81 (s, 3H) 4.34 (m, 1H) 5.04–5.30 (m, 6H) 6.88 (d, 2H) 7.26 (m, 7H)

c) 2-(N-CBZ-L-valyloxy)-propionic acid

To a solution of 4-methoxybenzyl 2-(N-CBZ-L-valyloxy)-propionate (7.8 g, 17.5 mmole) in dichloromethane (100 ml) was added trifluoroacetic acid (10 ml) and the solution was stirred for one hour at room temperature. The solution was evaporated under reduced pressure and the product was isolated by silica gel column chromatography. Yield: 5.0 g ¹H-NMR (CDCl₃) 0.94 (m, 6H) 1.56 (d, 3H) 2.30 (m, 1H) 4.42 (m, 1H) 5.12–5.30 (m, 4H) 7.28 (m, 5H)

EXAMPLE F-I-5

Succinic acid 2,3-bis-(N-CBZ-L-valyloxy)propyl ester

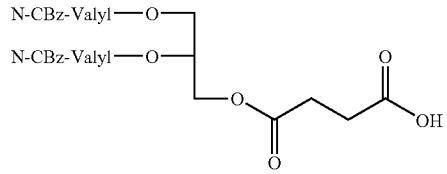

a) 4-Methoxybenzyl succinate monoester

To a mixture of succinic anhyride (75 g, 750 mmole) and 4-methoxybenzyl alcohol (69.1 g, 500 mmole) in 1,4-dioxane (300 ml) was added pyridine (79.1 g, 1000 mmole) and the mixture was stirred for five hours at 80° C. The mixture was evaporated under reduced pressure and 600 ml of ethyl acetate and 60 ml of acetic acid were added. The organic phase was washed three times with water, dried with sodium sulfate and evaporated under reduced pressure. The product was recrystallized from toluene. Yield: 104 g.

¹H-NMR (DMSO d-6) 2.48 (m, 4H) 3,72 (s, 3H) 5.00 (s, 2H) 6.90 (d, 2H) 7.28 (d, 2H)

b) Succinic acid 2,3-dihydroxy-propyl ester, 4-methoxybenzyl ester

To a solution of glycerol (23.0 g, 250 mmole), 4-methoxybenzyl succinate monoester (5.96 g, 25 mmole) and DMAP (0.36 g, 3 mmole) in DMF (200 ml) was added DCC (6.2 g 30 mmole) and the mixture was stirred overnight at room temperature. The mixture was evaporated under reduced pressure and 150 ml dichloromethane was added. The mixture was filtered and the solution washed twice with water. The water phase was extracted two times with dichloromethane and the combined organic phases were dried with sodium sulfate. The solution was evaporated under reduced pressure and the product was isolated by silica gel column chromatography.
Yield: 3.0 g ¹H-NMR (CDCl₃) 2.65 (m, 4H) 3.61 (m, 2H) 3.80 (s, 3H) 3.90 (m, 1H) 4.18 (m, 2H) 5.05 (s, 2H) 6.89 (d, 2H) 7.26 (d, 2H)

c) Succinic acid 2,3-bis-(N-CBZ-L-valyloxy)-propyl ester, 4-methoxybenzyl ester

To a stirred solution of succinic acid 2,3-dihydroxy-propyl ester, 4-methoxybenzyl ester (2.9 g, 9.28 mmole), N-CBZ-L-valine (5.03 g, 20 mmole) and DMAP (0.244 g, 2 mmole) in dichloromethane (60 ml) was added DCC (4.5 g, 22 mmole) and the mixture was stirred overnight at room temperature. The mixture was filtered and the solution was evaporated under reduced pressure. The product was isolated by silica gel column chromatography. Yield: 2.5 g ¹H-NMR (CDCl₃) 0.90 (m, 12H) 2,16 (m, 2H) 2.62 (m, 4H) 3.80 (s, 3H) 4.32 (m, 4H) 5.05–5.52 (m, 9H) 6.89 (d, 2H) 7.30 (m, 12H)

d) Succinic acid 2,3-bis-(N-CBZ-L-valyloxy)propyl ester

To a solution of the above intermediate (2.3 g, 2.95 mmole) in dichloromethane (25 ml) was added trifluoroacetic acid (2.5 ml) and the solution was stirred for two hours at roomtemperature. The solution was evaporated under reduced pressure and the product was isolated by silica gel column chromatography. Yield: 1,8 g $^1$H-NMR (CDCl$_3$) 0.92 (m, 12H) 2.12 (m, 2H) 2.64 (m, 4H) 4.32 (m, 4H) 5.10 (s, 4H) 5.22–5.50 (m, 3H) 7.34 (m, 10H)

EXAMPLE F-I-6

Succinic acid 1,3-bis-(N-CBZ-L-valyloxy)-2-propyl ester

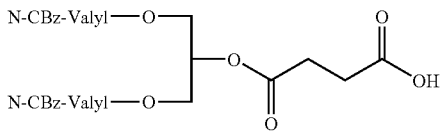

a) Succinic acid 1,3-dibromo-2-propyl ester, 4-methoxybenzyl ester

To a solution of 1,3-dibromopropan-2-ol (21.8 g, 100 mmole), succinic acid 4-methoxybenzyl ester (28.6 g, 120 mmole) and DMAP (1.22 g, 10 mmole) in dichloromethane (400 ml) was added DCC (24.8 g, 120 mmole) in portions at about 10° C. The mixture was stirred overnight at room temperature and cooled to about 5° C. The mixture was filtered and the solution was evaporated under reduced pressure. 600 ml of ethyl acetate was added and the organic phase was washed twice with 5% acetic acid, 5% sodium hydrogen carbonate and water. The solution was dried with sodium sulfate and evaporated under reduced pressure. The product was isolated by silica gel column chromatography. Yield: 34.8 g.

$^1$H-NMR (CDCl$_3$) 2.69 (m, 4H) 3.57 (m, 4H) 3.81 (s, 3H) 5.07 (s, 2H) 5.14 (m, 1H) 6,88 (d, 2H) 7.26 (d, 2H)

b) Succinic acid 1,3-bis-(N-CBZ-L-valyloxy)-2-propyl ester, 4-methoxybenzyl ester To a solution of N-CBZ-L-valine (58.5 g, 232.8 mmole) in dried DMF (300 ml) was added potassium-tert.-butoxide (24,68 g, 220 mmole) and the mixture was stirred for one hour at room temperature. A solution of succinic acid 1,3-dibromo-2-propyl ester, 4-methoxybenzyl ester (34 g, 77.6 mmole) in dried DMF (50 ml) was added and the mixture was stirred for eighteen hours at 60° C. The potassium bromide was filtered and the solution was evaporated under reduced pressure. 600 ml of ethyl acetate was added and the organic phase washed twice with 5% sodium hydrogen carbonate and with water. The organic phase was dried with sodium sulfate and evaporated under reduced pressure. The product was isolated by silica gel column chromatography. Yield: 45 g $^1$H-NMR (CDCl$_3$) 0.90 (m, 12H) 2.16 (m, 2H) 2.61 (m, 4H) 3.80 (s, 3H) 4.12–4.42 (m, 6H) 5.02 (s, 2H) 5.10 (s, 4H) 5.43 (m, 3H) 6.88 (d, 2H) 7.32 (m, 12H)

c) Succinic acid 1,3-bis-(N-CBZ-L-valyloxy)-2-propyl ester

To a cooled solution of the intermediate immediately above (44.5 g, 57.1 mmole) in dichloromethane (500 ml) was added trifluoroacetic acid (50 ml) between 5° C. and 10° C. and the solution was stirred for two hours at 10° C. The solution was evaporated under reduced pressure and two times coevaporated with toluene. 400 ml of ethanol was added and the mixture was stirred for 30 minutes at 40° C. The mixture was cooled and the biproduct filtered. The solution was evaporated under reduced pressure and the product was isolated by silica gel column chromatography. Yield: 33 g $^1$H-NMR (DMSO-d$_6$) 0.88 (m, 12H) 2.04 (m, 2H) 2.46 (m, 4H) 3.94–4.40 (m, 6H) 5.02 (s, 4H) 5.18 (m, 1H) 7.32 (m, 10H) 7,74 (d, 2H)

EXAMPLE F-I-7

Alternative route to succinic acid 1,3-bis-(N-CBZ-L-valyloxy)-2-propyl ester a) Succinic acid 1,3-dibromo-2-propyl ester, 1,1-dimethylethyl ester

To a solution of 1,3-dibromopropan-2-ol (10.9 g 50 mmole), succinic acid 1,1-dimethylethyl ester (J. Org.Chem 59 (1994) 4864) (10.45 g, 60 mmole) and DMAP (0.61 g, 5 mmole) in dichloromethane (180 ml) was added DCC (12.4 g, 60 mmole) in portions at about 10° C. The mixture was stirred overnight at room temperature and cooled to about 5° C. The mixture was filtered and the solution was evaporated under reduced pressure. 250 ml ethyl acetate was added and the organic phase was washed twice with 5% citric acid, 5% sodium hydrogen carbonate and water. The solution was dried with sodium sulfate and evaporated under reduced pressure. The product was distilled in vacuo. (bp 0,5 135–140° C.) Yield: 16.8 g $^1$H-NMR (CDCl$_3$) 1.45 (s, 9H) 2.58 (m, 4H) 3.61 (m, 4H) 5.12 (m, 1H)

b) Succinic acid 1,3-bis-(N-CBZ-L-valyloxy)-2-propyl ester, 1,1-dimethylethyl ester To a solution of N-CBZ-L-valine (18.85 g, 75 mmole) in dried DMF (100 ml) was added potassium tert.-butoxide (7.85 g, 70 mmole) and the mixture was stirred for one hour at room temperature. A solution of succinic acid 1,3-dibromo-2-propyl ester, 1,1-dimethylethyl ester (9.35 g, 25 mmole) in dried DMF (20 ml) was added and the mixture was stirred for eighteen hours at 60° C. The potassium bromide was filtered and the solution evaporated under reduced pressure. 300 ml of ethyl acetate were added and the organic phase washed twice with 5% sodium hydrogen carbonate and with water. The organic phase was dried with sodium sulfate and evaporated under reduced pressure. The product was isolated by silica gel column chromatography. Yield: 14 g $^1$H-NMR (CDCl$_3$) 0.90 (m, 12H) 1.42 (s, 9H) 2.14 (m, 2H) 2.52 (m, 4H) 4.32 (m, 4H) 5.10 (s, 4H) 5.32 (m, 3H) 7.26 (m, 10H)

c) 1,3-bis-(N-CBZ-L-valyloxy)-2-propyl succinate monoester

To a cooled solution of succinic acid 1,3-bis-(N-CBZ-L-valyloxy)-2-propyl ester, 1,1-dimethylethyl ester (13 g, 18.18 mmole) in dichloromethane (100 ml) was added trifluoroacetic acid (20 ml) and the solution was stirred for six hours at room temperature. The solution was evaporated under reduced pressure. 200 ml ethyl acetate was added and the organic phase was washed with 5% sodium hydrogen carbonate and water. The solution was evaporated under reduced pressure.
Yield: 11.7 g
$^1$H-NMR (DMSO-$d_6$) 0.88 (m, 12H) 2.04 (m, 2H) 2.46 (m, 4H) 3.94–4.40 (m, 6H) 5.02 (s, 4H) 5.18 (m, 1H) 7.32 (m, 10H) 7.74 (d, 2H)

EXAMPLE P-I-6

3-benzyloxycarbonylpropionic acid chloromethyl ester a) Succinic acid monobenzyl ester

Succinic anhydride (30 g, 300 mmole) was dissolved in methylene chloride (300 ml). To the solution were added benzyl alcohol (10.2 ml, 100 mmole), 4-dimethylaminopyridine (1.22 g, 10 mmole) and pyridine (48 ml). After 3 hours the reaction mixture was poured in to citric acid aqueous solution. The organic phase was concentrated to small volume and sodium hydrogen carbonate and water were added. Then mixture was stirred for 30 min. The aqueous phase was collected, and to it was added citric acid aqueous solution. The product precipitated out, was collected and dried. 15.3 g.
$^1$H-NMR (CDCl$_3$): 7.50 (m, 5H), 5.25 (s, 2H), 2.68 (m, 4H).

b) 3-benzyloxycarbonylpropionic acid chloromethyl ester

Succinic acid monobenzyl ester (4.16 g, 20 mmole) was dissolved in dioxane (20 ml). To the solution was added tetrabutylammonium hydroxide aqueous solution (40%, 11.6 ml, 18 mmole). The solution was dried in vacuo and coevaporated with toluene several times. The residue was dissolved in methylene chloride (60 ml) and then chloroiodomethane (14.5 ml, 200 mmole) was added to the solution. The reaction solution was stirred for 18 hr and then evaporated and the product was isolated with silica gel column chromatography. 3.64 g
$^1$H-NMR (CDCl$_3$): 7.35 (m, 5H), 5.67 (s, 2H), 5.13 (s, 2H), 2.72 (s, 4H).

c) 3-Benzyloxycarbonylpropionic acid iodomethyl ester

3-Benzyloxycarbonylpropionic acid chloromethyl ester (2 g, 1.38 mmole) was dissolved in acetonitrile (30 ml). Sodium iodide (1.6 g, 10.9 mmole) was added to the solution. After reaction at 70° C. for 3 hr, the reaction mixture was filtered and the residue was dissolved in methylene chloride (20 ml) and refiltered. The solution was dried and gave intermediate 3-benzyloxycarbonylpropionic acid iodomethyl ester in quantitative yield. This intermediate is bonded to an accessible function of a drug, such as a ring hydroxy or carboxy function using conventional alkylation/acylation conditions as described generally herein. Following deprotection of the terminal carboxy, a di/trifunctional linker bearing R$_2$, such as 1,3-bis-O-(L-valyl)glycerol or iodomethyloxy-L-valyl is acylated/alkylated thereon or R$_2$ amide bonded thereon by conventional techniques as described herein, such as with DCC coupling agent.

EXAMPLE B-I-1

4-(N-Boc-L-valyloxy)butyric acid

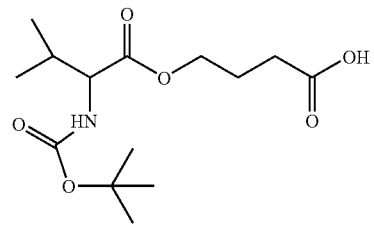

a) Preparation of 4-bromobutyric acid benzyl ester 4-bromobutyric acid (10.6 g, 60 mmole) was dissolved in thionyl chloride (20 mml), and the reaction was kept for 4 hr. The solution was evaporated and coevaporated with toluene several times. The residue was redissolved in dichloromethane (120 ml), and then benzyl alcohol (4.14 ml, 40 mmole) was added. The solution was cooled down to −50° C. and triethylamine (10 ml, 72 mmole) was added. The reaction mixture was slowly warmed to room temperature. After 3 hr, the reaction mixture was poured into sodium bicarbonate aqueous solution and the organic phase was washed with water and dried, giving the titled product, 6.8 g.
$^1$H-NMR (CDCl$_3$): 7.38 (m, 5H) 5.12 (m, 2H) 3.46 (t, 2H) 2.57 (t, 2H) 2.20 (m, 2H).

b) Preparation of 4-(N-Boc-L-valyloxy)butyric acid benzyl ester

N-Boc-L-valine (1.3 g, 6 mmole) was dissolved in dioxane (5 ml). To the solution was added tetrabutylammonium hydroxide aqueous solution (40%, 3.8 ml, 6 mmole), and the solution was evaporated and coevaporated with toluene several times. The residue was dissolved in DMF (15 ml) and 4-bromobutyric acid benzyl ester (1.28 g, 5 mmole) was added to it. The reaction was kept for 18 hr, and then poured into sodium bicarbonate aqueous solution and extracted with dichloromethane. The organic phase was dried and the product was isolated with silica gel column chromatography, 1.2 g.
$^1$H-NMR (CDCl$_3$): 7.35 (m, 5H) 5.13 (m, 2H) 5.00 (d, 1H) 4.28 (m, 3H), 2.48 (t, 2H), 2.05 (m, 2H) 1.46 (s, 9H) 0.93 (m, 6H).

c) 4-(N-Boc-L-valyloxy)butyric acid

To a solution of 4-(N-Boc-L-valyloxy)butyric acid benzyl ester (1.2 g, 3 mmole) in ethyl acetate/methanol (5 ml/5 ml) was added palladium black (20 mg). The reaction mixture was kept under hydrogen at atmospheric pressure for 2 hr. The suspension was filtered through Celite and dried, giving the title product, 840 mg.

¹H-NMR (CDCl₃): 5.05 (d, 1H) 4.20 (m, 3H) 2.48 (t, 2H) 2.00 (m, 2H) 1.46 (s, 9H) 0.96 (m, 6H).

A-I-1

Iodomethyl 2-methyl-2-(N-benzaloxycarbonyl-L-valyloxymethyl) propionate a) 4-Methoxybenzyl 2-(hydroxymethyl)-2-methyl propionate 2-(Hydroxymethyl)-2-methyl propionic acid was esterified by alkylation with 4-methoxybenzyl chloride by conventional means, namely treatment with aqueous NaOH, followed by evaporation and dissolution in an organic solvent such as DMF to which the 4-methoxybenzyl chloride is added and the reaction warmed and agitated, such as stirring at 60 C for one hour. The reaction mixture is cooled, concentrated by rotavapor and the resulting concentrated suspension partitioned between water and dichloromethane. The organic phase is evaporated and the reside subjected to silica gel column chromatography, for example with 0, 2, 4% EtOH in dichloromethane to yield the title compound (7.10 g). $R_f$ (2% MeOH/CHCl₃) 0.40.

¹H-NMR (CDCl₃): 7.26 (d, 2H), 6.90 (d, 2H), 5.07 (s, 2H), 3.80 (s, 3H), 3.55 (s, 2H), 2.44 (br, 1H), 1.19 (s, 6H).

b) 4-Methoxybenzyl 2-(N-benzyloxycarbonyl-L-valyloxymethyl)-2-methyl propionate

4-Methoxybenzyl 2-(hydroxymethyl)-2-methyl propionate (2.50 g, 10.5 mmol), N-benzyloxy carbonyl-L-valine (2.51 g, 10 mmole), 4-dimethylaminopyridine (183 mg) and 1-hydroxybenzotriazole (1.35 g, 10 mmole) were mixed and dissolved in N,N-dimethylformamide (90 ml). Then dicyclohexyl-carbodiimide (2.47 g 12 mmol) was added. After stirring for 3 days at room temperature the suspension was filtered and the filtrate evaporated in vacuo. The residue was partitioned between 0.1M citric acid and dichloromethane. The organic phase was then extracted with aqueous saturated NaHCO₃ and evaporated in vacuo. The residue was silica gel column chromatographed (0, 1, 2, 3% ethanol in dichloromethane). The appropriate fractions were pooled and evaporated in vacuo to give the title compound (2.72 g). $R_f$ (2% MeOH/CHCl₃) 0.75.

¹H-NMR (CDCl₃): 7.36 (s, 5H), 7.26 (d, 2H), 6.88 (d, 2H), 5.22 (d, 1H), 5.10 (s, 2H), 5.04 (s, 2H), 4.27 (d,d, 1H), 4.15 (d,d, 2H), 3.79 (s, 3H), 2.05 (m, 1H), 1.23 (s, 3H), 1.20 (s, 3H), 0.91 (d, 3H), 0.81 (d, 3H).

d) 2-(N-benzyloxycarbonyl-L-valyloxymethyl)-2-methyl propionic acid

To a solution of 4-methoxybenzyl 2-(N-benzyloxycarbonyl-L-valyloxymethyl)-2-methyl propionate (2.72 g, 5.76 mmole), was added trifluoroacetic acid (11.5 ml) and the emerging dark red solution was stirred for 30 min at room temperature. The solution was evaporated to dryness with dioxane and toluene. The residue was silica gel column chromatographed (2, 3, 4% ethanol in dichloromethane). The appropriate fractions were pooled and evaporated in vacuo to give the title compound (1.86 g). $R_f$ (2% MeOH/CHCl₃) 0.30.

¹H-NMR (CDCl₃): 7.32 (s, 5H), 5.32 (d, 1H), 5.10 (s, 2H), 4.32 (d,d, 1H), 4.21 (d,d, 2H), 2.13 (m, 1H), 1.26 (s, 3H), 1.25 (s, 3H), 0.95 (d, 3H), 0.86 (d, 3H).

c) Chloromethyl 2-(N-benzyloxycarbonyl-L-valyloxymethyl)-2-methyl propionate 2-(N-benzyloxycarbonyl-L-valyloxymethyl)-2-methyl propionic acid was esterified by conventional techniques, namely dissolution in an organic solvent such as dioxane and dropwise addition of aqueous tetrabutylammonium hydroxide, followed by evaporation. The residue is dissolved in dichloromethane and then chloroiodomethane and the mixture stirrred for 6 hours at room temperature, followed by partition, shaking the filtrate with aqueous sodium thiosulphate. 0.1M, filtration and evaporation. The title compound (1.40 g) was obtained after silica gel column chromatography (0, 1, 2, 3% ethanol in dichloromethane). $R_f$ (2% MeOH/CHCl₃) 0.80.

¹H-NMR (CDCl₃): 7.33 (s, 5H), 5.69 (s, 2H), 5.25 (d, 1H), 5.10 (s, 2H), 4.30 (d,d, 1H), 4.16 (d,d, 2H), 2.14 (m, 1H), 1.27 (s, 3H), 1.25 (s, 3H), 0.95 (d, 3H), 0.86 (d, 3H).

c) Iodomethyl 2-(N-benzyloxycarbonyl-L-valyloxymethyl)-2-methyl propionate

Chloromethyl 2-(N-benzyloxycarbonyl-L-valyloxymethyl)-2-methyl propionate was converted to iodide by conventional techniques, namely addition to NaI in acetonitrile, stirring and heating, for instance to 75 C for four hours. The resulting suspension is filtered and the filtrate evaporated, dissolved in organic solvent such as toluene and shaken with aqueous sodium thiosulphate (0.1M) and evaporation to give the title compound (1.25 g) practically pure. $R_f$ (2% MeOH/CHCl₃) 0.80.

¹H-NMR (CDCl₃): 7.35 (s, 5H), 5.90 (d,d, 2H), 5.24 (d, 1H), 5.10 (s, 2H), 4.31 (d,d, 1H), 4.14 (d,d, 2H), 2.16 (m, 1H), 1.22 (s, 6H), 0.96 (d, 3H), 0.87 (d, 3H).

EXAMPLE A-I-2

Iodomethyl 2-(N-benzyloxycarbonyl-L-valyloxyy-DL-propionate

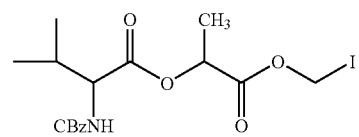

a) Chloromethyl 2-(N-benzyloxycarbonyl-L-valyloxy)-DL-propionate 2-(N-benzyloxycarbonyl-L-valyloxy) propionic acid (1 g) was esterified by the method described in Example A-I-1, step d. The title compound (0.76 g) was obtained after silica gel column chromatography (0, 1% ethanol in dichloromethane). $R_f$ (2% MeOH/CHCl₃) 0.75.

¹H-NMR (CDCl₃): 7.33 (s, 5H), 5.79 (d, 1H), 5.63 (d, 1H), 5.30 (d, 1H), 5.14 (q, 1H), 5.10 (s, 2H), 4.39 (d,d, 1H), 2.30 (m, 1H), 1.54 (d, 3H), 1.03 (d, 3H), 0.95 (d, 3H).

b) Iodomethyl 2-(N-benzyloxycarbonyl-L-valyloxy)-DL-propionate

Chloromethyl 2-N-benzyloxycarbonyl-L-valyloxymethyl)-2-methyl propionate was converted to iodide by the method described in Example A-I-1, step e to give the title compound (0.95 g) practically pure. $R_f$ (2% MeOH/CHCl$_3$) 0.75.

$^1$H-NMR (CDCl$_3$): 7.33 (s, 5H), 5.98 (d, 1H), 5.86 (d, 1H), 5.26 (d, 1H), 5.10 (s, 2H), 5.07 (q, 1H), 4.38 (d,d, 1H), 2.30 (m, 1H), 1.49 (d, 3H), 1.03 (d, 3H), 0.95 (d, 3H).

EXAMPLE A-I-3

Iodomethyl (1,3-di-(N-benzyloxycarbonyl)-L-valyloxy)-2-propyl carbonate

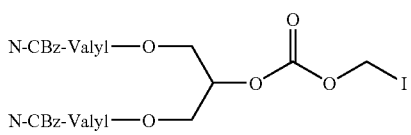

a) Chloromethyl (1,3-di-(N-benzyloxycarbonyl)-L-valyloxy)-2-propyl carbonate To a solution of 1,3-di-((N-benzyloxycarbonyl)-L-valyloxy)propan-2-ol (1.34 g, 2.4 mmole) in dichloromethane (10 ml) was added dry pyridine (1.15 ml, 14.4 mmol) and chloromethyl chloroformate (0.43 ml, 4.8 mmole) at 0° C. The reaction was then stirred for 30 min and then poured into aqueous 50% saturated sodium chloride/0.1M citric acid solution and extracted with dichloromethane. The organic phase was evaporated and the residue silica gel column chromatographed (0, 1, 1.5% ethanol in dichloromethane). The appropriate fractions were pooled and evaporated in vacuo to give the title compound (1.26 g). $R_f$ (2% MeOH/CHCl$_3$) 0.85.

$^1$H-NMR (CDCl$_3$): 7.34 (s, 10H), 5.68 (s, 2H), 5.21 (m, 3H), 5.10 (s, 4H), 4.50–4.12 (m, 6H), 2.14 (m, 2H), 0.97 (d, 6H), 0.88 (d, 6H).

b) Preparation of iodomethyl (1,3-di-(N-benzyloxycarbonyl)-L-valyloxy)-2-propyl carbonate Chloromethyl (1,3-di-(N-benzyloxycarbonyl)valyloxy)-2-propyl carbonate was converted to iodide by the method described in Example A-I-1, step e) to give the title compound (1.37 g) practically pure. $R_f$ (2% MeOH/CHCl$_3$) 0.85.

$^1$H-NMR (CDCl$_3$): 7.34 (s, 10H), 5.93 (d, 1H), 5.89 (d, 1H), 5.21 (m, 3H), 5.11 (s, 4H), 4.50–4.17 (m, 6H), 2.12 (m, 2H), 0.97 (d, 6H), 0.88 (d, 6H).

EXAMPLE A-I-4

Iodomethyl 2-(N-benzyloxycarbonyl-L-valyloxy)isobutgrate.

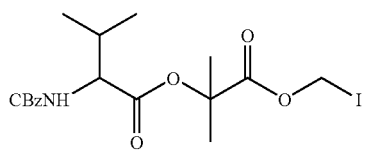

a) 4-Methoxybenzyl 2-hydroxyisobutyrate 2-hydroxy isobutyric acid (1.56 g) was esterified by alkylation with 4-methoxybenzyl chloride by the method described in Example A-I-1, step a). The title compound (2.65 g) was obtained after silica gel column chromatography (0, 1, 2% ethanol in dichloromethane). $R_f$ (2% MeOH/CHCl$_3$) 0.45.

$^1$H-NMR (CDCl$_3$): 7.26 (d, 2H), 6.89 (d, 2H), 5.12 (s, 2H), 3.80 (s, 3H), 3.17 (s, 1H), 1.42 (s, 6H).

b) 4-Methoxybenzyl 2-(N-benzyloxycarbonyl-L-valyloxy) isobutyrate.

4-methoxybenzyl 2-hydroxyisobutyrate was acylated with N-benzyloxycarbonyl-L-valine by the method described in Example A-I-1, step b). The title compound (3.21 g) was obtained after silica gel column chromatography (0, 1, 1.5% ethanol in dichloromethane). $R_f$ (2% MeOH/CHCl$_3$) 0.70.

$^1$H-NMR (CDCl$_3$): 7.33 (s, 5H), 7.26 (d, 2H), 6.88 (d, 2H), 5.22 (d, 1H), 5.10 (2xs, 4H), 4.28 (d,d, 1H), 3.79 (s, 3H), 2.15 (m, 1H), 1.56 (s, 3H), 1.54 (s, 3H), 0.95 (d, 3H), 0.84 (d, 3H).

c) 2-(N-benzyloxycarbonyl-L-valyloxy) isobutyric acid 4-methoxybenzyl 2-(N-benzyloxycarbonyl-L-valyloxy) isobutyrate was de-esterified by the method described in Example A-I-1 step c. The title compound (2.01 g) was obtained after silica gel column chromatography (2, 10, 20% ethanol in dichloromethane). $R_f$ (2% MeOH/CHCl$_3$) 0.30. This compound may be activated and esterified directly to a drug, or further modified as described below.

$^1$H-NMR (CDCl$_3$): 7.32 (s, 5H), 5.33 (d, 1H), 5.10 (s, 2H), 4.31 (d,d, 1H), 2.22 (m, 1H), 1.57 (s, 6H), 0.98 (d, 3H), 0.89 (d, 3H).

d) Chloromethyl 2-(N-benzyloxycarbonyl-L-valyloxy) isobutyrate 2-(N-benzyloxycarbonyl-L-valyloxy) isobutyric acid was esterified by the method described in Example A-I-1, step d. The title compound (1.90 g) was obtained after silica gel column chromatography (0, 1, 1.5% ethanol in dichloromethane). $R_f$ (2% MeOH/CHCl$_3$) 0.80.

$^1$H-NMR (CDCl$_3$): 7.33 (s, 5H), 5.68 (s, 2H), 5.25 (d, 1H), 5.11 (s, 2H), 4.30 (d,d, 1H), 2.21 (m, 1H), 1.59 (s, 3H), 1.57 (s, 3H), 1.00 (d, 3H), 0.90 (d, 3H).

e) Iodomethyl 2-(N-benzyloxycarbonyl-L-valyloxy) isobutyrate

Chloromethyl 2-(N-benzyloxycarbonyl-L-valyloxy) isobutyrate was converted to iodide by the method described in Example A-I-1, step e to give the title compound (2.32 g) practically pure. $R_f$ (2% MeOH/CHCl$_3$) 0.80.

$^1$H-NMR (CDCl$_3$): 7.33 (s, 5H), 5.89 (s, 2H), 5.22 (d, 1H), 5.11 (s, 2H), 4.29 (d,d, 1H), 2.21 (m, 1H), 1.55 (s, 3H), 1.53 (s, 3H), 1.00 (d, 3H), 0.93 (d, 3H).

EXAMPLE A-I-5

Iodomethyl 2-(N-benzyloxycarbonyl-L-valyloxy]-3-methyl-(S)-(+)-butyrate

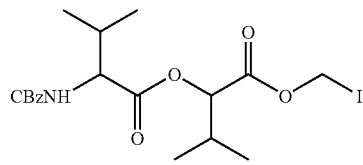

a) 4-Methoxybenzyl 2-hydroxy-3-methyl-(S)-(+)-butyrate 2-hydroxy-3-methyl-(S)-(+)-butyric acid (1.77 g) was esterified by alkylation with 4-methoxybenzyl chloride by the method described in Example A-I-1, step a. The title compound (3.10 g) was obtained after silica gel column chromatography (0, 1, 2% ethanol in dichloromethane). $R_f$ (2% MeOH/CHCl$_3$) 0.50.

$^1$H-NMR (CDCl$_3$): 7.27 (d, 2H), 6.90 (d, 2H), 5.19 (d, 1H), 5.12 (d, 1H), 4.05 (d,d, 1H), 3.81 (s, 3H), 2.70 (d, 1H), 2.06 (heptet, 1H), 3.55 (s, 2H), 0.98 (d, 3H), 0.80 (d, 3H).

b) 4-Methoxybenzyl 2-(N-benzyloxycarbonyl-L-valyloxy)-3-methyl-(S)-(+)-butyrate 4-Methoxybenzyl 2-hydroxy-3-methyl-(S)-(+)-butyrate was acylated with N-benzyloxycarbonyl-L-valine by the method described in Example A-I-1, step b. The title compound (5.74 g) was obtained after silica gel column chromatography (0, 1, 1.5% ethanol in dichloromethane). $R_f$ (2% MeOH/CHCl$_3$) 0.70.

$^1$H-NMR (CDCl$_3$): 7.36 (s, 5H), 7.27 (d, 2H), 6.87 (d, 2H), 5.27 (d, 1H), 5.10 (s, 4H), 4.88 (d, 1H), 4.40 (d,d, 1H), 3.80 (s, 3H), 2.25 (m, 2H), 1.01–0.81 (m, 12H).

c) 2-(N-benzyloxycarbonyl-L-valyloxy)-3-methyl-(S)-(+)-butyric acid 4-methoxybenzyl 2-(N-benzyloxycarbonyl-L-valyloxy)-3-methyl-(S)-(+)-butyrate was de-esterified by the method described in Example A-I-1, step c. The title compound (3.41 g) was obtained after silica gel column chromatography (2, 10, 20% ethanol in dichloromethane). $R_f$ (2% MeOH/CHCl$_3$) 0.45. The compound may be activated and esterified directly to a drug or further modified as described below:

$^1$H-NMR (CDCl$_3$): 7.36 (s, 5H), 5.38 (d, 1H), 5.11 (s, 4H), 4.90 (d, 1H), 4.41 (d,d, 1H), 2.28 (m, 2H), 1.04–0.89 (m, 12H).

d) Chloromethyl 2-(N-benzyloxycarbonyl-L-valyloxy)-3-methyl-(S)-(+)-butyrate 2-(N-benzyloxycarbonyl-L-valyloxy)-3-methyl-(S)-(+)-butyric acid was esterified by the method described in Example A-I-1, step d. The title compound (2.96 g) was obtained after silica gel column chromatography (0, 1, 2% ethanol in dichloromethane). $R_f$ (2% MeOH/CHCl$_3$) 0.85.

$^1$H-NMR (CDCl$_3$): 7.36 (s, 5H), 5.84 (d, 1H), 5.60 (d, 1H), 5.28 (d, 1H), 5.11 (s, 4H), 4.88 (d, 1H), 4.42 (d,d, 1H), 2.30 (m, 2H), 1.05–0.90 (m, 12H).

e) Iodomethyl 2-(N-benzyloxycarbonyl-L-valyloxy)-3-methyl-(S)-(+)butyrate

Chloromethyl 2-(N-benzyloxycarbonyl-L-valyloxy)-3-methyl-(S)-(+)-butyrate was converted to iodide by the method described in Example A-I-1, step e to give the title compound (3.64 g) practically pure. $R_f$ (2% MeOH/CHCl$_3$) 0.85.

$^1$H-NMR (CDCl$_3$): 7.36 (s, 5H), 6.00 (d, 1H), 5.83 (d, 1H), 5.28 (d, 1H), 5.11 (s, 4H), 4.83 (d, 1H), 4.41 (d,d, 1H), 2.29 (m, 2H), 1.05–0.90 (m, 12H).

EXAMPLE A-I-6

Iodomethyl 2-(N-benzyloxycarbonyl-L-valyloxy)-2-phenyl-DL-acetate

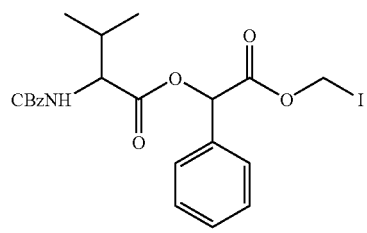

a) 4-Methoxybenzyl 2-hydroxy-2-phenyl-DL-acetate

DL-mandelic acid (2.28 g) was esterified by alkylation with 4-methoxybenzyl chloride by the method described in Example A-I-1, step a. The title compound (3.69 g) was obtained after silica gel column chromatography (0, 1, 1.5% ethanol in dichloromethane). $R_f$ (2% MeOH/CHCl$_3$) 0.55.

$^1$H-NMR (CDCl$_3$): 7.34 (m, 5H), 7.15 (d, 2H), 6.83 (d, 2H), 5.18 (d, 1H), 5.15 (d, 1H), 5.03 (d, 1H), 3.78 (s, 3H), 3.48 (s, 1H).

b) 4-Methoxybenzyl 2-(N-benzyloxycarbonyl-L-valyloxy)-2-phenyl-DL-acetate

4-Methoxybenzyl 2-hydroxy-2-phenyl-DL-acetate was acylated with N-benzyloxycarbonyl-L-valine by the method described in Example A-I-1, step b. The title compound (6.50 g) was obtained after silica gel column chromatography (0, 1, 1.5% ethanol in dichloromethane). $R_f$ (2% MeOH/CHCl$_3$) 0.75.

$^1$H-NMR (CDCl$_3$): 7.36 (m, 10H), 7.14 (2xd, 2H), 6.81 (d, 2H), 5.95 (d, 1H), 5.27 (m, 1H), 5.14–5.01 (m, 4H), 4.43 (m, 1H), 3.78 (s, 3H), 2.21 (m, 1H), 1.03–0.82 (m, 6H).

c) 2-(N-benzyloxycarbonyl-L-valyloxy)-2-phenyl-DL-acetic acid

4-Methoxybenzyl 2-(N-benzyloxycarbonyl-L-valyloxy)-2-phenyl-DL-acetate was deesterified by the method described in Example A-I-1, step c. The title compound (4.75 g) was obtained after silica gel column chromatography (2, 10, 20% ethanol in dichloromethane). $R_f$ (2% MeOH/CHCl$_3$) 0.40. The compound may be activated and esterified directly to a drug or further modified as described below.

$^1$H-NMR (CDCl$_3$): 7.36 (m, 10H), 5.91 (d, 1H), 5.27 (m, 1H), 5.04 (s, 2H), 4.57–4.40 (2xd,d, 1H), 2.30 (m, 1H), 1.01–0.82 (m, 6H).

d) Chloromethyl 2-(N-benzyloxycarbonyl-L-valyloxy)-2-phenyl-DLacetate 2-(N-benzyloxycarbonyl-L-valyloxy)-2-phenyl-DL-acetic acid was esterified by the method described in Example A-I-1, step d. The title compound (1.69 g) was obtained after silica gel column chromatography (0, 1, 2% ethanol in dichloromethane). $R_f$ (2% MeOH/CHCl$_3$) 0.80.

$^1$H-NMR (CDCl$_3$): 7.36 (m, 10H), 5.98, 5.95 (2xs, 1H), 5.74–5.61 (m, 2H), 5.32 (m, 1H), 5.10 (s, 2H), 4.43 (m, 1H), 2.30 (m, 1H), 1.07–0.5 (m, 6H).

e) Iodomethyl 2-(N-benzyloxycarbonyl-L-valyloxy)-2-phenyl-DL-acetate

Chloromethyl 2-(N-benzyloxycarbonyl-L-valyloxy)-2-phenyl-DL-acetate was converted to iodide by the method described in Example A-I-1, step e to give the title compound (1.89 g) practically pure. $R_f$ (2% MeOH/CHCl$_3$) 0.80.

$^1$H-NMR (CDCl$_3$): 7.36 (m, 10H), 5.94–5.82 (m, 3H), 5.28 (m, 1H), 5.10 (s, 2H), 4.46 (m, 1H), 2.21 (m, 1H), 1.08–0.85 (m, 6H).

EXAMPLE A-I-7

Iodomethyl 4-(N-benzyloxycarbonyl-L-valyloxy) benzoate

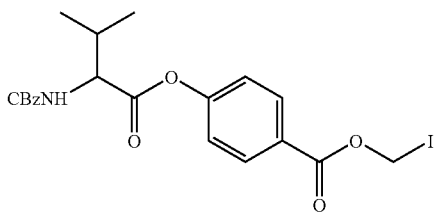

a) 4-Methoxybenzyl 4-hydroxybenzoate

4-Hydroxybenzoic acid (1.38 g) was esterified by alkylation with 4-methoxybenzyl chloride by the method described in Example A-I-1, step a. The title compound (2.06 g) was obtained after silica gel column chromatography (0, 1, 2, 3% ethanol in dichloromethane). $R_f$ (2% MeOH/CHCl$_3$) 0.40.

$^1$H-NMR (CDCl$_3$): 7.95 (d, 2H), 7.35 (d, 2H), 6.91 (d, 2H), 6.83 (d, 2H), 5.27 (s, 2H), 3.81 (s, 3H), 1.72 (s, 1H).

b) 4-Methoxybenzyl 4-(N-benzyloxycarbonyl-L-valyloxy) benzoate

4-Methoxybenzyl 4-hydroxybenzoate was acylated with N-benzyloxycarbonyl-Lvaline by the method described in Example A-I-1, step b. The title compound (2.71 g) was obtained after silica gel column chromatography (0, 1% ethanol in dichloromethane). $R_f$ (2% MeOH/CHCl$_3$) 0.70.

$^1$H-NMR (CDCl$_3$): 8.05 (d, 2H), 7.34 (m, 7H), 7.14 (d, 2H), 6.92 (d, 2H), 5.35 (d, 1H), 5.28 (s, 2H), 5.18 (s, 2H), 4.55 (d,d, 1H), 3.81 (s, 3H), 2.34 (m, 1H), 1.10 (s, 3H), 0.95 (d, 3H).

c) 4-(N-benzyloxycarbonyl-L-valyloxy) benzoic acid

4-Methoxybenzyl 4-(N-benzyloxycarbonyl-L-valyloxy) benzoate was de-esterified by the method described in Example A-I-1, step c. The title compound (1.86 g) was obtained after silica gel column chromatography (2, 10, 20% ethanol in dichloromethane). $R_f$ (2% MeOH/CHCl$_3$) 0.20. The compound can be activated and esterifed directly to a drug or further modifed as described below.

$^1$H-NMR (CDCl$_3$): 8.15 (d, 2H), 7.34 (m, 5H), 7.22 (d, 2H), 5.38 (d, 1H), 5.17 (s, 2H), 4.58 (d,d, 1H), 2.34 (m, 1H), 1.12 (s, 3H), 0.96 (d, 3H).

d) Chloromethyl 4-(N-benzyloxycarbonyl-L-valyloxy) benzoate 4-(N-benzyloxycarbonyl-L-valyloxy) benzoic acid was esterified by the method described in Example A-I-1, step d. The title compound (0.95 g) was obtained after silica gel column chromatography (0, 1% ethanol in dichloromethane). $R_f$ (2% MeOH/CHCl$_3$) 0.80.

$^1$H-NMR (CDCl$_3$): 8.12 (d, 2H), 7.36 (m, 5H), 7.20 (d, 2H), 5.94 (s, 2H), 5.32 (d, 1H), 5.15 (s, 2H), 4.55 (d,d, 1H), 2.34 (m, 1H), 1.10 (s, 3H), 1.03 (d, 3H).

e) Iodomethyl 4-(N-benzyloxycarbonyl-L-valyloxy) benzoate

Chloromethyl 4-(N-benzyloxycarbonyl-L-valyloxy) benzoate was converted to iodide by the method described in Example A-I-1, step e to give the title compound (1.16 g) practically pure. $R_f$ (2% MeOH/CHCl$_3$) 0.80.

$^1$H-NMR (CDCl$_3$): 8.11 (d, 2H), 7.35 (m, 5H), 7.21 (d, 2H), 6.15 (s, 2H), 5.32 (d, 1H), 5.14 (s, 2H), 4.55 (d,d, 1H), 2.34 (m, 1H), 1.10 (s, 3H), 1.03 (d, 3H).

EXAMPLE A-I-8

Iodomethyl 5-(N-CBz-L-valyloxy)-2,2-dimethylvalerate

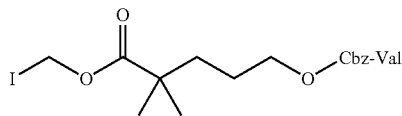

a) 4-Methoxybenzyl 2,2-dimethyl-4-pentenoate

To a solution of 2,2-dimethyl-4-pentenoic acid (11.5 g, 90 mmol) in DMF (250 mL) at room temperature, was added potassium tert-butoxide (11.1 g, 99 mmol). The reaction mixture was stirred at 60° C. for 1 h. 4-Methoxybenzyl chloride (16.9 g, 108 mmol) was added and the reaction mixture was stirred at 60° C. for 4 h. The DMF was evaporated under vacuum, the residue was dissolved in ether (500 mL) and washed with water (3×200 mL). The organic phase was dried with $Na_2SO_4$ and evaporated to give 21.4 g of 4-methoxybenzyl 2,2-dimethyl-4-pentenoate.

$^1$H-NMR ($CDCl_3$): 7.27 (d, J=8.7 Hz, 2H), 6.88 (d, J=8.7 Hz, 2H), 5.8–5.6 (m, 1H), 5.1–4.9 (m, 2H), 5.03 (s, 2H), 3.80 (s, 3H), 2.27 (d, 2H), 1.17 (s, 6H).

b) 4-Methoxybenzyl 5-hydroxy-2,2-dimethylvalerate

A mixture of 4-methoxybenzyl 2,2-dimethyl-4-pentenoate (9.50 g, 38 mmol) and 9-BBN (115 mL, 57 mmol, 0.5 M in THF) was stirred at 60° C. for 60 min, whereupon the reaction mixture was cooled to −5° C. $H_2O$ (35 mL) was added, the reaction mixture was stirred for 5 min at −5° C., an aqueous solution of NaOH (35 mL, 3M) was added and the reaction mixture was stirred for a further 10 min at −5° C. An aqueous solution of $H_2O_2$ (35 mL, 30%) was added dropwise and the temperature of the reaction mixture was allowed to assume room temperature, whereupon the reaction mixture was stirred for 30 min at room temperature. After evaporation, water (200 mL) was added and the resulting mixture was extracted with $CH_2Cl_2$ (5×200 mL). The combined organic layers were dried ($Na_2SO_4$) and concentrated under reduced pressure. The crude product was column chromatographed (silica gel, 1→8% MeOH in $CH_2Cl_2$), to give 6.32 g of 4-methoxybenzyl 5-hydroxy-2,2-dimethylvalerate.

$^1$H-NMR ($CDCl_3$): 7.27 (d, J=8.5 Hz, 2H), 6.87 (d, J=8.5 Hz, 2H), 5.03 (s, 2H), 3.79 (s, 3H), 3.53 (t, 2H), 1.88 (m, 1H), 1.61–1.52 (m, 2H), 1.49–1.38 (m, 2H), 1.16 (s, 6H).

c) 4-Methoxybenzyl 5-(N-CBz-L-valyloxy)-2,2-dimethylvalerate

To a mixture of DCC (9.41 g, 46 mmol), DMAP (0.586 g, 4.8 mmol) and N-CBz-Lvaline (12.1 g, 48 mmol) in $CH_2Cl_2$ (200 mL) at 0° C., was added dropwise a solution of 4-methoxybenzyl 5-hydroxy-2,2-dimethyl-valerate (6.40 g, 24 mmol) in $CH_2Cl_2$ (50 mL). After 1 h at 0° C., the temperature of the reaction mixture was allowed to assume room temperature and then the mixture was stirred for 5 h at room temperature. The mixture was filtered through a glass filter and the solvent was removed under reduced pressure. The crude product was column chromatographed (silica gel, 1→4% MeOH in $CH_2Cl_2$), to give 8.61 g 4-methoxybenzyl 5-(N-CBz-L-valyloxy)-2,2-dimethylvalerate.

$^1$H-NMR ($CDCl_3$): 7.36 (s, 5H), 7.28 (d, J=8.6 Hz, 2H), 6.89 (d, J=8.6 Hz, 2H), 5.39 (d, 1H), 5.12 (s, 2H), 5.05 (s, 2H), 4.30 (dd, 1H), 4.10–4.02 (m, 2H), 3.80 (s, 3H), 2.28–2.07 (m, 1H), 1.62–1.48 (m, 4H), 1.19 (s, 6H), 0.97 (d, 3H), 0.89 (d, 3H).

d) 5-(N-CBz-L-valyloxy)-2,2-dimethylvaleric acid

To a solution of 4-methoxybenzyl 5-(N-CBz-L-valyloxy)-2,2-dimethylvalerate (8.24 g, 16.5 mmol) in $CH_2Cl_2$ (100 mL) at room temperature, was added trifluoroacetic acid (5 mL). After 1 h at room temperature, the reaction mixture was concentrated under reduced pressure. The crude product was column chromatographed (silica gel, 3→5% MeOH in $CH_2Cl_2$), to give 6.00 g of 5-(N-CBz-L-valyloxy)-2,2-dimethylvaleric acid. The compound can be activated and directly esterified to a drug or further modified as described below.

$^1$H-NMR ($CDCl_3$): 10.94 (br s, 1H), 7.35 (s, 5H), 5.45 (d, 1H), 5.11 (s, 2H), 4.30 (dd, 1H), 4.21–4.00 (m, 2H), 2.28–2.07 (m, 1H), 1.68–1.51 (m, 4H), 1.21 (s, 6H), 0.97 (d, 3H), 0.89 (d, 3H).

e) Chloromethyl 5-(N-CBz-L-valyloxy)-2,2-dimethylvalerate

To a solution of 5-(N-CBz-L-valyloxy)-2,2-dimethylvaleric acid (5.88 g, 15.5 mmol) in dioxane (100 mL), was added dropwise a 40% aqueous solution of tetrabutylammonium hydroxide (10.1 g). After stirring for 5 min, the solution was evaporated to dryness through co-evaporation with dioxane and toluene. The residue was dissolved in dichloromethane (100 mL) and then chloroiodomethane (11.3 mL, 155 mmol) was added and the solution was stirred for 6 h at room temperature. The solution was concentrated under reduced pressure and the residue was shaken with hexane/ethyl acetate (1:1 v/v, 200 mL). The yellow crystalline solid was filtered off and the filtrate was washed with aqueous solution of sodium thiosulfate (0.1 M) and the filtered through anhydrous sodium sulfate and evaporated to dryness. The residue was column chromatographed (silica gel, 1–4% MeOH in $CH_2Cl_2$), to give 3.95 g of chloromethyl 5-(N-CBz-L-valyloxy)-2,2-dimethylvalerate.

$^1$H-NMR ($CDCl_3$): 7.34 (s, 5H), 5.69 (s, 2H), 5.35 (d, 1H), 5.10 (s, 2H), 4.29 (dd, 1H), 4.20–4.00 (m, 2H), 2.24–2.06 (m, 1H), 1.65–1.50 (m, 4H), 1.20 (s, 6H), 0.96 (d, 3H), 0.88 (d, 3H).

f) Iodomethyl 5-(N-CBz-L-valyloxy)-2,2-dimethylvalerate

To a solution of chloromethyl 5-(N-CBz-L-valyloxy)-2,2-dimethylvalerate (3.85 g, 9 mmol) in acetonitrile (50 mL), was added sodium iodide (5.40 g, 36 mmol). The solution was stirred for 4 h at 60° C. The resulting suspension was filtered and the filtrate was evaporated. The residue was dissolved in $CH_2Cl_2$ and washed with aqueous sodium thiosulfate (0.1 M). The organic phase was dried ($Na_2SO_4$) and concentrated under reduced pressure. The crude product was column chromatographed (silica gel, 1% MeOH in $CH_2Cl_2$), to give 4.26 g of iodomethyl 5(N-CBz-L-valyloxy)-2,2-dimethylvalerate $^1$H-NMR ($CDCl_3$): 7.34 (s, 5H), 5.90 (s, 2H), 5.32 (d, 1H), 5.10 (s, 2H), 4.29 (dd, 1H), 4.18–4.02 (m, 2H), 2.26–2.08 (m, 1H), 1.65–1.50 (m, 4H), 1.17 (s, 6H), 0.97 (d, 3H), 0.89 (d, 3H).

EXAMPLE A-I-9

2-(N-CBz-L-valyloxy)-ethyl iodomethyl carbonate

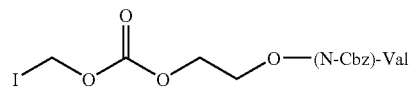

a) 2-(N-CBz-L-valyloxy)-ethanol

To a mixture of DCC (11.4 g, 55 mmol), DMAP (0.611 g, 5 mmol) and ethyleneglycol (55.8 mL, 1 mol) in $CH_2Cl_2$ (300 mL) at 0° C., was added dropwise a solution of N-CBz-L-valine (12.6 g, 50 mmol) in $CH_2Cl_2$ (100 ml). After 1 h at 0° C., the temperature of the reaction mixture was allowed to assume room temperature and then the mixture was stirred for 5 h at room temperature. The mixture was filtered through a glass filter and the solvent was removed under reduced pressure. The crude product was column chromatographed (silica gel, 5→10% MeOH in $CH_2Cl_2$), to give 12.0 g 2-(N-CBz-L-valyloxy)-ethanol.

$^1$H-NMR (CDCl$_3$): 7.30 (s, 5H), 5.77 (d, 1H), 5.06 (s, 2H), 4.29–4.12 (m, 3H), 3.80–3.66 (m, 2H), 3.46 (m, 1H), 2.22–2.04 (m, 1H), 0.94 (d, 3H), 0.88 (d, 3H).

b) 2-(N-CBz-L-valyloxy)-ethyl chloromethyl carbonate

To a mixture of 2-(N-CBz-L-valyloxy)-ethanol (12.0 g, 40.6 mmol) and pyridine (19.7 mL, 0.24 mmol) in $CH_2Cl_2$ (300 mL) at 0° C., was added dropwise chloromethyl chloroformate (10.5 g, 81.2 mmol). After 30 min at 0° C., the reaction mixture was washed with $H_2O$ (200 mL). The $H_2O$ phase was washed with $CH_2Cl_2$ (100 mL) and the solvent of the combined organic phases was removed under reduced pressure. The crude product was column chromatographed (silica gel, 0.5→1% MeOH in $CH_2Cl_2$), to give 8.26 g 2-(N-CBz-L-valyloxy)-ethyl chloromethyl carbonate.

$^1$H-NMR (CDCl$_3$): 7.35 (s, 5H), 5.71 (s, 1H), 5.28 (d, 1H), 5.11 (s, 2H), 4.48–4.26 (m, 5H) 2.28–2.10 (m, 1H), 0.97 (d, 3H), 0.89 (d, 3H).

c) 2-(N-CBz-L-valyloxy)-ethyl iodomethyl carbonate

To a solution of 2-(N-CBz-L-valyloxy)-ethyl chloromethyl carbonate (3.88 g, 10 mmol) in acetonitrile (50 mL), was added sodium iodide (7.50 g, 50 mmol). The solution was stirred for 4 h at 60° C. The resulting suspension was filtered and the filtrate was evaporated. The residue was dissolved in $CH_2Cl_2$ and washed with aqueous sodium thiosulfate (0.1 M). The organic phase was dried ($Na_2SO_4$) and concentrated under reduced pressure, to give 4.51 g 2-(N-CBz-L-valyloxy)-ethyl iodomethyl carbonate.

$^1$H-NMR (CDCl$_3$): 7.34 (s, 5H), 5.93 (s, 2H), 5.26 (d, 1H), 5.11 (s, 2H), 4.48–4.26 (m, 5H) 2.28–2.10 (m, 1H), 0.97 (d, 3H), 0.90 (d, 3H).

EXAMPLE A-I-10

2,2-dimethyl-3-(N-CBz-D-valyloxy)-propionic acid iodomethyl ester a) 2,2-dimethyl-3-(N-CBz-D-valyloxy)-propionic acid

To a solution of 2,2-dimethyl propionic acid 4-methoxybenzyl ester (4.7 g, 20 mmole) and N-CBz-D-valine (5.5 g, 22 mmole) in dichloromethane (100 ml) were added 4-dimethyaminopyridine (305 mg, 2.5 mmole) and DCC (5.15 g, 25 mmole). After 18 hr, the solution was washed successively with sodium bicarbonate aqueous solution, citric acid solution and water. The organic phase was dried and the residue was dissolved in dichloromethane (100 ml). To the solution was added trifluoroacetic acid (10 ml). After 3 hr, it was evaporated and the product was isolated with silica gel column chromatography. 4.5 g. The compound may be activated and esterified to a drug or further modified as described below.

$^1$H-NMR (CDCl$_3$): 7.36 (m, 5H) 5.11 (s, 2H) 4.30 (m, 1H) 4.18 (dd, 2H) 2.17 (m, 1H), 1.23 (d, 6H) 0.93 (m, 6H).

b) 2,2-dimethyl-3-(N-CBz-D-Valyloxy)-propionic acid chloromethyl ester (2,2-dimethyl-3-(N-CBz-D-valyloxy)-propionic acid (4.5 g, 12.8 mmole) was dissolved in dioxane (20 ml). To the solution was added tetrabutylammonium hydroxide aqueous solution (40%, 8.3 ml, 12.8 mmole). The solution was dried in vacuo, and it was coevaporated with toluene several times. The residue was dissolved in methylene chloride and then chloroiodomethane (18 ml, 260 mmole) was added to the solution. After 18 hr, the reaction solution was evaporated and the product was isolated with silica gel column chromatography. 3.5 g.

$^1$H-NMR (CDCl$_3$): 7.34 (m, 5H) 5.72 (s, 2H) 5.23 (d, 1H) 5.11 (s, 2H) 4.31(m, 1H) 4.14 (dd, 2H) 2.15 (m, 1H) 1.25 (d, 6H), 0.92 (m, 6H).

c) 2,2-dimethyl-3-(N-CBz-D-valyloxy)-propionic acid iodomethyl ester 2,2-Dimethyl-3-(N-CBz-D-valyloxy)-propionic acid chloromethyl ester (2.4 g, 6 mmole) was dissolved in acetonitrile (30 ml). Sodium iodide (1.26 g, 8.4 mmole) was added to the solution. After reaction at 70° C. for 2 hr, the reaction mixture was filtered and the residue was dissolved in methylene chloride (20 ml) and refiltered. The solution was dried and gave the titled product. 2.68 g.

$^1$H-NMR (CDCl$_3$): 7.36 (m, 5H) 5.90 (dd, 2H) 5.26 (d, 1H) 5.11 (s, 2H) 4.31 (m, 1H) 4.15 (dd, 2H) 2.18 (m, 1H) 1.22 (d, 6H) 0.92 (m, 6H).

EXAMPLE A-I-11

4-(N-CBz-L-valyloxy) butyric acid iodomethyl ester

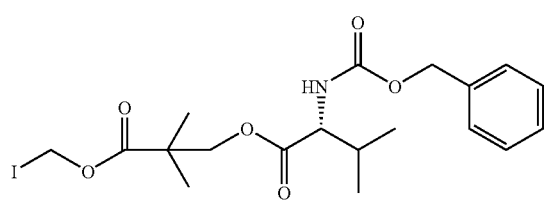

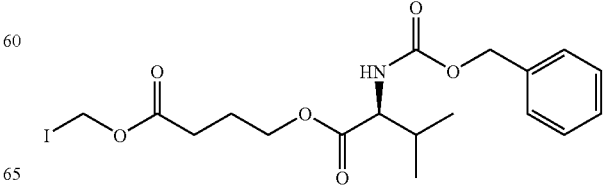

a) 4-(N-CBz-L-valyloxy) butyric acid t-butyl ester

N-CBz-L-valine (16.25 g, 65 mmole) was dissolved in DMF (40 ml). To the solution was added potassium t-butoxide (7.24 g, 65 mmole). After 10 min, 4-bromobutyric acid t-butyl ester (12 g, 53 mmole) was added. The reaction mixture was kept at 65° C. for 2.5 hr and then poured into sodium bicarbonate aqueous solution and extracted with dichloromethane. The organic phase was dried and the product was isolated with silica gel column chromatography. 20.1 g.

$^1$H-NMR (CDCl$_3$): 7.38 (m, 5H) 5.32 (d, 1H) 5.13 (s, 2H) 4.32 (dd, 1H) 4.28 (t, 2H) 2.31 (t, 2H) 2.18 (m, 1H) 1.97 (m, 2H) 1.45 (s, 9H) 0.97 (m, 6H).

b) 4-(N-CBz-L-valyloxy)butyric acid chloromethyl ester 4-(N-CBz-L-valyloxy) butyric acid t-butyl ester (20 g, 50.8 mmole) was treated with trifluoroacetic acid (30 ml) at 0° C. for 3 h and then evaporated. The residue was coevaporated with toluene several time. The intermediate acid (2.56 g, 7.6 mmole) was dissolved in dioxane (10 ml) and to the solution was added tetrabutylammonium hydroxide (40%, 4.66 ml. 7.2 mmole). The solution was dried and dissolved in dichloromethane (20 ml) and then chloroiodomethane (10 ml, 144 mmole) was added to the solution. After 18 hr, the reaction solution was evaporated and the product was isolated with silica gel column chromatography. Yield 2.1 g.

$^1$H-NMR (CDCl$_3$): 7.34 (m, 5H) 5.69 (dd, 2H) 5.29 (d, 1H) 5.11 (s, 2H) 4.29 (dd, 1H) 4.18 (t, 2H) 2.49 (t, 2H) 2.14 (m, 1H) 2.04 (m, 2H) 0.93 (dd, 6H).

c) 4-(N-CBz-L-valyloxy)butyric acid iodomethyl ester 4-(N-CBz-L-valyloxy) butyric acid chloromethyl ester (1.54 g, 4 mmole) was dissolved in acetonitrile (15 ml). Sodium iodide (840 mg, 5.6 mmole) was added to the solution. After reaction at 55° C. for 3 hr, the reaction mixture was filtered and the residue was dissolved in methylene chloride (20 ml) and refiltered. The solution was dried and gave the titled product. Yield 1.9 g.

$^1$H-NMR (CDCl$_3$): 7.36 (m, 5H) 5.90 (dd, 2H) 5.25 (d, 1H) 5.11 (s, 2H) 4.29 (dd, 1H 4.18 (t, 2H) 2.43 (t, 2H) 2.20 (m, 1H) 2.00 (m, 2H) 0.93 (dd, 6H).

EXAMPLE A-I-12

Iodomethyl 3-(N-benzyloxycarbonyl-L-valyloxy-benzoate

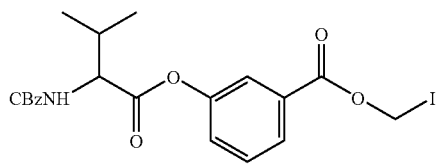

a) 4-Methoxybenzyl 3-hydroxybenzoate

To a solution of 3-hydroxybenzoic acid (6.9 g, 50 mmole) in DMF (100 ml) was added potassium-tert.-butoxide (6.17 g, 55 mmole) and the mixture was stirred at room temperature for one hour. 4-Methoxybenzyl chloride (9.4 g, 60 mmole) was added and the mixture was stirred for 16 hours at 60° C. The mixture was evaporated under reduced pressure and ethyl acetate (250 ml) were added. The organic phase was washed five times with water, dried with sodium sulfate and evaporated under reduced pressure. The product was isolated by silica gel column chromatography with toluene/acetone. Yield: 10.5 g=81%

$^1$H-NMR (CDCl$_3$) 3.82 (s, 3H) 5.29 (s, 2H) 6.90–7.61 (m, 8H)

b) 4-Methoxybenzyl 3-(N-benzyloxycarbonyl-L-valyloxy) benzoate

To a cooled solution of 4-methoxybenzyl 3-hydroxybenzoate (7.7 g, 29.8 mmole), 4-dimethylaminopyridine (0.73 g, 6 mmole) and N-benzyloxycarbonyl-L-valine (8.3 g, 33 mmole) in 100 ml dichloromethane was added dicyclohexylcarbodiimide (7.22 g, 35 mmole) and the mixture was stirred for 2 days at room temperature. The mixture was cooled and the urethane was filtered. The solution was evaporated and ethyl acetate (250 ml) was added. The organic phase was washed twice with 5% acetic acid; 5% sodium hydrogencarbonate and water. The organic phase was dried with sodium sulfate and evaporated under reduced pressure. The product was isolated by silica gel column chromatography with hexane/ethyl acetate. Yield: 13.9 g=94%

$^1$H-NMR (DMSO d-6) 0.98(m, 6H) 2.20 (m, 1H) 3.72 (s, 3H) 4.14 (m, 1H) 5.06 (s, 2H) 5.30 (s, 2H) 6.98–7.86 (m, 14H)

c) 3-(N-benzyloxycarbonyl-L-valyloxy) benzoic acid

To a solution of 4-methoxybenzyl-3-(N-benzyloxycarbonyl-L-valyloxy)-benzoate (13.7 g, 27.8 mmole) in dichloromethane (150 ml) was added trifluoroacetic acid (20 ml) and the mixture was stirred for 2 hours at room temperature. The solution was evaporated under reduced pressure and the product crystallized from toluene. Yield: 10.1 g=87%. The compound can be activated and esterified to a drug or further modified as described below $^1$H-NMR (DMSO d-6) 1.01 (m, 6H) 2.21 (m, 1H) 4.17 (d, d, 1H) 5.08 (s, 2H) 7.28–7.96 (m, 10H)

d) Chloromethyl 3-(N-benzyloxycarbonyl-L-valyloxy)-benzoate

To a solution of 3-(N-benzyloxycarbonyl-valyloxy)benzoic acid (7.42 g, 20 mmole) in 1,4-dioxane (100 ml) was added a 40% solution of tetrabutylammonium hydroxide (12.97 g, 20 mmole) and the mixture was stirred 2 hours at room temperature. The mixture was evaporated under reduced pressure and co-evaporated two times with 1,4-dioxane and two times with toluene. The dried product was dissolved in dichloromethane (50 ml) and chloroiodomethane (35.3 g, 200 mmole) was added. The solution was stirred for two days at room temperature and evaporated under reduced pressure. Ethyl acetate (100 ml) was added and the organic phase washed twice with water, dried with sodium sulfate and evaporated under reduced pressure: The product was isolated by silica gel column chromatography. Yield: 3.8 g=45%.

$^1$H-NMR (CDCl$_3$) 1.02 (m, 6H) 2.36 (m, 1H) 4.53 (d, d, 1H) 5.14 (s, 2H) 5.30 (d, 1H) 7.26 (m, 6H) 7.39 (t, 1H) 7.79 (s, 1H) 7.96 (d, 1H)

e) Iodomethyl 3-(N-benzyloxycarbonyl-L-valyloxy)-benzoate

To a solution of chloromethyl 3-(N-benzyloxycarbonyl-L-valyloxy)-benzoate (2.0 g, 4.76 mmole) in dry acetone (30 ml) was added sodium iodide (3.15 g, 21 mmole) and the mixture was stirred overnight at room temperature. The mixture was evaporated under reduced pressure and extracted with ethyl actate/water. The organic phase was washed with a 5% sodium thiosulfate solution, dried with sodium sulfate and evaporated under reduced pressure. Yield: 2.3 g=94%.

$^1$H-NMR (CDCl$_3$) 1.02 (m, 6H) 2.38 (m, 1H) 4.56 (d, d, 1H) 5.14 (s, 2H) 5.30 (d, 1H) 6.14 (s, 2H) 7.26–7.50 (m, 7H) 7.80(s, 1H) 7.96 (d, 1H)

EXAMPLE A-I-13

Iodomethyl 3-(N-benzyloxycarbonyl-L-valyloxy)-propionate

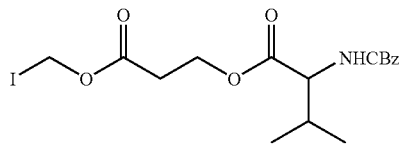

a) 3-buten-1-yl-3-(N-benzyloxycarbonyl)-propionate

To a solution of 3-buten-1-ol (2.16 g, 30 mmole), N-benzyloxycarbonyl-1-valine (8.29 g, 33 mmole) and 4-dimethylaminopyridine (0.37 g, 3 mmole) in dichloromethane (80 ml) was added dicyclohexyl-carbodiimide (7.22 g, 35 mmole) and the mixture was stirred overnight at room temperature. The mixture was cooled and the urethane was filtered. The solution was evaporated under reduced pressure and ethyl acetate (200 ml) was added. The organic phase was washed twice with 5% acetic acid, 5% sodium hydrogencarbonate and water. The organic phase was dried with sodium sulfate and evaporated under reduced pressure. The product was isolated by silica gel column chromatography with hexane/ethyl acetate. Yield: 8.3 g=90%.

$^1$H-NMR (CDCl$_3$) 0.92 (m, 6H) 2.18 (m, 1H) 2.40 (m, 2H) 4.20 (m, 3H) 5.10 (m, 4H) 5.26 (d, 1H) 5.75 (m, 1H) 7.30 (m, 5H)

b) 3-(N-benzyloxycarbonyl-L-valyloxy)-propanoic acid

To a solution of 3-buten-1-yl-3-(N-benzyloxycarbonyl-L-valyloxy)-propionate (9.2 g, 30 mmole) in 150 ml benzene was added tetrabutylammonium bromide (1.62 g, 5 mmole) and 100 ml water. The mixture was cooled to about 5° C. and potassium permanganate (14.82 g, 90 mmole) was added in portions. The mixture was stirred 2 hours at room temperature, diluted with water and decolorized by the addition of sodium bisulfite. The mixture was acidified with 2M hydrogen chloride and extracted 3 times with ethyl acetate. The combined organic phases were washed with water and dried with sodium sulfate. The solution was evaporated under reduced pressure and the product isolated by silica gel column chromatography with hexane/ethyl acetate. Yield: 5.4 g=55%. The compound can be activated and esterified to a drug or further modified as described below.

$^1$H-NMR (DMSO d-6) 0.90 (m, 6H) 2.5 (m, 2H) 3.88 (d, d, 1H) 4.32 (m, 2H) 5.03 (s, 2H) 7.36 (m, 5H) 7.68 (d, 1H)

c) Chloromethyl 3-(N-benzyloxycarbonyl-L-valyloxy)-propionate

To a solution of 3-(N-benzyloxycarbonyl-L-valyloxy)propanoic acid (5.2 g, 16.08 mmole) in 1,4-dioxane (50 ml) was added a 40% solution of tetrabutylammonium hydroxide (10.43 g, 16.08 mmole) and the mixture was stirred 2 hours at room temperature. The mixture was evaporated under reduced pressure and co-evaporated two times with 1,4-dioxane and two times with toluene. The dried product was dissolved in 40 ml dichloromethane and chloroiodomethane (28.4 g. 160 mmole) was added. The solution was stirred for two days at room temperature and evaporated under reduced pressure. Ethyl acetate (100 ml) was added and the organic phase washed twice with water, dried with sodium sulfate and evaporated under reduced pressure. The product was isolated by silica gel column chromatography. Yield: 2.2 g=35%

$^1$H-NMR (CDCl$_3$) 0.90 (m, 6H) 2.14 (m, 1H) 2.75 (m, 2H) 4.38 (m, 3H) 5.11 (s, 2H) 5.71 (s, 2H) 7.36 (m, 5H)

d) Iodomethyl3-(N-benzyloxycarbonyl-L-valyloxy)-propionate

To a solution of chloromethyl 3-(N-benzyloxycarbonyl-L-valyloxy)-propionate (2.05 g, 5.51 mmole) in dry acetone (50 ml) was added sodium iodide (4.12 g, 27.5 mmole) and the mixture was stirred overnight at room temperature. The mixture was evaporated under reduced pressure and extracted with ethyl acetate water. The organic phase was washed with a 5% sodium thiosulfate solution, dried with sodium sulfate and evaporated under reduced pressure. Yield: 2.35 g=92%.

$^1$H-NMR (CDCl$_3$) 0.94 (m, 6H) 2.17 (m, 1H) 2.68 (t, 2H) 4.40 (m, 3H) 5.12 (s, 2H) 5.91 (s, 2H) 7.26 (m, 5H).

EXAMPLE C-I-1

1,3-bis(N-tert-butoxycarbonyl-N-benzyloxycarbonyl-L-valyloxy)-2-propyl 1-iodoethyl carbonate

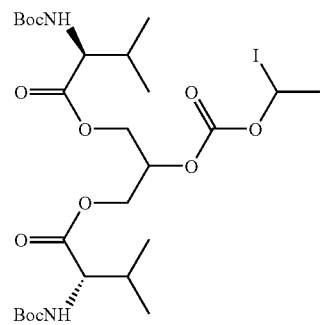

(a) 1,3-bis(N-tert-butoxycarbonyl-L-valyloxy)-2-propyl 1-chloroethyl carbonate

To a solution of 1,3-bis(N-tert-butoxycarbonyl-L-valyloxy)-2-propanol (0.545 g, 1.11 mmol) in 5 mL dry CH$_2$Cl$_2$ were added pyridine (540 µL, 6.68 mmol), with cooling and stirring in an ice bath, followed by 1-chloroethyl chloroformate (242 µL, 2.22 mmol). After 1 h, the reaction mixture was diluted with 5 mL $CH_2Cl_2$ and washed with water (5 mL) and brine (5 mL). The organic phase was dried over anhydrous $Na_2SO_4$ and concentrated on a rotavapor, coevapoating several times with toluene. Column chromatogaphy (silica, 4/1 petroleum ether—ethyl acetate) gave the chloride (596 mg, 90%) as a white solid.

$^1$H NMR (250 MHz, $CDCl_3$) δ 0.77 and 0.83 (2d, 6H each, J=6.8 Hz), 1.31 (s, 18H), 1.70 (d, 3H, J=5.8 Hz), 2.00 (m, 2H), 4.08–4.41 (m, 6H), 5.01–5.09 (m, 3H), 6.30 (q, 1H, J=5.7 Hz).

(b) 1,3-bis(N-tert-butoxycarbonyl-L-valyloxy)-2-propyl 1-iodoethyl carbonate

A mixture of the chloride (596 mg, 1.0 mmol) from step (a) and NaI (684 mg, 4.57 mmol) in 10 ml dry MeCN was refluxed at 80° C. for 4 h. The reaction mixture was concentrated under vacuum and then partitioned between 30 mL diethyl ether and 10 mL water. The organic phase was washed with 5% aqueous sodium thiosulfate (2×5 mL), and the last aqueous layer was reextracted with ether (5 mL). The organic phases were combined, washed with brine, dried over $Na_2SO_4$, and concentrated. Flash column chromatography (silica, 4/1 petroleum ether—ethyl acetate) gave a fraction (275 mg) containing 80% iodide, as determined from $^1$H NMR, and small amounts of the starting chloride and alkene from the elimination side reaction.

$^1$H NMR (250 MHz, $CDCl_3$) δ 0.81–0.85 (m, 6H), 0.88–0.92 (m, 6H), 1.37 (s, 18H), 2.05 (m, 2H), 2.17 (d, 3H, J=6.1 Hz), 4.12–4.46 (m, 6H), 5.00 (d, 2H, J=8.8 Hz), 5.11 (m, 1H), 6.68 and 6.69 (2 sets of q, 1H, J=6.1 Hz).

EXAMPLE A-I-14

3-(N-benzyloxycarbonyl-L-valyloxy)-2,2-dimethylpropyl iodomethyl carbonate

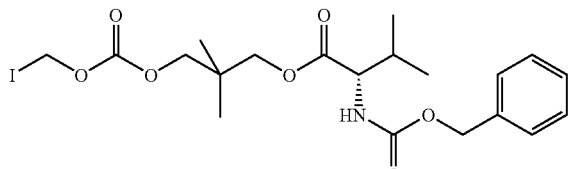

(a) 3-(N-benzyloxycarbonyl-L-valyloxy)-2,2-dimethyl-1-propanol

A mixture of N-benzyloxycarbonyl-L-valine (2.50 g, 10.0 mmol), 2,2-dimethyl-1,3-propanediol (5.30 g, 50.9 mmol), dicyclohexylcarbodiimide (2.60 g, 12.6 mmol), and 4-dimethylaminopyridine (125 mg, 1.0 mmol) in 100 mL dry $CH_2Cl_2$ was stirred for 23 h. The reaction mixture was filtered and washed successively with 50 mL each of water, saturated aqueous $NH_4Cl$, saturated aqueous $NaHCO_3$, and water. The organic phase was dried over anhydrous $Na_2SO_4$ and concentrated. The title compound (2.99 g, 87%) was isolated by flash column chromatography (silica, 2/1 petroleum ether ethyl acetate) as a white waxy solid.

$^1$H NMR (250 MHz, $CDCl_3$) δ 0.89 and 0.97 (2d, 3H each, J=6.8 Hz), 0.90 (s, 6H), 2.16 (m, 1H), 2.49 (br s, 1H), 3.25–3.37 (m, 2H), 3.96 (s, 2H), 4.28 (dd, 1H, J=8.9, 4.8 Hz), 5.09 (s, 2H), 5.41 (d, 1H, J=8.7 Hz), 7.34 (s, 5H).

(b) 3-(N-benzyloxycarbonyl-L-valyloxy)-2,2-dimethylpropyl chloromethyl carbonate Chloromethyl chloroformate (1.50 mL, 16.6 mmol) was added to a solution of the alcohol (2.74 g, 8.12 mmol) from step (a) and pyridine (4.9 mL, 61 mmol) in 40 mL dry $CH_2Cl_2$, in an ice bath. After stirring for 1 h, the mixture was diluted with $CH_2Cl_2$ and washed successively with water, saturated $NaHCO_3$, and brine. The organic phase was dried over anhydrous $Na_2SO_4$ and concentrated, coevaporating several times with toluene on a rotavapor. Flash column chromatography (silica, 2/1 petroleum ether—ethyl acetate) gave 3.31 g (95%) of the title compound.

$^1$H NMR (250 MHz, $CDCl_3$) δ 0.88 and 0.96 (2d, 3H each, J=6.9 Hz), 0.98 (s, 6H), 2.16 (m, 1H), 3.94 and 4.02 (2s, 2H each), 4.31 (dd, 1H, J=9.0, 4.7 Hz), 5.10 (s, 2H), 5.33 (d, 1H, J=9.0 Hz), 5.68 and 5.70 (ABq, 2H, $J_{AB}$=6.3 Hz), 7.34 (s, 5H).

(c) 3-(N-benzyloxycarbonyl-L-valyloxy)-2,2-dimethylpropyl iodomethyl carbonate

A mixture of the chloride (3.14 g, 7.30 mmol) from step (b) and NaI (4.37 g, 29.2 mmol) in 73 mL dry MeCN was refluxed at 80° C. for 3 h. After removal of solvent under vacuum, the mixture was partitioned between 80 mL ethyl acetate and 40 mL water. The organic phase was washed with 5% $Na_2S_2O_3$, and then brine, dried over anhydrous $Na_2SO_4$, and concentrated. Flash column chromatography (silica, petroleum ether—ethyl acetate) gave 3.68 g (97%) of the title compound.

$^1$H NMR (250 M[z, $CDCl_3$) δ0.88 and 0.96 (2d, 3H each), 0.98 (s, 6H), 2.18 (m, 1H), 3.94 and 4.02 (2s, 2H each), 4.32 (dd, 1H, J=9.0, 4.7 Hz), 5.11 (s, 2H), 5.26 (d, 1H), 5.92 and 5.93 (ABq, 2H, JAB=5.1 Hz), 7.35 (s, 5H).

EXAMPLE A-I-15

1-(N-benzyloxycarbonyl-L-valyloxy)-2-methyl-2-propyl iodomethyl carbonate

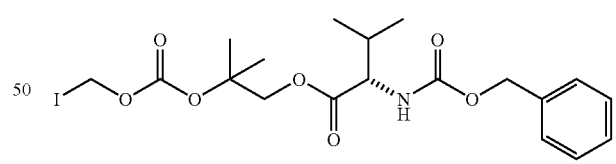

(a) 1-(N-benzyloxycarbonyl-L-valyloxy)-2-methyl-2-propanol

N-Benzyloxycarbonyl-L-valine (2.02 g, 8.0 mmol), 4-dimethylaminopyridine (100 mg, 0.8 mmol), and), and dicyclohexylcarbodiimide (2.04 g, 9.9 mmol, in 20 mL $CH_2Cl_2$) were added to 2-methyl-1,2-propanediol (12.2 mmol) in 30 mL dry $CH_2Cl_2$, with cooling in an ice bath. DMF (5 mL) was added. After stirring for 5 h at 10° C., the reaction mixture was filtered, concentrated, and then redissolved in ethyl acetate. The organic solution was washed with saturated NaCl, dried over anhydrous $Na_2SO_4$, and concentrated. Flash column chromatography (silica, 2/1 petroleum ether—ethyl acetate) gave 2.3 g of the title compound.

$^1$H NMR (250 MHz, CDCl$_3$) δ 0.91 (d, 3H), 0.98 (d, 3H), 1.23 (s, 6H), 2.17 m, 1H), 4.02 (s, 2H), 4.31 (m, 1H), 5.10 (s, 2H), 5.26 (m, 1H), 7.35 (s, 5H).

(b) 1-(N-benzyloxycarbonyl-L-valyloxy)-2-methyl-2-propyl chloromethyl carbonate All of the alcohol from above was dissolved in 35 mL dry CH$_2$Cl$_2$ and cooled in an ice bath. Pyridine (3.50 mL, 43.4 mmol) was added, followed by chloromethyl chloroformate (1.30 mL, 14.4 mmol). After 1 h, the ice bath was removed and stirring was continued for 2 h at ambient temperature. The mixture was diluted with CH$_2$Cl$_2$ (50 mL) and washed with water (50 mL), and then brine (2×25 mL). Drying over anhydrous Na$_2$SO$_4$ of the combined organic phases and concentration under vacuum, coevaporating several times with toluene, gave a yellow-brown oil that was subjected to flash column chromatography (silica, 2/1 petroleum ether—ethyl acetate) to yield 2.86 g (86% from N-benzyloxycarbonyl-L-valine) of the title compound.

$^1$H NMR (250 MHz, CDCl$_3$) δ 0.90 and 0.98 (2d, 3H each, J=6.9 Hz), 1.53 (s, 6H), 2.19 (m, 1H), 4.23 and 4.41 (ABq, 2H, $J_{AB}$=11.8 Hz), 4.36 (dd, 1H, J=9.1, 4.6 Hz), 5.11 (s, 2H), 5.26 (d, 1H, J=9.1 Hz), 5.65 and 5.67 (ABq, 2H, $J_{AB}$=6.3 Hz), 7.36 (br s, 5H).

(c) 1-(N-benzyloxycarbonyl-L-valyloxy)-2-methyl-2-propyl iodomethyl carbonate A mixture of the chloride (2.84 g, 6.84 mmol) from step (b) and NaI (4.15 g, 27.2 mmol) in 68 mL dry acetonitrile was refluxed at 75° C. for 4 h. After evaporation of solvent under vacuum, the residue was partitioned between ethyl acetate (80 mL) and water (40 mL), and the organic layer was washed with 5% Na$_2$S$_2$O$_3$ (15 mL) and brine (25 mL). Drying the organic phase over anhydrous Na$_2$SO$_4$ and concentration gave a yellow oil that was subjected to flash column chromatography (silica, 2/1 petroleum ether—ethyl acetate) to furnish 3.29 g (95%) of the title compound.

$^1$H NMR (250 MHz, CDCl$_3$) δ 0.90 and 0.94 (2d, 3H each, J=6.8 Hz), 1.52 (s, 6H), 2.17 (m, 1H), 4.35 (m, 1H), 4.22 and 4.39 (ABq, 2H, $J_{AB}$=11.7 Hz), 5.10 (s, 2H), 5.30 (d, 1H), 5.86 (s, 2H), 7.34 (s, 5H)

EXAMPLE A-I-16

Iodomethyl 3,4-di-(N-CBZ-L-valyloxy)hydrocinnamate

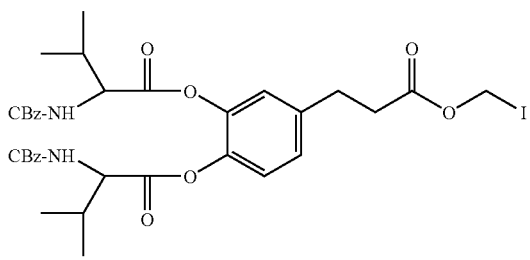

a) 4-Methoxybenzyl-3,4-dihydroxyhydrocinnamate 3,4-Dihydroxycinnamic acid (6.5 g, 35.7 mmol) was dissolved in DMF (50 ml) and cooled to 0° C. on an ice-bath. 4-Potassium tert-butoxide (35.7 mmol), was then added and the mixture was left for approximately 30 min at 0° C., followed by dropwise adition of 4-methoxy-benzylchloride (39 mmol) in DMF (25 ml). The mixture was allowed to reach room temperature and left over-night. The solvent was then evaporated and the crude product was purified by chromatography (ethyl acetate-hexane, 1:1) to give 6 g of the title compound (55%).

$^1$H NMR (CDCl$_3$ 45° C.): 7.24–6.57 (m, 7H), 5.03 (s, 2H), 3.80 (s, 3H), 2.83 (t, 2H), 2.58 (t, 3H).

b) 4-Methoxybenzyl-3,4-di-(N-CBZ-L-valyloxy)hydrocinnamate

4-Methoxybenzyl-3,4-dihydroxyhydrocinnamate (5 g, 16.5 mmol), N,N-dimethylaminopyridine (2 g, 16.5 mmol), N,N'-dicyclohexyl carbodiimide (8.5 g, 41.3 mmol) and Cbz-L-valine (10.4 g, 41.3 mmol) were dissolved in dichloromethane (50 ml). After 4 h, the the mixture was filtered and evaporated onto silica gel and purified by chromatography (hexane-EtOAc, 5:2→3:2) to give pure title product (10.1 g, 79%).

$^1$H NMR (CDCl$_3$ 45° C.): 7.24–6.49 (m, 17H), 5.6 (br s, 2H), 5.0 (m, 6H), 4.45 (m, 1H)), 3.79 (s, 3H), 2.94 (t, 2H), 2.65 (t, 2H), 2.4–2.25 (br m, 2H), 1.03 (m, 12H)

c) 3,4-Di-(N-CBZ-L-valyloxy)hydrocinnamic acid

4-Methoxybenzyl-3,4-di-(N-CBZ-L-valyloxy)hydrocinnamate (10 g, 13 mmol) was dissolved in dichloromethane and 1,1,1 trifluoroacetic acid (30 ml) and left at ambient temperature for 3.5 h. Evaporation under reduced pressure and purification by chromatography (chloroform-methanol, 10:1) yielded 6.7 g (80%) pure title product. The compound can be activated and esterified to a drug or further modified as described below.

$^1$H NMR (CDCl$_3$ 45° C.): 7.24–7.0 (m, 13H), 5.65 (br s, 1H), 5.55 (br s, 1H), 5.1 (m, 4H), 4.46 (m, 2H), 2.95 (t, 2H), 2.66 (t, 2H), 2.35 (m, 2H).

d) Chloromethyl 3,4-di-(N-CBZ-L-valyloxy)hydrocinnamate 3,4-Di-(N-CBZ-L-valyloxy)hydrocinnamic acid (4.2 g, 6.47 mmol) was dissolved in dioxane (70 ml). Tetrabutylammonium hydroxide was added dropwise until pH=8. The solvent was then removed under reduced pressure The solid was redissolved in dioxane (30 ml) and toluene (30 ml) and evaporated. The procedure was repeated twice (for removal of water). Dichloromethane (60 ml) and chloro-iodomethane was added in one portion and the mixture was left at ambient temperature for 6 h. Evaporation of the solvent and purification by chromatography yielded 1.7 g title product (38%).

$^1$H NMR (CDCl$_3$ 45° C.): 7.3–7.0 (m, 13H), 5.67 (s, 2H), 5.62 (br s, 2H), 5.14–5.0 (m, 4H), 4.46 (m, 2H), 2.95 (t, 2H), 2.67 (m, 2H), 1.07–0.99 (m, 12H)

e) Iodomethyl 3,4-di-(N-CBZ-L-valyloxy)hydrocinnamate

Chloromethyl 3,4-di-(N-CBZ-L-valyloxy)hydrocinnamate (1.9 g, 2.7 mmol) and sodium iodide (2 g, 13.3 mmol) were dissolved in acetonitrile (50 ml) and heated to 65° C. for 60 min. The solvent was removed under reduced pressure and the residue was taken up in dichloromethane and filtrated. Removal of the solvent and purification by chromatography (ethyl acetate-hexane, 2:5) gave pure title product (1.9 g, 90%)

$^1$H NMR (CDCl$_3$ 45° C.): 7.34–7.02 (m, 13H), 5.89 (s, 2H), 5.64 (br s, 2H), 5.14–5.02 (m, 4H), 4.47 (m, 2H), 2.96 (t, 2H), 2.64 (t, 2H), 2.33 (m, 2H), 1.08–0.99 (m, 12H)

EXAMPLE A-I-17

3-(N-CBZ-L-valyloxy)phenyl iodomethyl carbonate

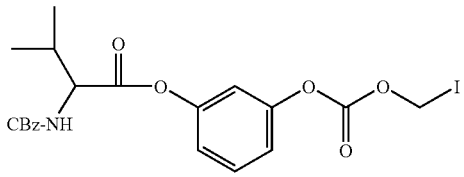

a) 3-(N-CBz-L-valyloxy)phenol

CBz-L-valine (10 g, 40 mmol), 1,3-dihydroxybenzene (8.7 g, 79 mmol) N,N'dicychlohexylcarbodiimide (10.2 g, 44 mmol) and 4-dimethylaminopyridine (2.4 g, 20 mmol) were dissolved in DMF (50 ml) and left at ambient temperature overnight. The reaction mixture was filtered, the solvent removed under reduced pressure and the crude product was taken up in dichloromethane and filtered. Removal of the solvent followed by purification by chromatography (chloroform-methanol, 10:1) yielded pure title product (10.9 g, 79%).

$^1$H NMR (CDCl$_3$ 45° C.): 7.36–7.32 (m, 6H, 7.20 (t, 1H), 6.71–6.55 (m, 2H), 5.2 (br s, 1H), 5.14 (s, 2H), 4.5 (br s, 1H), 2.4–2.3 (m, 1H), 1.09–1.01 (m, 6H)

b) (N-CBZ-L-valyloxy)phenyl chloromethyl carbonate 3-(N-CBz-L-valyloxy)phenol (5.4 g, 15 7 mmol) was dissolved in dichloromethane (70 ml) and cooled in an ice-bath. Pyridine (1.2 g, 23.5 mmol was added followed by dropwise addition of 1-chloro-methylchloroformate (2.3 g, 18.8 mmol) in dichloromethane (10 ml). The mixture was left at room temperature for 4 h. Water (25 ml) was then added and the phases were separated. The organic layer was washed with 0.01 M aqueous hydrochloric acid (25 ml). Purification by chromatography (ethyl acetate-hexane, 1:1) gave the title compound (4.5 g, 65%)

$^1$H NMR (CDCl$_3$ 45° C.): 7.38–7.02 (m, 9H), 5.81 (s, 2H), 5.2 (br s, 1H), 5.14 (s, 2H), 4.48 (m, 1H), 2.30 (m, 1H), 1.09–1.01 (m, 6H)

c) 3-(N-CBZ-L-valyloxy)phenyl iodomethyl carbonate (N-CBZ-L-valyloxy)phenyl chloromethyl carbonate (1.5 g, 3.44 mmol) and sodium iodide (2 g, 13.3 mmol) were stirred at 60° C. in acetonitrile (50 ml) for 4.5 h. The mixture was filered, the solvent removed and the crude product was taken up in 100 ml hexane-ethyl acetate, 1:1, and filtered through a sintered glass funnel, packed with 2 cm silica gel. Removal of the solvent yielded pure title product (1.68 g, 92%)

$^1$H NMR (CDCl$_3$ 45° C.): 7.38–7.02 (m, 9H), 6.03 (s, 2H), 5.2 (br s, 1H), 5.14 (s, 2H), 4.48 (m, 1H), 2.30 (m, 1H), 1.09–1.01 (m, 6H)

EXAMPLE A-I-18

Iodomethyl 2-(N-CBZ-L-valyloxy]phenylacetate

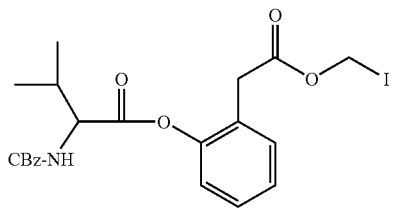

a) 4-Methoxybenzyl 2-hydroxyphenylacetate 2-hydroxyphenylacetic acid (10 g, 66 mmol) was dissolved in N,N-dimethylformamide (100 ml) and cooled on ice-bath. Potassium tert-butoxide (8.85 g, 78 mmol) was added. The mixture was left for 30 min and allowed to reach room temperature. 4-Methoxy-benzylchloride (11.7 g, 72 mmol) in N,N-dimethylformamide (30 ml) was then added dropwise, under nitrogen atmosphere and left over-night. The solvent was evaporated under reduced pressure and the crude mixture was dissolved in ether (100 ml) and washed with water (25 ml), brine and dried over sodium sulphate. Chromatography (hexane-ethyl acetate, 2:1) followed by recrystallization (hexane-ethyl acetate) gave the title compound (7.6 g, 42%).

$^1$H NMR (CDCl$_3$ 45° C.): 7.3–6.8 (m, 8H), 5.01 (s, 2H), 3.81 (s, 3H), 3.67 (s, 2H).

b)-4-Methoxybenzyl 2-(N-CBz-L-valyloxy)phenylacetate

4-Methoxybenzyl 2-hydroxyphenylacetate 3 g, 11 mmol), N,N,-dichyclohexyl-carbodiimide (2.7 g, 13.2 mmol), dimethylaminopyridine (0.134 g, 1.1 mmol) and CBz-L-valine (3.3 g, 13.2 mmol) were dissolved in dichloromethane (50 ml). After the weekend the solid was filtered off, the solvent removed under reduced pressure and the crude product purified by chromatography (ethyl acetate, hexane, 1:2) to give the title compound (5.2 g, 93%).

$^1$H NMR (CDCl$_3$ 45° C.): 7.36–6.80 (m, 13H), 5.4 (br s, 1H), 5.12 (s, 2H), 5.03 (s, 2H) 4.50 (m, 1H), 3.79 (s, 3H), 3.56 (s, 2H), 2.30 (m, 1H), 1.04 (d, 3H), 0.97 (d, 3H)

c) 2-(N-CBz-L-valyloxy)phenylacetic acid

4-Methoxybenzyl 2-(N-CBz-L-valyloxy)phenylacetate (4.25 g, 8.4 mmol), was dissolved in dichloromethane (40 ml). Triflouroacetic acid (8 ml) was added with cooling on ice. The mixture was allowed to reach room temperature and stirred for 40 min. The solvent was removed under reduced pressure and the crude product was recrystallized twice (hexan-ethyl acetate+a small amount of dichloromethane) to give the title compound (2.6 g, 80%). The compound can be activated and esterified to a drug or further modified as described below.

$^1$H NMR (CDCl$_3$ 45° C.): 7.35–7.08 (m, 9H), 5.35 (br s, 1H), 5.13 (s, 2H), 4.48 (m, 1H), 3.57 (s, 2H), 2.33 (m, 1H), 1.08 (d, 3H), 1.02 (d, 3H).

d) Chloromethyl 2-(N-CBZL-valyloxy)phenylacetate

This compound was prepared in poor yield from 2-(N-CBz-L-valyloxy)phenylacetic acid (5.5 g, 14.3 mmol) by an unoptimized procedure essentially as described in Example A-I-16 d). Yield: 0.265 g $^1$H NMR (CDCl$_3$ 45° C.): 7.28–7.01 (m, 9H), 5.55 (s, 2H), 5.2 (br s, 1H), 5.07 (s, 2H), 4.43 (m, 1H), 3.53 (s, 2H), 2.26 (m, 1H), 1.02 (d, 3H), 0.95 (d, 3H).

e) Iodomethyl 2-(N-CBZ-L-valyloxy)phenylacetate

Chloromethyl 2-(N-CBZ-L-valyloxy)phenylacetate is treated with NaI and purified as described in the Examples above to yield the title compound.

EXAMPLE A-I-19

Iodomethyl 4-(N-CBZ-L-valyloxyxy)phenylacetate

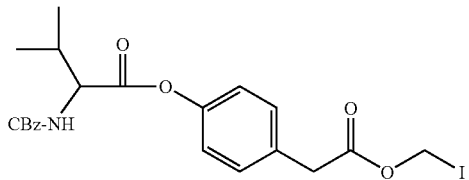

a) 4-Methoxybenzyl 4-hydroxyphenylacetate

Prepared from 4-hydroxyphenylacetic acid (10 g, 65.7 mmol) in 70% yield by the same procedure as for Example A-I-18 a) above, but wherein the solvent for the recrystallization was changed to hexane-ether.

$^1$H NMR (CDCl$_3$ 45° C.): 7.25 (d, 2H), 7.12 (d, 2H), 6.87 (d, 2H), 6.76 (d, 2H), 5.06 (s, 2H), 3.80 (s, 3H), 3.56 (s, 2H).

b) 4-Methoxybenzyl 4-(N-CBz-L-valyloxy)phenylacetate

Prepared from 4-methoxybenzyl 4-hydroxyphenylacetate (3 g, 11 mmol) by the same procedure as for Example A-I-18 b) in 87% yield. Solvent for chromatography: ethyl acetate-hexane, 1:2

$^1$H NMR (CDCl$_3$ 45° C.): 7.38–7.22 (m, 9H), 6.9 (d, 2), 6.86 (d, 2H), 5.3 (br s, 1H), 5.14 (s, 2H), 5.06 (s, 2H), 3.80 (s, 3H), 3.62 (s, 2H), 2.35 (m, 1H), 1.08 (d, 3H), 1.02 (d, 3H).

c) 4-(N-CBZ-L-valyloxy)phenylacetic acid

Prepared in 82% yield from 4-methoxybenzyl 4-(N-CBz-L-valyloxy)phenylacetate (1.6 g, 288 mmol) by the procedure described for Example A-I-18 c). Solvent for recrystallization: hexane-ether and a small amount of dichloromethane. The compound can be activated and esterified to a drug or further modified as described below.

$^1$H NMR (CDCl$_3$ 45° C.): 7.36–7.27 (m, 7H), 7.02 (d, 2H), 5.25 (d, 1H), 5.14 (s, 2H), 4.52 (m, 1H), 3.64 (s, 2H), 2.3 (m, 1H), 1.08 (d, 3H), 1.02 (d, 3H).

d) Chloromethyl 4-(N-CBZL-valyloxy)phenylacetate

Prepared from 4-(N-CBZ-L-valyloxy)phenylacetic acid (3 g, 7.8 mmol) in 26% yield by the same procedure as described for Example A-I-18 d). Solvent for chromatography: hexane-ether, 3:2.

$^1$H NMR (CDCl$_3$ 45° C.): 7.30–6.95 (m, 4H), 5.51 (s, 2H), 5.15 (br s, 1H), 5.07 (s, 2H), 4.43 (m, 1H), 3.60 (s, 2H) 2.25 (m, 1H), 1.00 (d, 3H), 0.95 (d, 3H).

e) Iodomethyl 4-(N-CBZL-valyloxy)phenylacetate

Chloromethyl 4-(N-CBZ-L-valyloxy)phenylacetate (0.83 g, 1.9 mmol) and sodium iodide (1.15 g, 7.6 mmol) were heated in acetonitril (45 ml) for 5 h. The mixture was filtered, the solvent removed, taken up in dichloromethane and filtrated again. Evaporation and purification by chromatography (ether-hexane, 2:3) yielded the title product (0.8 g, 80%).

$^1$H NMR (CDCl$_3$ 45° C.): 7.38–7.09 (m, 4H), 5.84 (s, 1H), 5.30 (br s, 1H), 5.15 (s, 2H), 4.5 (m, 1H), 3.56 (s, 2H), 2.36 (m, 1H), 1.10 (d, 3H), 1.00 (d, 3H).

EXAMPLE A-I-20

Iodomethyl 4-(2-N-benzyloxycarbonyl-L-valyloxyethyl) benzoate a) 4-(2-N-benzyloxycarbonyl-L-valyloxyethyl)toluene

To a cooled solution of 4-methylphenylethanol-2 (5.0 g, 36.7 mmole), 4-dimethylaminopyridine (0.98 g, 8 mmole) and N-benzyloxycarbonyl-L-valine (10.05 g, 40 mmole) in dichloromethane (120 ml) was added dicyclohexylcarbodiimide (9.1 g, 44 mmole) and the mixture was stirred overnight at room temperature. The mixture was cooled and the urethane was filtered. The solution was evaporated under reduced pressure and ethyl acetate (250 ml) was added. The organic phase was washed twice with 5% acetic acid, 5% sodium hydrogencarbonate and water. The organic phase was dried with sodium sulfate and evaporated under reduced pressure. The product was isolated by silica gel column chromatography with toluene/acetone. Yield: 13.3 g=97%

$^1$H-NMR (CDCl$_3$) 0.86 (m, 6H) 2.12 (m, 1H) 2.32 (s, 3H) 2.91 (m, 2H) 4.32 (m, 3H) 5.12 (s, 2H) 5.24 (d, 2H) 7.10–7.36 (m, 9H)

b) 4-(2-N-benzyloxycarbonyl-L-valyloxyethyl)-benzoic acid

To a cooled mixture of chromic anhydride (7.55 g, 75 mmole) in acetic acid (100 ml) was added dropwise a solution of 4-(2-N-benzyloxycarbonyl-L-valyloxyethyl) toluene (9.3 g, 25.1 mmole) in acetone (50 ml). The mixture was stirred at room temperature for 3 days and reduced to about 100 ml. 600 ml 10% sodium chloride solution was added and the mixture was extracted four times with ethyl acetate. The organic phase was washed with brine and dried with sodium sulfate. The solution was evaporated under reduced pressure and the product was islolated by silica gel column chromatography with dichloromethane/methanol. Yield: 2,1 g=21%. The product can be activated and esterified directly onto a drug or further modified as described below.

¹H-NMR (CDCl₃) 0.79 (d, 3H) 0.90 (d, 3H) 2.08 (m, 1H) 3.04 (t, 2H) 4.28 (d, d, 1H) 4.39 (m, 2H) 5.11 (s, 2H) 5.26 (d, 1H) 7.34 (m, 7H) 8.04 (d, 2H)

c) Chloromethyl 4-(2-N-benzyloxycarbonyl-L-valyloxyethyl)benzoate

To a solution of 4-(2-N-benzyloxycarbonyl-L-valyloxyethyl)benzoic acid (2.0 g, 5.0 mmole) in 1,4-dioxane (20 ml) was added a 40% solution of tetrabutylammonium hydroxide (3.1 g, 4.75 mmole) and the mixture was stirred 2 hours at room temperature. The mixture was evaporated under reduced pressure and coevaporated two times with 1,4-dioxane and two times with toluene. The dried product was dissolved in dichloromethane (10 ml) and iodochloromethane (13.2 g, 75 mmole) was added The solution was stirred overnight at room temperature and evaporated under reduced pressure. About 50 ml ethyl acetate were added and the organic phase washed twice with water, dried with sodium sulfate and evaporated under reduced pressure. The product was isolated by silica gel column chromatography. Yield: 0.5 g=23%

¹H-NMR (CDCl₃) 0.79 (d, 3H) 0.92 (d, 3H) 2.12 (m, 1H) 3.03 (t, 2H) 4.28 (d, d, 1H) 5.10 (s, 2H) 5.22 (d, 1H) 5.94(s, 2H) 7.34 (m, 7H) 8.02 (d, 2H)

d) Iodomethyl 4-(2-N-benzyloxycarbonyl-L-valyloxyethyl) benzoate

To a solution of chloromethyl 4-(2-N-benzyloxycarbonyl-L-valyloxyethyl) benzoate (0.5 g, 1.11 mmole). In dry acetone (10 ml) was added sodium iodide (0.75 g, 5.0 mmole) and the mixture was stirred overnight at room temperature. The mixture was evaporated under reduced pressure and extracted with ethyl actate/water. The organic phase was washed with a 5% sodium thiosulfate solution, dried with sodium sulfate and evaporated under reduced pressure. Yield: 0.53 g=88%.

¹H-NMR (CDCl₃) 0.88 (d, 3H) 0.90 (d, 3H) 2.08 (m, 1H) 3.02 (t, 2H) 4.28 (d, d, 1H) 4.38 (m, 2H) 5.10 (s, 2H) 5.22 (d, 1H) 6.15 (s, 2H) 7.35(m, 7H) 7.98 (d, 2H)

EXAMPLE A-I-21

Iodomethyl 2-(N-benzyloxycarbonyl-L-isoleucvloxymethyl) 2-methyl propionate a) 4-methoxybenzyl 2-(N-benzyloxycarbonyl-L-isoleucyloxymethyl)-2-methyl propionate To a cooled solution of 4-methoxybenzyl 2-(hydroxymethyl)-2-methyl propionate (6.0 g, 25 mmole), 4-dimethylaminopyridine (0.61 g, 5 mmole) and N-benzyloxycarbonyl-L-isoleucine (6.90 g, 26 mmole) in dichloromethane (100 ml) was added dicyclohexyl-carbodiimide (6.2 g, 30 mmole) and the mixture was stirred overnight at room temperature. The mixture was cooled and the urethane was filtered. The solution was evaporated and 200 ml ethyl acetate was added, The organic phase was washed twice with 5% acetic acid, 5% sodium hydrogencarbonate and water. The organic phase was dried with sodium sulfate and evaporated under reduced pressure. The product was isolated by silica gel column chromatography with toluene/acetone. Yield: 11.7 g=96%.

¹H-NMR (CDCl) 0.88 (m, 6H) 1.22 (m, 8H) 1.82 (m, 1H) 3.80 (s, 3H) 4.18 (d, d, 2H) 4.32 (d, d, 1H) 5.12 (m, 5H) 6.90 (d, 2H) 7.26 (m, 7H)

2-(N-benzyloxycarbonyl-L-isoleucyloxymethyl)-2-methyl) propionic acid.

To a solution of 4-methoxybenzyl 2-(N-benzyloxycarbonyl-L-isoleucyloxymethyl)-2-methyl propionate (11.0 g, 22.6 mmole) in 100 ml dichloromethane was added trifluoroacetic acid (15 ml) and the mixture was stirred overnight at room temperature. The solution was evaporated under reduced pressure and coevaporated two times with toluene. The residue was stirred 1 hour with 100 ml ethanol and the white solid was filtered (byproduct). The solution was evaporated under reduced pressure and the product was isolated by silica gel column chromatography with hexane/ethyl acetate. Yield: 7.4 g=89%. The product can be activated and esterified directly to a drug, or further modified as described below.

¹H-NMR (CDCl₃) 0.90 (m, 6H) 1.26 (m, 8H) 1.88 (m, 1H) 4.12 (d, d, 2H) 4.38 (d, d, 1H) 5.10 (s, 2H) 5.32 (d, 1H) 7.28 (m, 5H)

c) Chloromethyl 2-(N-benzyloxycarbonyl-L-isoleucyloxy)-2-methyl propionate

To a solution of 2-(N-benzyloxycarbony-L-isoleucyloxymethyl)-2-methyl propionic acid (7.0 g, 19 mmole) in 80 ml 1,4-dioxane was added a 40% solution of tetrabutylammonium hydroxide (12.4 g, 19 mmole) and the mixture was stirred 2 hours at room temperature. The mixture was evaporated under reduced pressure and co-evaporated two times with 1,4-dioxane and two times with toluene. The dried product was dissolved in 25 ml dichloromethane and iodochloromethane (33.7 g, 190 mmole) was added. The solution was stirred overnight at room temperature and evaporated under reduced pressure. About 100 ml ethyl actate was added and the organic phase washed twice with water, dried with sodium sulfate and evaporated under reduced pressure. The product was isolated by silica gel column chromatography with toluene/acetone. Yield: 4.2=54%

¹H-NMR (CDCl₃) 0.94 (m, 6H) 1.26 (m, 8H) 1.90 (m, 1H) 4.15 (d, d, 2H) 4.38 (d, d, 1H) 5.10 (s, 2H) 5.24 (d, 1H) 5.70 (s, 2H) 7.35 (m, 5H).

d) Iodomethyl 2-(N-benzyloxycarbonyl-L-isoleucyloxymethyl)-2-methyl propionate To a solution of chloromethyl 2-(N-benzyloxycarbonyl-L-isoleucyloxymethyl)-2-methyl propionate (3.0 g, 7.2 mmole) in 50 ml dry acetone was added sodium iodide (4.8 g, 32 mmole) and the mixture was stirred overnight at room temperature. The mixture was evaporated under reduced pressure and extracted with ethyl actate water. The organic phase was washed with a 5% sodium thiosulfate solution, dried with sodium sulfate and evaporated under reduced pressure. Yield: 3.3 g=90%.

¹H-NMR (CDCl₃) 0.93 (m, 6H) 1.23 (m, 8H) 4.12 (m, 2H) 4.38 (d, d, 1H) 5.10 (s, 2H) 5.26 (d, 1H) 5.92 (m, 2H) 5.35 (m, 5H)

EXAMPLE A-I-22

Iodomethyl 4-(N-benzyloxycarbonyl-L-valyloxy)cyclohexanoate a) 4-Methoxybenzyl 4-hydroxycyclohexanoate

To a solution of ethyl 4-hydroxycyclohexanoate (8.61 g, 50 mmole) in 50 ml ethanol was added a solution of potassium hydroxide 85% (3.63 g, 55 mmole) and the mixture was stirred for 6 hours at 70° C. The mixture was evaporated under reduced pressure, coevaporated two times with N,N-dimethylformamide and reduced to about 100 ml. 4-Methoxybenzyl chloride (9.4 g, 60 mmole) was added and the mixture was stirred for 18 hours at 60° C. The mixture was evaporated under reduced pressure and 250 ml ethyl acetate was added. The organic phase was washed five times with water, dried with sodiun sulfate and evaporated under reduced pressure. Yield: 13.2 g=100% (crude)

$^1$H-NMR (CDCl$_3$) 1.50–2.02 (m, 8H) 2.38 (m, 1H) 3.58–3.92 (m, 4H) 5.05 (d, 2H) 6.89 (m, 2H) 7.27 (m, 2H)

b) 4-methoxybenzyl 4-(N-benzyloxycarbonyl-L-valyloxy)cyclohexanoate

To a cooled solution of 4-methoxybenzyl 4-hydroxycyclohexanoate (7.5 g, 28 mmole), 4-dimethylaminopyridine (0.73 g, 6 mmole) and N-benzyloxycarbonyl-Lvaline (7.54 g, 30 mmole) in dichloromethane (90 ml) was added dicylohexylcarbodiimide (6.8 g, 33 mmole) and the mixture was stirred for 2 days at room temperature. The mixture was cooled and the urethane was filtered. The solution was evaporated and 250 ml ethyl acetate was added. The organic phase was washed twice with 5% acetic acid, 5% sodium hydrogencarbonate and water. The organic phase was dried with sodium sulfate and evaporated under reduced pressure. The product was isolated by silica gel column chromatography with toluene/acetone. Yield: 13 g=93%

$^1$H-NMR (DMSO d-6) 0.88 (m, 6H) 1.56–2.12 (m, 10H) 3.72 (s, 3H) 3.90 (m, 1H) 5.04 (d, 4H) 6.91 (d, 2H) 7.34 (m, 7H) 7.67 (d, 1H).

c) 4-(N-benzyloxycarbonyl-L-valyloxy) cyclohexanoic acid

To a solution of 4-methoxybenzyl 4-(N-benzyloxycarbonyl-L-valyloxy)cyclohexanoate (12 g, 24.1 mmole) in dichloromethane (100 ml) was added trifluoroacetic acid (20 ml) and the mixture was stirred for 3 hours at room temperature. The solution was evaporated under reduced pressure and coevaporated two times with toluene. The residue was stirred 1 hour with about 100 ml ethanol and the white solid was filtered (byproduct). The solution was evaporated under reduced pressure and the product was isolated by silica gel column chromatography with toluene/acetone. Yield: 6.8 g=74%. The product can be activated and esterified directly to a drug or further modified as described below.

$^1$H-NMR (CDCl$_3$) 0.91 (m, 6H) 1.52–2.54 (m, 10H) 4.28 (m, 1H) 4.82–5.08 (m, 1H) 5.11 (s, 2H) 5.28 (d, 1H) 7.36 (m, 5H)

d) Chloromethyl 4-(N-benzyloxycarbonyl-L-valyloxy)-cyclohexanoate

To a solution of 4-(N-benzyloxycarbonyl-L-valyloxy) cyclohexanoic acid (6.6 g, 20 mmole) in 1,4-dioxane (70 ml) was added a 40% solution of tetrabutylammonium hydroxide (11.34 g, 17.5 mmole) and the mixture was stirred 2 hours at room temperature. The mixture was evaporated under reduced pressure and co-evaporated two times with 1,4-dioxane and two times with toluene. The dried product was dissolved in 60 ml dichloromethane and iodochloromethane (30.9 g, 175 mmole) was added. The solution was stirred for two days at room temperature and evaporated under reduced pressure. About 100 ml ethyl actate was added and the organic phase washed twice with water, dried with sodium sulfate and evaporated under reduced pressure. The product was isolated by silica gel column chromatography with toluene/acetone. Yield: 4.1 g=55%.

$^1$H-NMR (CDCl$_3$) 0.92 (m, 6H) 1.54–2.58 (m, 10H) 4.32 (m, 1H) 4.78–5.08 (m, 1H) 5.11 (s, 2H) 5.72 (d, 2H) 7.36 (m, 5H)

e) Iodomethyl 4-(N-benzyloxycarbonyl-L-valyloxy)-cyclohexanoate

To a solution of chloromethyl 4-(N-benzyloxycarbonyl-L-valyloxy)-cyclohexanoate (4.0 g, 9.4 mmole) in dry acetone (50 ml) was added sodium iodide (6.3 g, 42 mmole) and the mixture was stirred overnight at room temperature. The mixture was evaporated under reduced pressure and extracted with ethyl actate water. The organic phase was washed with a 5% sodium thiosulfate solution, dried with sodium sulfate and evaporated under reduced pressure. Yield 4.5 g=93%.

$^1$H-NMR (CDCl$_3$) 0.90 (m, 6H) 1.52–2.02 (m, 8H) 2.18 (m, 1H) 2.43 (m, 1H) 4.30 (m, 1H) 4.76–5.08 (m, 1H) 5.11 (s, 2H) 5.26 (d, 1H) 5.91 (d, 2H) 7.34 (m, 5H)

EXAMPLE A-I-23

Iodomethyl 2-(N-benzyloxycarbonyl-L-valyloxymethyl)-2-ethyl butyrate

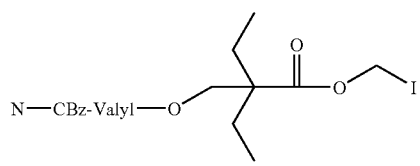

a) 2-(N-benzyloxycarbonyl-L-valyloxymethyl)-2-ethylbutan-1-ol

To a cooled solution of 2-ethyl-2-hydroxymethyl-butan-1-ol (33.1 g, 250 mmole), 4-dimethylaminopyridine (1.22 g, 10 mmole) and N-benzyloxycarbonyl-L-valine (12.6 g, 50 mmole) in 350 ml dichloromethane was added dropwise a solution of dicyclohexyl-carbodiimide (12.4 g, 60 mmole) in 50 ml dichloromethane. The mixture was stirred 2 days at room temperature and cooled. The urethane was filtered and the solution evaporated under reduced pressure. 350 ml ethyl acetate was added and the organic phase was washed twice with 5% acetic acid, 5% sodium-hydrogencarbonate and water. The organic phase was dried with sodium sulfat and evaporated under reduced pressure. The product was isolated by silica gel column chromatography with dichloromethane/methanol. Yield: 16.4 g=90%.

¹H-NMR (CDCl₃) 0.92 (m, 12H) 1.26 (m, 4H) 2.14 (m, 1H) 3.36 (d, 2H) 4.01 (d, 2H) 4.38 (d, d, 1H) 4.65 (br, 1H) 5.11 (s, 2H) 5.30 (d, 1H) 7.35 (m, 5H)

c) 2-(N-benzyloxycarbonyl-L-valyloxymethyl)-2-ethyl-butyric acid

To a cooled mixture of chromic anhydride (8.5 g, 85,2 mmole) in 100 ml acetic acid was added dropwise a solution of 2-(N-benzyloxycarbonyl-L-valyoxymethyl)-2-ethyl-butan-1-ol (10.4 g, 28.4 mmole) in 50 ml acetone and the mixture was stirred 24 hours at room temperature. The mixture was added to 1000 ml 10% sodium chloride solution and extracted four times with ethyl acetate. The organic phase was washed twice with brine, dried with sodium sulfate and evaporated under reduced pressure. The product was isolated by silica gel column chromatography with hexane/ethyl acetate. Yield: 7 g=65%. The product can be activated and esterified directly to a drug or futher modified as described below.

¹H-NMR (CDCl₃) 0.88 (m, 12H) 1.67 (m, 4H) 2.14 (m, 1H) 4.26 (m, 3H) 5.10 (s, 2H) 5.30 (d, 2H) 7.34 (m, 5H)

d) Chloromethyl 2-(N-benzyoxycarbonyl-L-valyloxymethyl-2-ethyl butyrate

To a solution of 2-(N-benzyloxycarbony-L-valyloxymethyl)₂-ethyl-butyric acid (7.2 g, 18,9 mmole) in 1,4-dioxane (80 ml) was added a 40% solution of tetrabutylammonium hydroxide (12.26 g, 18.9 mmole) and the mixture was stirred 2 hours at room temperature. The mixture was evaporated under reduced pressure and co-evaporated once with 1,4-dioxane and two times with toluene. The dried product was dissolved in 30 ml dichloromethane and iodochloromethane (49.4 g, 280 mmole) was added. The solution was stirred for two days at room temperature and evaporated under reduced pressure. About 100 ml ethyl actate were added and the organic phase washed twice with water, dried with sodium sulfate and evaporated under reduced pressure. The product was isolated by silica gel column chromatography. Yield: 5.2 g=63%.

¹H-NMR (CDCl₃) 0.92 (m, 12H) 1.68 (m, 4H) 2.18 (m, 1H) 4.28 (m, 3H) 5.10 (s, 2H) 5.24 (d, 1H) 5.72 (s, 2H) 7.35 (m, 5H).

e) Iodomethyl 2-(N-benzyloxycarbonyl-L-valyloxymethyl)-2-ethyl butyrate

To a solution of chloromethyl 2-(N-benzyloxycarbonyl-L-valyloxymethyl)-2-ethyl butyrate (5.0 g, 11.7 mmole) in dry acetone (60 ml) was added sodium iodide (7.5 g, 50 mmole) and the mixture was stirred overnight at room temperature. The mixture was evaporated under reduced pressure and extracted with ethyl actate water. The organic phase was washed with a 5% sodium thiosulfate solution, dried with sodium sulfate and evaporated under reduced pressure. Yield: 5.4 g=90%.

¹H-NMR (CDCl₃) 0.92 (m, 12H) 1.65 (m, 4H) 2.18 (m, 1H) 4.28 (m, 3H) 5.10 (s, 2H) 5.22 (d, 1H) 5.92 (s, 2H) 7.36 (m, 5H)

EXAMPLE A-I-24

2-(N-(iodomethoxycarbonyl)-amino)-2-methv-1-(N-benzyloxycarbonyl-L-valyloxy)-propane

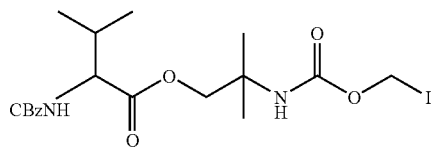

a) 2-(N-tert.-butyloxycarbonyl)-amino)-2-methyl-1-(N-benzyloxycarbonyl-L-valyloxy)-propane To a cooled solution of 2-(N-(tert.-butyloxycarbonyl)-amino)-2-methylpropan-1-ol (J. Am. Chem. Soc 113 (1991) p 8883) (4.73 g, 25 mmole), 4-dimethylaminopyridine (0.61 g, 5 mmole) and N-benzyloxycarbonyl-L-valine (6.28 g, 25 mmole) in dichloromethane (70 ml) was added dicyclohexyl-carbodiimide (6.19 g, 30 mmole) and the mixture was stirred 2 days at roommtemperature. The mixture was cooled, the urethane was filtered and the solution evaporated under reduced pressure. Ethyl acetate (200 ml) was added and the organic phase was washed twice with 5% acetic acid, 5% sodium hydrogencarbonate and water. The organic phase was dried with, sodium sulfate and evaporated under reduced pressure. The product was isolated by silica gel column chromatography with hexane/ethyl acetate. Yield: 10.2 g=96%.

¹H-NMR (CDCl₃) 0.96 (m, 6H) 1.32 (s, 6H) 1.42 (s, 9H) 2.20 (m, 1H) 4.08–4.58 (m, 3H) 5.11(s, 2H) 5.32 (d, 1H) 7.36 (m, 5H)

b) 2-amino-2-methyl-1-(N-benzyloxycarbonyl-L-valyloxy)-propane

To a solution of 2-(N-(tert.-butyloxycarbonyl)-amino)₂-methyl-1-(N-benzyloxycarbonyl-L-valyloxy)-propane (10 g, 23 mmole) in dichloromethane (150 ml) was added trifluoroacetic acid (30 ml) and the mixture was stirred for 1 hour at room temperature. The solution was evaporated under reduced pressure and 10% sodium carbonate solution was added. The product was extracted four times with dichloromethane, dried with sodium sulfate and evaporated under reduced pressure.

The product was isolated by silica gel column chromatography with dichloromethane/methanol. Yield: 3.0 g=40% (crude)

c) 2-(N-(chloromethoxycarbonyl)-amino)-2-methyl-1-(N-benzyloxycarbonyl-L-valyloxy)-propane To a solution of 2-amino-2-methyl-1-(N-benzyloxycarbonyl-L-valyloxy)-propane (2.9 g, 9 mmole) and pyridine (2 ml) in dichloromethane (50 ml) was added chloromethyl chloroformate(1.55 g, 12 mmole) and the mixture was stirred for 3 hours at room temperature. The mixture was evaporated under reduced pressure and ethyl acetate was added. The organic phase was washed with water, dried with sodium sulfate and evaporated under reduced pressure. The product was isolated by silica gel column chromatography with hexane/ethyl acetate. Yield: 1.1 g=29%.

¹H-NMR (CDCl₃) 0.92 (m, 6H) 1.35 (s, 6H) 2.10 (m, 1H) 3.87 (m, 1H) 4.36 (m, 2H) 5.11 (s, 2H) 5.30 (d, 1H) 5.70 (s, 2H) 5.78 (s, 1H) 7.35 (m, 5H).

d) 2-(N-(iodomethoxycarbonyl)-amino)-2-methyl-1-(N-benzyloxycarbonyl-L-valyloxy)-propane To a solution of 2-(N-(chloromethoxycarbonyl)-amino)-2-methyl-1-(N-benzyloxycarbonyl-L-valyloxy)propane (1.05 g, 2.53 mmole) in dry acetone (20 ml) was added sodium iodide (1.8 g, 12 mmole) and the mixture was stirred for 36 hours at room temperature. The mixture was evaporated under reduced pressure and ethyl acetate and water were added. The organic phase was washed with 10% sodium thiosulfate solution and water. The organic phase was dried with sodium sulfate and evaporated under reduced pressure. Yield: 1.04 g=81%.

¹H-NMR (CDCl₃) 0.92 (m, 6H) 1.35 (s, 6H) 2.10 (m, 1H) 3.88 (m, 1H) 4.35 (m, 2H) 5.11 (s, 2H) 5.32 (d, 1H) 5.82 (s, 1H) 5.91 (s, 2H) 7.35 (m, 5H)

EXAMPLE A-I-25

1-(2-N-CBz-L-valyloxyethyl)-6-oxo-1,6-dihydro-pyridine-3-carboxylic acid iodomethyl ester

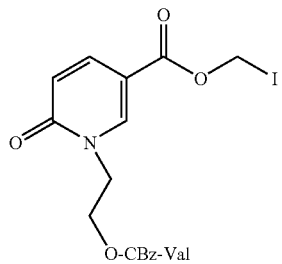

a) 6-oxo-1,6-dihydro-pyridine-3-carboxylic acid 4-methoxybenzyl ester

To a solution of 6-hydroxynicotinic acid (4.87 g, 35 mmol) in DMF (100 mL) at room temperature, was added potassium tert-butoxide (3.93 g, 35 mmol). The reaction mixture was stirred at 60° C. for 1 h. 4-Methoxybenzylchloride (8.30 g, 53 mmol) was added and the reaction mixture was stirred at 60° C. for 4 h. The DMF was evaporated under vacuum, the residue was dissolved in ether (200 mL) and washed with water (3×100 mL). The organic phase was dried with Na₂SO₄ and evaporated to give 4.41 g of 6-oxo-1,6-dihydro-pyridine-3-carboxylic acid 4-methoxybenzyl ester.

¹H-NMR (CDCl₃): 8.20 (d, J=2.5 Hz, 1H), 8.01 (dd, J=9.5, 2.5 Hz, 1H), 7.33 (d, J=8.7 Hz, 2H), 6.90 (d, J=8.7 Hz, 2H), 6.54 (d, J=9.5 Hz, 1H), 5.22 (s, 2H), 3.81 (s, 3H).

b) 1-(2-Hydroxyethyl)-6-oxo-1,6-dihydro-pyridine-3-carboxylic acid 4-methoxybenzyl ester To a solution of 6-oxo-1,6-dihydro-pyridine-3-carboxylic acid 4-methoxybenzyl ester (4.41 g, 17 mmol) and K₂CO₃ (2.58 g, 18.7 mmol) in DMF (100 mL) at room temperature, was added 2-bromoethanol (2.02 g, 16.2 mmol). The reaction mixture was stirred at 80° C. for 30 h, whereupon the DMF was evaporated under vacuum. The crude product was column chromatographed (silica gel, 2→5% MeOH in CH₂Cl₂), to give 3.91 g of 1-(2-hydroxyethyl)-6-oxo-1,6-dihydro-pyridine-3-carboxylic acid 4-methoxybenzyl ester.

¹H-NMR (CDCl₃): 8.26 (d, J=2.5 Hz, 1H), 7.85 (dd, J=9.5, 2.5 Hz, 1H), 7.34 (d, J=8.7 Hz, 2H), 6.90 (d, J=8.7 Hz, 2H), 6.47 (d, J=9.5 Hz, 1H), 5.21 (s, 2H), 4.09 (t, 2H), 3.90 (m, 2H), 3.81 (s, 3H), 3.64 (br s, 1H).

c) 1-(2-N-CBz-L-valyloxyethyl)-6-oxo-1,6-dihydro-pyridine-3-carboxylic acid 4-methoxybenzyl ester To a mixture of DCC (5.06 g, 24.5 mmol), DMAP (318 mg, 2.6 mmol) and N-CBz-L-valine (6.48 g, 25.8 mmol) in CH₂Cl₂ (200 mL) at 0° C., was added dropwise a solution of 1-(2-hydroxyethyl)-6-oxo-1,6-dihydro-pyridine-3-carboxylic acid 4-methoxybenzyl ester (6.40 g, 24 mmol) in CH₂Cl₂ (200 mL). After 1 h at 0° C., the temperature of the reaction mixture was allowed to assume room temperature and then the mixture was stirred for 5 h at room temperature. The mixture was filtered through a glass filter and the solvent was removed under reduced pressure. The crude product was column chromatographed (silica gel, 2→5% MeOH in CH₂Cl₂), to give 6.81 g 1-(2-N-CBz-L-valyloxyethyl)-6-oxo-1,6-dihydro-pyridine-3-carboxylic acid 4-methoxybenzyl ester.

¹H-NMR (CDCl₃): 8.15 (d, J=2.5 Hz, 1H), 7.83 (dd, J=9.6, 2.5 Hz, 1H), 7.37–7.25 (m, 7H), 6.88 (d, 2H), 6.49 (d, J=9.6 Hz, 1H), 5.35 (d, 1H), 5.21 (s, 2H), 5.06 (s, 2H), 4.48–4.05 (m, 5H), 3.78 (s, 3H), 2.10–1.98 (m, 1H), 0.85 (d, 3H), 0.75 (d, 3H).

d) 1-(2-N-CBz-L-valyloxyethyl)-2-pyridone-5-carboxylic acid

To a solution of 1-(2-N-CBz-L-valyloxyethyl)-6-oxo-1,6-dihydro-pyridine-3-carboxylic acid 4-methoxybenzyl ester (6.46 g, 12 mmol) in CH₂Cl₂ (85 mL) at room temperature, was added trifluoroacetic acid (15 mL). After 1 h at room temperature, the reaction mixture was concentrated under reduced pressure. The crude product was column chromatographed (silica gel, 3→6% MeOH in CH₂Cl₂), to give 4.91 g 1-(2-N-CBz-L-valyloxyethyl)-2-pyridone-5-carboxylic acid. The product can be activated and esterified direct to a drug or further modified as described below.

¹H-NMR (CDCl₃): 12.15 (br s, 1H), 8.29 (d, J=2.2 Hz, 1H), 7.93 (dd, J=9.5, 2.2 Hz, 1H), 7.31 (m, 5H), 6.69 (d, J=9.5 Hz, 1H), 5.53 (d, 1H), 5.07 (s, 2H), 4.52–4.05 (m, 5H), 2.20–2.00 (m, 1H), 0.90 (d, 3H), 0.81 (d, 3H).

e) 1-(2-N-CBz-L-valyloxyethyl)-6-oxo-1,6-dihydro-pyridine-3-carboxylic acid chloromethyl ester To a solution of 1-(2-N-CBz-L-valyloxyethyl)-2-pyridone-5-carboxylic acid (4.91 g, 11.8 mmol) in dioxane (200 mL), was added dropwise a 40% aqueous solution of tetrabutylammonium hydroxide (7.65 g). After stirring for 5 min, the solution was evaporated to dryness through co-evaporation with dioxane and toluene. The residue was dissolved in dichloromethane (200 mL) and then chlor-oiodomethane (8.74 mL, 120 mmol) was added and the solution was stirred for 12 h at room temperature. The solution was concentrated under reduced pressure and the residue was shaken with hexane/ethyl acetate (1:1 v/v, 200 mL). The yellow crystalline solid was filtered off and the filtrate was washed with aqueous solution of sodium thiosulfate (0.1 M) and the filtered through anhydrous sodium sulfate and evaporated to dryness. The residue was column chromatographed (silica gel, 2–4% MeOH in $CH_2Cl_2$), to give 1.80 g of 1-(2-N-CBz-L-valyloxyethyl)-6-oxo-1,6-dihydro-pyridine-3-carboxylic acid chloromethyl ester.

$^1$H-NMR (CDCl$_3$): 8.24 (d, J=2.5 Hz, 1H), 7.83 (dd, J=9.6, 2.5 Hz, 1H), 7.33 (m, 5H), 6.54 (d, J=9.6 Hz, 1H), 5.86 (s, 2H), 5.34 (d, 1H), 5.09 (s, 2H), 4.56–4.08 (m, 5H), 2.20–2.00 (m, 1H), 0.92 (d, 3H), 0.83 (d, 3H).

f) 1-(2-N-CBz-L-valyloxyethyl)-6-oxo-1,6-dihydro-pyridine-3-carboxylic acid iodomethyl ester To a solution of 1-(2-N-CBz-L-valyloxyethyl)-6-oxo-1,6-dihydro-pyridine-3-carboxylic acid chloromethyl ester (1.80 g, 3.87 mmol) in acetonitrile (30 mL), was added sodium iodide (2.32 g, 15.5 mmol). The solution was stirred for 4 h at 60° C. The resulting suspension was filtered and the filtrate was evaporated. The residue was dissolved in $CH_2Cl_2$ and washed with aqueous sodium thiosulfate (0.1 M). The organic phase was dried ($Na_2SO_4$) and concentrated under reduced pressure. The crude product was column chromatographed (silica gel, 1% MeOH in $CH_2Cl_2$), to give 2.04 g 1-(2-N-CBz-L-valyloxyethyl)-6-oxo-1,6-dihydro-pyridine-3-carboxylic acid iodomethyl ester.

$^1$H-NMR (CDCl$_3$): 8.19 (d, J=2.5 Hz, 1H), 7.79 (dd, J=9.6, 2.5 Hz, 1H), 7.32 (m, 5H), 6.52 (d, J=9.6 Hz, 1H), 6.04 (s, 2H), 5.38 (d, 1H), 5.07 (s, 2H), 4.54–4.06 (m, 5H), 2.20–2.00 (m, 1H), 0.91 (d, 3H), 0.81 (d, 3H).

EXAMPLE A-I-26

Iodomethyl 5-[(N-benzyloxycarbonyl-L-valyloxy)methyl]-2-furoate

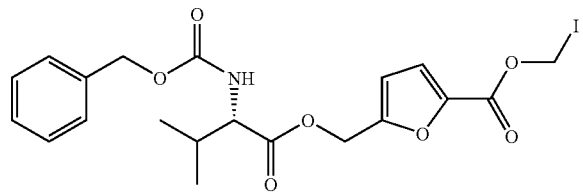

(a) 5-[(N-Benzyloxycarbonyl-L-valyloxy)methyl]-2-furaldehyde

A solution of 5-(hydroxymethyl)-2-furaldehyde (1.00 g, 7.69 mmol) in 5 mL dry $CH_2Cl_2$ was added to a mixture of N-benzyloxycarbonyl-L-valine (2.40 g, 9.57 mmol), N,N-dicyclohexylcarbodiimide (2.00 g, 9.69 mmol), and 4-dimethylaminopyridine (117 mg, 0.96 mmol) in 45 mL $CH_2Cl_2$. After stirring overnight, the reaction slurry was filtered, concentrated under vacuum, and subjected to flash column chromatography (silica, 2/1 petroleum ether—ethyl acetate to give the valine ester (quantitative yield).

$^1$H NMR (250 MHz, CDCl$_3$) δ 0.86 and 0.94 (2d, 3H each, J=6.9 Hz), 2.16 (m, 1H), 4.34 (dd, 1H, J=9.0, 4.7 Hz), 5.10 (s, 2H), 5.13–5.27 (m, 3H), 6.59 (d, 1H, J=3.4 Hz), 7.19 (d, 1H, J=3.5 Hz), 7.35 (s, 5H), 9.63 (s, 1H).

(b) 5-[(N-Benzyloxycarbonyl-L-valyloxy)methyl]-2-furoic acid

A solution of NaClO$_2$ (2.8 mmol) in 3 mL water was added dropwise to a stirred solution of 5-[(N-benzyloxycarbonyl-L-valyloxy)methyl]-2-furaldehyde (798 mg, 2.22 mmol) from step (a) in 3 mL MeCN, with cooling in an ice bath. After 2.5 h, the ice bath was removed, 2 mL more MeCN was added, and the two-phase liquid reaction mixture was stirred at room temperature for 25 h. The reaction mixture was diluted with water, made basic with saturated NaHCO$_3$, and extracted with ethyl acetate (3×50 mL). The separated aqueous solution was acidified to pH 2 with 5% aqueous HCl and extracted with ethyl acetate (3×50 mL). This second ethyl acetate solution was washed with brine, dried over anhydrous Na$_2$SO$_4$, and evaporated to dryness under vacuum to give the carboxylic acid (287 mg, 34%) which was used in the next step without further purification. The compound can be activated and esterified direct to a drug or further modified as described below.

$^1$H NMR (250 MHz, CDCl$_3$) δ 0.84 and 0.93 (2d, 3H each, J=6.8 Hz), 2.15 (m, 1H), 4.35 (dd, 1H, J=9.0, 4.7 Hz), 5.10–5.24 (m, 4H), 5.44 (d, 1H, J=9.0 Hz), 6.54 (d, 1H, J=3.3 Hz), 7.23 (d, 1H, J=3.3 Hz), 7.33 (s, 5H), 11.05 (br s, 1H).

(c) Chloromethyl 5-[(N-benzyloxycarbonyl-L-valyloxy)methyl]-2-furoate

Tetrabutylammonium hydroxide (40 wt. % solution in water, 0.55 mL, 0.84 mmol) was added to the carboxylic acid (286 mg, 0.76 mmol) from step (b) in 5 mL dioxane. The yellow solution was concentrated under vacuum, coevaporating several times with dioxane, toluene, and, lastly, $CH_2Cl_2$. The residue was charged with 10 mL dry $CH_2Cl_2$ and chloroiodomethane (0.55 mL, 7.55 mmol) was added. After stirring for 20.5 h, the reaction mixture was concentrated and subjected to flash column chromatography (silica, 2/1 petroleum ether—ethyl acetate) to give the chloromethyl ester (137 mg, 42%).

$^1$H NMR (250 MHz, CDCl$_3$) δ 0.85 and 0.93 (2d, 3H each, J=6.9 Hz), 2.14 (m, 1H), 4.33 (dd, 1H, J=9.0, 4.8 Hz), 5.09–5.22 (m, 4H), 5.37 (d, 1H, J=8.9 Hz), 5.88 (s, 2H), 6.53 (d, 1H, J=3.4 Hz), 7.23 (d, 1H, J=3.5 Hz), 7.32 (s, 5H).

(d) Iodomethyl 5-[(N-benzyloxycarbonyl-L-valyloxy)methyl]-2-furoate

All of the chloromethyl ester (137 mg, 0.32 mmol) from step (c) was refluxed with NaI (195 mg, 1.3 mmol) in 3.2 mL dry MeCN at 70° C. for 4 h. The solvent was removed under vacuum and the residue was subjected to flash column chromatography (silica, 3/1 petroleum ether—ethyl acetate) to give the iodomethyl ester (152 mg, 92%).

$^1$H NMR (250 MHz, CDCl$_3$) δ 0.84 and 0.93 (2d, 3H each, J=6.8 Hz), 2.16 (m, 1H), 4.33 (dd, 1H, J=9.1, 4.7 Hz), 5.09–5.21 (m, 4H), 5.36 (d, 1H, J=9.1 Hz), 6.08 (s, 2H), 6.52 (d, 1H, J=3.4 Hz), 7.19 (d, 1H, J=3.5 Hz), 7.33 (s, 5H).

EXAMPLE A-I-27

4-(2-N-benzyloxycarbonyl-L-valyloxyethyl)benzoic acid a) 4-Methoxybenzyl 4-(2-hydroxyethoxy)benzoate To a solution of 4-methoxybenzyl 4-hydroxybenzoate (7.0 g, 27 mmole) in dry NN-dimethylformamide (50 ml) was added potassium carbonate (4.15 g, 30 mmole) and 2-bromoethanol. The mixture was stirred 48 hours at 80° C., evaporated under reduced pressure and ethyl acetate and water were added. The organic phase was washed five times with water and dried with sodium sulfate. The solution was evaporated under reduced pressure and the product was isolated by silica gel column chromatography with hexane/ethyl acetate.

Yield: 6.8 g=83%.

$^1$H-NMR (CDCl$_3$) 3.81 (s, 3H) 4.00 (m, 2H) 4.12 (m, 2H) 5.26 (s, 2H) 6.90 (m, 4H) 7.38 (d, 2H) 8.00 (d, 2H)

b) 4-methoxybenzyl 4-(2-N-benzyloxycarbonyl-L-valyloxyethoxy)benzoate

To a solution of 4-methoxybenzyl 4-(2-hydroxyethoxy) benzoate (6.6 g, 21.8 mmole), 4-dimethylaminopyridine (0.61 g, 5 mmole) and N-benzyloxycarbonyl-Lvaline (6.3 g, 25 mmole) in dichloromethane (80 ml) was added dicyclohexylcarbodiimide (5.2 g, 25 mmole) and the mixture was stirred overnight at room temperature. The mixture was cooled and the urethane was filtered. The solution was evaporated and ethyl acetate (200 ml) was added. The organic phase was washed twice with 5% acetic acid, 5% sodium hydrogencarbonate and water. The organic phase was dried with sodium sulfate and evaporated under reduced pressure. The product was isolated by silica gel column chromatography with dichloromethane/methanol. Yield: 10.6 g=90%.

$^1$H-NMR (CDCl$_3$) 0.90 (m, 6H) 2.18 (m, 1H) 3.82 (s, 3H) 4.14–4.64 (m, 5H) 5.10 (s, 2H) 5.27 (s, 2H) 6.90 (m, 4H) 7.34 (m, 7H) 7.99 (d, 2H)

c) 4-(2-N-benzyloxycarbonyl-L-valyloxyethoxy)-benzoic acid

To a solution of 4-methoxybenzyl 4-(2-N-benzyloxycarbonyl-L-valyloxyethoxy) benzoate (10.2 g, 19.04 mmole) in dichloromethane (100 ml) was added trifluoroacetic acid (20 ml) and the mixture was stirred 3 hours at room temperature. The solution was evaporated under reduced pressure and co-evaporated two times with toluene. The product was isolated by silica gel column chromatography. Yield: 6.9 g=87%. The product may be activated and esterified direct to a drug or converted to iodomethyl 4-(2-N-benzyloxycarbonyl-L-valyloxyethoxy)-benzoic acid as described above, that is by treatment with a base, chloroiodomethane, separation and then treatment with NaI.

$^1$H-NMR (CDCl$_3$) 0.94 (m, 6H) 2.18 (m, 1H) 4.22–4.68 (m, 5H) 5.10 (s, 2H) 6.94 (d, 2H) 7.35 (m, 5H) 8.05 (d, 2H)

EXAMPLE 1

2-(stearoyloxymethyl)-2-(N-(fluorenylmethoxycarbonyl)-L-valyloxymethyl)-propionic acid To a solution of 2,2-bis(hydroxymethyl) propionic acid (28.16 g, 210 mmole) in water (50 ml), was added potassium hydroxide (11.78 g, 210 mmole). After 5 min, the solution was evaporated in vacuo and the residue was coevaporated with dry DMF for three times. The residue was then dissolved in DMF (500 ml), and to the solution was added benzyl bromide (3.57 ml, 30 ml). After stirring for 30 min, the reaction mixture was filtered through the Celite, poured into sodium hydrogen carbonate aqueous solution and extracted with dichloromethane. The organic phase was collected and then washed with sodium hydrogen carbonated aqueous solution. It was then evaporated in vacuo to give benzyl 2,2-bis(hydroxymethyl) propionate (4.37 g).

$^1$H-NMR (CDCl$_3$): 7.35 (s, 5H), 5.20 (d, 2H), 3.91–3.71 (m, 4H), 1.10 (s, 3H).

To a solution of benzyl 2,2-bis(hydroxymethyl) propionate (4.37 g, 19.5 mmole) in pyridine (58 ml) was added dropwise stearoyl chloride (4.13 g, 13.6 mmole) in dichloromethane over 40 min. The reaction was then kept for 16 hr and then poured into sodium hydrogen carbonate aqueous solution and extracted with dichloromethane. The organic phase was collected and evaporated in vacuo. The product benzyl-2-(hydroxymethyl)-2-(stearoyloxymethyl) propionate was isolated by silica gel column chromatography (1.97 g)

$^1$H-NMR (CDCl$_3$): 7.34 (s, 5H), 5.17 (d, 2H), 4.28 (dd, 2H) 3.69 (dd, 2H), 2.24 (t, 2H), 1.57 (m, 2H, 1.25 (s, 28H), 1.22 (s, 3H), 0.87 (t, 3H).

Benzyl-2-(hydroxymethyl)-2-(stearoyloxymethyl) propionate (1.86 g, 3.8 mmole) was dissolved in pyridine (30 ml). To the solution were added toluenesulfonic acid (73 mg, 0.39 mmole), N-fluorenylmethoxycarbonyl-L-valine (3.94 g, 11.6 mmole), and DCC (3.58 g, 17.4 mmole). The reaction was kept at 4° C. for 16 hr and then filtered through Celite. The filtrate was poured into sodium hydrogen carbonate aqueous solution and extracted with dichloromethane. The organic phase was collected and evaporated in vacuo. The product, benzyl-2-(N-fluorenyl-methoxycarbonyl)-L-valyloxymethyl)-2-(stearoyloxymethyl)propionate, was isolated by silica gel column chromatography. Yield: 2.38 g.

$^1$H-NMR (CDCl$_3$): 7.78–7.25 (m, 13H), 5.29 (m, 1H), 5.15 (d, 2H), 4.38–4.23 (m, 7H), 2.19 (t, 2H), 2.10 (m, 1H), 1.55 (m, 2H), 1.24 (m, 31H), 0.94–0.83 (m, 9H).

To the solution of benzyl 2-(N-(fluorenylmethoxycarbonyl)-L-valyloxymethyl)-2(stearoyloxymethyl) propionate (1.86 g, 3.8 mmole) in a mixed solvent of THF/methanol (16 ml/8 ml) were added ammonium formate (376 mg, 6 mmole), formic acid (1.87 ml), and palladium black (40 mg). The reaction was kept at room temperature for 16 hr, and then filtered through Celite. After evaporation, the product was isolated by silica gel column chromatography. Yield: 1.05 g.

EXAMPLE 2

1-O-stearoyl-2-O—(N-CBz-L-valyl)glycerol a) Preparation of 1-O-stearoylglycerol

To a mixture of glycerol (30 g, 326 mmol) and pyridine (25 ml) dissolved in DMF (300 ml) was added dropwise stearoyl chloride (10 g, 33 mmol) dissolved in DMF 100 ml9. The mixture was cooled on an ice bath until addition was complete, whereupon the reaction was maintained under an N$_2$ atmosphere overnight. After 15 hours CH$_2$CL$_2$ (300 ml) and saturated NaHCO3 (aq) was added. The phases were separated and the organic phase washed with water (50 ml) and dried with Na$_2$ SO$_4$. The solvent and any pyridine were evaporated under vacuum. The crude product was chromatographed on a silica column (CH$_2$Cl$_2$-MeOH, 20:1) and recrystallised (CH$_2$Cl$_2$-ether) to yield around 7 grams.

b) Preparation of pixyl chloride

Acetyl chloride (150 ml, 2.1 mol) is added to a magnetically stirred suspension of 9-hydroxy-9-phenylxanthene (20 g 72 mmol) in benzene (100 ml). An homogenous deep red solution is obtained. The solution is stirred for 30 min. at 20° C. The volatiles are removed under reduced pressure. Excess AcCl is neutralised by careful addition to ethanol. The residue is coevaporated with toluene (2×30 ml) and with cyclohexane (2×30 ml) to obtain a crystalline residue which is stored airtight. Pixyl chloride is alternatively available from Aldrich.

c) Preparation of 1-O-stearoyl, 3-O-pixylglycerol

The product from a) above (2.28 g) and pyridine (25 ml) were mixed and heated until dissolved. After cooling in an icebath pixyl chloride (1.92 g) from step b) was added. The mixture was maintained under agitation and an argon atmosphere in an icebath for half an hour and then at room temperature for 1.5 h. The pyridine was evaporated under vacuum, the residue dissolved in $CH_2Cl_2$ (70 ml) and washed with 0.5 M citricacid to remove remaining pyridine. The residue was dried with $Na_2SO_4$, evaporated and chromatographed (ether-hexane 1:3) to give 1.25 g pure product with a TLC $R_f$ around 0.2.

d) Preparation of 1-O-stearoyl, 2-O—(N-CBz-L-valyl), 3-O-pixylglycerol

The product of step c) (237 mg, 0.39 mmol), CBz-L-valine (116 mg, 0.46 mmol), DCC (96 mg, 0.46 mmol) and DMAP (4.7 mg, 0.04 mmol) were dissolved in $CH_2Cl_2$ (4 ml). The mixture was maintained under agitation in a nitrogen atmosphere overnight. After 18 hours the mixture was filtered through a glass filter and chromatographed on a silica gel column (ether-hexane 1:4) to yield 230 mg with a TLC $R_f$ of 0.2 e) Preparation of 1-O-stearoyl-2-O—(N-CBz-L-valyl)glycerol

The pixyl group in the product of step d) was removed by selective deprotection by the method described in Example 3, step d to yield the title compound.

$^1$H-NMR ($CDCl_3$): δ 7.35 (m, 5H), 5.3–4.9 (m, 4H), 4.35–4.25 (m, 3H), 3.8–3.6 (m, 2H), 2.31–2.25 (m, 2H), 2.20–2.10 (m, 1H), 1.60 (m, 2H), 1.02–0.86 (m, 9H).

EXAMPLE 3

1-O—(N-CBz-L-valyl)-2-O-stearoylglycerol a) Preparation of 1-O—(N-CBz-L-valyl)glycerol CBz-L-valine (4.35 g, 17.3 mmol) was added to a fivefold excess of glycerol (8 ml, 86.9 mmol) togehter with dicyclohexylcarbodiimide (4.29 g 20.8 mmol) and 4-dimethylaminopyridine (0.212 g) at room temperature. After stirring overnight the suspension was filtered and DMF removed in vacuo from the filtrate. The residue was redissolved in $CH_2Cl_2$, washed successively with saturated $NaHCO_3$, brine, and water and then dried. The crude material was chromatographed on silica gel with 4/1 EtOAc—hexane as eluent to yield 2.465 g. $R_f$ (4/1 EtOAc—hexane) 0.17, (20/1 $CH_2Cl_2$-methanol) 0.12.

b) Preparation of 1-O-(N-CBz-L-valyl)-3-O-pixylglyerol

The product of step a) (0.672 g, 20.1 mmol) was dissolved in dry pyridine (3.5 ml) under nitrogen. 9-Chloro-9-phenylxanthene (pixyl chloride, 0.65 g, 22.0 mmol, 1.1 eq—prepared as above) was added and the mixture stirred at room temperature for 1.5 h. MeOH (1.5 ml) was added and the mixture partitioned between 10 ml $Et_2O$ and 10 ml saturated $NaHCO_3$. The aqueous layer was extracted with more ether. The organic layers were combined, dried and concentrated several times with toluene to give a white solid. The crude material was chromatographed on silica gel with 3/1 hexane—EtOAc as eluent to give 0.681 g.

Alternatively a pixyl group can be put on by the procedure described by Gaffney et al, Tetrahedron Lett 1997, 38, 2539–2542 using PxOH and acetic acid.

c) Preparation of 1-O-(N-CBz-L-valyl)-2-O-stearoyl-3-O-pixyl glycerol

Stearoyl chloride (496 ml, 1.3 eq) in 1.5 ml $CH_2Cl_2$ was added dropwise to a solution of the product of step b) (0.658 g, 1.13 mmol) in 11 ml pyridine with stirring under $N_2$ in an ice bath. After 15 minutes the mixture was stirred at room temperature overnight. The mixture was diluted with 20 ml $Et_2O$ and washed with 10 ml saturated $NaHCO_3$. The aqueous layer was extracted with more $Et_2O$. The organic layers were combined, washed with brine (20 ml), dried over $Na_2SO_4$ and concentrated several times with toluene. The crude material (1.37 g) was chromatographed on 130 g silica gel with 6/1 hexane—EtOAc. An initial fraction of 500 ml was taken followed by 100 ml fractions. The desired material eluted in fractions 2–5 yielding 0.748 g.

d) Preparation of 1-O—(N-CBz-L-valyl)-2-O-stearoylglycerol

To a solution of the product of step c) (0.748 g, 0.872 mmol) dissolved in 35 ml $CH_2Cl_2$ to make 0.025 M) was added pyrrole (16.5 mol eq) and dichloroacetic acid (5.5 mol eq) at room temperature. TLC after 5 minutes showed complete reaction. The mixture was diluted with 300 ml $CH_2Cl_2$ and washed with 30 ml saturated $NaHCO_3$. The aqueous layer was extracted with more $CH_2Cl_2$. The organic phases were combined, washed with brine (30 ml), dried over $Na_2SO_4$ and concentrated. Crude material was chromatographed on silica gel with 2/1 hexane—EtOAc (with 0.3% acetic acid) as eluent to yield 0.363 g with $R_f$ (2/1 hexane—EtOAc) 0.21.

$^1$H NMR ($CDCl_3$) δ ppm 0.86–0.99 (m, 9H), 1.25 (s, 28H), 1.61 (m, 2H), 2.16 (m, 1H), 2.32 (m, 2H), 3.74 (br s, 2H), 4.28–4.44 (m, 3H), 5.09 (m, 1H), 5.11 (s, 2H), 5.22 (d, 1H), 7.36 (m, 5H)

EXAMPLE 4

1-O-stearoyl-3-O—(NCBz-L-valyl)glycerol

The product of Example 2, part a) (2.86 g, 7.99 mmol), DCC (0.9 g, 4.36 mmol) 4-(N,N-dimethyl)aminopyridine (DMAP) (0.048 mg, 0.39 mmol) and N-CBz-L-valine (1 g, 3.98 mmol) were dissolved in $CH_2Cl_2$ (60 ml) and DMF (6 ml). The reaction was left at ambient temperature for 18 hours and then filtrated. The solvent was evaporated under reduced pressure. The residue was dissolved in $CH_2Cl_2$ (100 ml) and filtrated. The crude title compound was purified by chromatography [$SiO2$, ether/hexane (1:2)] to yield 1.3 g of the desired product. Unreacted 1-stearoylglycerol may be recovered by eluting with $CH_2Cl_2$/MeOH (20:1).

$^1$H-NMR ($CDCl_3$): δ 5.25 (d, 1H), 5.11 (s, 2H), 4.30–4.05 (m, 6H), 2.65 (d, 1H), 2.35 (t, 2H), 2.06 (m, 1H), 1.62 (m, 2H), 1.26 (s, 28H), 1.00–0.84 (m, 9H).

EXAMPLE 5

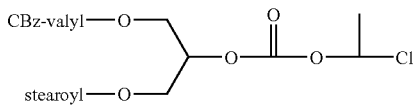

To an ice cooled solution of 1-chloroethyl chloroformate (1.89 g, 13.2 mmol) in dry CH$_2$Cl$_2$ (5 ml), was added the compound of Example 4 in CH$_2$Cl$_2$ (20 ml) followed by dry pyridine (1.2 ml, 29.6 mmol). The reaction mixture was stirred with cooling under argon atmosphere until TLC (ether/hexane, 1:2) indicated consumption of the starting material. After 1.5 h, the mixture was washed with water (3×5 ml), sat. NaHCO$_3$ (5 ml) and dried (Na$_2$SO$_4$). Purification by chromatography [SiO$_2$ (etherhexane (1:2)] yielded the title compound (4.0 g).

$^1$H-NMR (CDCl$_3$): δ7.36–7.32 (m, 5H), 6.40 (m, 1H), 5.24 (m, 1H), 5.11 (s, 2H), 4.30 (m, 6H), 2.32 (m, 2H), 2.15 (m, 1H), 1.82 (m, 3H), 1.60 (m, 2H), 1.25 (br s, 28H), 0.97 (m, 3H), 0.86 (m, 6H).

EXAMPLE 6

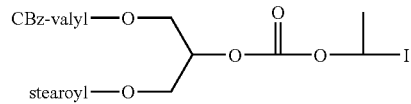

To a solution of the compound of Example 5 (3.4 g, 4,87 mmol) in dry acetonitrile (47 ml), was added sodium iodide (3.65 g, 24.3 mmol). The solution obtained was refluxed under argon atmosphere until NMR indicated consumption of the starting material. After 4.5 h, ether (50 ml) was added and the mixture was filtrated. The solvent was removed by evaporation and the crude product dissolved in ether (50 ml). The ether solution was washed with water (2×10 ml) and dried (Na$_2$SO$_4$) and evaporated under reduced pressure. Purification by chromatography [SiO$_2$, etherhexane (1:2)] yielded the title compound (2.15 g).

$^1$H-NMR (CDCl$_3$): δ7.37 (m, 5H), 6.75 (m, 1H), 5.22 (m, 1H), 5.15 (s, 1H), 4.3 (m, 6H), 2.32 (m, 1H), 2.22 (m, 2H), 1.6 (m, 2H), 1.25 (s, 28H), 0.95 (m, 9H).

EXAMPLE 7

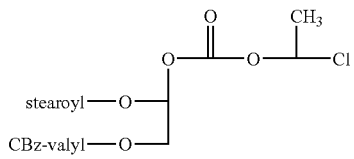

A solution of the compound of Example 3 (810 mg, 1.37 mmol) in 2.2 mL dry dichloromethane was cooled in an ice bath with stirring under argon. 1-Chloroethyl chloroformate (298 µL, 2.74 mmol) was added, followed by the dropwise addition of pyridine (665 µL, 8.22 mmol) in 2.5 mL dichloromethane. After 2.5 hr, the mixture was diluted with 25 mL dichloromethane and washed successively with 10 mL water and 10 mL brine. The organic phase was dried over anhydrous sodium sulfate and concentrated several times with toluene to give a yellow oil. Purification by flash column chromatography on silica gel with 40/1 dichloromethane-diethyl ether gave the title compound as an oil (96 mg, quantitative yield).

$^1$H NMR (CDCl$_3$) δ ppm 0.85–0.98 (m, 9H), 1.25 (s, 28H), 1.60 (m, 2H), 1.83 (d, 3H, J=5.8 Hz), 2.17 (m, 1H), 2.31 (t, 2H), 4.19–4.48 (m, 5H), 5.11 (s, 2H), 5.22 (d, 1H), 5.27 (m, 1H), 6.38–6.43 (m, 1H), 7.36 (m, 5H).

EXAMPLE 8

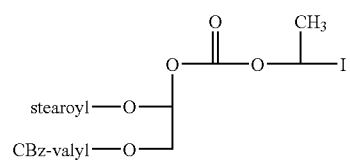

A solution of the compound of Example 7 (1.896 g, 2.71 mmol) and sodium iodide (1.80 g, 12.0 mmol) in acetonitrile (27 mL) was refluxed at 80° C. under nitrogen. After 4.5 hours the reaction mixture was diluted with 100 mL 1/1 hexane-diethyl ether and washed with 25 mL water. The aqueous phase was extracted with more solvent (25 mL). The organic phases were combined, washed successively with 5% aqueous sodium thiosulfate solution (25 mL) and brine (25 mL), dried over anhydrous sodium sulfate, and concentrated in vacuo. Purification by flash column chromatography on silica gel with 80/1 dichloromethane-methanol as eluant gave an oil (1.45 g) containing 90% of the title compound with 10% of the compound of Example 7.

$^1$H NMR (CDCl$_3$) δ ppm 0.85–0.99 (m, 9H), 1.25 (s, 28H), 1.60 (m, 2H), 2.17 (m, 1H), 2.23 (d, 3H, J=6 Hz), 2.31 (t, 2H), 4.16–4.49 (m, 5H), 5.10 (s, 2H), 5.20–5.29 (m, 2H), 6.69–6.79 (m, 1H), 7.36 (m, 5H).

EXAMPLE 9

4-Benzyloxy-2-(N-trityl-L-valyloxymethyl)-1-stearoyloxybutane a) Synthesis of diethyl-2-(2-benzyloxyethyl) malonate To a freshly prepared solution of sodium (0.95 g, 41.4 mmole) in 50 ml ethanol was added a solution of diethylmalonate (6.4 g, 40 mmole) in 10 ml ethanol and the mixture was stirred for 15 minutes. Then a solution of 2-benzyloxy-1-iodoethane (11.5 g, 41,35 mmole) was added drppwise. The mixture was refluxed for four hours and than evaporated in vacuo. 100 ml of water was added and the mixture was extracted three times with 50 ml portions of diethylether. The organic phase was dried with sodium sulfate and evaporated in vacuo and the product was isolated by silica gel column chromatography. Yield: 8.6 g $^1$H-NMR (CDCl$_3$) 1.26 (m, 6H) 2.26 (m, 2H) 3.54 (m, 3H) 4.16 (m, 4H) 4.57 (s, 2H) 7.32 (m, 5H)

b) Synthesis of 4-benzyloxy-2-hydroxymethyl-butanol-1

To a stirred suspension of lithium aluminium hydride (3.0 g, 80 mmol) in 100 ml diethylether was added dropwise a solution of diethyl-2-(2-benzyloxyethyl) malonate (8.5 g, 28.8 mmol) in 20 ml diethylether at about 15° C. The mixture was refluxed for two hours. About 4 ml water was dropwise added while cooling. The mixture was filtered and washed with dioxane. The filtrate was evaporated under reduced pressure and the product was isolated by silica gel column chromatography.

Yield: 3.4 g $^1$H-NMR (CDCl$_3$) 1.60 (m, 2H) 1.82 (m, 1H) 3.00 (m, 2H) 3.56 (t, 2H) 3.69 (m, 4H) 4.50 (s, 2H) 7.32 (m, 5H)

c) Synthesis of 4-benzyloxy-2-(N-trityl-L-valyloxymethyl)-butanol-1

To a solution of N-trityl-L-valine (4.66 g, 13 mmol) and 4-benzyloxy-2-hydroxymethyl-butanol-1 (3.3 g, 15.6 mmole) in 50 ml dichloromethane was added DCC (3.0 g, 14.5 mmole) and DMAP (0.18 g, 1.45 mmole) and the mixture was stirred for three days. The mixture was cooled to 5° C. and the urethane was filtered. The solution was evaporated under reduced pressure and the product was isolated by silica gel column chromatography.

Yield: 2.5 g $^1$H-NMR (CDCl$_3$) 1.00 (m, 6H) 1.55 (m, 4H) 1.72 (m, 1H) 2.18 (m, 1H) 2.70 (m, 1H) 3.27 (m, 2H) 3.43 (m, 3H) 4.50 (s, 2H) 7.26 (m, 20H)

d) Synthesis of 4-benzyloxy-2-(N-trityl-L-valyloxymethyl)-1-stearoyloxybutane To a solution of 4-benzyloxy-2-(N-trityl-1-valyloxymethyl)-butanol-1 (2,4 g, 4.35 mmol) in 50 ml dichloromethane was added pyridine (1.72 g, 21.7 mmol). The solution was cooled to 10° C. and a solution of stearoyl chloride (2.64 g, 8.7 mmol) in 10 ml dichloromethane was added dropwise between 10° C. and 15° C. The mixture was stirred overnight at room temperature. 100 ml of 5% sodium hydrogen carbonate solution was added and the mixture stirred for 30 minutes. The organic phase was seperated and the water phase was extracted two times with dichloromethane. The combined organic phases were dried with sodium sulfate and concentrated in vacuo. The product was isolated by silica gel column chromatography.

Yield: 3.0 g $^1$H-NMR (CDCl$_3$) 0.98 (m, 9H) 1.26 (m, 28H) 1.54 (m, 2H) 1.94 (m, 1H) 2.25 (m, 2H) 3.23 (m, 2H) 3.44 (m, 2H) 3.58 (m, 1H) 3.91 (m, 2H) 4.10 (m, 1H) 4.47 (s, 2H) 7.28 (m, 20H)

EXAMPLE 10

5-(N-trityl-L-valyloxymethyl)-6-stearoyloxyhexanoic acid a) Preparation of 2-allyl 1,3-propanediol

Diethyl allylmalonate (20 ml, 101 mmol) in anhydrous ether (100 ml) was added dropwise to a stirred solution of lithium aluminium hydride (9.6 g, 253 mmol) at 0° C. The reaction was warmed up to room temperature and kept for 5 hours. It was cooled down to 0° C. and water (12 ml) was carefully added dropwise. After stirring for 30 min, the mixture was filtered through Celite and then washed with ethanol (2×500 ml). The solution was dried under vacuum giving 9.5 g product $^1$H-NMR (CDCl$_3$): 5.78 m, 1H), 5.03 (m, 2H), 3.78 (m, 2H), 3.69 (m, 2H), 2.06 (t, 2H), 1.87 (m, 1H).

b) Preparation of 1-O-(N-trityl-L-valyl)-2-allyl-1,3-propandiol

To a solution of N-trityl-L-valine (5.5 g, 15.2 mmole), 2-allyl-1,3-propandiol (4.4 g, 38 mmol), N,N-dimethylamino pyridine (183 mg, 1.5 mmol) in dichloromethane (120 ml) was added DCC (3.5 g, 16.7 mmol). The reaction was kept under reflux overnight. After filtration through Celite, the organic phase was washed with sodium hydrogen carbonate aqueous solution and dried. Silica gel column chromatography gave 4.6 g intermediate 1-O-(N-trityl-L-valyl)-2-allyl-1,3-propandiol.

c) Preparation of 1-O-(N-trityl-L-valyl)-2-allyl-3-stearoyl-1,3-propandiol

To a solution of 1-O-(N-trityl-L-valyl)-2-allyl-1,3-propandiol (1.83 g, 4 mmol) in dichloromethane (40 ml) and pyridine (3.2 ml, 40 mmol) at 0° C. was added dropwise stearoyl chloride (3.62 g, 12 mmol) in dichloromethane. The solution was warmed up to room temperature, and kept for 3 hr. It was then washed with sodium hydrogen carbonate aqueous solution and dried. The product was isolated by silica gel column chromatography. 1.9 g $^1$H-NMR (CDCl$_3$): 7.30 (m, 15H), 5.70 (m, 1H), 4.99 (m, 2H), 3.93 (m, 2H), 3.55 (m, 1H), 3.27 (m, 2H), 2.68 (m, 1H), 2.30 (m, 2H), 2.23 (m, 1H), 2.01 (m, 2H), 1.85 (m, 1H), 1.62 (m, 2H), 1.3 (m, 28H), 0.98 (dd, 6H), 0.91 (t, 3H).

d) Preparation of 3-(N-trityl-L-valyloxymethyl)-4-stearoyloxy-butyraldehyde

1-O-(N-trityl-L-valyl)-2-allyl-3-stearoyl-1,3-propandiol (580 mg, 0.8 mmol) was dissolved in dioxane (5 ml). To the solution were added osmium tetraoxide (20 mg, 0.08 mmole) and pyridine (0.05 ml, 0.64 mmole). A solution of sodium periodate in water (3.5 ml) was added to the reaction mixture. The reaction was kept overnight and then cooled down to 0° C. An aqueous solution of sodium hydrogen sulfite was added and the mixture was extracted with dichloromethane. The organic phase was dried and purified by silica gel column chromatography. Yield. 250 mg $^1$H-NMR (CDCl$_3$): 9.68 (s, 1H), 7.25 (m, 15H), 3.92 (m, 2H), 3.58 (m, 1H), 2.32 (m, 2H), 2.68 (m, 1H), 2.34 (m, 7H), 1.58 (m, 2H), 1.53 (m, 28H), 0.96 (dd, 6H), 0.86 (t, 3H).

f) Preparation of benzyl 3-(N-trityl-L-valyloxymethyl)-4-stearoyloxyhexen-2-oate To the solution of 3-(N-trityl-L-valyloxymethyl)-4-stearoyloxy-butyraldehyde (15.8 g, 21.8 mmole) in cichloromethanewere added (benzyloxycarbonylmethyl) triphenylphosphonium bromide (10.7 g, 21.8 mmole) and triethylamine (2.21 g, 21.8 mmole). The reaction was kept overnight at room temperature, and the mixture was evaporated. To the residue was added diethyl ether (200 ml and kept at 4° C. for two hours. It was then filtered and the filtrate was evaporated and the product was purified by silica gel column chromatography. Yield. 10 g $^1$H-NMR (CDCl$_3$): 7.30 (m, 20H), 6.89 (m, 1H), 5.88 (d, 1H), 5.19 (d, 2H), 3.95 (m, 2H), 3.57 (m, 1H), 3.29 (, 2H), 2.68 (m, 1H), 2.23 (m, 5H), 1.93 (m, 1H), 1.60 (m, 2H), 1.32 (m, 28H), 0.95 (dd, 6H), 0.89 (t, 3H).

g) Preparation of 3-(N-trityl-L-valyloxymethyl)-4-stearoyloxyhexanoate

To a solution of benzyl 3-(N-trityl-L-valyloxymethyl)-4-stearoyloxyhexen-2-oate (70 mg, 0.08 mmole) in methanaol (3 ml) and ethyl acetate (1 ml) was added sodium hydrogen carbonate (10 mg) and palladium black (20 mg). The reaction was kept under hydrogen at atmospheric pressure for 2 hr. The mixture was filtered and evaporated. The residue was dissolved in dichloromethane and washed successively with aqueous EDTA solution and cold aqueous 2% citric solution. The organic phase was evaporated to give 61 mg product $^1$H-NMR (CDCl$_3$): 7.30 (m, 15H), 3.93 (m, 2H), 3.57 (m, 1H), 3.25 (m, 2H), 2.30 (dt, 4H), 2.20 (m, 1H), 1.70 (m, 1H), 1.62 (m, 4H), 1.30 (m, 28H), 0.95 (dd, 6H), 0.87 (t, 3H).

EXAMPLE 11

3-(N-benzyloxycarbonyl-L-valyloxymethyl)-4-stearoyloxy-butvric acid a) Preparation of 1-O-(N-benzyloxycarbonyl-L-valyl)-2-allylyl-1,3-propandiol To a solution of 2-allyl-1,3-propandiol (4.6 g, 40 mmole) and N-benzyloxycarbonyl valine (5.02 g, 20 mmole) in dichloromethane was added dimethylaminopyridine (244 mg, 2 mmol), and DCC (4.5 g, 22 mmol). After two hours, the mixture was filtered through Celite, evaporated and the product, 1-O-(N-benzyloxycarbonyl-L-valyl)-2-allylyl-1,3-propandiol, isolated to yield 5.01 g.

$^1$H-NMR (CDCl$_3$): 7.36 (m, 5H), 5.78 (m, 1H), 5.26 (d, 1H), 5.11 (s, 2H), 5.06 (d, 2H), 4.22 (m, 3H), 3.59 (m, 2H), 2.13 (m, 3H), 1.98 (m, 2H), 0.94 (dd, 6H).

b) Preparation of 1-O-(N-benzyloxycarbonyl-L-valyl)-2-allylyl-3-O-stearoyl-1,3-propandiol To a solution of 1-O-(N-benzyloxycarbonyl-L-valyl)-2-allylyl-1,3-propandiol (4.46 g, 12.7 mmol) in dichloromethane (70 ml) and pyridine (6.1 ml, 76 mmole) in ice bath was added stearoyl chloride (7.8 g, 26 mmole). The reaction mixture was warmed up to room temperature and kept for one hour. It was then poured into aqueous sodium hydrogen carbonate solution, the organic phase was dried and the product 1-O-(N-benzyloxycarbonyl-L-valyl)-2-allylyl-3-O-stearoyl-1,3-propandiol was purified by silica gel column chromatography. 6.7 g $^1$H-NMR (CDCl$_3$): 7.34 (m, 5H), 5.77 (m, 1H), 5.30 (d, 1H), 5.11 (s, 2H), 5.08 (d, 2H), 4.32 (m, 1H), 4.10 (m, 4H), 2.29 (t, 2H), 2.13 (m, 4H), 1.62 (m, 3H), 1.25 (m, 28H), 0.90 (m, 9H).

c) Preparation of 3-(N-benzyloxycarbonyl-L-valyloxymethyl)-4-stearoyloxy-butyric acid Potassium permanganate (756 mg, 4.8 mmole) was dissolved in water (7.5 ml). The solution was kept under strong stirring for 10 min. A solution of 1-O-(N-benzyloxycarbonyl-L-valyl)-2-allylyl-3-O-stearoyl-1,3-propandiol (1 g, 1.6 mmol) and tetrabutylammonium bromide (77 mg, 0.24 mmole) in benzene (5 ml) was added. The slurry was stirred for 1.5 hr, and dichloromethane was added. A sodium bisulfite aqueous solution was added to the slurry until the mixture discolored. The organic phase was acidified with acetic acid and washed with water. After evaporation, the product 3-(N-benzyloxycarbonyl-L-valyloxymethyl)-4-stearoyloxybutyric acid (390 mg) was isolated by silica gel column chromatography.

$^1$H-NMR (CDCl$_3$): 7.33 (m, 5H), 5.38 (d, 1H), 5.11 (s, 2H), 4.14 (m, 5H); 2.60 (m, 1H), 2.45 (m, 2H), 2.29 (t, 2H), 2.18 (m, 1H), 1.58 (m, 2H), 1.25 (m, 28H), 0.90 (m, 9H).

EXAMPLE 12

2' 3'-dideoxy-3'-fluoro-5'-O-[5-(L-valyloxymethyl)-6-stearoyloxyhexanoyl]guanosine a) Preparation of 2',3'-dideoxy-3'-fluoro-5'-O-[5-(N-trityl-L-valyloxymethyl)-6-stearoyloxyhexanoyl] guanosine To a solution of 5-(N-trityl-L-valyloxymethyl)-6-stearoyloxyhexanoic acid (462 mg, 0.6 mmole) and 2',3'-dideoxy-3'-fluoroguanosine (340 mg, 1.25 mmol) in DMF (3 ml) were added dimethylaminopyridine (7 mg, 0.06 mmole), and DCC (136 mg, 0.66 mmol). The reaction was kept at room temperature overnight, and then at 40° C. for two hours. The reaction mixture was filtered through Celite and poured into dichloromethane, and washed with aqueous sodium hydrogen carbonate solution. The product 2',3'-dideoxy-3'-fluoro-5'-O-[5-(N-trityl-L-valyloxymethyl)-6-stearoyloxyhexanoyl) guanosine was isolated by silica gel column chromatography. (93 mg)

$^1$H-NMR (DMSO δ-6): 7.88 (s, 1H), 7.29 (m, 15H), 6.52 (s, 2H), 6.17 (dd, 1H), 5.45 (m, 1H), 4.35 (m, 1H), 4.20 (m, 2H), 3.82 (m, 2H), 3.50–2.60 (m, 5H), 2.30 (m, 4H), 2.10 (m, 1H), 1.70 (m, 1H), 1.50 (m, 4H), 1.22 (m, 28H), 0.85 (m, 9H).

b) Preparation of 2',3'-dideoxy-3'-fluoro-5'-O-[5-(L-valyloxymethyl)-6-stearoyloxyhexanoyl] guanosine The compound of step b) (90 mg, 0.088 mmole) was N-deprotected by treatment with 80% acetic acid (5 ml) at room temperature for 30 min. It was evaporated and product was purified by silica gel column chromatography to yield 72 mg of the title compound.

$^1$H-NMR (DMSO δ-6): 7.88 (s, 1H), 6.54 (s, 2H), 6.18 (dd, 1H), 5.48 (dd, 1H), 4.27 (dt, 1H), 4.19 (m, 2H), 3.98 (m, 4H), 3.17–2.55 (m, 4H), 2.29 (m, 4H), 1.95 (m, 1H), 1.75 (m, 1H), 1.50 (m, 4H), 1.21 (m, 28H), 0.84 (m, 9H).

EXAMPLE 13

2,3'-Dideoxy-3'-fluoro-5'-O-[3-(L-valyloxymethyl-4-stearoyloxy-butanoyl]guanosine a) Preparation of 2',3'-dideoxy-3'-fluoro-5'-O-[3-(N-benzyloxycarbonyl-L-valyloxy)-4-stearoyloxy-butanoyl]guanosine To a solution of 2',3'-dideoxy-3'-fluoroguanosine (113 mg, 0.42 mmol) and 3-(N-benzyloxycarbonyl-L-valyloxymethyl)-4-stearoyloxy-butyric acid (140 mg, 0.21 mmol) in DMF (2 ml) were added dimethylaminopyridine (3 mg, 0.02 mmol) and DCC (52 mg, 0.25 mmol). After two days, dichloromethane (10 ml) and a few drops of acetic acid were added and the organic phase was filtered through Celite. The filtrate was washed with aqueous sodium hydrogen carbonate solution and the product 2',3'-dideoxy-3'-fluoro-5'-O-[3-(N-benzyloxycarbonyl-L-valyloxymethyl)-4-stearoyloxybutanoyl]guanosine was isolated by silica gel column chromatography to yield 51 mg.

$^1$H-NMR (CDCl$_3$): 7.79 (d, 1H), 7.26 (m, 5H), 6.38 (s, 2H), 6.23 (t, 1H), 5.44 (m, 2H), 5.08 (s, 2H), 4.50–4.10 (m, 8H), 3.15–2.40 (m, 5H), 2.30 (t, 2H), 2.14 (m, 1H), 1.58 (m, 2H), 1.24 (m, 28H), 0.87 (m, 9H).

b) Preparation of 2',3'-Dideoxy-3'-fluoro-5'-O-[3-(L-valyloxymethyl)-4-stearoyloxy-butanoyl]guanosine The product of step a) (76 mg, 0.084 mmole) was dissolved in a mixed solvent of methanol (3 ml), ethyl acetate (0.5 ml) and acetic acid (0.01 ml). To the solution was added palladium black (10 mg). After 2 hr, additional 10 mg palladium black was added. After 3 hr, the mixture was filtered and evaporated. The residue was dissolved in dichlorometahne and washed with aqueous EDTA solution. The organic phase was dried and coevaporated with toluene giving the title compound as the acetate salt.

Yield 65 mg.

$^1$H-NMR (DMSO δ-6+D$_2$O): 7.87 (s, 1H), 5.16 (dd, 1H), 5.37 (dd, 1H), 4.24 (m, 3H), 4.01 (m, 4H), 3.10–2.60 (m, 3H), 2.40 (m, 2H), 2.24 (t, 2H), 1.70 (m, 1H), 1.48 (m, 2H), 1.25 (m, 28H), 0.82 (m, 9H).

EXAMPLE 14

3-[1-(N-CBz-L-valyl)-2-stearoyl]propyl chloroformate 1-(N-CBz-L-valyl)-2-stearoyl) glycerol (300 mg, 0.5 mmole) was dissolved in 20% phosgene in toluene (15 ml). After 18 h, the solution was evaporated and the residue was coevaporated with toluene for several time, giving title product in quantitative yield. This product forms a carbonate with the target nucleoside using standard methodology, for instance reacting in a 10:1 DMF/pyridine solution at 0° C. for 3 to 24 hours, pouring into NaHCO$_3$ solution and extraction with dichloromethane. The amino acid is deprotected, for instance with palladium black in a methanol, ethyl acetate, acetic acid solution to yield the nucleoside-O-[1-(L-valyl)-2-stearoyl-3-propyloxy carbonyl]

$^1$H-NMR (CDCl$_3$): 7.40 (m, 5H), 5.28 (m, 2H), 5.10 (s, 2H), 4.35 (m, 5H), 2.35 (m, 2H), 2.17 (m, 1H), 1.56 (m, 2H), 1.30 (m, 28H), 0.95 (m, 9H).

EXAMPLE 15

5-(N-FMOC-L-valyloxy)-4-stearoyloxy-pentanoic acid a) Benzyl 4,5-dihydroxy-2-pentenoate A mixture of DL-glycerinaldehyde (4,5 g, 50 mmole) and (benzyloxycarbonylmethyl)-triphenyl-phosphoniumbromide (24.57 g, 50 mmole) in 100 ml 1,2-epoxybutane was refluxed overnight. The mixture was evaporated under vacuum and the product was isolated by silica gel column chromatography.

Yield: 8 g=71%

$^1$H-NMR (CDCl$_3$) 2.50 (s, 1H) 2.96 (s, 1H) 3.54 (m, 1H) 3.70 (m, 1H) 4.38 (m, 1H) 5.12 (s, 2H) 6.14 (m, 1H) 6.90 (m, 1H) 7.30 (m, 5H)

b) Benzyl 5-(N-FMOC-L-valyloxy)-4-hydroxy-2-pentenoate

A mixture of benzyl 4,5-dihydroxy-2-pentenoate (4.4 g, 20 mmole), N-FMOC-L-valine (5.8 g, 17 mmole) and DMAP (0.21 g, 1,7 mmole) in 100 ml dichloromethane was cooled to about 10° C. A solution of DCC (4.2 g, 20 mmole) in 25 ml dichloromethane was added dropwise at the same temperature and the mixture was stirred overnight at room temperature. The mixture was cooled to 5° C. and the urethane was filtered. The filtrate was evaporated under reduced pressure and the product was isolated by silica gel column chromatography.

Yield: 6,6 g=71%

$^1$H-NMR(CDCl$_3$) 0.91 (m, 6H)2.12 (m, 1H) 4.38 (m, 5H) 5.14(s, 2H) 5.24 (m, 1H) 6.20 (m, 1H) 6.92 (m, 1H) 7.30 (m, 13H)

c) Benzyl-5-(N-FMOC-L-valyloxy)-4-stearoyloxy-2-pentenoate

To a solution of benzyl-5-(N-FMOC-L-valyloxy)-4-hydroxy-2-pentenoate (6.5 g, 12 mmol) and pyridine (2.0 g, 25 mmole) in 100 ml dichloromethane at 10° C. was added dropwise a solution of stearoylchloride (4.55 g, 15 mmol) in 25 ml dichloromethane. The mixture was stirred overnight. 100 ml of 5% sodium hydrogencarbonate solution was added and the mixture was stirred for 30 minutes. The organic phase was seperated and the water phase was extracted two times with dichloromethane. The combined organic phases were dried with sodium sulfate and concentrated in vacuo. The product was isolated by silica gel column chromatography Yield: 7,8 g=80%

$^1$H-NMR (CDCl$_3$) 0.88 (m, 9H) 1.25 (m, 28H) 1.58 (m, 2H) 2.14 (m, 1H) 2.32 (m, 2H) 4.22 (m, 5H) 5.19 (s, 2H) 5.25 (m, 1H) 6.12 (m, 1H) 6.85 (m, 1H) 7.35 (m, 13H).

d) 5-(N-FMOC-L-valyloxy)-4-stearoyloxy-pentanoic acid

A solution of benzyl 5-(N-FMOC-L-valyloxy)-4-stearoyloxy-2-pentenoate (3.8 g, 4.69 mmole) in 50 ml ethyl acetate was hydrogenated with 10% palladium on charcoal (0,5 g) at normal pressure for five hours at room temperature. The catalyst was filtered and washed with ethyl acetate and 1,4-dioxane. The solution was evaporated under reduced pressure Yield: 3.3 g=99%

$^1$H-NMR (CDCl$_3$) 0.92 (m, 9H) 1.25 (m, 28H) 1.54 (m, 2H) 1.98 (m, 2H) 2.18 (m, 1H) 2.28 (m, 2H) 2.41 (m, 2H) 4,32 (m, 5H) 5.13 (m, 1H) 5.33 (m, 1H) 7.50 (m, 8H)

EXAMPLE 16

3-(N-FMOC-L-valyloxy)-2-stearoyloxypropionic acid a) Benzyl 2,3-dihydroxypropionate A mixture of D,L-glyceric acid, calcium salt dihydrate (2.9 g, 10 mmole) and benzylbromide (3.8 g, 22 mmole) in 25 ml DMF was stirred at 60° C. overnight. The mixture was evaporated under reduced pressure and the product was isolated by silica gel chromatography. Yield: 4 g=100%

$^1$H-NMR (CDCl$_3$) 3.26 (s, 1H) 3.90 (m, 2H) 4.32 (m, 1H) 5.25 (s, 2H) 7.28 (m, 5H)

b) Benzyl 3-(N-FMOC-L-valyloxy)-2-hydroxypropionate

A solution of benzyl-2,3-dihydroxypropionate (4,0 g, 20 mmole) N-FMOC-Lvaline (5.4 g, 16 mmole) and DMAP (0.2 g, 1.6 mmole) in 80 ml dichloromethane was cooled to about 10° C. A solution of DCC (4.12 g, 20 mmole) in 25 ml was added dropwise at the same temperature and the mixture was stirred overnight at room temperature. The mixture was cooled to 5° C. and the urethane was filtered.

The solution was evaporated under reduced pressure and the product was isolated by silica gel chromatography. Yield: 4.7 g=45%

$^1$H-NMR (CDCl$_3$) 0.88 (m, 6H) 2.05 (m, 1H) 4.40 (m, 6H) 5.23 (m, 3H) 7.50 (m, 13H)

c) Benzyl 3-(N-FMOC-L-valyloxy)-2-stearoyloxypropionate

To a stirred solution of benzyl 3-(N-FMOC-L-valyloxy)-2-hydroxypropionate (4.6 g 8.89 mmole) and pyridine (1.41 g, 17.8 mmole) in 80 ml dichloromethane was added dropwise a solution of stearoylchloride (3.64 g, 12 mmole) in 20 ml dichloromethane and the mixture was stirred overnight at room temperature. 100 ml of 5% sodium hydrogencarbonate solution was added and the mixture stirred for 30 minutes. The organic phase was seperated and the water phase was extracted two times with dichloromethane. The combined organic phases were dried with sodium sulfate and concentrated in vacuo. The product was isolated by silica gel chromatography. Yield: 6.1 g=87%

$^1$H-NMR (CDCl$_3$) 0.88 (m, 9H) 1.26 (m, 28H) 1.56 (m, 2H) 2.06 (m, 1H) 2.34 (m, 2H) 4.36 (m, 6H) 5.19 (s, 2H) 5.32 (m, 1H) 7.50 (m, 13H)

d) 3-(N-FMOC-L-valyloxy)-2-stearoyloxypropionic acid

A solution of benzyl 3-(N-FMOC-L-valyloxy)-2-stearoyloxypropionate (0.78 g, 1 mmole) in 20 ml ethyl acetate was hydrogenated with 10% palladium on charcoal (0.2 g) at normal pressure for three hours at room temperature. The catalyst was filtered and washed with ethyl acetate and 1,4-dioxane. The solution was evaporated under reduced pressure. Yield: 0.63 g=90%

$^1$H-NMR (CDCl$_3$) 0.88 (m, 9H) 1.24 (m, 28H) 1.40 (m, 2H) 2.12 (m, 3H) 4.30 (m, 5H) 5.16 (m, 1H) 5.60 (m, 1H) 7.40 (m, 8H)

EXAMPLE 17

1-(N-Benzyloxycarbonyl-L-valyloxymethyl)-2-stearoyloxyethoxycarbonyl chloride

Bis(trichloromethyl) carbonate (160 mg; 0.54 mmol) was added with stirring to a solution of 1-(N-benzyloxycarbonyl-L-valyl)-3-stearoylglycerol; 1-(N-benzyloxycarbonyl-L-valyloxy)-3-stearoyloxy-2-propanol; preparative example 4; (660 mg; 1.12 mmol) and triethylamine (200 mg; 2.0 mmol) in dichloromethane (5 ml) at room temperature. After 1 h, n-hexane (10 ml) was added and the precipitated triethylamine hydrochloride was filtered off through a short column of silica gel, the product eluted with a further amount of n-hexane, and the solvent evaporated in vacuum to yield 650 mg (89%) of the title compound.

$^{13}$C NMR (CDCl$_3$, 62.975 MHz): δ 172.8 (stear-COO); 171.2 (Val-COO); 155.9 (CONH); 154.1 (COCl); 136.0 (Ph-C1-Val); 128.1–127.7 (Ph); 67.2 (CHOH); 66.7 (PhCH$_2$); 63.1 (ValCOOCH$_2$); 61.8 (stear-COOCH$_2$); 58.7 (Val-αC); 33.7 (stear-C2); 31.6 (stear-C16); 31.0 (Val-βC); 29.3–28.8 (stear-C4-15); 24.5 (stear-C3); 18.6 and 17.1 (Val 2 CH$_3$); 13.8 (stear-C18).

EXAMPLE 18

3-(N-CBz-L-valyloxymethyl)-4-stearoyloxybutyl-chloroformate a) 3-(N-CBz-L-valyoxymethyl)-4-stearoyloxy-butanol

To a stirred solution of 4-stearoyloxy-3-(N-CBz-L-valyloxymethylbutyraldehyde (prepared analogously to preparative example 6, step d) using CBz protected valine) (2.0 g, 3.2 mmole) in 25 ml methanol at 10° C. was added sodium borohydride (0.6 g, 16 mmole) in small portions. The mixture was stirred for 30 minutes and then acidified with acetic acid. The mixture was diluted with water and extracted three times with dichloromethane. The organic phase was dried with sodium sulfate and concentrated in vacuo. The product was isolated by silica gel column chromatography. Yield: 1,5 g=75%.

$^1$H-NMR (CDCl$_3$) 0.88 (m, 9H) 1.25 (m, 28H) 1.52 (m, 4H) 2.24 (m, 3H) 3.68 (m, 2H) 4.12 (m, 4H) 4.24 (m, 1H) 5.08 (s, 2H) 5.22 (m, 1H) 7.36 (m, 5H)

b) 3-(N-CBz-L-valyloxymethyl)-4-stearoyloxybutyl chloroformate

A solution of the intermediate of step a) in 20 ml of a 20% solution of phosgene in toluene was stirred overnight. The mixture was evaporated under reduced pressure to yield the title compound. Yield 1.5 g=97%.

$^1$H-NMR (CDCl$_3$) 0.88 (m, 9H) 1.28 (m, 28H) 1.58 (m, 2H) 1.72 (m, 2H) 2.15 (m, 1H) 2.31 (m, 2H) 4.08–4.42 (m, 5H) 5.10 (s, 2H) 5.22 (m, 1H) 7.36 (m, 5H)

EXAMPLE 19

2',3'-dideoxy-3'-fluoro-5'-O-[1-(L-valyloxy)-2-stearoyloxy-3-propyloxy carbonyl] guanosine a) Synthesis of 2',3'-dideoxy-3'-fluoro-5'-O-[1-(N-CBz-L-valyloxy)-2-stearoyloxy-3-propyloxy carbonyl] guanosine To a solution of 2',3'-dideoxy-3'-fluoro-guanosine (270 mg, 1 mmole) in DMF (10 ml) and pyridine (1 ml) was added 3-{1-(N-CBz-L-valyl)-2-stearoyl} propyl chloroformate (619 mg, 0.5 mmole) at 0° C. After 3 h, the reaction mixture was poured into sodium hydrogen carbonate solution and extracted with dichloromethane. The organic phase was dried in vacuo, and 2',3'-dideoxy-3'-fluoro-5'-O-[1-(N-CBz-L-valyloxy)-2-stearoyloxy-3-propyloxy carbonyl] guanosine was isolated by silica gel column chromatography (195 mg).

$^1$H-NMR (CDCl$_3$): 7.69 (s, 1H), 7.31 (m, 5H), 6.50 (m, 2H), 6.32 (m, 1H), 5.3 (m, 2H), 5.09 (m, 2H), 4.35 (m, 7H), 2.60 (m, 2H), 2.31 (t, 2H), 2.20 (m, 1H), 1.58 (m, 2H), 1.23 (m, 28H), 0.92 (m, 9H).

b) Synthesis of 2',3'-dideoxy-3'-fluoro-5'-O-[1-(L-valyloxy)-2-stearoyloxy-3-propyloxy carbonyl] guanosine 2',3'-dideoxy-3'-fluoro-5'-O-[1-(N-CBz-L-valyloxy)-2-stearoyloxy-3-propyloxy carbonyl] guanosine (190 mg), was dissolved in a mixed solvent of methanol (6 ml), ethyl acetate (2 ml) and acetic acid (1 ml). To the solution was added palladium black (30 mg), and the reaction mixture was kept under hydrogen for 2 h. It was then filtered and the filtrate was evaporated and the titled product was isolated by silica gel column. 110 mg.

$^1$H-NMR (DMSO-δ6): 7.86 (ds, 1H), 6.51 (s, 2H), 6.17 (dd, 1H), 5.48 (m, 1H), 5.20 (m, 1H), 4.25 (m, 7H), 2.70 (m, 2H), 2.27 (m, 2H), 1.72 (m, 1H), 1.47 (m, 2H), 1.22 (m, 28H), 0.84 (m, 9H).

EXAMPLE 20

2', 3'-dideoxy-3'-fluoro-5'-O-[5-(L-valyloxy)-4-stearoyloxy-pentanoyl] guanosine To a solution of 2',3'-dideoxy-3'-fluoroguanosine (0.27 g, 1 mmole) and 5-(N-FMOC-L-valyloxy)-4-stearoyloxypentanoic acid (0.94 g, 1.3 mmole) in 30 ml DMF was added DMAP (16 mg, 0.13 mmol) HOBT (0.176 g, 1.3 mmole) and DCC (0.248 g, 1.2 mmole). The mixture was stirred for three days at room temperature. 4 g silica gel were added and the mixture evaporate in vacuo. The product, 2', 3'-dideoxy-3'-fluoro-5'-O-[5-(FMOC-L-valyloxy)-4-stearoyloxy-pentanoyl]guanosine was separated by silica gel chromatography. Yield: 0.45 g $^1$H-NMR (DMSOδ-6) 0.88 (m, 9H) 1.20 (m, 28H) 1.45 (m, 2H) 1.78 (m, 2H) 2.18 (m, 2H) 2.36 (m, 1H) 2.62 (m, 2H) 3.88 (m, 1H) 4.22 (m, 6H) 4.92 (m, 1H) 5,45 (m, 1H) 6.19 (m, 1H) 6.52 (s, 2H) 7.26–7.88 (m, 8H)

The protected intermediate is deprotected as shown above to yield the title compound.

EXAMPLE20

2', 3'-dideoxy-3'-fluoro-5'-O-[3-(N-FMOC-L-valyloxy)-2-stearoyloxypropanoyl]guanosine To a stirred mixture of 3-(N-FMOC-L-valyloxy)-2-stearoyloxypropanoic acid (0.61 g, 0.88 mmol) in 5 ml dry diethlether was added one drop DMF and thionyl chloride (0.52 g, 4.4 mmole). The mixture was refluxed for two hours and then evaporated under reduced pressure. The product was dissolved in dry dichloromethane and added dropwise to a solution of 2',3'-dideoxy-3'-fluoroguanisine (0.215 g, 0.8 mmole) and pyridine (0.35 g, 4.4 mmole) in 20 ml DMF. The solution was stirred overnight. Two grammes of silica gel were added and the mixture was evaporated in vacuo. The product was isolated by silica gel chromatography. Yield: 0.19 g=25%

$^1$H-NMR (CDCl$_3$) 0.88 (m, 9H) 1.25 (m, 28H) 1.62 (m, 2H) 2.12(m, 1H) 2.38 (m, 2H) 2.58 (m, 2H) 4.12–4.76 (m, 6H) 5.32 (m, 2H) 6.12 (m, 1H) 6.26 (m, 1H) 6.44 (m, 1H) 7.12–7.78 (m, 8H).

EXAMPLE 21

1-(N-CBz-L-valyl)-3-stearoyl-2-propyl succinate monoester 1-(N-CBz-L-valyl)-3-stearoyl-glycerol (886 mg, 1.5 mmole) and succinic anhydride (450 mg, 4.5 mmole) were dissolved in a mixed solvent of DMF (15 ml) and pyridine (1 ml). The reaction was kept at room temperature for 3 h, and then at 60° C. for 5 h. The reaction mixture was poured into a solution of acetic acid and water and extracted with dichloromethane. The organic phase was washed with water and evaporated, and the product was isolated by silica gel column chromatography to yield 900 mg.

$^1$H-NMR (CDCl$_3$): 7.43 (m, 5H), 5.27 (m, 1H), 5.09 (m, 2H), 4.21 (m, 5H), 2.54 (m, 4H), 2.29 (t, 2H), 2.13 (m, 1H), 1.59 (m, 2H), 1.25 (m, 28H), 0.90 (m, 9H).

EXAMPLE 22

2',3'-dideoxy-3'-fluoro-5'-O-{3-[1-(L-valyloxy)-3-stearoyloxy-2-propyloxy carbonyl]-propanoyl} guanosine To a solution of 2',3'-dideoxy-3'-fluoro-guanosine (351 mg, 1.3 mmole) and 1-(N-CBz-L-valyl)-3-stearoyl-2-propyl succinate monoester (900 mg, 1.3 mmole) in DMF (15 ml) were added dimethylaminopyridine (24 mg, 0.2 mmole), 1-hydroxybenzotriazole (175 mg, 1.3 mmole), DCC (321 mg, 1.56 mmole). After 48 h, the reaction mixture was filtered. The filtrate was poured into sodium hydrogen carbonate solution and extracted with dichloromethane. The product 2',3'-dideoxy-3'-fluoro-5'-O-{3-[1-(N-CBz-L-valyl)-3-stearoyl glyceroloxy carbonyl]propanoyl} guanosine was isolated by silica gel column chromatography. 780 mg $^1$H-NMR (DMSO-d$_6$): 7.89 (s, 1H), 7.34 (m, 5H), 6.50 (s, 2H), 6.17 (dd, 1H), 5.46 (m, 1H), 5.38 (m, 1H), 5.02 (s, 2H), 4.22 (m, 7H), 3.32 (s, 4H), 2.80 (m, 2H), 2.57 (m, 2H), 2.31 (t, 2H), 2.05 (m, 1H), 1.48 (m, 2H), 1.21 (m, 28H), 0.84 (m, 9H).

To the solution of 2',3'-dideoxy-3'-fluoro-5'-O-{3-[1-(N-CBz-L-valyl)-3-stearoyl-2-propyloxy carbonyl]propanoyl}guanosine (460 mg, 0.5 mmole) in a mixed solvent of methanol (10 ml), ethyl acetate (3 ml) and acetic acid (2 ml) was added palladium black (50 mg). After reaction under hydrogen atmosphere for 2 h, the mixture was filtered and the filtrate was dried. The titled product was isolated by silica gel column chromatography. 360 mg.

$^1$H-NMR (DMSO-d$_6$): 7.89 (s, 1H), 6.51 (s, 2H), 6.16 (dd, 1H), 5.48 (m, 1H), 5.17 (m, 1H), 4.28 (m, 7H), 2.90 (m, 2H), 2.58 (m, 4H), 2.28 (t, 2H), 1.85 (m, 1H), 1.49 (m, 2H), 1.22 (m, 28H), 0.85 (m, 9H).

EXAMPLE 23

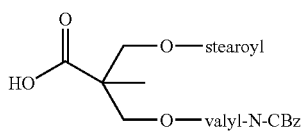

A solution of stearoyl chloride (12.1 g, 40 mmol, 1.0 eq) in CH$_2$Cl$_2$ (100 ml) was slowly (1 h) added to a solution of 2,2-bis(hydroxymethyl)propionic acid (26.8 g, 200 mmol, 5.0 eq) in pyridine (400 ml) at room temperature. The reaction mixture was stirred at room temperature overnight and thereafter concentrated (100 ml) under vacuum. The reaction mixture was slowly treated with saturated NaHCO$_3$ (400 ml) and thereafter extracted with CH$_2$Cl$_2$ (3×300 ml). The organic layers were combined, washed with brine, dried over Na$_2$SO$_4$ and concentrated in vacuum. The crude material was chromatographed on silica gel (500 g) with 19/1 to 4/1 CH$_2$Cl$_2$-MeOH as eluent, to yield the monostearoyl ester, R$_f$ (9/1 CH$_2$Cl$_2$-MeOH) 0.33. 12.5 g (78%).

A solution of N-Cbz-L-valine (18.85 g, 75 mmol, 2.4 eq) and DMAP (855 mg, 7 mmol, 0.22 eq) in CH$_2$Cl$_2$ (800 ml) was cooled to 0° C. and treated with DCC (14.4 g, 70 mmol, 2.2 eq). The reaction mixture was stirred at room temperature for 30 min and thereafter slowly (1 h) treated with a solution of the above monostearoyl ester (12.5 g, 31.2 mmol, 1 eq) in CHCl$_3$ (200 ml, free of ethanol). After stirring overnight the suspension was filtered and the filtrate was washed with brine, dried with Na$_2$SO$_4$ and concentrated in vacuum. The crude material was chromatographed on silica gel (500 g) with 19/1 to 4/1 CH$_2$Cl$_2$-MeOH as eluent, to yield the above depicted diester. R$_f$ (9/1 CH$_2$Cl$_2$-MeOH) 0.46. 13.8 g (70%).

$^1$H-NMR (250 MHz, CDCl$_3$) δ 7.35–7.3 (m, 5H, ArH), 5.32 (d, 1H, CH), 5.10 (s, 2H, CH$_2$Ph), 4.33–4.18 (m, 4H, CH$_2$), 2.28 (t, 2H, CH$_2$), 2.22–2.05 (m, 1H, CH), 1.65–1.50 (m, 2H, CH$_2$) 1.35–1.15 (m, 31H), 1.00–0.82 (m, 9H, Me).

EXAMPLE 24

2',3'-Dideoxy-3'-fluoro-5'-O-[5-(L-valyloxyl)-4-stearoyloxy-pentanoyl]guanosine a) Synthesis of 2',3'-di deoxy-3'-fluoro-5'-O-[5-(N-FMOC-L-valyoxy)-4-stearoyloxy-pentanoyl] guanosine A mixture of 2',3'-dideoxy-3'-fluoroguanosine (269 mg, 1.0 mmole), 5-(N-FMOCL-valyoxy)-4-stearoyloxy-pentanoic acid (940 mg, 1.3 mmole), DMAP (16 mg, 0.13 mmole) and HOBT (176 mg, 1.3 mmole) was coevaporated two times with DMF and reduced to about 30 ml. DCC (248 mg, 1.2 mmole) was added and the mixture was stirred overnight at room temperature. The mixture was filtered and the solution was evaporated under reduced pressure. Ethyl acetate (50 ml) was added and the organic phase was washed two times with 5% acetic acid, with 5% sodium hydrogen carbonate and with water. The organic phase was dried with sodium sulfate and evaporated under reduced pressure. The product is isolated by silica gel column chromatography. Yield: 450 mg $^1$H-NMR (DMSO d-6) 0.88 (m, 9H) 1.22 (m, 28H) 1.45 (m, 2H) 1.83 (m, 2H) 2.21 (m, 2H) 2.37 (m, 1H) 3.90 (m, 1H) 5.36–5.58 (m, 1H) 6.18 (m, 1H) 6.50 (s, 2H) 7.28–7.91 (m, 10H)

b) Synthesis of 2',3'-dideoxy-3'-fluoro-5'-O-[5-(L-valyloxy)-4-stearoyloxy-pentanoyl] guanosine A mixture of 2', 3'-dideoxy-3'-fluoro-5'-O-[5-(N-CBZ-L-valyloxy)-4-stearoyloxy-pentanoyl] guanosine (300 mg, 0.308 mmole) in 5 ml N,N-diisopropylethylamine and 5 ml DMF was stirred for three days at room temperature. Acetic acid (5 ml) was added and the mixture was evaporated under reduced pressure. The product was isolated as the acetate salt by silica gel column chromatography. Yield: 90 mg $^1$H-NMR (DMSO d-6) 0.88 (m, 9H) 1.24 (m, 28H) 1.55 (m, 2H) 1.91 (m, 2H) 2.31 (m, 2H) 2.44 (m, 1H) 2.56–3.08 (m, 2H) 3.15 (m, 1H) 4.00–4.49 (m, 5H) 5.08 (m, 1H) 5.40–5.62 (m, 1H) 6.24 (m, 1H) 6.54 (s, 2H) 7.96 (s, 1H)

EXAMPLE 25

2', 3'-Dideoxy-3'-fluoro-5'-O-[3-(L-valyloxyy-2-stearoyloxy-propanoyl] guanosine a) Synthesis of 2',3'-Dideoxy-3'-fluoro-5'-O-[3-(N-CBZ-L-valyloxy)-2-stearoyloxy-propanoyl]guanosine A mixture of 2',3'-dideoxy-3'-fluoroguanosine (404 mg, 1.5 mmole), 3-(N-CBZ-L-valyloxy)-2-stearoyloxy-propanoic acid (1.06 g, 1.75 mmole), DMAP (24 mg, 0.2 mmole) and HOBT (264 mg, 1.82 mmole) was coevaporated two times with DMF and reduced to about 30 ml. DCC (372 mg, 1.8 mmole) was added and the mixture was stirred overnight at room temperature. The mixture was filtered and the solution was evaporated under reduced pressure. Ethyl acetate (50 ml) was added and the organic phase was washed twice with 5% acetic acid, with 5% sodium hydrogen carbonate and with water. The organic phase was dried with sodium sulfate and evaporated under reduced pressure. The product was isolated by silica gel column chromatography. Yield: 0.73 g $^1$H-NMR (DMSO d-6) 0.82 (m, 9H) 1.22 (m, 28H) 1.48 (m, 2H) 2.31 (m, 2H) 2.50–3.00 (m, 2H) 3.91 (m, 1H) 4.18–4.52 (m, 5H) 5.00 (s, 2H) 5.30–5.61 (m, 2H) 6.16 (m, 1H) 6.50 (s, 2H) 7.32 (m, 5H) 7.71 (m, 1H) 7.92 (s, 1H) 10.18 (s, 1H)

b) Synthesis of 2',3'-dideoxy-3'-fluoro-5'-O-[3-(L-valyloxy)-2-stearoyloxypropanoyl]guanosine A solution of 2',3'-dideoxy-3'-fluoro-5'-O-[3-(N-CBZ-L-valyloxy)-2-stearoyloxypropanoyl]guanosine (350 mg, 0.4 mmole) in ethyl acetate (25 ml), methanol (5 ml) and acetic acid (5 ml) was hydrogenated with palladium black (300 mg) with normal pressure for three hours. The catalyst was filtered and washed with ethyl acetate and methanol. The solution was evaporated under reduced pressure and the product was isolated as the acetate salt by silica gel column chromatography. Yield: 120 mg $^1$H-NMR (DMSO d-6) 0.84 (m, 9H) 1.22 (m, 28H) 1.50 (m, 2H) 2.32 (m, 2H) 2.50–3.00 (m, 2H) 3.07 (m, 1H) 4.21–4.59 (m, 5H) 5.38–5.59 (m, 2H) 6.17 (m, 1H) 6.0 (s, 2H) 7.90 (s, 1H)

EXAMPLE 26

2', 3'-Dideoxy-3'-fluoro-5'-O-[3,3-bis(L-valyloxymethyl)-propionic acid] guanosine a) Synthesis of 4,4-bis (N-CBZ-L-valyloxymethyl)-but-1-ene To a solution of 2-allyl-1,3-propandiol (2.32 g, 20 mmole), N-CBZ-L-valine (10.06 g, 40 mmole) and DMAP (0.488 g, 4 mmole) in 120 ml dichloromethane was added DCC (9.08 g, 44 mmole) in portions and the mixture was stirred overnight at room temperature. The mixture was cooled to 5° C. and the urethane was filtered. The filtrate was evaporated and the product was isolated by silica gel column chromatography. Yield: 9.0 g $^1$H-NMR (CDCl$_3$) 0.89 (m, 12H) 5.11 (s, 2H) 5.73 (m, 1H)

b) Synthesis of 3,3-Bis (N-CBZ-L-valyloxymethyl)-propionic acid. To a cooled solution of 4,4-bis (N-CBZ-L-valyloxymethyl)-but-1-ene (14.6 g, 25 mmole) and tetrabutylammonium bromide (1.3 g, 4 mmole) in 120 ml benzene was added 100 ml water. Under strong stirring potassium permanganate (15.8 g, 100 mmole) was addded in portions and the mixture was stirred for 2 hours between 15° C. and 20° C. A sodium bisulfite aqueous solution was added to the slurry until the mixture was discolored. The mixture was acidified with 2N hydrochloric acid and extracted four times with ethyl acetate. The organic phase was washed two times with water, dried with sodium sulfate and evaporated under reduced pressure. The product was isolated by silica gel column chromatography. Yield: 7.5 g $^1$H-NMR (CDCl$_3$) 0.89 (m, 12H) 2.05 (m, 2H) 2.46 (m, 2H) 2.62 (m, 1H) 4.20 (m, 6H) 5.11 (s, 4H) 5.30 (m, 2H) 7.35 (m, 10H)

c) Synthesis of 2',3'-dideoxy-3'-fluoro-5'-O-[3,3-bis (N-CBZ-L-valyloxymethyl)-propionyl]guanosine A solution of 2',3'-dideoxy-3'-fluoroguanosine (1.35 g, 5 mmole), 3,3-bis (N-CBZ-L-valyloxymethyl)-propionic acid (3.6 g, 6 mmole), DMAP (0.061 g, 0.5 mmole) and HOBT (0.81 g, 6 mmole) was coevaporated two times with DME and reduced to about 120 ml. DCC (1.24 g, 6 mmole) was added and the mixture was stirred overnight at room temperature. The mixture was filtered and the solution was evaporated under reduced pressure. Ethyl acetate (200 ml) was added and the organic phase washed twice with 5% acetic acid, 5% sodium hydrogen carbonate and water.

The organic phase was dried with sodium sulfate and evaporated under reduced pressure. The product was isolated by silica gel column chromatography. Yield: 2.7 g $^1$H-NMR (DMSO d-6) 0.88 (m, 12H) 2.00(m, 2H) 2.50–3.00 (m, 2H) 3.90–4.43 (m, 10H) 5.08 (s, 4H) 5.32–5.59 (m, 1H) 6.17 (m, 1H) 6.50 (s, 2H) 7.28 (m, 10H) 7.72 (m, 2H) 7.90 (s, 1H)

d) Synthesis of 2',3'-Dideoxy-3'-fluoro-5'-O-[3,3-bis (L-valyloxymethyl)-propionicacid] guanosine A solution of 2',3'-dideoxy-3'-fluoro-5'-O-[3,3-bis (N-CBZ-L-valyloxymethyl)-propionyl] guanosine (2.6 g, 3.1 mmole) in 80 ml ethyl acetate, 20 ml methanol and 20 ml acetic acid was hydrogenated with palladium black (0.3 g) for two hours under normal pressure. The catalyst was filtered and washed with ethyl acetate and methanol. The solution was evaporated under reduced pressure and the product was isolated as the bisacetate salt by silica gel column chromatography. Yield: 1.2 g $^1$H-NMR (DMSO d-6) 0.90 (m, 12H) 1.78 (m, 2H) 2.50–3.00 (m, 2H) 3.09 (m, 2H) 4.02–4.45 (m, 8H) 5.34–5.59 (m, 1H) 6.17 (m, 1H) 6.62 (s, 2H) 7.88 (s, 1H)

EXAMPLE 27

2', 3'-Dideoxy-3'-fluoro-5'-O-[3-(L-valyloxymethyl)-4-stearoyloxy-butoxycarbonyl] guanosine a) Synthesis of 2',3'-Dideoxy-3'-fluoro-5'-O-[3-(N-CBZ-L-valyloxymethyl)-4-stearoyloxy-butoxycarbonyl] guanosine To a solution of 2',3'-dideoxy-3'-fluoroguanosine (269 mg, 1.0 mmole in absolute DMF were added pyridine (198 mg, 2.5 mmole) and a solution of 3-(N-CBZ-L-valyloxymethyl)-4-stearoyloxy-butoxycarbonyl chloride (750 mg, 1.1 mmole) in 5 ml dichloromethane. The mixture was stirred for three days at room temperature. The solution was evaporated under reduced pressure and the product was isolated by silica gel column chromatography. Yield: 120 mg $^1$H-NMR (DMSO d-6) 0.88 (m 9H) 1.24 (m, 28H) 5.08 (s, 2H) 6.24 (m, 1H) 8.00 (s, 1H)

b) Synthesis of 2',3'-Dideoxy-3'-fluoro-5'-O-[3-(L-valyloxymethyl)-4-stearoyloxy-butoxycarbonyl] guanosine A mixture of 2',3'-dideoxy-3'-fluoro-5-O-[3-(N-CBZ-L-valyloxymethyl)-4-stearoyloxy-butoxycarbonyl]guanosine in 15 ml ethyl acetate, 2 ml methanol and 2 ml acetic acid was hydrogenated with palladium black (40 mg) under normal pressure for two hours. The catalyst was filtered and washed with ethyl acetate and methanol. The solution was evaporated and the product isolated as the acetate salt by silica gel column chromatography. Yield: 78 mg $^1$H-NMR (DMSO d-6) 0.87 (m, 9H) 1.22 (m, 28H) 1.48 (m, 2H) 1.68 (m, 2H) 2.12 (m, 1H) 2.26 (m, 2H) 2.50–3.00 (m, 2H) 4.00–4.42 (m, 10H) 5.34–5.58 (m, 1H) 6.18 (m, 1H) 6.52 (s, 2H) 7.82 (s, 1H)

EXAMPLE 28

2',3'-Dideoxy-3'-fluoro-5'-O-[2-(L-valyloxy) stearoyl]guanosine a) Synthesis of benzyl 2-hydroxystearate To a stirred solution of DL-2-hydroxystearic acid (3.0 g, 10 mmole) in 20 ml dry DMF was added potassium tert-butoxide (1.23 g, 11 mmole) and the mixture was stirred for one hour at 60° C. Benzyl bromide (2.14 g, 12.5 mmole) was added and the mixture was stirred for six hours at 80° C. The mixture was evaporated under reduced pressure and 100 ml ethyl acatate was added. The organic phase was separated and washed four times with water. The organic phase was dried with sodium sulfate and concentrated in vacuo. The product was isolated by silica gel column chromatography. Yield: 3.3 g $^1$H-NMR (CDCl$_3$) 0.88 (m, 3H) 1.26 (m, 28H) 1.62 (m, 2H) 4.20 (m, 1H) 5.20 (s, 2H) 7.36 (m, 5H)

b) Synthesis of benzyl-2-(N-FMOC-L-valyloxy)stearate

To a solution of benzyl-2-hydroxystearate (3.2 g, 8.2 mmole), N-FMOC-L-valine (3.4 g, 10 mmole) and DMAP (0.12 g, 1 mmole) in 80 ml dichloromethane was added a solution of DCC (2.5 g, 12 mmole) and the mixture was stirred overnight at room temperature. The mixture was cooled to 5° C. and the urethane was filtered. The filtrate was evaporated and the product was isolated by silica gel column chromatography. Yield: 4.5 g $^1$H-NMR (CDCl$_3$) 0.90 (m, 6H) 1.26 (m, 6H) 1.82 (m, 2H) 2.16 (m, 1H) 4.21 (m, 1H) 4.36 (m, 2H) 5.10 (m, 1H) 5.18 (s, 2H) 5.28 (m, 1H) 7.20–7.80 (m, 13H)

c) Synthesis of 2-(N-FMOC-L-valyloxy) stearic acid

A solution of benzyl-2-(N-FMOC-L-valyloxy)stearate (4.4 g, 6.2 mmole) in 50 ml ethyl acetate was hydrogenated with 10% palladium on charcoal (0.5 g) with normal pressure for two hours. The catalyst was filtered and washed with ethyl acetate and 1,4-dioxane. The solution was evaporated under reduced pressure and the product was isolated by silica gel column chromatography. Yield: 3.4 g $^1$H-NMR (CDCl$_3$) 0.88 (m, 6H) 1.26 (m, 28H) 1.82 (m, 2H) 2.28 (m, 1H) 4.20 (m, 1H) 4.40 (m, 2H) 5.00 (m, 1H) 5.41 (m, 1H) 7.26–7.82 (m, 8H)

d) Synthesis of 2',3'-Dideoxy-3'-fluoro-5'-O-[2-(N-FMOC-L-valyloxy)stearoyl] guanosine A mixture of 2',3'-dideoxy-3'-fluoroguanosine (404 mg, 1.5 mmole), 2-(N-FMOC-L-valyloxy)stearic acid (1.24 g, 2 mmole), DMAP (24 mg, 0.2 mmole) and HOBT (264 mg, 1,95 mmole) was coevaporated two times with DMF and reduced to about 30 ml. DCC (372 mg, 1.8 mmole) was added and the mixture was stirred overnight at room temperature. The mixture was filtered and the solution was evaporated under reduced pressure. Ethyl acetate (50 ml) was added and the organic phase washed twice with 5% acetic acid, with 5% sodium hydrogen carbonate and with water. The organic phase was dried with sodium sulfate and evaporated under reduced pressure.

The product was isolated as the acetate salt by silica gel column chromatography.

Yield: 1.2 g $^1$H-NMR (DMSO d-6) 0.80–0.90 (m, 9H) 1.22 (m, 28H) 2.12 (m, 1H) 2.50–3.00 (m, 2H) 3.98 (m, 1H) 4.96 (m, 1H) 6.17 (m, 1H) 6.50 (s, 2H) 7.32–7.95 (m, 10H)

e) Synthesis of 2',3'-dideoxy-3'-fluoro-5'-O-[2-(L-valyloxy)-stearoyl] guanosine To a solution of 2',3'-dideoxy-3'-fluoro-5'-O-[2-(N-FMOC-L-valyloxy) stearoyl] guanosine (800 mg, 0.89 mmole) in 15 ml DMF was added DBU (1.35 g, 8.9 mmole) and the mixture was stirred for 5 minutes at room temperature. Acetic acid (2 ml) was added and the mixture was evaporated under reduced pressure. Water (20 ml) were added and the mixture was extracted three times with dichloromethane. The organic phase was dried with sodium sulfate and evaporated under reduced pressure. The product was isolated by silica gel column chromatography. Yield: 165 mg $^1$H-NMR (DMSO d-6) 0.87 (m, 9H) 1.22 (m, 28H) 1.70 (m, 2H) 1.88 (m, 1H) 2.50–3.00 (m, 2H) 3.20 (m, 1H) 4.32 (m, 3H) 4.94 (m, 1H) 5.32–5.54 (m, 1H) 6.14 (m, 1H) 6.49 (s, 2H) 7.89 (s, 1H)

EXAMPLE 29

2', 3'-Dideoxy-3'-fluoro-5'-O-3-[1,3-bis-(L-valyloxy]-2-propyloxycarbonyl propanoyl]guanosine a) Synthesis of 1,3-dibenzyloxy-2-propyl succinate monoester

A solution of 1,3-dibenzyloxypropan-2-ol (6.8 g, 25 mmole) and succinic anhydride (7.5 g, 75 mmole) and DMAP (12.2 g, 100 mmole) was stirred for one hour at 60° C. The mixture was evaporated under reduced pressure, acidified with 2N HCl and extracted two times with ethyl actate. The combined organic phase was washed three times with water, dried with sodium sulfate and evaporated under reduced pressure. The product was isolated by silica gel column chromatography. Yield: 7.8 g b) Synthesis of 2',3'-dideoxy-3'-fluoro-5'-O-[3-(1,3-dibenzyloxy-2-propyloxycarbonyl)-propanoyl] guanosine A mixture of 2',3'-dideoxy-3'-fluoroguanosine (1.61 g, 6 mmole), HOBT (0.972 g, 7.2 mmole), DMAP (73.3 mg, 0.6 mmole) and 1,3-dibenzyloxy-2-propyl succinate monoester (2.68 g, 7,2 mmole) was coevaporated two times with DMF and reduced to about 150 ml. DCC (1.55 g, 7.5 mmole) was added and the mixture was stirred 72 hours at room temperature. The mixture was filtered and the solution was evaporated under reduced pressure. Ethyl acetate (200 ml) was added and the organic phase washed twice with 5% acetic acid, 5% sodium hydrogen carbonate and water. The organic phase was dried with sodium sulfate and evaporated under reduced pressure. The product was isolated by silica gel column chromatography. Yield: 3.3 g c) Synthesis of 2',3'-dideoxy-3'-fluoro-5'-O [3-(1,3-dihydoxy-2-propyloxy carbonyl)propanoyl]guanosine A solution of 2',3'-dideoxy-3'-fluoro-5'-O-[3-(1,3-dibenzyloxy-2-propyloxy carbonyl)propanoyl]guanosine (3.2 g, 5.13 mmole) in 50 ml ethyl acetate, 50 ml methanol and 10 ml acetic acid was hydrogenated with palladium black (0.6 g) under 40 psi overnight. The catalyst was filtered and washed with methanol, The solution was evaporated under reduced pressure and the product was isolated by silica gel column chromathography. Yield: 1.64 g d) Synthesis of 2',3'-dideoxy-3'-fluoro-5'-O-{3-[1,3-Bis (N-CBZ-L-valyloxy)-2-propyloxycarbonyl]propanoyl} guanosine A mixture of 2',3'-dideoxy-3'-fluoro-5'-O-[3-(1,3-dihydroxy-2-propyloxy carbonyl)propanoyl]guanosine (1.93 g, 2.93 mmole), N-CBZ-L-valine (1.76 g, 7 mmole), HOBT (0.95 g, 7 mmole) and DMAP (85.5 mg, 0.7 mmole) was coevaporated two times with DMF and reduced to about 60 ml. DCC (1.55 g, 7.5 mmole) was added and the mixture was stirred overnight at room temperature. The mixture was warmed for four hours at 60° C. and then cooled to about 10° C. The mixture was filtered and the solution was reduced under reduced pressure. Ethyl acetate (150 ml) was added and the organic phase was washed twice with 5% acetic acid, 5% sodium hydrogen carbonate and water. The organic phase was dried with sodium sulfate and evaporated under reduced pressure. The product was isolated by silica gel column chromatography. Yield: 1.6 g.

e) Synthesis of 2',3'-dideoxy-3'-fluoro-5'-O-{3-[1,3-bis-(L-valyloxy)-2-propyloxycarbonyl]-propanoyl}guanosine A solution of 2',3'-dideoxy-3'-fluoro-5'-O-{3-[1,3-bis-(N-CBZ-L-valyloxy)-2-propyloxycarbonyl) propanoyl}guanosine(1.6 g, 1.75 mmole) in 80 ml ethyl acetate, 20 ml methanol and 20 ml acetic acid was hydrogenated with palladium black (0.3 g) for two hours at room temperature and normal pressure. The catalyst was filtered and washed with methanol. The solution was evaporated under reduced pressure and the product was isolated as the diacetate salt by silica gel column chromatography. Yield: 1.02 g $^1$H-NMR (DMSO d-6) 0.84 (m, 12H) 1.85(m, 2H) 2.58 (m, 4H) 2.60–3.10 (m, 2H) 3.11 (m, 2H) 3.61–4.39 (m, 7H) 5.19 (m, 1H) 5.35–5.56 (m, 1H) 6.16 (m, 1H) 6.62 (s, 2H) 7.89 (s, 1H)

EXAMPLE 30

2',3'-Dideoxy-3'-fluoro-5'-O-{3-[1-(L-valyloxy)-3-hydroxy-2-propyloxy carbonyl]-propanoyl}guanosine a) Synthesis of 2',3'-dideoxy-3'-fluoro-5'-O-{3-[1-(N-CBZ-L-valyloxy)-3-hydroxy-2-propyloxy carbonyl]-propanoyl} guanosine A mixture of 2',3'-dideoxy-3'-fluoro-5'-O-[3-(1,3-dihydroxy-2-propyloxy carbonyl)-propanoyl] guanosine (1.3 g, 2.93 mmole), N-CBZ-L-valine (1.00 g, 4 mmole), HOBT (0.54 g, 4 mmole) and DMAP (48.8 mg, 0.4 mmole) was coevaporated two times with DMF and reduced to about 60 ml. DCC (0.91 g, 4.4 mmole) was added and the mixture was stirred for 72 hours at room temperature. The mixture was filtered and the solution evaporated under reduced pressure. Ethyl acetate (150 ml) was added and the organic phase washed twice with 5% acetic acid, 5% sodium hydrogen carbonate and water. The organic phase was dried with sodium sulfate and evaporated under reduced pressure. The product was isolated by silica gel column chromatography. Yield: 0.99 g b) Synthesis of 2',3'-dideoxy-3'-fluoro-5'-O-{3-[1-(L-valyloxy)-3-hydroxy-2-propyloxycarbonyl]-propanoyl} guanosine A solution of 2',3'-dideoxy-3'-fluoro-5'-O-{3-[1-(N-CBZ-L-valyloxy)-3-hydroxy-2-propyloxycarbonyl)-propanoyl}guanosine (0.82 g, 1.21 mmole) in 30 ml ethyl acetate, 15 ml methanol and 15 ml acetic acid was hydrogenated with palladium black (0.15 g) for two hours at room temperature and normal pressure. The catalyst was filtered and washed with methanol. The solution was evaporated under reduced pressure and the product was isolated as th acetate salt by silica gel column chromatography. Yield: 0.5 g $^1$H.NMR (DMSO d-6) 0.84 (m, 6H) 1.86 (m, 1H) 2.58 (m, 4H) 2.63–3.02 (m, 2H) 3.10–4.38 (m, 9H) 5.34–5.55 (m, 1H) 6.16 (m, 1H) 6.56 (s, 2H) 7.90 (s, 1H)

EXAMPLE 31

5'-L-valyl-2',3'-dideoxy-3'-fluoroguanosine

To a solution of 2',3'—dideoxy-3'—fluoroguanosine (810 mg, 3 mmole) and 4-dimethylaminopyridine (73 mg, 0.6 mmole), N-CBz-L-valine (1.5 g, 6 mmole) and 1-hydroxybenzotriazole (810 mg, 6 mmole) in DMF (20 ml) was added DCC (1.36 g, 6.6 mmole). After 72 h, the reaction mixture was filtered and concentrated in vacuo. 5'-(N-CBz-L-valyl)-2',3'-dideoxy-3'-fluoroguanosine was isolated by silica gel column chromatography (1.15 g).

This intermediate (503 mg, 1 mmole) was dissolved in a mixed solvent of ethyl acetate (10 ml), methanol (20 ml) and acetic acid (2 ml). To the mixture was added palladium black (100 mg) and the reaction mixture was kept under hydrogen at atmospheric pressure for 3 h. After filtration and concentration, the titled product was isolated by silica gel column chromatography (370 mg).

$^1$H-NMR (DMSO d-6): 7.94 (s, 1H), 6.52 (s, 2H), 6.17 (dd, 1H), 5.47 (dd, 1H), 4.15 (m, 3H), 3.15 (d, 1H), 3.01–2.62 (m, 2H), 1.80 (m, 1H), 0.82 (dd, 6H).

EXAMPLE 32

2', 3'-Dideoxy-3'-fluoro-5-O-[2-(-L-valyloxy)-propionyl]guanosine a) Synthesis of 4-methoxybenzyl-2-hydroxypropionate To a stirred solution of DL –2 hydroxypropionic acid (9.0 g, 100 mmole) in 100 ml dry DMF was added potassium tert-butoxide (12.34 g, 110 mmole) and the mixture was stirred for one hour at 60° C. 4-methoxybenzyl chloride (18.8 g 120 mmole) was added and the mixture was stirred for eight hours at 60° C. The mixture was evaporated under reduced pressure and 250 ml ethyl acatate was added. The organic phase was washed four times with water. The organic phase was dried with sodium sulfate and concentrated in vacuo. Yield: 16.8 g $^1$H-NMR (CDCl$_3$) 1.40 (m, 3H) 3.81 (s, 3H) 4.26 (m, 1H) 5.14 (s, 2H) 6.90 (d, 2H) 7,28 (d, 2H)

b) Synthesis of 4-methoxybenzyl-2-(N-CBZ-L-valyloxy)propionate

To a solution of 4-methoxybenzyl-2-hydroxypropionate (4.2 g, 20 mmole), N-CBZ-Lvaline (5.02 g, 20 mmole) and DMAP (0.24 g, 2 mmole) in 100 ml dichloromethane was added a solution of DCC (4.54 g, 22 mmole) and the mixture was stirred overnight at room temperature. The mixture was cooled to 5° C. and the urethane was filtered. The filtrate was evoporated and the product was isolated by silica gel column chromatography. Yield: 7.9 g $^1$H-NMR (CDCl$_3$) 0.88 (m, 6H) 1.50 (m, 3H) 2.26 (m, 1H) 3.81 (s, 3H) 4.34 (m, 1H) 5.04–5.30 (m, 6H) 6.88 (d, 2H) 7.26 (m, 7H)

c) Synthesis of 2-(N-CBZ-L-valyloxy)-propionic acid

To a solution of 4-methoxybenzyl-2-(N-CBZ-L-valyloxy)-propionate (7.8 g, 17.5 mmole) in dichloromethane (100 ml) was added trifluoroacetic acid (10 ml) and the solution was stirred for one hour at room temperature. The solution was evaporated under reduced pressure and the product was isolated by silica gel column chromatography.Yield: 5.0 g $^1$H-NMR (CDCl$_3$) 0.94 (m, 6H) 1.56 (d, 3H) 2.30 (m, 1H) 4.42 (m, 1H) 5.12–5.30 (m, 4H) 7.28 (m, 5H)

d) Synthesis of 2',3'-dideoxy-3'-fluoro-5-O-[2-(N-CBZ-L-valyloxy)prop ionyl] guanosine A mixture of 2',3'-dideoxy-3'-fluoroguanosine (404 mg, 1.5 mmole), 2-(N-CBZ-L-valyloxy)-propionic acid (0.582 g, 1.8 mmole), DMAP (22 mg, 0.18 mmole) and HOBT (243 mg, 1.8 mmole was coevaporated two times with DMF and reduced to about 30 ml. DCC (412 mg, 2.0 mmole) was added and the mixture was stirred overnight at room temperature. The mixture was filtered and the solution was evaporated under reduced pressure. 100 ml ethyl acetate was added and the organic phase was washed twice with 5% acetic acid, with 5% sodium hydrogen carbonate and with water. The organic phase was dried with sodium sulfate and evaporated under reduced pressure. The product was isolated by silica gel column chromatography.Yield: 0.72 g $^1$H-NMR (DMSO d-6) 0.92 (m, 6H) 1.40 (d, 3H) 2.10 (m, 1H) 2.50–3.06 (m, 2H) 4.03 (m, 1H) 4.20–4.44 (m, 3H) 5.04 (s, 2H) 5.12 (m, 1H) 5.44–5.58 (m, 1H) 6.18 (t, 1H) 6.52 (s, 2H) 7.36 (m, 5H) 7.70 (d, 2H) 7.92 (s, 1H)

e) Synthesis of 2',3'-dideoxy-3'-fluoro-5-O-[2-(L-valyloxy)-propanoyl] guanosine A solution of 2',3'-dideoxy-3'-fluoro-5-O-[2-(N-CBZ-L-valyloxy)-propanoyl] guanosine (0.6 g, 1.04 mmole) in 20 ml ethyl acetate, 10 ml methanol and 10 ml acetic acid was hydrogenated with palladium black (0.1 g) for two hours at room temperature and normal pressure. The catalyst was filtered and washed with methanol. The solution was evaporated under reduced pressure to yield the title compound as the acetate salt. Yield: 0.5 g $^1$H-NMR (DMSO d-6) 0.88 (m, 6H) 1.40 (d, 3H) 1.92 (m, 4H) 2.52–3.04 (m, 2H) 3.18 (m, 1H) 4.18–4.42 (m, 3H) 5.06 (m, 1H) 5.32–5.58 (m, 2H) 6.18 (m, 1H) 6.52 (s, 2H) 7.90 (s, 1H)

EXAMPLE 33

2', 3'-Dideoxy-3'-fluoro-5'-O-3-[2,3-bis-(L-valyloxy)-1-propyloxycarbonvl]-propanoyl guanosine a) Synthesis of 4-methoxybenzyl succinate monoester To a mixture of succinic anhyride (75 g, 750 mmole) and 4-methoxybenyl alcohol (69.1 g, 500 mmole) in 1,4-dioxane (300 ml) was added pyridine (79.1 g, 1000 mmole) and the mixture was stirred for five hours at 80° C. The mixture was evaporated under reduced pressure and 600 ml of ethyl acetate and 60 ml of acetic acid were added. The organic phase was washed three times with water, dried with sodium sulfate and evaporated under reduced pressure. The product was recrystallized from toluene. Yield: 104 g.

$^1$H-NMR (DMSO d-6) 2.48 (m, 4H) 3,72 (s, 3H) 5.00 (s, 2H) 6.90 (d, 2H) 7.28 (d, 2H)

b) Synthesis of succinic acid 2,3-dihydroxy-propyl ester, 4-methoxybenzyl ester

To a solution of glycerol (23.0 g, 250 mmole), 4-methoxybenzyl succinate monoester (5.96 g, 25 mmole) and DMAP (0.36 g, 3 mmole) in DMF (200 ml) was added DCC (6.2 g 30 mmole) and the mixture was stirred overnight at room temperature. The mixture was evaporated under reduced pressure and 150 ml dichloromethane was added. The mixture was filtered and the solution washed twice with water. The water phase was extracted two times with dichloromethane and the combined organic phases were dried with sodium sulfate. The solution was evaporated under reduced pressure and the product was isolated by silica gel column chromatography.

Yield: 3.0 g $^1$H-NMR (CDCl$_3$) 2.65 (m, 4H) 3.61 (m, 2H) 3.80 (s, 3H) 3.90 (m, 1H) 4.18 (m, 2H) 5.05 (s, 2H) 6.89 (d, 2H) 7.26 (d, 2H)

c) Synthesis of succinic acid 2,3-bis-(N-CBZ-L-Valyloxy)-propyl ester, 4-methoxybenzyl ester To a stirred solution of succinic acid 2,3-dihydroxy-propyl ester, 4-methoxybenzyl ester (2.9 g, 9.28 mmole), N-CBZ-L-valine (5.03 g, 20 mmole) and DMAP (0.244 g, 2 mmole) in dichloromethane (60 ml) was added DCC (4.5 g, 22 mmole) and the mixture was stirred overnight at room temperature. The mixture was filtered and the solution was evaporated under reduced pressure. The product was isolated by silica gel column chromatography. Yield: 2.5 g $^1$H-NMR (CDCl$_3$) 0.90 (m, 12H) 2,16 (m, 2H) 2.62 (m, 4H) 3.80 (s, 3H) 4.32 (m, 4H) 5.05–5.52 (m, 9H) 6.89 (d, 2H) 7.30 (m, 12H)

d) Synthesis of succinic acid 2,3-bis-(N-CBZ-L-valyloxy)propyl ester

To a solution of the above intermediate (2.3 g, 2.95 mmole) in dichloromethane (25 ml) was added trifluoroacetic acid (2.5 ml) and the solution was stirred for two hours at roomtemperature. The solution was evaporated under reduced pressure and the product was isolated by silica gel column chromatography. Yield: 1,8 g $^1$H-NMR (CDCl$_3$) 0.92 (m, 12H) 2.12 (m, 2H) 2.64 (m, 4H) 4.32 (m, 4H) 5.10 (s, 4H) 5.22–5.50 (m, 3H) 7.34 (m, 10H)

e) Synthesis of 2',3'-dideoxy-3'-fluoro-5'-O-{3-[2,3-bis (N-CBZ-L-valyloxy)-1-propyloxycarbonyl]propanoyl} guanosine A mixture of 2', 3'-dideoxy-3'-fluoroguanosine (0.538 g, 2 mmole), HOBT (0.327 g, 2.42 mmole), DMAP(29.3 mg, 0.24 mmole) and succinci acid 2,3-bis-(N-CBZ-L-valyloxy)-1-propyl ester (1.6 g, 2.42 mmole) was coevaporated two times with DMF and reduced to about 50 ml. DCC (0.536 g, 2.6 mmole) was added and the mixture was stirred 72 hours at room temperature. The mixture was filtered and the solution was evaporated under reduced pressure. 100 ml of ethyl acetate was added and the organic phase washed twice with 5% acetic acid, 5% sodium hydrogen carbonate and water. The organic phase was dried with sodium sulfate and evaporated under reduced pressure. The product was isolated by silica gel column chromatography.

Yield: 0.65 g.

$^1$H-NMR (DMSO-d$_6$) 0.88 (m, 12H) 2.08 (m, 2H) 2.58–3.04 (m, 6H) 3.92 (m, 2H) 4.10–4.46 (m, 7H) 5.00 (s, 4H) 5.22 (m, 1H) 5.32–5.56 (m, 1H) 6.17 (m, 1H) 6.50 (s, 2H) 7.32 (m, 10H) 7.70 (d, 2H) 7.92 (s, 1H)

f) Synthesis of 2',3'-dideoxy-3'-fluoro-5'-O-{3-[2,3-bis-(L-valyloxy)-1-propyloxycarbonyl]-propanoyl} guanosine A solution of the intermediate immediately above (0.57 g, 0.626 mmole) in 20 ml ethyl acetate, 10 ml methanol and 10 ml acetic acid was hydrogenated with palladium black (0.1 g) for two hours at room temperature and normal pressure. The catalyst was filtered and washed with methanol. The solution was evaporated under reduced pressure and the product was isolated by silica gel column chromatography. The product was dissolved in dichloromethane and 1M hydrogen chloride in ether (1.1 ml) was added. The mixture was evaporated under reduced pressure and dried in vacuo to yield the title compound as the dihydrochloride salt. Yield: 0.37 g $^1$H-NMR (DMSO d-6) 0.92 (m, 12H) 2.12 (m, 2H) 2.58–3.04 (m, 6H) 3.75 (m, 2H) 4.16–4.50 (m, 7H) 5.19–5.60 (m, 2H) 6.18 (m, 1H) 6.76 (s, 2H) 7.92 (s, 1H)

EXAMPLE 34

2', 3'-Dideoxy-3'-fluoro-5'-O-3-[1,3-bis-(L-valyloxy]-2-propyloxycarbonyl]propanoyl guanosine, dihydrochloride salt a) Synthesis of succinic acid 1,3-dibromo-2-propyl ester, 4-methoxybenzyl ester To a solution of 1,3-dibromopropan-2-ol (21.8 g, 100 mmole), succinic acid 4-methoxybenzyl ester (28.6 g, 120 mmole) and DMAP (1.22 g, 10 mmole) in dichloromethane (400 ml) was added DCC (24.8 g, 120 mmole) in portions at about 10° C. The mixture was stirred overnight at room temperature and cooled to about 5° C. The mixture was filtered and the solution was evaporated under reduced pressure. 600 ml of ethyl acetate was added and the organic phase was washed twice with 5% acetic acid, 5% sodium hydrogen carbonate and water. The solution was dried with sodium sulfate and evaporated under reduced pressure. The product was isolated by silica gel column chromatography. Yield: 34.8 g.

$^1$H-NMR (CDCl$_3$) 2.69 (m, 4H) 3.57 (m, 4H) 3.81 (s, 3H) 5.07 (s, 2H) 5.14 (m, 1H) 6,88 (d, 2H) 7.26 (d, 2H)

b) Synthesis of succinic acid 1,3-bis-(N-CBZ-L-valyloxy)-2-propyl ester, 4-methoxybenzyl ester To a solution of N-CBZ-L-valine (58.5 g, 232.8 mmole) in dried DMF (300 ml) was added potassium-tert.-butoxide (24,68 g, 220 mmole) and the mixture was stirred for one hour at room temperature. A solution of succinic acid 1,3-dibromo-2-propyl ester, 4-methoxybenzyl ester (34 g, 77.6 mmole) in dried DMF (50 ml) was added and the mixture was stirred for eighteen hours at 60° C. The potassium bromide was filtered and the solution was evaporated under reduced pressure. 600 ml of ethyl acetate was added and the organic phase washed twice with 5% sodium hydrogen carbonate and with water. The organic phase was dried with sodium sulfate and evaporated under reduced pressure. The product was isolated by silica gel column chromatography. Yield: 45 g $^1$H-NMR (CDCl$_3$) 0.90 (m, 12H) 2.16 (m, 2H) 2.61 (m, 4H) 3.80 (s, 3H) 4.12–4.42 (m, 6H) 5.02 (s, 2H) 5.10 (s, 4H) 5.43 (m, 3H) 6.88 (d, 2H) 7.32 (m, 12H)

c) Synthesis of succinic acid 1,3-bis-(N-CBZ-L-valyloxy)-2-propyl ester

To a cooled solution of the intermediate immediately above (44.5 g, 57.1 mmole) in dichloromethane (500 ml) was added trifluoroacetic acid (50 ml) between 5° C. and 10° C. and the solution was stirred for two hours at 10° C. The solution was evaporated under reduced pressure and two times coevaporated with toluene. 400 ml of ethanol was added and the mixture was stirred for 30 minutes at 40° C. The mixture was cooled and the biproduct filtered. The solution was evaporated under reduced pressure and the product was isolated by silica gel column chromatography.

Yield: 33 g $^1$H-NMR (DMSO-d$_6$) 0.88 (m, 12H) 2.04 (m, 2H) 2.46 (m, 4H) 3.94–4.40 (m, 6H) 5.02 (s, 4H) 5.18 (m, 1H) 7.32 (m, 10H) 7,74 (d, 2H)

d) Synthesis of 2',3'-dideoxy-3'-fluoro-5'-O-{3-[1,3-bis-(N-CBZ-L-valyloxy)-2-propyloxycarbonyl]propanoyl} guanosine A mixture of 2',3'-dideoxy-3'-fluoroguanosine (17.8 g, 66 mmole), HOBT (10.64 g, 78.8 mmole), succinic acid 1,3-bis-(N-CBZ-L-valyloxy)-2-propyl ester (52 g, 78.8 mmole) and DMAP (0.96 g, 7.88 mmole) was coevaporated two times with DMF and redued to about 500 ml. DCC (17.3 g, 84 mmole) was added and the mixture was stirred overnight at room temperature. The mixture was warmed for six hours at 60° C. and then cooled to about 10° C. The mixture was filtered and the solution was reduced under reduced pressure. 1200 ml of ethyl acetate was added and the organic phase was washed twice with 5% acetic acid, 5% sodium hydrogen carbonate and water. The organic phase was dried with sodium sulfate and evaporated under reduced pressure. The product was isolated by silica gel column chromatography.

Yield: 42 g.

$^1$H-NMR (DMSO-d$_6$) 0.90 (m, 12H) 2.02 (m, 2H) 2.5–3.02 (m, 6H) 3.94 (m, 2H) 4.22 (m, 7H) 5.02 (s, 4H) 5.18 (m, 1H) 5.22–5.50 (m, 1H) 6.16 (m, 1H) 6.50 (s, 2H) 7.32 (m, 10H) 7.72 (d, 2H) 7.92 (s, 1H)

e) Synthesis of 2',3'-dideoxy-3'-fluoro-5'-O-{3-[1,3-bis-(L-valyloxy)-2-propyloxycarbonyl]-propanoyl}guanosine dihydrochloride salt A solution of 2',3'-dideoxy-3'-fluoro-5'-O-{3-[1,3-bis-(N-CBZ-L-valyloxy)-2-propyloxy carbonyl]propanoyl} guanosine (5.0, 5.9 mmole) in 75 ml ethyl acetate and 75 ml methanol was hydrogenated with palladium on activated carbon 10% Pd (1 g) one hour at room temperature and normal pressure. The catalyst was filtered and washed with methanol. The solution was evaporated under reduced pressure. The product was dissolved in dichloromethane and a solution of 1M hydrogen chloride in ether (6 ml) was added, while cooling. The mixture was evaporated under reduced pressure. Yield: 3.5 g $^1$H-NMR (DMSO d-6) 0.94 (m, 12H) 2.18 (m, 2H) 2.5–3.04 (m, 6H) 4.20–4.54 (m, 7H) 5.24 (m, 1H) 5.34–5.64 (m, 1H) 6.22 (m, 1H) 6.92 (s, 2H) 8.30 (s, 1H) 8.62 (s, 6H)

EXAMPLE 35

Alternative synthesis of 2',3'-dideoxy-3'-fluoro-5'-O-3-[1,3-bis-(L-valyloxy)-2-propyloxycarbonyl] propanoyl guanosine a) Synthesis of succinic acid 1,3-dibromo-2-propyl ester, 1,1-dimethylethyl ester To a solution of 1,3-dibromopropan-2-ol (10.9 g 50 mmole), succinic acid 1,1-dimethylethyl ester (J. Org.Chem 59 (1994) 4864) (10.45 g, 60 mmole) and DMAP (0.61 g, 5 mmole) in dichloromethane (180 ml) was added DCC (12.4 g, 60 mmole) in portions at about 10° C. The mixture was stirred overnight at room temperature and cooled to about 5° C. The mixture was filtered and the solution was evaporated under reduced pressure. 250 ml ethyl acetate was added and the organic phase was washed twice with 5% citric acid, 5% sodium hydrogen carbonate and water. The solution was dried with sodium sulfate and evaporated under reduced pressure. The product was distilled in vacuo. (bp 0,5 135–140° C.) Yield: 16.8 g $^1$H-NMR (CDCl$_3$) 1.45 (s, 9H) 2.58 (m, 4H) 3.61 (m, 4H) 5.12 (m, 1H)

b) Synthesis of succinic acid 1,3-bis-(N-CBZ-L-valyloxy)-2-propyl ester, 1,1-dimethylethyl ester To a solution of N-CBZ-L-valine (18.85 g, 75 mmole) in dried DMF (100 ml) was added potassium tert.-butoxide (7.85 g, 70 mmole) and the mixture was stirred for one hour at room temperature. A solution of succinic acid 1,3-dibromo-2-propyl ester, 1,1-dimethylethyl ester (9.35 g, 25 mmole) in dried DMF (20 ml) was added and the mixture was stirred for eighteen hours at 60° C. The potassium bromide was filtered and the solution evaporated under reduced pressure. 300 ml of ethyl acetate were added and the organic phase washed twice with 5% sodium hydrogen carbonate and with water. The organic phase was dried with sodium sulfate and evaporated under reduced pressure. The product was isolated by silica gel column chromatography. Yield: 14 g $^1$H-NMR (CDCl$_3$) 0.90 (m, 12H) 1.42 (s, 9H) 2.14 (m, 2H) 2.52 (m, 4H) 4.32 (m, 6H) 5.10 (s, 4H) 5.32 (m, 3H) 7.26 (m, 10H)

c) Synthesis of 1,3-bis-(N-CBZ-L-valyloxy)-2-propyl succinate monoester

To a cooled solution of succinic acid 1,3-bis-(N-CBZ-L-valyloxy)-2-propyl ester, 1,1-dimethylethyl ester (13 g, 18.18 mmole) in dichloromethane (100 ml) was added trifluoroacetic acid (20 ml) and the solution was stirred for six hours at room temperature. The solution was evaporated under reduced pressure. 200 ml ethyl acetate was added and the organic phase was washed with 5% sodium hydrogen carbonate and water. The solution was evaporated under reduced pressure.

Yield: 11.7 g $^1$H-NMR (DMSO-d$_6$) 0.88 (m, 12H) 2.04 (m, 2H) 2.46 (m, 4H) 3.94–4.40 (m, 6H) 5.02 (s, 4H) 5.18 (m, 1H) 7.32 (m, 10H) 7.74 (d, 2H)

d) Synthesis of 2',3'-dideoxy-3'-fluoro-5'-O-3-[1,3-bis-(L-valyloxy)-2-propyloxycarbonyl] propanoyl guanosine The intermediate from step c) is esterified to FLG as shown in example 34 step d) and the N-protecting groups on the valyl moieties removed by conventional techniques, such as shown in Example 35 step e) or Example 29 step e).

EXAMPLE 36

2',3'-Dideoxy-3'-fluoro-5'-O-[(S)-(+)-2-(L-valyloxy]-propanoyl]guanosine a) 2',3'-Dideoxy-3'-fluoro-5-O-[(S)-(+)-2-(N-CBZ-L-valyloxy)propionyl]guanosine A mixture of 2',3'-dideoxy-3'-fluoroguanosine (2.69 g, 10 mmole), (S)-(+)-2-(N-CBZ-L-valyloxy)-propionic acid (4.2 g, 13 mmole), DMAP (0.244 g, 2 mmole) and HOBT (1.76 g, 13 mmole) was coevaporated two times with DMF and reduced to about 150 ml. DCC (3.1 g, 15 mmole) was added and the mixture was stirred overnight at room temperature and two hours at 60° C. The mixture was filtered and the solution was evaporated under reduced pressure. 300 ml ethyl acetate was added and the organic phase was washed twice with 5% acetic acid, with 5% sodium hydrogen carbonate and with water. The organic phase was dried with sodium sulfate and evaporated under reduced pressure. The product was isolated by silica gel column chromatography. Yield: 5.0 g=87%

$^1$H-NMR (DMSO d-6) 0.92 (m, 6H) 1.40 (d, 3H) 2.10 (m, 1H) 2.55–3.06 (m, 2H) 4.03 (m, 1H) 4.20–4.44 (m, 3H) 5.04 (s, 2H) 5.12 (m, 1H) 5.44–5.58 (m, 1H) 6.18 (t, 1H) 6.52 (s, 2H) 7.36 (m, 5H) 7.70 (d, 2H) 7.92 (s, 1H)

b) 2',3'-Dideoxy-3'-fluoro-5'-O-[(S)-(+)2-(L-valyloxy)propanoyl] guanosine

A solution of 2',3'-dideoxy-3'-fluoro-5-O-[(S)-(+)-2-(N-CBZ-L-valyloxy)propanoyl]guanosine (3.0 g, 5.22 mmole) in 120 ml ethyl acetate and 40 ml acetic acid was hydrogenated with palladium black (1.0 g) for 2.5 hours at room temperature and 40 psi. The catalyst was filtered and washed with ethyl acetate and acetic acid. The solution was evaporated under reduced pressure to yield the hydrochloride salt. Yield: 2.4 g=95%

$^1$H-NMR (DMSO d-6+D$_2$O) 0.88 (m, 6H) 1.42 (d, 3H) 2.20 (m, 1H) 2.52–3.04 (m, 2H) 3.92 (m, 1H) 4.38–4.49 (m, 3H) 5.18 (m, 1H) 5.36–5.64 (m, 2H) 6.22 (m, 1H) 8.12 (s, 1H)

EXAMPLE 37

2', 3'-Dideoxy-3'-fluoro-5'-O-[2,3-bis-(L-valyloxy) propanoyl]guanosine a) 2',3'-Dideoxy-3'-fluoro-5'-O-[2,3-bis-(N-CBZ-L-valyloxy)propanoyl]guanosine (MSS-138)

A mixture of 2',3'-dideoxy-3'-fluoroguanosine (2.15 g, 8 mmole), 2,3-bis-(N-CBZ-L-valyloxy)-propanoic acid (6.2 g, 10.8 mmole), DMAP (244 mg, 2 mmole) and HOBT (1.46 g, 10.8 mmole) was coevaporated two times with DMF and reduced to about 120 ml. DCC (2.48 g, 12 mmole) was added and the mixture was stirred for two days at room temperature. The mixture was filtered and the solution was evaporated under reduced pressure. 150 ml ethyl acetate was added and the organic phase was washed twice with 5% acetic acid, with 5% sodium hydrogen carbonate and with water. The organic phase was dried with sodium sulfate and evaporated under reduced pressure. The product was isolated by silica gel column chromatography.

Yield: 2,25 g=35%

$^1$H-NMR (DMSO d-6) 0.88 (m, 12H) 2,12 (m, 2H) 2.50–3.00 (m, 2H) 3.88–4.14 (m, 2H) 4.22–4.62 (m, 6H) 5.04 (s, 4H) 5.30–5.61 (m, 2H) 6.16 (m, 1H) 6.50 (s, 2H) 7.32 (m, 10H) 7.70 (m, 2H) 7.92 (s, 1H)

b) 2',3'-Dideoxy-3'-fluoro-5'-O-[2,3-bis-(L-valyloxy) propanoyl] guanosine

A solution of 2',3'-dideoxy-3'-fluoro-5'-O-[2,3-bis-(N-CBZ-L-valyloxy)propanoyl]guanosine (0.41 g, 0.5 mmole) in ethyl acetate (40 ml) and acetic acid (20 ml) was hydrogenated with palladium black (200 mg) at 30 psi for two hours at room temperature. The catalyst was filtered and washed with ethyl acetate and acetic acid. The solution was evaporated under reduced pressure and the product was dried in vacuo to give the dihydrochloride salt. Yield: 0.3 g=95%

$^1$H-NMR (DMSO d-6 and D$_2$O) 0.94 (m, 12H) 2.18(m, 2H) 2.52–3.00 (m, 2H) 3.88–4.09 (m, 2H) 4.36–4.72 (m, 6H) 5.42–5.72.

EXAMPLE 38

N1,N6-bis {(1 S,2R)-1-[2-(4-(L-valyloxy)-butanoyloxy)]-indanyl}-(2R,3R,4R,5R)-2,5-di(benzyloxy)-3,4-dihydroxyhexanediamide $^1$H-NMR (CDCl$_3$): 7.23 (m, 18H) 5.58 (m, 4H) 5.16 (d, 2H) 4.70–3.80 (m, 12H) 3.08 (dd, 4H) 2.20 (m, 4H), 1.80 (m, 4H) 1.35 (m, 18H) 0.78 (dd, 12H)

b) N1,N6-bis{(1S,2R)-1-[2-(4-(L-valyloxy)-butanoyloxy)]-indanyl}-(2R,3R,4R,5R)-2,5-di(benzyloxy)-3,4-dihydroxyhexanediamide N1,N6-bis{(1S,2R)-1-[2-(4-(N-Boc-L-valyloxy)-butanoyloxy)]-indanyl}-(2R,3R,4R, 5R)-2,5-di(benzyloxy)-3,4-dihydroxyhexanediamide (90 mg) was treated with trifluoroacetic acid (6 ml) at 0° C. for 2 hr. The solution was dried and coevaporated with toluene and methanol successively, giving the titled product in quantitative yield.

$^1$H-NMR (DMSO-d$_6$+D$_2$O): 7.22 (m, 18H) 5.61 (m, 4H) 4.60–3.65 (m, 12H), 3.12 (dd, 4H) 2.15 (m, 4H) 1.80 (m, 4H) 0.90 (m, 12H).

EXAMPLE 39

N1-{(1 S,2R)-2-[4-(L-valyloxy)butanoyloxy]-2,3-dihydro-1H-1-indenyl}-N-6-[(1S)-2-methyl-1-(methylcarbamoyl)propyl]-(2R,3R,4R,5R)-2,5-di[4-(2-thiazolyl)benazloxy]-3-hydroxy-4-[4-(L-valyloxy) butanoyloxy]hexanediamide bis-trifluoroacetate a) N1-[(1S,2R)-2-Hydroxy-2,3-dihydro-1H-1-indenyl]-N-6-[(1S)-2-methyl-1-(methylcarbamoyl)propyl]-(2R,3R,4R,5R)-2,5-di[4-(2-thiazolyl)benzyloxy]-3,4-dihydroxyhexanediamide A mixture of N1-[(1S,2R)-2-hydroxy-2,3-dihydro-1H-1-indenyl]-N-6-[(1S)-2-methyl-1-(methylcarbamoyl)propyl]-

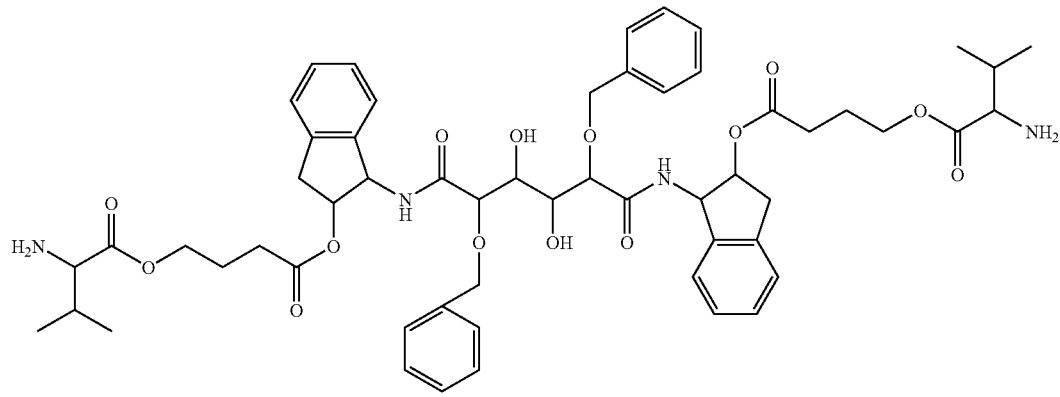

a) N1,N6-bis{(1S,2R)-1-[2-(4-(N-Boc-L-valyloxy)-butanoyloxy)]-indanyl}-(2R,3R,4R,5R)-2,5-di(benzyloxy)-3, 4-dihydroxyhexanediamide To N1,N6-bis [(1S,2R)-1-(2-hydroxy)-indany]-(2R,3R, 4R,5R)-2,5-di-(benzyloxy)-3,4-dihydroxyhexanediamide from WO 98/45330 (326 mg, 0.5 mmole) and 4-(NBoc-L-valyloxy)butyric acid (295 mg, 1 mmole) in dichloromethane (3 ml) were added 4-dimethylaminopyridine (12 mg, 0.1 mmole). The solution was cooled to −10° C. and DCC (206 mg, 1 mmole) in dichloromethane (2 ml) was added dropwise over 2 hr. The reaction mixture was slowly warmed to room temperature, and kept for 18 hr. It was then filtered through Celite and poured into sodium bicarbonate aqueous solution. The organic phase was dried and the product was isolated with silica gel column chromatography. 103 mg.

(2R,3R,4R,5R)-2,5-di(4-bromobenzyloxy)-3,4-dihydroxyhexanediamide, prepared analagously to Example 11 of WO98/45330 using 4-bromobenzyl (130 mg, 0.164 mmol), tributyl-2-thiazolyltin (554 mg, 1.47 mmol), PdCl$_2$(PPh$_3$)$_2$ (120 mg, 0.5 M suspension in DMF), and dry DMF (3 ml) was twice degassed and flushed with argon and then stirred at 90° C./16 h, evaporated to near dryness, washed with a little ether and purified by silica gel column chromatography (chloroform-methanol 20: 1) to yield 95.5 mg (73%) of off-white solid.

$^{13}$C NMR (CDCl$_3$; 62.9 MHz) δ 17.2, 19.4, 26.0, 29.5, 39.3, 57.6, 58.2, 71.8, 72.2, 72.4, 81.0, 81.4, 118.8, 124.0, 125.3, 127.0, 127.1, 128.2, 128.3, 128.4, 133.2, 138.5, 139.9, 140.6, 143.5, 167.5, 171.0, 171.3.

b) N1-{(1S,2R)-2-[4-(N-Boc-L-valyloxy)butanoyloxy]-2,3-dihydro-1H-1-indenyl}-N-6-[(1S)-2-methyl-1-(methylcarbamoyl)propyl]-(2R,3R,4R,5R)-2,5-di[4-(2-thiazolyl)benzyloxy]-3-hydroxy-4-[(N-Boc-L-valyloxy)butanoyloxy] hexanediamide To obtain the di-acylated derivative, a solution of the intermediate of step a) (49.5 mg, 0.062 mmol), 4-(L-valyloxy)butyric acid (100 mg, 0.33 mmol), dicyclohexylcarbodiimide (50 mg, 0.24 mmol), and 4-(N,N-dimethylamino)pyridine (10 mg, 0.082 mmol) in dichloromethane (1 ml) was kept at room temperature overnight. The precipitated dicyclohexylurea was filtered off and the solution evaporated to small volume and then purified by silica gel column chromatography (chloroform-hexane-methanol 20:10:1) to yield the title compound as a glass (71 mg, 84%).

$^{13}$C NMR (CDCl$_3$; 62.9 MHz) δ 17.2, 17.3, 18.9, 19.1, 23.8, 25.0, 28.2, 30.4, 31.0, 37.3, 58.0, 58.5, 63.8, 70.5, 71.0, 71.1, 71.6, 75.6, 79.4, 80.0, 118.8, 123.7, 125.0, 126.5, 127.1, 128.2, 128.6, 128.8, 133.3, 138.2, 139.0, 140.1, 143.5, 155.4, 168.5, 170.5, 171.5, 172.0.

c) N1-{(1S,2R)-2-[4-(L-valyloxy)butanoyloxy]-2,3-dihydro-1H-1-indenyl}-N6-[(1S)-2-methyl-1-(methylcarbamoyl)propyl]-(2R,3R,4R,5R)-2,5-di[4-(2-thiazolyl)benzyloxy]-3-hydroxy-4-[(L-valyloxy)butanoyloxy]hexanediamide bis-trifluoroacetate The intermediate of step b) (71 mg, 0.0518 mmol) was dissolved in 1 ml of neat trifluoroacetic acid with cooling and kept at room temperature for 1 h. The solution was evaporated to small volume, lyophilized with dioxane, then with water containing 10% of dioxane, to give 66.6 mg (92%) of the title compound as offwhite, light powder.

$^{13}$C NMR (CDCl$_3$; 62.9 MHz) δ 17.5, 18.0, 23.6, 30.0, 31.1, 58.5, 65.0, 71.2, 71.6, 119.1, 123.2, 124.0, 126.8, 128.2, 128.5, 128.8, 133.4, 137.9, 139.3, 143.5, 161.7, 168.8, 169.1, 171.3.

EXAMPLE 40

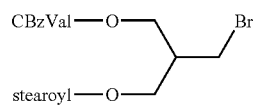

a) Synthesis of 3-bromo-2-hydroxy-1-(N-CBz-L-valyloxy)-propane

To a stirred solution of 3-bromo-1,2-propanediol (10.85 g, 70 mmole), N-CBz-L-valine (10.05 g, 40 mmole) and DMAP (0.49 g, 4 mmol) in 250 ml dichloromethane was added dropwise a solution of DCC (9.1 g, 44 mmol) in 50 ml dichloromethane at about 10° C. The mixture was stirred for two days at room temperature and then cooled to 5° C. The urethane was filtered and the solution was evaporated under reduced pressure. The product was isolated by silica gel column chromatography.

Yield: 8 g $^1$H-NMR (CDCl$_3$) 0.93 (m, 6H) 1.24 (m, 1H) 2.15 (m, 1H) 3.10 (m, 1H) 3.45 (m, 2H) 4.10 (m, 1H) 4.27 (m, 2H) 5.11 (s, 2H) 7.31 (m, 5H)

b) Synthesis of 3-bromo-2-stearoyloxy-1-(N-CBz-L-valyloxy)-propane

To a stirred solution of 3-bromo-2-hydroxy-1-(N-CBZ-L-valyloxy)-propane (7.9 g, 20 mmol) and pyridin (3.2 g, 40 mmol) in 250 ml dichloromethane was added dropwise a solution of stearoyl chloride (9.1 g, 30 mmol) in 50 ml dichloromethane between 10° C. and 15° C. The solution was stirred overnight at room temperature. 150 ml of 5% sodium hydrogen carbonate solution was added and the mixture stirred for 30 minutes. The organic phase was separated and the water phase was extracted two times with dichloromethane. The combined organic phases were dried with sodium sulfate and concentrated in vacuo. The product was isolated by silica gel column chromtography.

Yield:10.5 g $^1$H-NMR (CDCl$_3$) 0.88 (m, 9H) 1.25 (m, 28H) 1.58 (m, 2H) 2.08 (m, 1H) 2.22 (m, 2H) 3.42 (m, 2H) 4.25 (m, 3H) 5.08 (s, 2H) 5.20 (m, 2H) 7.35 (m, 5H)

EXAMPLE 41

1-chloroethyl ester of 3-(N-benzyloxycarbonyl-L-valyloxymethyl)-4-stearoyloxy-butyric acid a) Preparation of 1-O-(N-benzyloxycarbonyl-L-valyl)-2-allylyl-1,3-propandiol To a solution of 2-allyl-1,3-propandiol (4.6 g, 40 mmole) and N-benzyloxycarbonyl valine (5.02 g, 20 mmol) were added dimethylaminopyridine (244 mg, 2 mmol), and DCC (4.5 g, 22 mmol). After two hr, the mixture was filtered through Celite and evaporated. The product 1-O-(N-benzyloxycarbonyl-L-valyl)-2-allylyl-1,3-propandiol was isolated. 5.01 g $^1$H-NMR (CDCl$_3$): 7.36 (m, 5H), 5.78 (m, 1H), 5.26 (d, 1H), 5.11 (s, 2H), 5.06 (d, 2H), 4.22 (m, 3H), 3.59 (m, 2H), 2.13 (m, 3H), 1.98 (m, 2H), 0.94 (dd, 6H).

b) Preparation of 1-O-(N-benzyloxycarbonyl-L-valyl)-2-allylyl-3-O-stearoyl-1,3-propandiol To a solution of 1-O-(N-benzyloxycarbonyl-L-valyl)-2-allylyl-1,3-propandiol (4.46 g, 12.7 mmole), in dichloromethane (70 ml) and pyridine (6.1 ml, 76 mmol) in an ice bath was added stearoyl chloride (7.8 g, 26 mmol). The reaction mixture was warmed up to room temperature and kept for one hr. It was then poured into aqueous sodium hydrogen carbonate solution and the organic phase was dried and the product 1-O-(N-benzyloxycarbonyl-L-valyl)-2-allylyl-3-O-stearoyl-1,3-propandiol was purified by silica gel column chromatography. 6.7 g $^1$H-NMR (CDCl$_3$): 7.34 (m, 5H, 5.77 (m, 1H), 5.30 (d, 1H), 5.11 (s, 2H), 5.08 (d, 2H), 4.32 (m, 1H), 4.10 (m, 4H), 2.29 (t, 2H), 2.13 (m, 4H), 1.62 (m, 3H), 1.25 (m, 28H), 0.90(m, 9H).

c) Preparation of 3-(N-benzyloxycarbonyl-L-valyloxy)-4-stearoyloxy-butyric acid Potassium permanganate (756 mg, 4.8 mmole) was dissolved in water (7.5 ml). The solution was kept under strong stirring for 10 min. A solution of product 1-O-(N-benzyloxycarbonyl-L-valyl)-2-allylyl-3-O-stearoyl-1,3-propandiol (1 g, 1.6 mmole) and tetrabutylammonium bromide (77 mg, 0.24 mmol) in benzene (5 ml) was added. The slurry was stirred for 1.5 hr, and dichloromethane was added. A sodium bisulfite aqueous solution was added to the slurry until the mixture discolored. The organic phase was acidified with acetic acid and washed with water. After evaporation, the product 3-(N-benzyloxycarbonyl-L-valyloxy)-4-stearoyloxy-butyric acid (390 mg) was isolated by silica gel column chromatography.

$^1$H-NMR (CDCl$_3$): 7.33 (m, 5H), 5.38 (d, 1H), 5.11 (s, 2H), 4.14 (m, 5H); 2.60 (m, 1H), 2.45 (m, 2H), 2.29 (t, 2H), 2.18 (m, 1H), 1.58 (m, 2H), 1.25 (m, 28H), 0.90 (m, 9H).

d) Preparation of 3-(N-benzyloxycarbonyl-L-valyloxy)-4-stearoyloxy-butyroyl chloride 3-(N-benzyloxycarbonyl-L-valyloxymethyl)-4-stearoyloxy-butyric acid (1.26 g, 2 mmol), was treated with thionyl chloride (50 ml) at 35° C. for 3 hr, evaporated and coevaporated to give the product 3-(N-benzyloxycarbonyl-L-valyloxy)-4-stearoyloxy-butyroyl chloride (1.3 g).

$^1$H-NMR (CDCl$_3$): 7.37 (m, 5), 5.30 (d, 1H), 4.20 (m, 5H), 3.05 (m, 2H), 2.70 (m, 1H), 2.35 (t, 2H), 2.15 (m, 1H), 1.70 (m, 4H), 1.25 (m, 28H), 0.91 (m, 9H).

f) Preparation of 1-chloroethyl ester of 3-(N-benzyloxycarbonyl-L-valyloxymethyl)-4-stearoyloxy-butyric acid To a mixture of 3-(N-benzyloxycarbonyl-L-valyloxymethyl)-4-stearoyloxy-butyroyl chloride (650 mg, 1 mmol) and acetaldehyde (0.062 ml, 1.1 mmol) was added 1 M zinc chloride (0.02 ml, 0.02 mmol). After 2 hr, the reaction mixture was loaded on a silica gel column and the titled product was isolated. 470 mg.

$^1$H-NMR (CDCl$_3$): 7.34 (m, 5H), 6.53 (q, 1H), 5.38 (d, 1H), 5.10 (s, 2H), 4.16 (m, 5H), 2.60 (m, 1H), 2.48 (m, 5H), 2.15 (m, 1H), 1.68 (d, 3H), 1.60 (m, 2H), 1.25 (m, 28H), 0.90 (m, 9H).

EXAMPLE 42

Application of a Trifunctional Linker to the Carboxy Function of a Drug

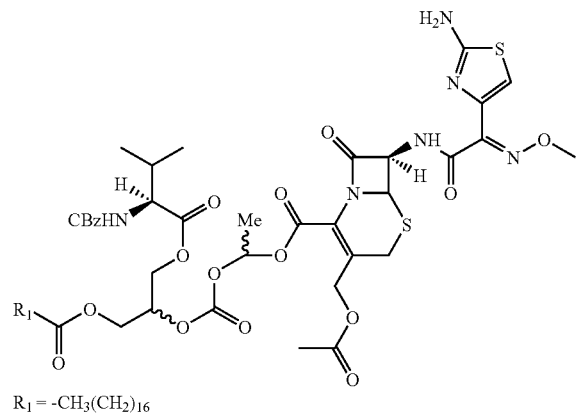

$R_1 = -CH_3(CH_2)_{16}$

To a solution of cefotaxime sodium salt (0.338 g, 0.71 mmol) in DMF (5 ml) was added the compound of Example 6 (0.5 g, 0.63 mmol) in DMF (1 ml). The mixture was stirred under nitrogen atmosphere at 40° C. until TLC indicated consumption of the starting material. After 16 h, the solvent was removed in vacuum and the residue dissolved in ethyl acetate (50 ml) and filtrated. The ethyl acetate was evaporated and the crude product purified by chromatography [SiO$_2$, ethyl acetate/hexane (3:2)]. Evaporation and drying in vacuum gave the above depicted compound (0.27 g)

$^1$H-NMR (CDCl$_3$): δ 7.30 (m, 5H), 5.82 (m, 1H), 5.30 (m, 1H), 5.06 (m, 2H), 4.6–4.02 (m, 5H4.0 (s, 3H, =N—OMe), 3.48 (m, 1H), 2.29 (t, 2H), 2.15 (m, 1H), 2.05 m, 5H), 1.55 (m, 2H1.23 (m, 28H), 0.9 (m, 9H).

The CBz protecting group on the α-amine of the amino acid is removed by conventional deprotection treatments as described above.

EXAMPLE 43

Application of an Alternative Trifunctional Linker to a Carboxyl Function

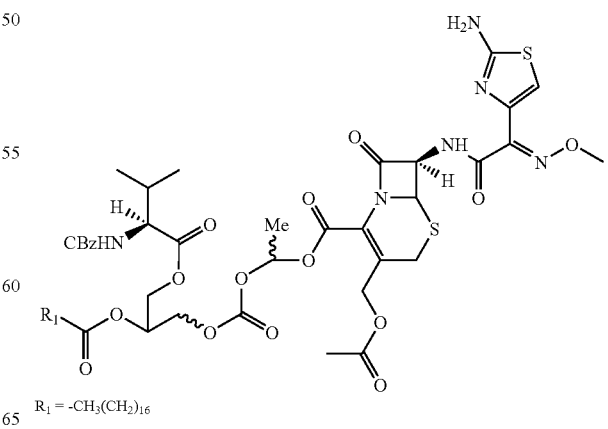

$R_1 = -CH_3(CH_2)_{16}$

A solution of the compound of Example 8 (220 mg, 0.28 mmol) and the sodium salt of Claforan (111 mg, 0.23 mmol in dry N,N-dimethylformamide (4.6 mL) was stirred at ambient temperature under nitrogen for 23 hr. After removal of solvent in vacuo, the residue was purified by flash column chromatography on silica gel eluted successively with 1/1 hexane-diethyl ether, 80/1 dichloromethane-methanol, and 40/1 dichloromethane-methanol to give the above depicted compound as a light yellow solid (161 mg).

$^1$H NMR (CDCl$_3$) d ppm 0.83–0.97 (m, 9H), 1.23 (s, 28H), 1.57 (m, 5H), 2.07 (s, 3H), 2.13 (m, 1H), 2.28 (m, 2H), 3.50 (AB q, 2H), 4.02 (s, 3H), 4.10–4.50 (m, 5H), 4.80–4.87 (m, 1H), 5.05–5.45 (m, 6H), 5.80–6.12 (m, 1H), 6.65–7.70 (m, 2H), 7.33 (m, 5H).

The CBz protecting group on the α-amine of the amino acid is removed by conventional deprotection treatments as described above.

EXAMPLE 44

Application of an Alternative Trifunctional Linker to a Carboxyl Function

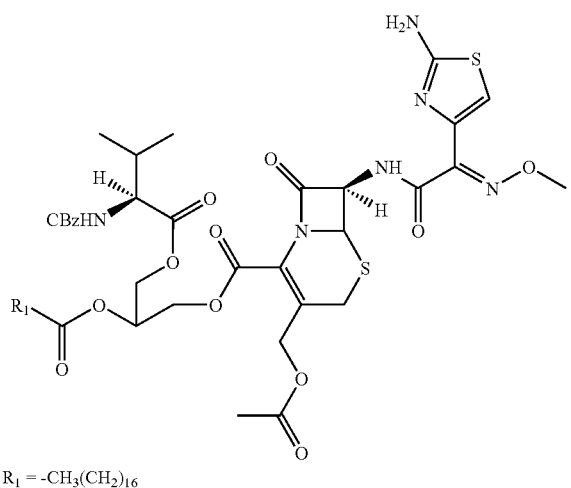

$R_1 = -CH_3(CH_2)_{16}$

A mixture of claforan sodium salt (477,5 mg, 1,0 mmole) and 3-bromo-2-stearoyloxy-1-(N-CBz-L-valyloxy)-propane (785.7 mg, 1.2 mmole) in 20 ml DMF was stirred for one week at room temperature. The solution was evaporated under reduced pressure and the product isolated by silica gel column chromatography.

Yield: 310 mg $^1$H-NMR (CDCl$_3$) 0,88 (m, 9H) 1,25 (m, 28H) 2,10 (m, 3H) 3,48 (m, 2H) 4,04 (m, 3H) 4,26 (m, 5H) 5,06 (m, 4H).

The CBz protecting group on the α-amino group is removed with conventional deprotection conditions as described above.

EXAMPLE 45

Application of a Trifunctional Linker to an Hydroxyl Bearing DRUG a) 6/18/20-O-mono-(6-(N-tritylvalyloxy)-5-(1-stearoyloxy methyl) hexanoyl) rifabutin Dried rifabutin (343 mg, 0.42 mmol) and 6-(N-tritylvalyloxy)-5-(1-stearoyloxy methyl) hexanoic acid (323 mg, 0.42 mmol) were dissolved together in dry dichloromethane (3.5 ml). Then dimethylaminopyridine (6 mg, 0.05 mmol) and dicyclohexylcarbodiimide (93 mg, 0.45 mmol) were added and the reaction mixture was stirred for 24 h at 20° C. The mixture was filtered and extracted with 5% aqueous sodium bicarbonate and dichloromethane three times. The residue obtained by evaporation of the organic phase was chromatographed on silica gel and the product was eluted with 0%→2% EtOH/dichloromethane. (Yield 316 mg). R$_f$ (5% MeOH/CHCl$_3$): 0.75.

b) 6/18/20-O-mono-(6-(valyloxy)-5-(1-stearoyloxy methyl) hexanoyl) rifabutin. The product from step a) (316 mg, 0.2 mmol) was dissolved in dioxane (2 ml) and then 80% acetic acid (20 ml) was added and the solution was stirred for 5 min at 20° C. The solution was evaporated and coevaporated with dioxane two times and toluene one time. The residue was chromatographed on silica gel and the product was eluted with 0%→5% EtOH/dichloromethane. (Yield 230 mg). R$_f$ (5% MeOH/CHCl$_3$): 0.50.

$^1$H-NMR (CHCl$_3$): 8.35 (br, 1H); 7.77 (s, 1H); 6.42 (d,d, 1H); 6.12 (m, 2H); 5.91 (d,d, 1H); 5.12 (d, 1H); 5.07 (d,d, 1H); 4.94 (d, 1H); 4.18–3.96(m, 4H); 3.46 (d, 1H); 3.31 (d,d, 1H); 3.05 (s, 3H); 2.98 (m, 2H); 2.86 (d,d, 1H); 2.65 (m, 2H); 2.48 (q, 1H); 2.38–2.32 (m, 5H); 2.30 (s, 3H); ); 2.13 (t, 2H); 2.05 (s, 3H); 2.01 (s, 3H); 2.00 (m, 2H); 1.85–1.73 (m, 1H); 1.78 (s, 3H); 1.68–1.50 (m, 5H); 1.25 (m, 28H); 1.15 (m, 2H); 1.05–0.85 (m, 21H); 0.47 (d, 3H); −0.18 (d, 3H).

EXAMPLE 46

Application of a Trifunctional Linker to an Alternative Hydroxy Drug a) Preparation of dibenzyl ester of 1,3-bis-(2-carboxychromon-5-yloxy)propan-2-ol 1,3-bis(2-carboxychromon-5-yloxy)-propan-2-ol disodium salt (2.5 g, 5.2 mmol), was suspended in DMF. To the suspension was added benzyl bromide (0.734 ml, 6.2 mmol) and the reaction was kept overnight under stirring. An additional portion of benzyl bromide (0.734 ml, 6.2 mmol) was added. After 24 hr, the reaction mixture was poured into sodium hydrogen carbonate aqueous solution and extracted dichloromethane. The organic phase was washed with water two times and evaporated to give the dibenzyl ester of 1,3-bis-(2-carboxychromon-5-yloxy)propan-2-ol (1.72 g).

$^1$H-NMR (CDCl$_3$): 7.58 (t, 2H), 7.40 (m, 10H), 7.16 (d, 2H), 6.98 (s, 2H), 6.95 (d, 2H), 5.39 (s, 4H), 4.53 (m, 5H).

b) Preparation of the dibenzyl ester of 2-[5-(N-trityl-L-valyloxymethyl)-6-stearoyloxyhexanoyloxy]-1,3-bis-(2-carboxychromon-5-yloxy)propane To a solution of the dibenzyl ester of 1,3-bis-(2-carboxychromon-5-yloxy)propan-2-ol (270 mg, 0.42 mmole), 5-(N-Trityl-L-valyloxymethyl)-6-stearoyloxyhexanoic acid (323 mg, 0.42 mmol) and dimethylaminopyridine (6 mg, 0.05 mmol) in dichloromethane was added DCC (92 mg, 0.45 mmol). After 3 days, the reaction mixture was filtered through Celite and the filtrate was washed with sodium hydrogen carbonate aqueous solution and dried. The product dibenzyl ester of 2-[5-(N-trityl-L-valyloxymethyl)-6-stearoyloxyhexanoyloxy]-1,3-bis-(2-carboxychromon-5-yloxy)propane was isolated from silica gel column chromatography. 250 mg.

¹H-NMR (CDCl₃): 7.60–7.20 (m, 27H), 7.18 (d, 2H), 6.93 (d, 2H), 6.88 (s, 2H), 5.65 (m, 1H), 5.37 (s, 4H), 4.60 (m, 5H), 3.87 (m, 2H), 3.55 (m, 1H), 3.22 (m, 2H), 2.38 (t, 2H), 2.24 (t, 2H), 2.20 (m, 1H), 1.70 (m, 5H), 1.25 (m, 28H), 0.91 (m, 9H).

c) Preparation of 2-[5-(L-valyloxymethyl)-6-stearoyloxyhexanoyloxy]-1,3-bis-(2-carboxychromon-5-yloxy)propane Dibenzyl ester of 2-[5-(N-trityl-L-valyloxymethyl)-6-stearoyloxyhexanoyloxy]-1,3-bis-(2-carboxychromon-5-yloxy)propane (238 mg, (0.17 mmol) was dissolved in ethyl acetate (1.5 ml). To the solution was added 80% acetic acid (10 ml). After two hr, the solution was evaporated and purified by column chromatography to yield 197 mg of 2-[5-(L-valyloxymethyl)-6-stearoyloxyhexanoyloxy]-1,3-bis-(2-carboxychromon-5-yloxy)propane.

¹H-NMR (CDCl₃): 7.57 (t, 2H), 7.44 (m, 10H), 7.08 (d, 2H), 6.95 (d, 2H), 6.90 (s, 2H), 5.65 (m, 1H), 5.37 (s, 4H), 4.58 (m, 4H), 4.07 (m, 4H), 3.40 (m, 2H), 2.43 (t, 2H), 2.27 (t, 2H), 2.10–1.40 (m, 8H), 1.24 (m, 28H), 0.90 (m, 9H).

Preparation of 2-[5-(L-valyloxymethyl)-6-stearoyloxy-hexanoyloxy]-1,3-bis-(2-carboxychromon-5-yloxy)propane 2-[5-(L-valyloxymethyl)-6-stearoyloxyhexanoyloxy]-1,3-bis-(2-carboxychromon-5-yloxy)propane (190 mg, 0.16 mmole) was dissolved in a mixed solvent of methanol (6 ml), ethyl acetate (2 ml) and acetic acid (0.5 ml) and hydrogenated on palladium black (30 mg) for 1 hr. After filtration, the solution was dried and coevaporated with toluene giving 160 mg titled product.

¹H-NMR (DMSO δ-6): 7.77 (t, 2H), 7.27 (d, 2H), 7.12 (d, 2H), 6.68 (s, 2H), 5.60 (m, 1H), 4.60 (m, 4H), 4.05 (m, 5H), 2.50–2.10 (m, 6H), 1.90–1.50 (m, 6H), 1.26 (m, 28H), 0.93 (m, 9H).

EXAMPLE 46

Iodomethyl 3-[3-{1-(N-benzyloxycarbonyl)-L-valyloxy-3-stearoyloxypropyl-2-oxycarbonyl} propionyloxy]-2,2-dimethylpropionate a) Preparation of (1-(N-benzyloxycarbonyl)-L-valyloxy)-3-stearoyloxypropyl-2-oxycarbonyl) propionic acid To a solution of (1-(N-benzyloxycarbonyl)-L-valyloxy)-3-stearoyloxypropan-2-ol (8.1 g, 13.7 mmole) in N,N-dimethylformamide (135 ml) and pyridine (10 ml) was added succinic anhydride (4.1 g, 41.1 mmole) and the solution was stirred for 72 hr at 60° C. The reaction was cooled to room temperature and acetic amhydride (13 ml) was added and the solution was stirred over night. The reaction was quenched by addition of aqueous sodium hydrogen carbonate solution (3 ml). After concentration on rotavapor, the residual concentrated solution was poured into aqueous sodium hydrogen carbonate solution and extracted with dichloromethane. The organic phase was evaporated and the residue silica gel column chromatographed (20, 30, 50, 80% ethyl acetate in hexane). The appropriate fractions were pooled and evaporated in vacuo to give the title compound (6.8 g). $R_f$ (5% MeOH/CHCl₃) 0.65.

¹H-NMR (CDCl₃): δ 7.36 (m, 5H), 5.34 (m, 2H), 5.11 (s, 2H), 4.50–4.05 (m, 5H), 2.64 (br s, 4H), 2.31 (t, 2H), 2.14 (m, 1H), 1.60 (m, 2H), 1.28 (br s, 28H), 0.95 (d, 3H), 0.86 (m, 6H).

b) Preparation of 4-methoxybenzyl 3-[3-{1-(N-benzyloxycarbonyl)-L-valyloxy-3-stearoyloxypropyl-2-oxycarbonyl} propionyloxy]-2,2-dimethylpropionate (1-(N-benzyloxycarbonyl)-L-valyloxy)-3-stearoyloxypropyl-2-oxycarbonyl) propionic acid (5.8 g, 8.38 mmol), 4-methoxybenzyl 2-(hydroxymethyl)-2-methyl propionate (2.09 g, 8.80 mmole), 4-dimethylaminopyridine (153 mg) and 1-hydroxybenzotriazole (1.13 g, 8.38 mmole) were mixed and dissolved in N,N-dimethylformamide (70 ml). Then dicyclohexyl-carbodiimide (2.07 g 10.06 mmol) was added. After stirring for 4 days at room temperature the suspension was filtered and the filtrate evaporated in vacuo. The residue was partitioned between 0.1M citric acid and dichloromethane. The organic phase was then extracted with aqueous saturated NaHCO₃ and evaporated in vacuo. The residue was silica gel column chromatographed (20, 30, 60, 100% ethyl acetate in hexane). The appropriate fractions were pooled and evaporated in vacuo to give the title compound (5.73 g). $R_f$ (2% MeOH/CHCl₃) 0.80.

¹H-NMR (CDCl₃): δ 7.32 (m, 5H), 7.26 (d, 2H), 6.88 (d, 2H), 5.27 (m, 2H), 5.10 (s, 2H), 5.06 (s, 2H), 4.36–4.12 (m, 5H), 4.10 (s, 2H), 3.80 (s, 3H), 2.54 (br s, 4H), 2.31 (t, 2H), 2.14 (m, 1H), 1.60 (m, 2H), 1.26 (br s, 34H), 0.95 (d, 3H), 0.86 (m, 6H).

c) Preparation of 3-[3-{1 i-(N-benzyloxycarbonyl)-L-valyloxy-3-stearoyloxypropyl-2-oxycarbonyl} propionyloxy]-2,2-dimethylpropionic acid 4-methoxybenzyl 3-[3-{1-(N-benzyloxycarbonyl)-L-valyloxy-3-stearoyloxypropyl-2-oxycarbonyl} propionyloxy]-2,2-dimethylpropionate was treated with trifluoroacetic aicd by the method described in Example II, step c. The title compound (4.08 g) was obtained after silica gel column chromatography (20, 30, 50, 80% ethyl acetate in hexane). $R_f$ (2% MeOH/CHCl₃) 0.55.

¹H-NMR (CDCl₃): 7.34 (s, 5H), 5.26 (m, 2H), 5.11 (s, 2H), 4.39–4.15 (m, 5H), 4.10 (s, 2H), 2.61 (br s, 4H), 2.31 (t, 2H), 2.17 (m, 1H), 1.60 (m, 2H), 1.26 (br s, 34H), 0.95 (d, 3H), 0.86 (m, 6H).

d) Preparation of chloromethyl 3-[3-{1-(N-benzyloxycarbonyl)-L-valyloxy-3-stearoyloxypropyl-2-oxycarbonyl} propionyloxy]-2,2-dimethylpropionate The propionic acid derivative of step c was esterified by the method described in Example A-I-1, step d. The title compound (3.3 g) was obtained after silica gel column chromatography (20, 30% ethyl acetate in hexane). $R_f$ (2% MeOH/CHCl₃) 0.85.

¹H-NMR (CDCl₃): ): 7.34 (s, 5H), 5.71 (s, 2H), 5.27 (m, 2H), 5.11 (s, 2H), 4.39–4.14 (m, 5H), 4.08 (s, 2H), 2.61 (s, 4H), 2.31 (t, 2H), 2.15 (m, 1H), 1.60 (m, 2H), 1.26 (br s, 34H), 0.98 (d, 3H), 0.86 (m, 6H).

e) Preparation of iodomethyl 3-[3-{1-(N-benzyloxycarbonyl)-L-valyloxy-3-stearoyloxypropyl-2-oxycarbonyl} propionyloxy]-2,2-dimethylpropionate The chloromethyl ester of step d was converted to iodide by the method described in Example I, step e to give the title compound (1.96 g) practically pure. $R_f$ (2% MeOH/CHCl₃) 0.85.

¹H-NMR (CDCl₃): 7.34 (s, 5H), 5.91 (s, 2H), 5.29 (m, 2H), 5.11 (s, 2H), 4.39–4.14 (m, 5H), 4.08 (s, 2H), 2.61 (s, 4H), 2.31 (t, 2H), 2.15 (m, 1H), 1.60 (m, 2H), 1.26 (br s, 34H), 0.98 (d, 3H), 0.86 (m, 6H).

EXAMPLE 47

Iodomethyl 5-(N-CBz-L-valyloxy)-4-stearoyloxy-2,2-dimethylvalerate a) 4-Methoxybenzyl 2,2-dimethyl-4-pentenoate To a solution of 2,2-dimethyl-4-pentenoic acid (11.5 g, 90 mmol) in DMF (250 mL) at room temperature, was added potassium tert-butoxide (11.1 g, 99 mmol). The reaction mixture was stirred at 60° C. for 1 h. 4-Methoxybenzylchloride (16.9 g, 108 mmol) was added and the reaction mixture was stirred at 60° C. for 4 h. The DMF was evaporated under vacuum, the residue was dissolved in ether (500 mL) and washed with water (3×200 mL). The organic phase was dried with Na₂SO₄ and evaporated to give 21.4 g of 4-methoxybenzyl 2,2-dimethyl-4-pentenoate.

¹H-NMR (CDCl₃): 7.27 (d, J=8.7 Hz, 2H), 6.88 (d, J=8.7 Hz, 2H), 5.8–5.6 (m, 1H), 5.1–4.9 (m, 2H), 5.03 (s, 2H), 3.80 (s, 3H), 2.27 (d, 2H), 1.17 (s, 6H).

b) 4-Methoxybenzyl 4,5-dihydroxy-2,2-dimethylvalerate

To a mixture of 4-methoxybenzyl 2,2-dimethyl-4-pentenoate (22.5 g, 91 mmol), NMO (36.7 g, 272 mmol) and tert-butanol (100 mL) in THF (400 mL) at 0° C., was added osmium tertoxide (230 mg, 0.9 mmol).). After 1 h at 0° C., the temperature of the reaction mixture was allowed to assume room temperature and then the mixture was stirred for 4 h at room temperature. After evaporation, water (300 mL) was added and the resulting mixture was extracted with CH₂Cl₂ (5×300 mL). The combined organic layers were dried (Na₂SO₄) and concentrated under reduced pressure. The crude product was column chromatographed (silica gel, 3→>10% MeOH in CH₂Cl₂), to give 20.4 g of 4-methoxybenzyl 4,5-dihydroxy-2,2-dimethylvalerate.

¹H-NMR (CDCl₃): 7.27 (d, J=8.7 Hz, 2H), 6.87 (d, J=8.7 Hz, 2H), 5.03 (s, 2H), 3.8–3.7 (m, 1H), 3.79 (s, 3H), 3.51 (dd, 1H), 3.36 (dd, 1H), 3.04 (br s, 1H), 2.74 (br s, 1H), 1.87 (dd, 1H), 1.46 (dd, 1H), 1.24 (s, 6H).

c) 4-Methoxybenzyl 5-(N-CBz-L-valyloxy)-4-hydroxy-2,2-dimethylvalerate

To a mixture of DCC (14.8 g, 72 mmol), DMAP (0.88 g, 7.2 mmol) and 4-methoxybenzyl 4,5-dihydroxy-2,2-dimethyl-valerate (20.3 g, 72 mmol) in CH₂Cl₂ (400 mL) at 0° C., was added dropwise a solution of N-CBz-L-valine (16.2 g, 65 mmol) in CH₂Cl₂ (100 mL). After 1 h at 0° C., the temperature of the reaction mixture was allowed to assume room temperature and then the mixture was stirred for 5 h at room temperature. The mixture was filtered through a glass filter and the solvent was removed under reduced pressure. The crude product was column chromatographed (silica gel, 2→5% MeOH in CH₂Cl₂), to give 22.4 g 4-methoxybenzyl 5-(N-CBz-L-valyloxy)-4-hydroxy-2,2-dimethylvalerate.

¹H-NMR (CDCl₃): 7.35 (s, 5H), 7.28 (d, J=8.7 Hz, 2H), 6.88 (d, J=8.7 Hz, 2H), 5.26 (d, 1H), 5.11 (s, 2H), 5.04 (s, 2H), 4.29 (dd, 1H), 4.1–3.9 (m, 2H), 3.80 (s, 3H), 2.50 (br s, 1H), 2.3–2.1 (m, 1H), 2.0–1.8 (m, 1H), 1.6–1.4 (m, 1H), 1.24 (s, 6H), 0.98 (d, 3H), 0.90 (d, 3H).

d) 4-Methoxybenzyl 5-(N-CBz-L-valyloxy)-4-stearoyloxy-2,2-dimethylvalerate

To a mixture of 4-methoxybenzyl 5-(N-CBz-L-valyloxy)-4-hydroxy-2,2-dimethylvalerate (20.6 g, 40 mmol), Pyridine (31.6 g, 400 mmol) in CH₂Cl₂ (500 mL) at 0° C., was added dropwise a solution of stearoyl chloride (18.2 g, 60 mmol) in CH₂Cl₂ (100 mL). After 1 h at 0° C., the temperature of the reaction mixture was allowed to assume room temperature and then the mixture was stirred for 5 h at room temperature. The mixture was extracted with a 10% aqueous solution of NaHCO₃ (300 mL) and the aqueous phase was washed with CH₂Cl₂ (200 mL). The combined organic layers were dried (Na₂SO₄) and concentrated under reduced pressure. The crude product was column chromatographed (silica gel, 1→5% MeOH in CH₂Cl₂), to give 27.2 g of 4-methoxybenzyl 5-(N-CBz-L-valyloxy)-4-stearoyloxy-2,2-dimethylvalerate.

¹H-NMR (CDCl₃): 7.37 (s, 5H), 7.28 (d, J=8.7 Hz, 2H), 6.88 (d, J=8.7 Hz, 2H), 5.3–5.0 (m, 4H), 5.11 (s, 2H), 4.4–4.2 (m, 2H), 4.1–3.9 (m, 1H), 3.80 (s, 3H), 2.22.0 (m, 4H), 1.8–1.5 (m, 3H), 1.3–1.1 (m, 34H), 1.0–0.8 (m, 9H).

e) 5-(N-CBz-L-valyloxy)-4-stearoyloxy-2,2-dimethylvaleric acid

To a solution of 4-methoxybenzyl 5-(N-CBz-L-valyloxy)-4-stearoyloxy-2,2-dimethylvalerate (25.5 g, 33 mmol) in CH₂Cl₂ (400 mL) at room temperature, was added trifluoroacetic acid (40 mL). After 1 h at room temperature, the reaction mixture was concentrated under reduced pressure. The crude product was column chromatographed (silica gel, 3→5% MeOH in CH₂Cl₂), to give 19.8 g of 5-(N-CBz-L-valyloxy)-4-stearoyloxy-2,2-dimethylvaleric acid.

¹H-NMR (CDCl₃): 7.37 (s, 5H), 5.3–5.1 (m, 2H), 5.11 (s, 2H), 4.4–4.2 (m, 2H), 4.1–3.9 (m, 1H), 2.2–2.0 (m, 4H), 1.8–1.5 (m, 3H), 1.3–1.1 (m, 34H), 1.0–0.8 (m, 9H).

f) Chloromethyl 5-(N-CBz-L-valyloxy)-4-stearoyloxy-2,2-dimethylvalerate

To a solution of 5-(N-CBz-L-valyloxy)-4-stearoyloxy-2,2-dimethylvaleric acid (16.0 g, 24 mmol) in dioxane (500 mL), was added dropwise a 40% aqueous solution of tetrabutylammonium hydroxide (14.3 mL). After stirring for 5 min, the solution was evaporated to dryness through co-evaporation with dioxane and toluene. The residue was dissolved in dichloromethane (500 mL) and then chloroiodomethane (17.5 mL, 240 mmol) was added and the solution was stirred for 6 h at room temperature. The solution was concentrated under reduced pressure and the residue was shaken with hexane/ethyl acetate (1:1 v/v, 400 mL). The yellow crystalline solid was filtered off and the filtrate was washed with aqueous solution of sodium thiosulfate (0.1 M) and the filtered through anhydrous sodium sulfate and evaporated to dryness. The residue was column chromatographed (silica gel, 1% MeOH in CH₂Cl₂), to give 11.0 g of chloromethyl 5-(N-CBz-L-valyloxy)-4-stearoyloxy-2,2-dimethylvalerate.

¹H-NMR (CDCl₃): 7.35 (s, 5H), 5.8–5.6 (m, 2H), 5.3–5.1 (m, 2H), 5.11 (s, 2H), 4.4–4.2 (m, 2H), 4.1–3.9 (m, 1H), 2.3–2.1 (m, 4H), 1.8–1.5 (m, 3H), 1.3–1.1 (m, 34H), 1.0–0.8 (m, 9H).

g) Iodomethyl 5-(N-CBz-L-valyloxy)-4-stearoyloxy-2,2-dimethylvalerate

To a solution of chloromethyl 5-(N-CBz-L-valyloxy)-4-stearoyloxy-2,2-dimethylvalerate (7.8 g, 11 mmol) in acetonitrile (100 mL), was added sodium iodide (6.5 g, 44 mmol). The solution was stirred for 4 h at 60° C. The resulting suspension was filtered and the filtrate was evaporated. The residue was dissolved in $CH_2Cl_2$ and washed with aqueous sodium thiosulfate (0.1 M). The organic phase was dried ($Na_2SO_4$) and concentrated under reduced pressure. The crude product was column chromatographed (silica gel, 1% MeOH in $CH_2Cl_2$), to give 7.84 g of iodomethyl 5(N-CBz-L-valyloxy)-4-stearoyloxy-2,2-dimethylvalerate $^1$H-NMR ($CDCl_3$): 7.34 (s, 5H), 6.0–5.8 (m, 2H), 5.3–5.1 (m, 2H), 5.10 (s, 2H), 4.4–4.2 (m, 2H), 4.1–3.9 (m, 1H), 2.3–2.0 (m, 4H), 1.8–1.5 (m, 3H), 1.3–1.1 (m, 34H), 1.0–0.8 (m, 9H).

EXAMPLE A-1

4-amino-1-hydroxybutylidene-1,1-bisphosphonic acid, tri(2-methyl-2-(L-valyloxymethyl) propionyloxymethyl) ester a) 4-Benzyloxycarbonylamino-1-hydroxybutylidene-1,1-bisphosphonic acid, tri(2-methyl-2-(N-benzyloxycarbonyl-L-valyloxymethyl) propionyl-oxymethyl) ester and 4-benzyloxycarbonylamino-1-hydroxybutylidene-1,1-bisphosphonic acid, di(2-methyl-2-(N-benzyloxycarbonyl-L-valyloxymethyl) propionyloxymethyl) ester.

4-Benzyloxycarbonylamino-1-hydroxybutylidene-1,1-bisphosphonic acid is prepared by the methodology in Kieczykowski et al, J Org Chem 1995, 60, 8310–8312, and the 4-amino group CBz protected as shown in U.S. Pat. No. 5,227,506. To a solution thereof (195 mg, 0.51 mmole) in dry N,N-dimethylformamide (2 ml), was added diisopropylethylamine (0.27 ml, 1.53 mmole), followed by an injection of a solution of iodomethyl 2-methyl-2-(N-benzyloxycarbonyl-L-valyloxymethyl) propionate (626 mg, 1.27 mmole) in N,N-dimethylformamide (2 ml). After stirring under argon for 2,5 h at room temperature, the solution was concentrated on rotavapor and treated with ethyl acetate (10 ml). Crystals were filtered off and the filtrate was extracted with brine containing a small amount of sodium thiosulfate. The organic phase was filtered through anhydrous sodium sulfate and evaporated. The title compounds were isolated by silica gel column chromatography (0–4, 7–8, 20–30% ethanol in dichloromethane).

Triester (70 mg). $R_f$ (10% MeOH/$CHCl_3$) 0.45. $^1$H-NMR ($CDCl_3$): 7.30 (m, 20H), 5.85–5.43 (m, 9H), 5.08 (m, 8H), 4.36–3.95 (m, 9H), 3.10 (m, 2H), 2.15–1.75 (m, 7H), 1.19 (s, 18H), 0.86 (m, 18H). $^{31}$P-NMR ($CDCl_3$+1% $CD_3OD$) ($H_3PO_4$ reference): δ 23.8 (d), 11.8(d);

Diester (185 mg), $R_f$(10% MeOH/$CHCl_3$) 0.10 (at the center of oval spot from baseline). $^1$H-NMR ($CDCl_3$+1% $CD_3OD$): 7.31 (m, 15H), 5.79–5.63 (m, 4H), 5.08 (m, 6H), 4.35–4.10 (m, 6H), 3.10 (m, 2H), 2.18–1.70 (m, 6H), 1.19 (m, 12H), 0.87 (m, 12H). $^{31}$P-NMR ($CDCl_3$+1% $CD_3OD$) ($H_3PO_4$ reference): δ 16.6 (s).

b) 4-Amino-1-hydroxybutylidene-1,1-bisphosphonic acid, tri(2-methyl-2(L-valyloxymethyl) propionyloxymethyl) ester A solution of 4-benzyloxycarbonylamino-1-hydroxybutylidene-1,1-bisphosphonic acid tri(2-methyl-2-(N-benzyloxycarbonyl-L-valyloxymethyl) propionyloxymethyl) Ester (203 mg, 0.136 mmol) in methanol/ethyl acetate/acetic acid (2:1:1 v/v/v) (8.7 ml) was hydrogenated over a Pd-black catalyst (93 mg) at 40 psi of hydrogen for 16 h. The suspension was filtered through Celite on a fine pore sized glassinter and washed with methanol/ethyl acetate (2:1). The filtrate was evaporated to dryness in vacuo and the title compound as the tetra acetate was obtained as a white solid after a few co-evaporations with dioxane and hexane.

$^{31}$P-NMR ($CDCl_3$+5% $CD_3OD$)($H_3PO4$ reference): 623.1 (m), 11.1 (m).

EXAMPLE A-2

4-Amino-1-hydroxybutylidene-1,1-bisphosphonic acid, di(2-methyl-2-(L-valyloxymethyl) propionyloxymethyl) ester 4-Benzyloxycarbonylamino-1-hydroxybutylidene-1,1-bisphosphonic acid, di(2-methyl-2-(N-benzyloxycarbonyl-L-valyloxymethyl) propionyloxymethyl) ester (130 mg, 0.112 mmol) was hydrogenated over Pd-black (48 mg) by the method of Example A-I b), to give the title compound as the triacetate as a white solid (90 mg).

$^{31}$P-NMR ($CDCl_3$+5% $CD_3OD$)($H_3PO_4$ reference): δ 16.2 (br, s).

EXAMPLE A-3

4-Amino-1-hydroxybutylidene-1,1-bisphosphonic acid, di(2-methyl-2-(L-valylox) propionyloxymethyl) ester a) 4-Benzyloxycarbonylamino-1-hydroxybutylidene-1,1-bisphosphonic acid, di(2-methyl-2-(N-benzyloxycarbonyl-L-valyloxy) propionyloxymethyl) ester 4-Benzyloxycarbonylamino-1-hydroxybutylidene-1,1-bisphosphonic acid (306 mg, 0.80 mmole) was esterifi-ed by the method described in Example A-1-a. After silica gel column chromatography (2–4, 6–12, 15–20% ethanol in dichloromethane), the pure fractions containing the title compound were pooled together and evaporated. The residue was then dissolved in ethyl acetate and the solution extracted twice with aqueous saturated sodium bicarbonate and then twice with 5% aqueous EDTAdisodium salt. (116 mg of title compound). $R_f$(20% MeOH/$CHCl_3$) 0.20 (at the center of oval spot from baseline).

$^1$H-NMR ($CDCl_3$+1% $CD_3OD$): 7.28 (m, 15H), 5.60 (m, 4H), 5.05 (m, 6H), 4.13 (m, 2H), 3.09 (m, 2H), 2.19–1.72 (m, 6H), 1.49 (m, 12H), 0.89 (m, 12H). $^{31}$P-NMR ($CDCl_3$+ 1% $CD_3OD$)($H_3PO_4$ reference): δ15.3 (s).

b) 4-Amino-1-hydroxybutylidene-1,1-bisphosphonic acid, di(2-methyl-2-(L-valyloxy) propionyloxymethyl) ester 4-Benzyloxycarbonylamino-1-hydroxybutylidene-1,1-bisphosphonic acid, di(2-methyl-2-(N-benzyloxycarbonyl-L-valyloxy) propionyloxymethyl) ester (116 mg, 0.107 mmol) was hydrogenated over Pd-black (46 mg) by the method of Example A1-b, to give the title compound as the triacetate as a white solid (71 mg).

$^{31}$P-NMR (CDCl$_3$+5% CD$_3$OD)(H$_3$PO$_4$ reference): δ 14.9 (s).

EXAMPLE A-4

4-Amino-1-hydroxybutylidene-11'-bisphosphonic acid, di (2-(L-valyloxy)-3-methyl-(S)-(+)-butyryloxymethyl) ester a) 4-Benzyloxycarbonylamino-1-hydroxybutylidene-11,1-bisphosphonic acid, di (2-(N-benzyloxycarbonyl-L-valyloxy)-3-methyl-(S)-(+)-butyryloxymethyl) ester 4-Benzyloxycarbonylamino-1-hydroxybutylidene-1,1-bisphosphonic acid (383 mg, 1 mmole) was esterified by the method described in Example A-3-a to yield 184 mg of title compound. R$_f$ (20% MeOH/CHCl$_3$) 0.20 (at the center of oval spot from baseline).

$^1$H-NMR (CDCl$_3$+1% CD$_3$OD): 7.27 (m, 15H), 5.62 (m, 4H), 5.15–4.72 (m, 8H), 4.32 (m, 2H), 3.08 (m, 2H), 2.16–1.73 (m, 6H), 0.88 (m, 24H). $^{31}$P-NMR (CDCl$_3$+1% CD$_3$OD)(H$_3$PO$_4$ reference): δ15.5 (s).

b) 4-Amino-1-hydroxybutylidene-1,1-bisphosphonic acid, di (2-(L-valyloxy)-3-methyl-(S)-(+)-butyryloxymethyl) ester 4-Benzyloxycarbonylamino-1-hydroxybutylidene-1,1-bisphosphonic acid, di (2-(N-benzyloxycarbonyl-L-valyloxy)-3-methyl-(S)-(+)-butyryloxymethyl) ester (184 mg, 0.166 mmol) was hydrogenated over Pd-black (71 mg) by the method of Example A1-b, to give the title compound as the triacetate as a white solid (95 mg).

$^{31}$P-NMR (CDCl$_3$+5% CD$_3$OD)(H$_3$PO$_4$ reference): δ 14.6 (s).

EXAMPLE A-5

4-amino-1-hydroxybutylidene-1,1-bisphosphonic acid mono (2-methyl-2-(L-valyloxymethyl) propionyloxymethyl) ester a) 4-Benzyloxycarbonylamino-1-hydroxybutylidene-1,1-bisphosphonic acid, tribenzyl mono (2-methyl-2-(N-benzyloxycarbonyl-L-valyloxymethyl) propionyloxymethyl) ester To a solution of 4-benzyloxycarbonylamino-1-hydroxybutylidene-1,1-bisphosphonic acid (1.54 g, 4 mmole) in dry N,N-dimethylformamide (24 ml), heated at 50° C., was added diisopropylethylamine (2.78 ml, 16 mmole), followed by dropwise addition of benzylbromide (1.9 ml, 16 mmole). After stirring under argon for 4 h, the solution was concentrated on rotavapor and treated with ethyl acetate (20 ml). Crystals were filtered off and the filtrate was extracted with brine. The organic phase was filtered through anhydrous sodium sulfate and evaporated. The 4-benzyloxycarbonylamino-1-hydroxybutylidene-1,1-bisphosphonic acid, tribenzylester was isolated by silica gel column chromatography (2–4, 7–10, 15–20% ethanol in dichloromethane). The pure fractions containing the pure triester were pooled together and evaporated. The residue was then dissolved in ethyl acetate and the solution extracted three times with 2M aqueous solution of citric acid. Triester (990 mg); R$_f$ (20% MeOH/CHCl$_3$) 0.15 (at the center of oval spot from baseline);

$^{31}$P-NMR (CDCl$_3$) (H$_3$PO$_4$ reference): δ 20.4.(d), 13.3 (d); $^1$H-NMR (CDCl$_3$): 7.35–7.10 (m, 20H), 5.20–4.91 (m, 8H), 4.60 (br, 1H), 3.00 (m, 2H), 2.12–1.75 (m, 4H).

b) Dried tribenzyl ester (395 mg) was dissolved in dry N,N-dimethylformamide (3 ml), followed by addition of diisopropylethylamine (99 ml) and a solution of iodomethyl 2-methyl-2-(N-benzyloxycarbonyl-L-valyloxymethyl) propionate (737 mg) in N,N-dimethylformamide (1 ml). After stirring under argon for 4 h at 30° C., the solution was concentrated to dryness on rotavapor and treated with ethyl acetate (10 ml). Crystals were filtered off and the filtrate was extracted with brine brine containing a small amount of sodium thiosulfate. The organic phase was filtered through anhydrous sodium sulfate and evaporated. The title compound (84 mg) was isolated by silica gel column chromatography (1, 2, 3% ethanol in dichloromethane). R$_f$ (2% MeOH/CHCl$_3$) 0.60;

$^{31}$P-NMR (CDCl$_3$) (H$_3$PO$_4$ reference): δ 16.4(m). $^1$H-NMR (CDCl$_3$): 7.28 (m, 25H), 5.22 (d, 1H), 5.62–5.53 (m, 3H), 5.07, 5.04 (2xs, 10H), 4.93 (br, 1H), 4.27 (d,d, 1H), 4.15 (d,d, 2H), 3.11 (m, 2H), 2.13–1.77 (m, 5H), 1.17 (s, 6H), 0.92 (d, 3H), 0.83 (d, 3H).

c) 4-amino-1-hydroxybutylidene-1,1-bisphosphonic acid, mono (2-methyl-2-(L -valyloxymethyl) propionyloxymethyl) ester 4-Benzyloxycarbonylamino-1-hydroxybutylidene-1,1-bisphosphonic acid tribenzyl mono (2-methyl-2-(N-benzyloxycarbonyl-L-valyloxymethyl) propionyloxymethyl) ester (84 mg, 0.083 mmol) was hydrogenated over Pd-black (60 mg) by the method of Example A-I-b, to give the title compound as a white solid (35 mg).

$^{31}$P-NMR (CDCl$_3$+5% CD$_3$OD)(H$_3$PO$_4$ reference): δ 14.5 (m).

EXAMPLE A-6

4-amino-1-hydroxybutylidene-1,1-bisphosphonic acid, di (2-(-L-valyloxy)-2-phenyl-DL-acetyloxymethyl) ester 4-Benzyloxycarbonylamino-1-hydroxybutylidene-1,1-bisphosphonic acid (192 mg, 0.5 mmole) was esterified by the method described in Example A-3-a to yield 72 mg of the title compound as the tri-N-CBz protected form, ready for deprotection. R$_f$ (20% MeOH/CHCl$_3$) 0.20 (at the center of oval spot from baseline).

$^1$H-NMR (CDCl$_3$+i % CD$_3$OD): 7.44–7.10 (m, 25H), 5.94 (m, 2H), 5.59 (m, 2H), 5.18–4.85 (m, 6H), 4.36 (m, 2H), 3.00 (m, 2H), 2.12–1.63 (m, 6H), 0.95 (m, 12H). $^{31}$P-NMR (CDCl$_3$+1% CD$_3$OD)(H$_3$PO$_4$ reference): δ 15.5 (s).

EXAMPLE A-7

4-amino-1-hydroxybutylidene-1,1-bisphosphonic acid, di ((1,3-di-valyloxy)propyl-2-oxycarbonyloxy methyl) ester 4-Benzyloxycarbonylamino-1-hydroxybutylidene-1,1-bisphosphonic acid (141 mg, 0.37 mmole) was esterified by the method described in Example A-1-a to yield 90 mg of title compound as the tri CBz protected form, ready for deprotection. R$_f$ (10% MeOH/CHCl$_3$) 0.20 (at the center of oval spot from baseline). (153 mg of mixture of the diester and triester).

$^1$H-NMR (CDCl$_3$+1% CD$_3$OD) of title compound: 7.29 (m, 25H), 5.65 (m, 4H), 5.14–4.85 (m, 12H), 4.45–4.05 (m, 12H), 3.11 (m, 2H), 2.14–1.76 (m, 8H), 0.87 (m, 24H). $^{31}$P-NMR (CDCl$_3$+1% CD$_3$OD)(H$_3$PO$_4$ reference): δ 16.7 (s).

EXAMPLE A-8

4-Amino-1-hydroxybutylidene-1,1-bisphosphonic acid, di (2-L-valyloxy)-DL-propionyloxymethyl) ester 4-Benzyloxycarbonylamino-1-hydroxybutylidene-1,1-bisphosphonic acid (158 mg, 0.41 mmole) was esterified by the method described in Example A-3-a to yield 110 mg of the title compound as the tri N-Boc protected from, ready for deprotection. R$_f$ (20% MeOH/CHCl$_3$) 0.15 (at the center of oval spot from baseline).

$^1$H-NMR (CDCl$_3$+1% CD$_3$OD): 7.29 (m, 15H), 5.65 (m, 4H), 5.15–4.95 (m, 8H), 4.33 (m, 2H), 3.09 (m, 2H), 2.22–1.74 (m, 6H), 1.52 (m, 6H), 0.92 (m, 12H). $^{31}$P-NMR (CDCl$_3$+1% CD$_3$OD)(H$_3$PO$_4$ reference): δ 16.8 (s).

EXAMPLE A-9

4-Amino-1-hydroxybutylidene-1,1-bisphosphonic acid di-(5-(L-valyloxy)-2,2-dimethylvaleryloxymethyl) ester a) 4-Benzyloxy carbonylamino-1-hydroxybutylidene-1,1-bisphosphonic acid di-(5-(N-CBz-L-valyloxy)-2,2-dimethylvaleryloxymethyl) ester To a solution of 4-benzyloxycarbonylamino-1-hydroxybutylidene-1,1-bisphosphonic acid (575 mg, 1.50 mmol) in DMF (10 mL), was added diisopropylamine (0.78 mL, 4.5 mmol), followed by an injection of a solution of give iodomethyl 5-(N-CBz-L-valyloxy)-2,2-dimethylvalerate (1.95 g, 3.75 mmol) in DMF (5 mL). After stirring under argon for 1.5 h at room temperature, the solution was concentrated on rotavapor and treated with ethyl acetate (100 mL). Crystals were filtered off and the filtrate was extracted with brine containing a small amount of sodium thiosulfate. The organic phase was filtered through anhydrous sodium sulfate and evaporated. After silica gel column (silica gel, 4→20% MeOH in CH$_2$Cl$_2$), the pure fractions containing the title compound were combined and evaporated. The residue was then dissolved in ethyl acetate and the solution extracted twice with aqueous saturated sodium bicarbonate and then twice with 5% aqueous EDTA-disodium salt. The ethyl acetate phase was evaporated, to give 171 mg of 4-benzyloxy carbonylamino-1-hydroxybutylidene-1,1-bisphosphonic acid di-(5-(N-CBz-L-valyloxy)-2,2-dimethylvaleryloxymethyl) ester.

$^1$H-NMR (CDCl$_3$): 7.30 (br s, 15H), 5.85–5.25 (m, 4H), 5.20–4.95 (m, 6H), 4.30–3.95 (m, 6H), 3.18–3.00 (m, 2H), 2.20–1.75 (m, 6H), 1.7–1.4 (m, 8H), 1.3–1.0 (s, 12H), 1.0–0.8 (m, 12H).

$^{31}$P-NMR (CDCl$_3$)(H$_3$PO$_4$ reference): 16.0 (s).

b) 4-Amino-1-hydroxybutylidene-1,1-bisphosphonic acid di-(5-(L-valyloxy)-2,2-dimethylvaleryloxymethyl) ester A solution of 4-benzyloxy carbonylamino-1-hydroxybutylidene-1, 1-bisphosphonic acid di-(5-(N-CBz-L-valyloxy)-2,2-dimethylvaleryloxymethyl) ester (171 mg, 0.147 mmol) in methanol/ethyl acetate/acetic acid (2:1:1 v/v/v) (20 mL) was hydrogenated over a Pd-black catalyst (30 mg) at 40 psi of hydrogen for 6 h. The suspension was filtered through celite and the filtrate was evaporated to dryness under reduced pressure, to give 95 mg of 4-amino-1-hydroxybutylidene-1,1-bisphosphonic acid di-(5-(L-valyloxy)-2,2-dimethylvaleryloxymethyl) ester was obtained as a white solid.

$^1$H-NMR (CDCl$_3$): 5.75–5.30 (m, 4H), 5.20–4.95 (m, 6H), 4.20–3.80 (m, 6H), 3.00–2.80 (m, 2H), 2.20–1.40 (m, 14H), 1.3–1.0 (m, 12H), 1.0–0.8 (m, 12H).

$^{31}$P-NMR (CDCl$_3$+CD$_3$OD)(H$_3$PO$_4$ reference): δ 17.3 (br s)

EXAMPLE A-10

4-Amino-1-hydroxybutylidene-1,1-bisphosphonic acid di-((2-(L-valyloxy)-ethoxycarbonyloxy) methyl) ester a) 4-benzyloxy carbonylamino-1-hydroxybutylidene-1,1-bisphosphonic acid di-((2-(N-CBz-L-valyloxy)-ethoxycarbonyloxy) methyl) ester To a solution of 4-benzyloxycarbonylamino-1-hydroxybutylidene-1,1-bisphosphonic acid (550 mg, 1.44 mmol) in DMF (10 mL), was added diisopropylamine (0.75 mL, 4.32 mmol), followed by an injection of a solution of 2-(N-CBz-L-valyloxy)-ethyl iodomethyl carbonate (1.40 g, 3.60 mmol) in DMF (5 mL). After stirring under argon for 1.5 h at room temperature, the solution was concentrated on rotavapor and treated with ethyl acetate (100 mL). Crystals were filtered off and the filtrate was extracted with brine containing a small amount of sodium thiosulfate. The organic phase was filtered through anhydrous sodium sulfate and evaporated. After silica gel column (silica gel, 4→20% MeOH in CH$_2$Cl$_2$), the pure fractions containing the title compound were combined and evaporated. The residue was then dissolved in ethyl acetate and the solution extracted twice with aqueous saturated sodium bicarbonate and then twice with 5% aqueous EDTA-disodium salt. The ethyl acetate phase was evaporated, to give 160 mg of 4-benzyloxy carbonylamino-1-hydroxybutylidene-1,1 bisphosphonic acid di-((2-(N-CBz-L-valyloxy)-ethoxycarbonyloxy) methyl) ester.

$^1$H-NMR (CDCl$_3$): 7.29 (br s, 15H), 5.90–5.30 (m, 4H), 5.15–4.90 (m, 6H), 4.50–4.00 (m, 10H), 3.18–3.00 (m, 2H), 2.20–1.50 (m, 6H), 1.05–0.80 (m, 12H). $^{31}$P-NMR (CDCl$_3$) (H$_3$PO$_4$ reference): 16.5 (s).

b) 4-Amino-1-hydroxybutylidene-1,1-bisphosphonic acid di-((2-(L-valyloxy)-ethoxycarbonyloxy) methyl) ester A solution of 4-benzyloxy carbonylamino-1-hydroxybutylidene-1,1-bisphosphonic acid di-((2-(N-CBz-L-valyloxy)-ethoxycarbonyloxy) methyl) ester (160 mg, 0.147 mmol) in methanol/ethyl acetate/acetic acid (2:1:1 v/v/v) (20 mL) was hydrogenated over a Pd-black catalyst (30 mg) at 40 psi of hydrogen for 7 h. The suspension was filtered through celite and the filtrate was evaporated to dryness under reduced pressure, to give 100 mg of 4-amino-1-hydroxybutylidene-1,1 bisphosphonic acid di-((2-(L-valyloxy)-ethoxycarbonyloxy) methyl) ester was obtained as a white solid.

$^1$H-NMR (CDCl$_3$): 5.80–5.40 (m, 4H), 4.70–4.05 (m, 101H), 4.4–4.2 (m, 4H), 3.00–2.80 (m, 2H), 2.20–1.50 (m, 6H), 1.05–0.80 (m, 12H).

$^{31}$P-NMR (CDCl$_3$+CD$_3$OD)(H$_3$PO$_4$ reference): δ17.5 (br s).

EXAMPLE A-11

4-Amino-1-hydroxybutyliden-1,1-bisphosphonic acid bis [2,2-dimethyl-3-D-valyloxy)-propionyloxymethyl] ester a) 4-Benzyloxycarbonylamino-1-hydroxybutyliden-1,1-bisphosphonic acid bis [2,2-dimethyl-3-(N-CBZ-D-valyloxy)-propionyloxymethyl] ester To a solution of 4-benzyloxycarbonylamino-1-hydroxybutyliden-1,1-bisphosphonic acid (382 mg, 1 mmole) and diisopropylethyl (0.43 ml, 2.5 mmole) in DME (3 ml) at −40° C. was added 2,2-dimethyl-3-(N-CBz-D-valyloxy)-propionic acid iodomethyl ester (1.23 g, 2.5 mmole) in DMF (4 ml). The reaction was kept at 0° C. for 2.5 hr and then at 4° C. for 18 hr. The reaction mixture was evaporated in vacuo and ethyl acetate (20 ml) was added. The precipitate was filtered off and the organic phase was washed with sodium bicarbonate aqueous solution and dried. The product was isolated with silica gel column chromatography. 125 mg.

$^1$H-NMR (CDCl$_3$): 7.31 (m, 15H) 5.71 (m, 4H) 5.58 (d, 2H) 5.12 (s, 4H) 5.05 (s, 2H) 4.30 (dd, 2H) 4.12 (m, 4H) 3.18 (m, 2H) 2.05 (m, 6H) 0.92 (dd, 12H). $^{31}$P-NMR (CDCl$_3$): 15.1 b) 4-Amino-1-hydroxybutyliden-1,1-bisphosphonic acid bis [2,2-dimethyl-3-(D-valyloxy)-propionyloxymethyl] ester 4-Benzyloxycarbonylamino-1-hydroxybutyliden-1,1-bisphosphonic acid bis [2,2-dimethyl-3-(N-CBZ-D-valyloxy)-propionyloxymethyl] ester (130 mg) was dissolved in a mixed solvent of EtOAc/MeOH/AcOH (6 ml/3 ml/1.5 ml). To the solution was added palladium black (60 mg). The reaction was kept under hydrogen atmosphere (40 psi) until sampling showed the complete deprotection of the benzyloxycarbonyl groups. The reaction mixture was filtered, and then dried and coevaporated with toluene and methanol, giving the titled product. 102 mg.

$^{31}$P-NMR (CDCl$_3$+CD$_3$OD): 14.1

EXAMPLE A-12

4-Amino-1-hydroxybutyliden-1,1-bisphosphonic acid bis [4-(N-CBz-L-valyloxy)-butanoyloxymethyl] ester a) 4-Benzyloxycarbonylamino-1-hydroxybutyliden-1,1-bisphosphonic acid bis [4-(N-CBz-L-valyloxy)-butanoyloxymethyl] ester 4-Benzyloxycarbonylamino-1-hydroxybutyliden-1,1-bisphosphonic acid (573 mg, 1.5 mmole) was dissolved in dioxane (10 ml). To the solution was added tetrabutylammonium hydroxide (40%, 2.43 ml, 3.75 mmole). The solution was evaporated and coevaporated with DMF several times. The residue was dissolved in DMF (5 ml). To the solution was added 4-(N-CBz-L-valyloxy) butyric acid iodomethyl ester (1.79 g, 3.75 mmole) in DMF (5 ml) portionwise in one hour. The reaction was kept at room temperature for 3 hr and then evaporated in vacuo. Later, ethyl acetate (20 ml) was added. The precipitate was filtered off and the organic phase was washed with sodium bicarbonate aqueous solution and dried. The product was isolated with silica gel column chromatography. 135 mg.

$^1$H-NMR (CDCl$_3$):7.25 (m, 15H) 5.60 (m, 6H) 5.05 (m, 8H) 4.30–3.90 (m, 6H) 3.10 (m, 2H) 2.50–1.80 (m, 14H) 0.85 (m, 12H). $^{31}$P-NMR (CDCl$_3$): 13.7.

b) 4-amino-1-hydroxybutyliden-1,1-bisphosphonic acid bis 4-(L-valyloxy)-butanoyloxymethyl] ester 4-Benzyloxycarbonylamino-1-hydroxybutyliden-1,1-bisphosphonic acid bis [4-(N-CBz-L-valyloxy)-butanoyloxymethyl] ester (100 mg) was dissolved in a mixed solvent of EtOAc/MeOH/AcOH (6 ml/3 ml/1.5 ml). To the solution was added palladium black (80 mg). The reaction was kept under hydrogen atmosphere (40 psi) until sampling showed the complete deprotection of the benzyloxycarbonyl groups. The reaction mixture was filtered, and then dried and coevaporated with toluene and methanol, giving the titled product. 70 mg. $^{31}$P-NMR (CD$_3$OD): 17.7

EXAMPLE A-13

4-amino-1-hydroxybutyliden-1,1-bisphosphonic acid di-(3-(L-valyloxy) benzoyloxymethyl) ester a) 4-Benzyloxycarbonylamino-1-hydroxybutyliden-1,1-bisphonic acid, di-(3-(N-benzyloxycarbonyl-L-valyloxy) benzoyloxymethyl) ester To a solution of 4-benzyloxycarbonylamino-1-hydroxybutyliden-1,1-biphosphonic acid (0.59 g, 1.5 mmole) and diisopropylethyl-amine (0.64 g, 5 mmole) in N,N-dimethylformamide (40 ml) was added dropwise a solution of iodomethyl-3-(N-benzyloxycarbonyl-L-valyloxy)-benzoate (2.2 g, 4.3 mmole) in N,N-dimethylformamide (5 ml). The mixture was stirred 2 hours at room temperature under argon. The mixture was evaporated under reduced pressure. Ethyl acetate (50 ml) was added and the mixture was filtered after 2 hours. The organic phase was washed twice with 5% sodium hydrogencarbonate solution and dried with sodium sulfate. The product was isolated by silica gel column chromatography.

Yield: 0.23 g=15%

$^1$H-NMR (CDCl$_3$+5% CD$_3$OD) 0.89 (m, 12H) 1.58–2.28 (m, 6H) 2.92 (m, 2H) 4.26 (m, 2H) 5.00 (m, 6H) 5.46–6.02 (m, 4H) 6.78–7.86 (8 m, 23H)

$^{31}$P-NMR (CDCl$_3$+5% CD$_3$OD) 16.5 (s)

b) 4-amino-1-hydroxybutyliden-1,1-bisphosphonic acid, di-(3-(L-valyloxy) benzoyloxymethyl) ester Deprotection of the CBz groups of 4-benzyloxycarbonylamino-1-hydroxybutylidenl, 1-bisphonic acid, di-(3-(N-benzyloxycarbonyl-L-valyloxy) benzoyloxymethyl) ester using mild conditions as specified in Greene, "Protecting Groups in Organic Synthesis, (John Wiley & Sons, New York, 1981) yields the title compound.

EXAMPLE A-14

4-Amino-1-hydroxybutyliden-1,1-bisphosphonic acid di-(3-(L-valyloxy)-propionyloxymethyl) ester a) 4-Benzyloxycarbonylamino-1-hydroxybutyliden-1,1-bisphosphonic acid, di-(3-(N-benzyloxycarbonyl-L-valyloxy)-propionyloxymethyl) ester To a solution of 4-benzyloxycarbonylamino-1-hydroxybutyliden-1,1-bisphosphonic acid (0.88 g, 2,5 mmole) and diisopropylethyl-amine (0.78 g, 6 mmole) in N,N-dimethylformamide (40 ml) was added dropwise a solution of iodomethyl-3-(N-benzyloxycarbonyl-L-valyloxy)-propionate (2.3 g, 4.95 mmole) in N,N-dimethylformamide (5 ml). The mixture was stirred 2 hours at room temperature under argon and evaporated under reduced pressure. Ethyl acetate (50 ml) was added and the mixture was filtered after 2 hours. The organic phase was washed twice with 5% sodium hydrogencarbonate solution and dried with sodium sulfate. The product was isolated by silica gel column chromatography. Yield: 0.19 g=8%

$^1$H-NMR (CDCl$_3$+5% CD$_3$OD) 0.89 (m, 12H) 1.62–2.16 (m, 6H) 2.60 (m, 4H) 3.08 (m, 2H) 4.12 (m, 2H) 4.30 (m, 4H) 5.02 (m, 6H) 5.42–5.64 (m, 4H) 7.24 (m, 15H)

$^{31}$P-NMR (CDCl$_3$+5% CD$_3$OD) 16,9 (s)

b) 4-Amino-1-hydroxybutyliden-1,1-bisphosphonic acid, di-(3-(L-valyloxy)-propionyloxymethyl) ester Deprotection of the CBz groups of 4-benzyloxycarbonylamino-1-hydroxybutyliden-1,1-bisphosphonic acid, di-(3-(N-benzyloxycarbonyl-L-valyloxy)propionyloxymethyl) ester using mild conditions as specified in Greene, "Protecting Groups in Organic Synthesis, (John Wiley & Sons, New York, 1981) yields the title compound.

EXAMPLE C-1

1-[(1,3-bis(L-valyloxy)-2-propoxy)carbonyloxy]ethyl (7R)-3-acetoxymethyl-7-[(Z)-2-(2-aminothiazol-4-yl)-2-(methoxyimino)acetamido]-3-cephem-4-carboxylate

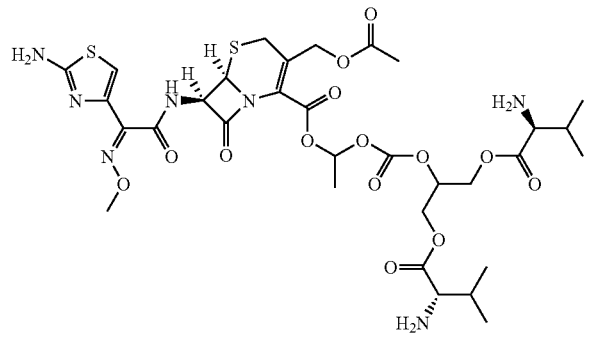

a) 1-[(1,3-bis(N-tert-butoxycarbonyl-L-valyloxy)-2-propoxy)carbonyloxy]ethyl (7R)-3-acetoxymethyl-7-[(Z)-2-(2-aminothiazol-4-yl)-2-(methoxyimino)acetamido]-3-cephem-4-carboxylate A solution of 1,3-bis(N-tert-butoxycarbonyl-L-valyloxy)-2-propyl 1-iodoethyl carbonate (0.156 mmol) and cefotaxime sodium (67.8 mg, 0.142 mmol) in 3.2 mL dry N,N'-dimethylformamide was stirred under argon for 22 h. The reaction mixture was concentrated and subjected to column chromatography (silica, 2/1 petroleum ether—ethyl acetate, and then 20/1 CH$_2$Cl$_2$-methanol) to yield an oil enriched in the desired product. The oil was dissolved in 10 mL ethyl acetate, washed with water, dried, and concentrated. A second chromatography (silica, 40/1 CH$_2$Cl$_2$-methanol) gave the title compound (59.7 mg) as cream-colored solids.

$^1$H NMR (250 MHz, CDCl$_3$) δ 0.84–0.89 (m, 6H), 0.91–0.96 (m, 6H), 1.43 (s, 18H), 1.57 (d, 3H, J=5.5 Hz), 2.07 and 2.08 (2s, 3H total), 2.04–2.18 (br, 2H), 3.40–3.64 (m, 2H), 4.03 and 4.04 (2s, 3H total), 4.18–4.51 (m, 6H), 4.82–5.19 (m, 6H), 5.64 (br s, 2H), 6.10 (m, 1H), 6.72 (s, 1H), 6.88 and 7.00 (2q, 1H total, J=5.6 Hz), 8.03 and 8.14 (2d, 1H total, J=9.9 Hz).

b) 1-[(1,3-bis(L-valyloxy)-2-propoxy)carbonyloxy]ethyl (7R)-3-acetoxymethyl-7-[(Z)-2-(2-aminothiazol-4-yl)-2-(methoxyimino)acetamido]-3-cephem-4 carboxylate A solution of the Boc-protected cefotaxime ester (247 mg) prepared as in step (a) was dissolved in 1.5 mL CH$_2$Cl$_2$ and 1.5 mL CF$_3$COOH. After 7 min, the solvent was removed under vacuum to give fine, light yellow solids of the title compound as the trifluoroacetate salt.

$^1$H NMR (250 MHz, DMSO-d$_6$) δ0.94–1.04 (m, 12H), 1.53 (d, 3H, J=5.4 Hz), 2.07 and 2.08 (2s, 3H total), 2.19 (m, 2H), 3.57–3.77 (m, 2H), 3.92 (s, 3H), 4.03 (br s, 2H), 4.37–4.68 (m, 4H), 4.72–4.97 (ABq, 2H), 5.18–5.27 (br, 1H), 5.23 (d, 1H, J=4.9 Hz), 5.88 (m, 1H), 6.80–6.95 (m, 2H), 8.50 (br s), 9.74 and 9.79 (2d, 1H total, J=8.1 Hz).

EXAMPLE A-15

4-amino-1-hydroxybutylidene-1,1-bisphosphonic acid, di-(4-(L-valyloxy) benzoyloxymethyl) ester a) 4-Benzyloxycarbonylamino-1-hydroxybutylidene-1,1-bisphosphonic acid, di-(4-(N-benzyloxycarbonyl-L-valyloxy) benzoyloxymethyl) ester 4-benzyloxycarbonylamino-1-hydroxybutylidene-1,1-bisphosphonic acid (141 mg, 0.37 mmole) was esterified by the method described in Example A-3-a) to yield 55 mg of title compound. R$_f$ (20% MeOH/CHCl$_3$) 0.15 (at the center of oval spot from baseline).

$^1$H-NMR (CDCl$_3$+1% CD$_3$OD): 7.82 (m, 4H), 7.29 (m, 15H), 6.97 (m, 4H), 5.85 (m, 4H), 5.11 (m, 6H), 4.46 (m, 2H), 3.10 (m, 2H), 2.30–1.77 (m, 6H), 1.52 (m, 6H), 0.99 (m, 12H).

$^{31}$P-NMR (CDCl$_3$+1% CD$_3$OD)(H$_3$PO$_4$ reference): δ15.6(s).

b) 4-Amino-1-hydroxybutylidene-1,1-bisphosphonic acid, di-(4-(L-valyloxy) benzoyloxymethyl) ester 4-Benzyloxycarbonylamino-1-hydroxybutylidene-1,1-bisphosphonic acid, di-(4-(N-benzyloxycarbonyl-L-valyloxy) benzoyloxymethyl) ester is CBz deprotected using mild conditions as prescribed in Greene, "Protecting Groups in Organic Synthesis, (John Wiley & Sons, New York, 1981) to yield the title compound.

EXAMPLE C2

1-[(1,3-bis(L-valyloxy)-2-propoxy)carbonyloxy] ethyl (Z)-7-[2-(2-aminothiazol-4-yl)-2-methoxyiminoacetamido]-3-cephem-4-carboxylate

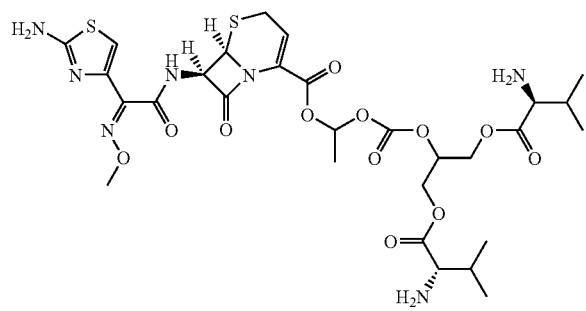

a) 1-[(1,3-bis(N-tert-butoxycarbonyl-L-valyloxy)-2-propoxy)carbonyloxy]ethyl (Z)-7-[2-(2-aminothiazol-4-yl)-2-methoxyiminoacetamido]-3-cephem-4-carboxylate A mixture of ceftizoxime sodium (550 mg, 1.36 mmol) and 1,3-bis(N-tert-butoxycarbonyl-L-valyloxy)-2-propyl 1-iodoethyl carbonate (1.5 mmol) in 27 mL dry DMF was stirred under nitrogen for 3 h. DMF was removed under vacuum and the residue was partitioned between ethyl acetate and water. The organic phase was washed successively with 5% $Na_2S_2O_3$ and brine, stirred with anhydrous $Na_2SO_4$ and activated carbon for 15 min, filtered through celite, and concentrated. Silica gel column chromatography (2/1 petroleum ether—ethyl acetate, 20/1 $CH_2Cl_2$ Substitute methanol) yielded fractions enriched in the desired product. A second column chromatography (silica, 40/1 $CH_2Cl_2$-methanol) gave the title compound (410 mg).

$^1$H NMR (250 MHz, $CDCl_3$) δ 0.84–0.88 (m, 6H), 0.92–0.97 (m, 6H), 1.42 (s, 18H), 1.56–1.59 (m, 3H), 2.11 (br, 2H), 3.40–3.68 (m, 2H), 4.04 (s, 3H), 4.17–4.51 (m, 6H), 4.97–5.14 (m, 4H), 5.73 (br s, 2H), 6.08 (m, 1H), 6.66 (m, 1H), 6.76 (s, 1H), 6.85–6.95 (m, 1H), 7.93 (br d, 1H).

b) 1-[(1,3-bis(L-valyloxy)-2-propoxy)carbonyloxy] ethyl (Z)-7-[2-(2-aminothiazol-4-yl)-2-methoxyiminoacetamido]-3-cephem-4-carboxylate The Boc-protected ceftizoxime ester (347 mg) from step (a) was dissolved in 2.5 mL $CH_2Cl_2$ and 2.5 mL $CF_3COOH$. After 15 min, the solvent was removed under vacuum to give fine light yellow solids of the title compound as the trifluoroacetate salt.

$^1$H NMR (250 MHz, DMSO-$d_6$) δ 0.95–1.04 (m, 12H), 1.54 (d, 3H, J=5.4 Hz), 2.20 (m, 2H), 3.64–3.66 (m, 2H), 3.88 (s, 3H), 3.97 (br s, 2H), 4.37–4.66 (m, 4H), 5.15–5.20 (m, 2H), 5.87 (dd, 1H, J=8.1, 5.0 Hz), 6.67 (m, 1H), 6.78 (s, 1H), 6.82 (q, 1H), 8.46 (br s), 9.54 and 9.55 (2d, 1H total, J=8 Hz)

EXAMPLE A-16

4-Amino-1-hydroxybutylidene-1,1-bisphosphonic acid di-(3-(3,4-di-(L-valyloxy) phenyl) propionyloxymethyl) ester a) 4-benzyloxycarbonylamino-1-hydroxybutylidene-1,1-bisphosphonic acid, di-(3-(3,4-di(N-benzyloxycarbonyl-L-valyloxy) phenyl) propionyloxy-methyl) ester 4-benzyloxycarbonylamino-1-hydroxybutylidene-1,1-bisphosphonic acid (143 mg, 0.37 mmole) was esterified by the method described in Example A-3-a) to yield 169 mg of the title compound. $R_f$ (20% MeOH/$CHCl_3$) 0.15 (at the center of oval spot from baseline).

$^1$H-NMR ($CDCl_3$+1% $CD_3OD$): 7.40–6.85 (m, 31H), 5.62 (m, 4H), 5.02 (m, 10H), 4.43 (m, 4H), 3.10 (m, 2H), 2.84 (m, 4H), 2.61 (m, 4H), 2.35–1.73 (m, 8H), 1.52 (m, 6H), 0.99 (m, 24H). $^{31}$P-NMR ($CDCl_3$+1% $CD_3OD$)($H_3PO_4$ reference): δ 14.3 (s).

b) 4-Amino-1-hydroxybutylidene-1,1-bisphosphonic acid, di-(3-(3,4-di(L-valyloxy) phenyl) propionyloxymethyl) ester 4-Benzyloxycarbonylamino-1-hydroxybutylidene-1,1-bisphosphonic acid, di-(3-(3,4-di(N-benzyloxycarbonyl-L-valyloxy) phenyl) propionyloxy-methyl) ester is CBz deprotected using mild conditions as prescribed in Greene, "Protecting Groups in Organic Synthesis, (John Wiley & Sons, New York, 1981) to yield the title compound.

EXAMPLE A-17

4-Amino-1-hydroxybutylidene-1,1-bisphosphonic acid, tri(3-(L-valyloxy)-2,2-dimethylpropoxycarbonyloxymethyl) ester a) 4-Benzyloxycarbonylamino-1-hydroxybutylidene-1,1-bisphosphonic acid tri(3-(N-benzyloxycarbonyl-L-valyloxy)-2,2-dimethylpropoxycarbonyl oxymethyl) ester To a solution of 4-benzyloxycarbonylamino-1-hydroxybutylidene-1,1-bisphosphonic acid (174 mg, 0.45 mmol) in dry DMF (1 mL) were added diisopropylethylamine (240 μL, 1.38 mmol), followed by 3-(N-benzyloxycarbonyl-L-valyloxy)-2,2-dimethylpropyl iodomethyl carbonate (592 mg, 1.14 mmol). After stirring for 5 h at ambient temperature, under nitrogen, the reaction mixture was concentrated on a rotavapor, treated with ethyl acetate (15 mL), and filtered. The organic solution was washed with 5% $Na_2S_2O_3$, followed by brine. Drying over anhydrous $Na_2SO_4$ and concentration gave a yellow oil that was subjected to column chromatography (silica, 2/1 petroleum ether—ethyl acetate, 2.5–20% methanol in $CH_2Cl_2$) to give fine, white solids (147 mg) enriched in the triester. The solids were dissolved in ethyl acetate, washed twice with 5% aqueous EDTA-disodium salt, dried over anhydrous $Na_2SO_4$, and evaporated to dryness under vacuum.

R$_f$ (10% methanol in CH$_2$Cl$_2$) 0.30; $^1$H NMR (250 MHz, CDCl$_3$+1% CD$_3$OD) δ 0.85–0.95 (m, 36H), 1.70–2.20 (m, 7H), 3.10 (br s, 2H), 3.85–3.95 (br, 12H), 4.25 (m, 3H), 5.05 (s, 8H), 5.52–6.0 (m, 10H), 7.30 (s, 20H); $^{31}$P NMR (101 MHz, CDCl$_3$+1% CD$_3$OD) δ 13.6 and 24.6 (2d, J=47 Hz). The diester was a minor component: $^{31}$P NMR δ 18.6 (s).

(b) Removal of Benzyloxycarbonyl Protecting Groups

The triester (110 mg) from step (a) was hydrogenated at 40 psi over Pd black (14 mg) in 4.2 mL solvent (2/1/1 ethyl acetate—methanol—acetic acid) for 18.5 h. The suspension was filtered through a small column of celite and washed with ethyl acetate—methanol. The filtrate was evaporated to dryness under vacuum to give white solids (97 mg). Because proton NMR showed incomplete deprotection, the material was resubmitted for hydrogenation (14 mg Pd, 10 mL solvent) overnight to give the deprotected triester (as the acetate salt, 79 mg) as shown by the disappearance of peaks for the benzyloxy group at δ 5.05 and 7.30.

$^{31}$P NMR (101 MHz, CDCl$_3$) δ 12.5 and 24.0.

EXAMPLE A-18

4-Amino-1-hydroxybutylidene-1,1-bisphosphonic acid, di(2-methyl-1-(L-valyloxy)-2-propoxycarbonyloxymethyl) ester a) 4-Benzyloxycarbonylamino-1-hydroxybutylidene-1,1-bisphosphonic acid di(1-(N-benzyloxycarbonyl-L-valyloxy)-2-methyl-2-propoxycarbonyloxymethyl) ester 4-Benzyloxycarbonylamino-1-hydroxybutylidene-1,1-bisphosphonic acid (460 mg, 1.2 mmol) was esterified by the method described in Example A-17 a) with 1-(N-benzyloxycarbonyl-L-valyloxy)-2-methyl-2-propyl iodomethyl carbonate (1.54 g, 3.0 mmol) for 2 h. After column chromatography (silica, 4–20% methanol in CH$_2$Cl$_2$), the pure fractions containing the title compound were pooled together and concentrated. The residue was dissolved in ethyl acetate, washed twice with 5% aqueous EDTA-disodium salt, and then, water, dried over Na$_2$SO$_4$, and evaporated to dryness under vacuum to give the diester as off-white solids (92 mg).

$^{31}$P NMR (101 MHz, CDCl$_3$+1% CD$_3$OD) δ 19.5 (s); $^1$H NMR (250 MHz, CDCl$_3$+1% CD$_3$OD) δ 0.76–1.41 (m, 24H), 1.74 (br s, 4H), 2.05 (m, 2H), 3.02 (br s, CH$_2$N), 3.90–4.30 (m, CH$_2$OC=O and CHα valine), 4.93–5.01 (m, 6H), 5.30–5.90 (m, OCH$_2$O and NHC=O), 7.22 (s, 15H).

(b) 4-Amino-1-hydroxybutylidene-1,1-bisphosphonic acid, di(2-methyl-1 (L-valyloxy)-2-propoxycarbonyloxymethyl) ester The benzyloxycarbonyl-protected diester (86 mg) from step (a) was hydrogenated by the method described in Example A-17 b) to give the title compound (as the acetate salt) as a white powder (72 mg).

$^{31}$P NMR (101 MHz, CDCl$_3$) δ 19.2 (s).

EXAMPLE A-19

4-amino-1-hydroxybutylidene-1,1-bisphosphonic acid di (2-methyl-2-(N-benzyloxycarbonyl-L-isoleucyloxymethyl)propionyloxymethyl) ester a) 4-N-benzyloxycarbonylamino-1-hydroxybutylidene-1,1-bisphosphonic acid di (2-methyl-2-(N-benzyloxycarbonyl-L-isoleucyloxymethyl)propionyl-oxymethyl) ester To a solution of 4-benzyloxycarbonylamino-1-hydroxybutyliden-1,1-bisphosphonic acid (824 mg, 2.1 mmole) and diisopropylethylamine (0.8 g, 6.3 mmole) in dry N,N-dimethylformamide (15 ml) was added dropwise a solution of iodomethyl 2-methyl-2-(N-benzyloxycarbonyl-L-isoleucyloxymethyl) propionate (3.1 g, 5.21 mmole) in N,N-dimethylformamide (6 ml). The mixture was stirred 2 hours at room temperature and evaporated under reduced pressure. Ethyl acetate (70 ml) was added and after 1 hour the crystals were filtered. The organic phase was washed two times with saturated sodium hydrogencarbonate solution, dried with sodium sulfate and evaporated under reduced pressure. The product was isolated by silica gel column chromatography with dichloromethane/methanol. Yield: 0.36 g $^1$H-NMR (CDCl$_3$) 0.86(m, 12H) 1.20 (m, 16H) 1.60–2.20 (m, 6H) 3.10 (m, 2H) 3.80–4.40 (m, 6H) 5.08 (m, 6H) 5.45 (m, 4H) 7.29 (m, 15H) $^{31}$P-NMR (CDCl$_3$+5% CD$_3$OD) 14.2 (s)

b) 4-amino-1-hydroxybutylidene-1,1-bisphosphonic acid di (2-methyl-2-(isoleucyloxymethyl)propionyloxymethyl) ester To a solution of 4-benzyloxycarbonylamino-1-hydroxybutylidene-1,1-bisphosphonic acid di (2-methyl-2-(N-benzyloxycarbonylamino-L-isoleucyloxymethyl)propionyloxymethyl) ester (0.195 g, 0.171 mmole) in ethyl acetate (10 ml), methanol (10 ml) and acetic acid (5 ml) was added palladium black (100 mg). The mixture was hydrogenated overnight at 45 psi. The catalyst was filtered and washed with ethyl acetate, methanol and acetic acid. The solution was evaporated under reduced pressure and the product was dried in vacuo to yield the title compound as the triacetate salt. Yield: 150 mg.

31P-NMR (CDCl$_3$+5% CD$_3$OD) 18.1 (s)

EXAMPLE A-20

4-amino-1-hydroxybutylidene-1,1-bisphosphonic acid di (4-(L-valyloxy)-cyclohexanoyloxymethyl) ester a) 4-N-benzyloxycarbonylamino-1-hydroxybutylidene-1,1-bisphosphonic acid di (4-(N-benzyloxycarbonyl-L-valyloxy)-cyclohexanoyloxymethyl) ester To a solution of 4-benzyloxycarbonylamino-1-hydroxybutylidene-1,1-biphosphonic acid (0.706 g, 1.8 mmole) and diisopropylethylamine (07 g, 5.4 mmole) in N,N-dimethylformamide (15 ml) was added dropwise a solution of iodomethyl 4-(N-benzyloxycarbonyl-L-valyloxy)-cyclohexanoate (2.35 g, 4.5 mmole) in N,N-dimethylformamide (5 ml). The mixture was stirred 2 hours at room temperature under argon. The mixture was evaporated under reduced pressure. Ethyl acetate (60 ml) was added and the solid was filtered after 2 hours. The organic phase was washed twice with saturated sodium hydrogencarbonate and brine. The organic phase was dried with sodium sulfate and evaporated under reduced pressure. The products were isolated by silica gel column chromatography with dichloromethane/methanol. After silica gel column chromatography the fractions were dissolved in ethyl acetate and washed three times with 5% aqueous EDTA-disodium salt solution, dried with sodium sulfate, evaporated under reduced pressure and dried in vacuo to yield 298 mg $^1$H-NMR (CDCl$_3$) 0.84 (m, 12H) 1.35–2.35 (m, 24H) 3.10 (m, 2H) 4.08 (m, 2H) 5.02 (m, 8H) 5.55 (m, 4H) 7.24 (m, 15H)

$^{31}$P-NMR (CDCl$_3$+5% CD$_3$OD) 15.2 (s)

b) 4-amino-1-hydroxybutylidene-1,1-bisphosphonic acid di (4-(L-valyloxy)-cyclohexanoyloxymethyl) ester 4-N-benzyloxycarbonylamino-1-hydroxybutylidene-1,1-bisphosphonic acid di (4-(N-benzyloxycarbonyl-L-valyloxy)-cyclohexanoyloxymethyl) ester is de-CBz protected using conventional conditions as exemplified above to yield the title compound.

EXAMPLE A-21

4-amino-1-hydroxybutylidene-1,1-bisphosphonic acid tri (4-(L-valyloxy)-cyclohexanoyloxymethyl) ester The appropriate fraction of Example A-20, step a) was dissolved in ethyl acetate and washed three times with 5% aqueous EDTA-disodium salt solution, dried with sodium sulfate, evaporated under reduced pressure and dried in vacuo to yield 320 mg which is deprotected using conventional conditions as exemplified above to yiled the title compound.

$^1$H-NMR (protected form) (CDCl$_3$) 0.86 (m, 18H) 1.3–2.5 (m, 34H) 3.10 (m, 2H) 4.22 (m, 3H) 4.55–5.10 (m, 1H) 5.50 (m, 6H) 7.28 (m, 20H)

$^{31}$P-NMR (CDCl$_3$+5% CD$_3$OD) 20.8 (d) 10.0 (d)

EXAMPLE A-22

4-amino-1-hydroxybutylidene-1,1'-bisphosphonic acid di (1-(L1-valyloxy)-2-methylpropane-2-aminocarbonyloxymethyl) ester a) 4-N-benzyloxycarbonylamino-1-hydroxybutylidene-1,1-bisphosphonic acid di (1-(N-benzloxycarbonyl-L-valyloxy)-2-methylpropane-2-amino-carbonyloxymethyl) ester To a solution of 4-benzyloxycarbonylamino-1-hydroxybutylidene-1,1-biphosphonic aid (0.1 g, 0. mmole) and diisopropylethylamine (0.31 g, 2.4 mmole) in N,N-dimethylformamide (5 ml) was added dropwise a solution of 2-(N-(iodomethoxy-carbonyl)-amino)-2-methyl-1-(N-benzyloxycarbonyl-L-valyloxy)-propane in N,N-dimethylformamide (2.5 ml). The mixture was stirred 2 hours at room temperature under argon. The mixture was evaporated under reduced pressure. Ethyl acetate (40 ml) was added and the solid was filtered after 2 hours. The organic phase was washed twice with saturated sodium hydrogencarbonate and brine. The organic phase was dried with sodium sulfate and evaporated under reduced pressure. The product was isolated by silica gel column chromatography with dichloromethane/methanol acetic acid. After silica gel column chromatography the fractions were dissolved in ethyl acetate and washed three times with 5% aqueous EDTA-disodium salt solution, dried with sodium sulfate, evaporated under reduced pressure and dried in vacuo.

Yield: 165 mg.

$^1$H-NMR (CDCl$_3$) 0.80 (m, 12H) 1.20 (m, 12H) 1.88 (m, 6H) 3.00 (m, 2H) 3.64 (m, 4H) 4.20 (m, 2H) 5.00 (m, 6H) 5.50 (m, 4H) 7.26 (m, 15H)

$^{31}$P-NMR (CDCl$_3$+5% CD$_3$OD) 14.8 (s)

b) 4-amino-1-hydroxybutylidene-1,1-bisphosphonic acid di (1-(L-valyloxy)-2-methylpropane-2-aminocarbonyloxymethyl) ester 4-N-benzyloxycarbonylamino-1-hydroxybutylidene-1,1-bisphosphonic acid di (1-(N-benzloxycarbonyl-L-valyloxy)-2-methylpropane-2-aminocarbonyloxymethyl) ester is deCBz protected as exemplified above to yield the title compound.

EXAMPLE A-23

4-Benzyloxy carbonylamino-1-hydroxybutylidene-1,1-bisphosphonic acid di-(1-(2-N-CBz-L-valyloxy-ethyl)-6-oxo-1,6-dihydro-pyridine-3-carbonyloxymethyl) ester a) 4-Benzyloxy carbonylamino-1-hydroxybutylidene-1,1-bisphosphonic acid di-(1-(2-N-CBz-L-valyloxyethyl)-6-oxo-1,6-dihydro-pyridine-3-carbonyloxymethyl) ester To a solution of 4-benzyloxycarbonylamino-1-hydroxybutylidene-1,1-bisphosphonic acid (565 mg, 1.44 mmol) in DME (10 mL), was added diisopropylamine (0.75 mL, 4.32 mmol), followed by an injection of a solution of give 1-(2-N-CBz-L-valyloxyethyl)-6-oxo-1,6-dihydro-pyridine-3-carboxylic acid iodomethyl ester (2.00 g, 3.60 mmol) in DMF (5 mL). After stirring under argon for 1.5 h at room temperature, the solution was concentrated and treated with ethyl acetate (100 mL). Crystals were filtered off and the filtrate was extracted with brine containing a small amount of sodium thiosulfate. The organic phase was filtered through anhydrous sodium sulfate and evaporated. After silica gel column (silica gel, 4→20% MeOH in CH$_2$Cl$_2$), the pure fractions containing the title compound were combined and evaporated. The residue was then dissolved in ethyl acetate and the solution extracted twice with aqueous saturated sodium bicarbonate and then twice with 5% aqueous EDTA-disodium salt. The ethyl acetate phase was evaporated, to give 205 mg of 4-benzyloxy carbonylamino-1-hydroxybutylidene-1,1-bisphosphonic acid di-(1-(2-N-CBz-L-valyloxyethyl)-6-oxo-1,6-dihydro-pyridine-3-carbonyloxymethyl) ester.

$^1$H-NMR (CDCl$_3$): 8.35–7.95 (m, 2H), 7.85–7.50 (m, 2H), 7.26 (br s, 15H), 6.60–6.20 (m, 2H), 5.90–5.35 (m, 4H), 5.15–4.80 (m, 6H1), 4.50–4.00 (m, 10H), 3.18–3.00 (m, 2H), 2.45–1.55 (m, 6H), 1.00–0.80 (m, 12H).

$^{31}$P-NMR (CDCl$_3$)(H$_3$PO$_4$ reference): 16.8 (s).

b) 4-amino-1-hydroxybutylidene-1,1-bisphosphonic acid di-(1-(2-N-CBz-L-valyloxyethyl)-6-oxo-1,6-dihydro-pyridine-3-carbonyloxymethyl) ester A solution of 4-benzyloxy carbonylamino-1-hydroxybutylidene-1,1-bisphosphonic acid di-(1-(2-N-CBz-L-valyloxyethyl)-6-oxo-1,6-dihydro-pyridine-3-carbonyloxymethyl) ester (180 mg, 0.145 mmol) in methanol/ethyl acetate/acetic acid (2:1:1 v/v/v) (20 mL) was hydrogenated over a Pd-black catalyst (30 mg) at 40 psi of hydrogen for 10 h. The suspension was filtered through celite and the filtrate was evaporated to dryness under reduced pressure, to give 85 mg of 4-amino-1-hydroxybutylidene-1,1-bisphosphonic acid di-(1-(2-L-valyloxyethyl)-6-oxo-1,6-dihydro-pyridine-3-carbonyloxymethyl) ester was obtained as a white solid.

$^1$H-NMR (CDCl$_3$): 8.65–8.20 (m, 2H), 7.95–7.65 (m, 2H), 6.65–6.30 (m, 2H), 5.90–5.35 (m, 4H), 4.70–4.00 (m, 10H), 3.18–3.00 (m, 2H), 2.45–1.55 (m, 6H), 1.00–0.80 (m, 12H).

$^{31}$P-NMR (CDCl$_3$)(H$_3$PO$_4$ reference): 13.9 (s).

EXAMPLE P-1

(1S. 2S)-N-{cis-2-[6-fluoro-2-(L-isoleucyloxymethyloxy)-3-propionylphenyl]cyclopropyl}-N'-[2-(5-cyanopyridyl)]urea (MST-041)

a) (1S, 2S)-N-{cis-2-[6-fluoro-2-(N-BOC-L-isoleucyloxymethyloxy)-3-propionylphenyl] cyclopropyl}-N'-[2-(5-cyanopyridyl)]urea To a solution of (1S, 2S)-N-{cis-2-[6-fluoro-2-hydroxy-3-propionylphenyl] cyclopropyl}-N'-[2-(5-cyanopyridyl)]urea (2.03 g, 5.5 mmol) in THF (50 mL) at 20° C., was added NaH (60%, 220 mg, 5.5 mmol). After the mixture was stirred 1.5 h at 20° C., N-BOC-L-isoleucine iodomethyl ester (16.5 g, 16.5 mmol) was added. The solution was stirred for 6 h at room temperature and then concentrated under reduced pressure. The crude product was column chromatographed (aluminium oxide 90, 1% MeOH in CH$_2$Cl$_2$), to give 1.76 g of the title product.

$^1$H-NMR (CDCl$_3$): 9.75 (br s, 1H), 9.15 (br s, 1H), 8.16 (s, 1H), 7.71 (dd, 1H), 7.52 (dd, 1H), 7.00–6.87 (m, 2H), 5.81 (d, 1H), 5.68 (d, 1H), 5.00 (d, 1H), 4.21 (dd, 1H), 3.40–3.25 (m, 1H), 2.99–2.72 (m, 2H), 2.10 (dd, 1H), 1.85–1.68 (m, 1H), 1.60–1.47 (m, 1H), 1.41 (s, 9H), 1.32–1.05 (m, 3H), 1.13 (t, 3H), 0.88–0.78 (m, 6H).

b) (1S, 2S)-N-{cis-2-[6-fluoro-2-(L-isoleucyloxymethyloxy)-3-propionylphenyl] cyclopropyl}-N'-[2-(5-cyanopyridyl)]urea To TFA (30 mL) at 0° C., was added (1S, 2S)-N-{cis-2-[6-fluoro-2-(N-BOC-L-isoleucyloxymethyloxy)-3-propionylphenyl] cyclopropyl}-N'-[2-(5-cyanopyridyl)]urea(1.81 g, 2.96 mmol). The reaction mixture was stirred at 0° C. for 30 min and then concentrated under reduced pressure at 0° C. The crude product was column chromatographed (silica gel, 10% MeOH in CH$_2$Cl$_2$), to give 1.48 g of the title compound as the TFA-salt.

$^1$H-NMR (CDCl$_3$): 9.50 (br s, 1H), 9.42 (br s, 1H), 8.34 (s, 1H), 7.73 (dd, 1H), 7.27 (m, 1H), 7.10 (d, 1H), 6.81 (dd, 1H), 6.16 (d, 1H), 5.73 (d, 1H), 3.87 (d, 1H), 3.39 (m, 1H), 3.05–2.68 (m, 2H), 2.29 (dd, 1H), 2.10–1.88 (m, 2H), 1.57–1.21 (m, 3H), 1.09 (t, 3H), 1.02 (d, 3H), 0.91 (t, 3H).

EXAMPLE P-2

(1S, 2S)-N-{cis-2 ξ-fluoro-2-(L-valyloxymethyloxy)-3-propionylphenyl)]cyclopropyl}-N'-[2-(5-cyanopyridyl)]urea a) (1S, 2S)-N-{cis-2-[6-fluoro-2-(N-CBz-L-valyloxymethyloxy)-3-propionylphenyl)]cyclopropyl}-N'-[2-(5-cyanopyridyl)]urea To a solution of (1S, 2S)-N-{cis-2-[6-fluoro-2-hydroxy-3-propionylphenyl]cyclopropyl}-N'-[2-(5-cyanopyridyl)]urea (368 mg, 1 mmole) in THF (5 ml) was added sodium hydride in paraffin (60%, 38 mg, 0.95 mmole). After 1.5 hour, N-CBz-L-valyloxymethyl iodide (1.09 g, 2.8 mmole) prepared analogously to the N-BOC-L-isoleucyloxymethyl iodide described above was added to the solution and reaction was kept 18 hours. The mixture was filtered through Celite and poured into sodium hydrogen carbonate aqueous solution, and extracted with methylene chloride. The organic phase was dried and the product was isolated with silica gel column chromatography to yield 210 mg.

$^1$H-NMR (CDCl$_3$): 8.16 (s, 1H), 7.70 (dd, 1H), 7.49 (t, 1H), 7.35 (m, 5H), 6.93 (m, 2H), 5.78 (dd, 2H), 5.27 (d, 1H), 5.11 (s, 2H), 4.28 (m, 1H), 3.34 (m, 1H), 2.84 (m, 2H), 2.09 (m, 2H), 1.54 (m, 1H), 1.34 (m, 1H), 1.10 (t, 3H), 0.87 (dd, 6H).

b) (1S, 2S)-N-{cis-2-[-fluoro-2-(L-valyloxymethyloxy)-3-propionylphenyl)]cyclopropyl}-N'-[2-(5-cyanopyridyl)]urea (1S, 2S)-N-{cis-2-[6-fluoro-2-(N-CBz-L-valyloxymethyloxy)-3-propionylphenyl)]cyclopropyl}-N'-[2-(5-cyanopyridyl)]urea (200 mg, 0.32 mmole) was dissolved in a mixed solvent of methanol (5 ml), ethylacetate (2 ml) and acetic acid (1 ml). To the solution was added palladium black (35 mg). It was kept under hydrogen at atmospheric pressure for two hours. After filtration, the solution was evaporated and the product was purified by silica gel column chromatography yielding 66 mg.

$^1$H-NMR (CDCl$_3$) 8.20 (d, 1H), 7.73 (dd, 1H), 7.44 (dd, 1H), 6.94 (m, 2H), 5.80 (dd, 2H), 3.37 (1H), 2.88 (m, 2H), 2.10 (m, 2H), 1.60 (m, 1H), 1.46 (m, 1H), 1.08 (t, 3H), 0.94 (m, 6H).

EXAMPLE P-3

(1S, 2S)-N-{cis-2 [6-fluoro-2-(2,2-dimethyl-3-(L-valyloxy)-propionyloxy-methyloxy)-3-propionylphenyl]-cyclopropyl}-N'-[2-(5-cyanopyridyl)] urea a) (1S, 2S)-N-{cis-2-[6-fluoro-2-(2,2-dimethyl-3-(N-Boc-L-valyloxy)propionyloxy-methyloxy)-3-propionylphenyl]cyclopropyl}-N'-[2-(5-cyanopyridyl)]urea To a solution of (1S, 2S)-N-[cis-2-(6-fluoro-2-hydroxy-3-propionylphenyl) cyclopropyl]-N'-[2-(5-cyanopyridyl)]urea (368 mg, 1 mmole) in THF (5 ml) was added sodium hydride in paraffin (60%, 38 mg, 0.95 mmole). After one hour, 2,2-dimethyl-3-(N-Boc-L-valyloxy)propionic acid iodomethyl ester (1.35 g, 3 mmole) was added to the solution. After 5 hr at room temperature, it was then raised to 50° C. and reaction was kept 18 hours. The reaction mixture was poured into sodium hydrogen carbonate aqueous solution and extracted with methylene chloride. The organic phase was dried and the product was isolated with alumina column chromatography. 140 mg.

$^1$H-NMR (CDCl$_3$): 8.39–6.70 (m, 5H) 5.77 (m, 2H) 5.15 (d, 1H) 4.00 (m, 3H) 3.40 (m, 1H) 2.90 (m, 2H) 2.30 (m, 1H) 2.20 (m, 1H) 1.70 (m, 1H) 1.42 (s, 9H) 1.16 (d, 6H) 0.92 (m, 9H)

b) (1S, 2S)-N-{cis-2-[6-fluoro-2-(2,2-dimethyl-3-(L-valyloxy)propionyl-oxymethyloxy)-3-propionylphenyl]-cyclopropyl}-N'-[2-(5-cyanopyridyl)] urea (1S, 2S)-N-{cis-2-[6-fluoro-2-(2,2-dimethyl-3-(N-Boc-L-valyloxy)-propionyloxy-methyloxy)-3-propionylphenyl)]cyclopropyl}-N'-[2-(5-cyanopyridyl)] urea (120 mg) was treated with trifluoroacetic acid at 0° C. for 20 min. The solution was evaporated and coevaporated with toluene and methanol succesively, giving the titled product in quantitative yield.

$^1$H-NMR (CDCl$_3$): 8.33 (d, 1H) 7.89 (d, 1H) 7.48 (t, 1H) 7.16 (m, 1H) 6.96 (t, 1H) 5.70 (dd, 2H) 4.18 (dd, 2H) 4.01 (m, 1H) 3.38 (m, 1H) 2.88 (m, 2H) 2.16 (m, 1H) 1.58 (m, 2H) 1.25 (d, 6H) 1.04 (m, 9H).

EXAMPLE P-4

(1S, 2S)-N-{cis-2-[6-fluoro-2-(3,3-bis-(L-valyloxymethyl)propionyloxy-methyloxy)-3-propionylphenyl]cyclopropyl}-N'-[2-(5-cyanopyridyl)]urea a) (1S, 2S)-N-{cis-2-[6-fluoro-2-(3,3-bis (N-CBz-L-valyloxymethyl) propionyloxymethyloxy)-3-propionylphenyl)]cyclopropyl}-N'-[2-(5-cyanopyridyl)] urea To a solution of (1S, 2S)-N-{cis-2-[6-fluoro-2-hydroxy-3-propionylphenyl] cyclopropyl}-N'-[2-(5-cyanopyridyl)] urea (331 mg, 1 mmole) in THF (5 ml) was added sodium hydride in paraffin (60%, 32 mg, 0.81 mmole). After one hour, 3,3-bis-(N-CBz-L-valyloxymethyl) propionic acid iodomethyl ester (1.3 g, 1.8 mmole) was added to the solution. After 5 hr at room temperature, it was then raised to 50° C. and reaction was kept 18 hours. The mixture was poured into sodium hydrogen carbonate aqueous solution, and extracted with methylene chloride. The organic phase was dried and the product was isolated with alumina column chromatography. 185 mg.

$^1$H-NMR (CDCl$_3$): 8.19 (s, 11H) 7.89 (dd, 1H) 7.32 (m, 111H) 7.10 (m, 11H) 6.90 (t, 1H) 5.79 (dd, 2H) 5.09 (s, 2H) 4.31 (m, 2H) 4.08 (m, 4H) 2.95 (m, 2H) 2.50 (m, 3H) 2.17 (m, 3H) 1.55 (m, 1H) 1.07 (t, 3H) 0.88 (dd, 12H).

b) (1S, 2S)-N-{cis-2-[6-fluoro-2-(3,3-bis (L-valyloxymethyl) propionyloxy-methyloxy)-3-propionylphenyl]cyclopropyl}-N'-[2-(5-cyanopyridyl)] urea (1S, 2S)-N-{cis-2-[6-fluoro-2-(3,3-bis (N-CBz-L-valyloxymethyl) propionyloxy-methyloxy)-3-propionylphenyl]cyclopropyl}-N'-[2-(5-cyanopyridyl)] urea (170 mg, 0.17 mmole) was dissolved in a mixed solvent of methanol (5 ml), ethyl acetate (2 ml) and acetic acid (1 ml). To the solution was added palladium black (30 mg). It was kept under hydrogen at atmospheric pressure for four hours. After filtration, the solution was evaporated and the product was purified by silica gel column chromatography. 80 mg.

$^1$H-NMR (DMSO-d$_6$): 8.38 (d, 1H) 8.02 (d, 1H) 7.42 (m, 2H) 7.12 (t, 1H) 5.70 (dd, 2H) 4.00 (s, 4H) 3.16 (m, 1H) 3.08 (d, 2H) 2.80 (m, 2H) 2.40 (m, 2H), 2.11 (m, 1H) 1.52 (m, 1H) 0.95 (t, 3H) 0.98 (dd, 12H).

EXAMPLE P5

(1S, 2S)-N-{cis-2-[6-fluoro-2-(2-(L-valyloxy)-ethoxycarbonyloxymethyloxy)-3-propionylphenyl)]cyclopropyl}-N'-[2-(5-cyanopyridyl)]urea a) (1S, 2S)-N-{cis-2-[6-fluoro-2-(2-(N-CBz-L-valyloxy)-ethoxycarbonyloxymethyloxy)-3-propionylphenyl)]cyclopropyl}-N'-[2-(5-cyanopyridyl)] urea To a solution of (1S, 2S)-N-{cis-2 [6-fluoro-2-hydroxy-3-propionylphenyl]cyclopropyl}-N'-[2-(5-cyanopyridyl)] urea (368 mg, 1 mmole) in THF (5 ml) was added sodium hydride in paraffin (60%, 38 mg, 0.95 mmole). After 1.5 hr, 2-(N-CBz-L-valyloxy)ethoxycarbonyloxymethyl iodide (864 mg, 1.7 mmole) was added to the solution. The reaction was kept for 48 hours. The mixture was poured into sodium hydrogen carbonate aqueous solution, and extracted with methylene chloride. The organic phase was dried and the product was isolated with silica gel column chromatography. 210 mg.

$^1$H-NMR (CDCl$_3$): 8.21 (d, 1H) 7.72 (d, 1H) 7.28 (m, 6H) 6.90 (m, 2H) 5.75 (dd, 2H) 5.09 (s, 2H) 4.35 (m, 4H) 2.85 (m, 2H) 2.50 (m, 2H) 2.16 (m, 1H), 1.65 (m, 1H) 1.11 (t, 3H) 0.93 (dd, 6H).

b) 1S, 2S)-N-{cis-2-[6-fluoro-2-(2-(L-valyloxy)-ethoxycarbonyloxymethyloxy)-3-propionylphenyl)]cyclopropyl}-N'-[2-(5-cyanopyridyl)] urea (1S, 2S)-N-{cis-2-[6-fluoro-2-(2-(N-CBz-L-valyloxy) ethoxycarbonyloxymethyloxy)-3-propionylphenyl)]cyclopropyl}-N'-[2-(5-cyanopyridyl)] urea is deprotected by conventional techniques such as palladium black in a mixed solvent of methanol, ethyl acetate and acetic acid under hydrogen at atmospheric pressure followed by conventional work up such as filtration, evaporation and silica gel column chromatorgraphy.

EXAMPLE P-6

(I1S, 2S)-N-[cis-2-(6-fluoro-2-(1, 3-bis-L-valyloxy-2-(propoxycarbonyloxmethyloxy)-3-propionylphenyl)cyclopropyl]-N'-[2-(5-cyanopyridyl)]urea a) (1S, 2S)-N-[cis-2-(6-fluoro-2-(1,3-bis-(N-BOC-L-valyloxy-2-(propoxycarbonyloxymethyloxy)-3-propionylphenyl)cyclopropyl]-N'-[2-(5-cyanopyridyl)]urea NaH (121 mg, 60% w/w in mineral oil, 3.0 mmol) was added to a mixture of (1S, 2S)-N-[cis-2-(6-fluoro-2-hydroxy-3-propionylphenyl)cyclopropyl]-N'-[2-(5-cyanopyridyl)]urea (1.05 g, 2.85 mmol) in 15 mL dry THF under N$_2$. After 1 h, the solution was concentrated to dryness and redissolved in 10 mL DMF. 2-O-iodomethoxycarbonyl-1,3-di-O-(N-tert-butoxycarbonyl-L-valyl)glycerol (2.96 g, 4.39 mmol) in 15 mL DMF was added and the reaction mixture was stirred for 20 h. Removal of solvent under vacuum followed by flash column chromatography (silica gel, 2/1 ethyl acetate—petroleum ether) gave 1.46 g (56%) of the title product as a white solid.

$^1$H NMR (250 MHz, CD$_3$OD) δ 0.94 and 0.97 (2d overlap, 12H), 1.11 (t, 3H), 1.23 (m, 1H), 1.46 (s, 18H), 1.64 (m, 1H), 2.07–2.24 (m, 3H), 2.90 (m, 2H), 3.32 (m, 1H), 4.06 (d, 2H), 4.28–4.52 (m, 4H), 5.13 (m, 1H), 5.78 and 5.88 (AB q, 2H), 7.07–7.19 (m, 2H), 7.62 (dd, 1H), 7.92 (dd, 1H), 8.31 (d, 1H).

b) (1S,2S)-N-[cis-2-(6-fluoro-2-(1,3-bis-L-valyloxy-2-(propoxycarbonyloxymethyloxy)-3-propionylphenyl)cyclopropyl]-N'-[2-(5-cyanopyridyl)]urea Ice-cold trifluoroacetic acid (30 mL) was added to the intermediate of step a (1.69 g, 1.85 mmol) in an ice bath, under $N_2$. After 7 min, the reaction mixture was concentrated under vacuum, coevaporating several times with, initially, toluene and, finally, $CH_2Cl_2$. The oily residue was chromatographed immediately on a silica gel column with 10–20% methanol in $CH_2Cl_2$ to give 1.37 g of the product as a trifluoroacetate salt.

$^1$H NMR (250 MHz, $CD_3OD$) δ 1.07–1.12 (m, 15H), 1.26 (m, 1H), 1.63 (m, 1H), 2.19 (m, 1H), 2.35 (m, 2H), 2.89 (m, 2H), 4.08 (m, 2H), 4.44–4.71 (m, 4H), 5.26 (m, 1H), 5.79 and 5.91 (AB q, 2H), 7.10–7.18 (m, 2H), 7.59 (dd, 1H), 7.93 (dd, 1H), 8.30 (d, 1H).

$^{19}$F NMR (235 MHz, $CD_3OD$) δ -103.5, −73.5.

EXAMPLE P-7

(1S,2S)-N-[cis-2-(6-fluoro-2-(L-valyloxy)methoxycarbonylox-3-propionylphenyl)cyclopropyl]-N'-[2-(5-cyanopyridyl)]urea a) (1S,2S)-N-[cis-2-(6-fluoro-2-chloromethoxycarbonyloxy-3-propionylphenyl)cyclopropyl]-N'-[2-(5-cyanopyridyl)]urea Chloromethyl chloroformate (2.3 mL, 25 mmol) was added by syringe to a mixture of (1 S,2S)-N-[cis-2-(6-fluoro-2-hydroxy-3-propionylphenyl)cyclopropyl]-N'-[2-(5-cyanopyridyl)]urea (4.695 g, 12.7 mmol) and pyridine (6.1 mL, 76 mmol) in 65 mL dry $CH_2Cl_2$ with cooling in an ice bath, under $N_2$. After 10 min, the ice bath was removed and the mixture was stirred at room temperature for 1 h 40 min. The mixture was diluted with 100 mL $CH_2Cl_2$ and washed with 50 mL $H_2O$. The aqueous phase was reextracted with 25 mL $CH_2Cl_2$. The combined organic phases were washed with 50 mL saturated $NaHCO_3$, followed by 2×50 mL brine. Drying over $Na_2SO_4$ and concentration under vacuum gave a crude material that was subjected to flash column chromatography (silica gel, 1/1 ethyl acetate—petroleum ether) to give 4.05 g (69%) title product.

$^1$H NMR (250 MHz, $CDCl_3$) δ 1.15 (t, 3H), 1.30 (m, 1H), 1.59 (m, 1H), 2.02 (m, 1H), 2.87 (q, 2H), 3.29 (m, 1H), 5.87 (s, 2H), 6.97 (d, 1H), 7.09 (m, 1H), 7.72 (dd, 1H), 7.76 (dd, 1H), 8.10 (dd, 1H), 9.26 (br s, 1H), 10.09 (brs, 1H).

b) (1S,2S)-N-[cis-2-(6-fluoro-2-iodomethoxycarbonyloxy-3-propionylphenyl)cyclopropyl]-N'-[2-(5-cyanopyridyl)]urea (1S,2S)-N-[cis-2-(6-fluoro-2-chloromethoxycarbonyloxy-3-propionylphenyl) cyclopropyl]-N'-[2-(5-cyanopyridyl)]urea (3.97 g, 8.6 mmol) and NaI (5.17 g, 34.5 mmol) in 85 mL dry acetonitrile were refluxed at 70° C. for 4 h under $N_2$. The solvent was removed in vacuo, the residue was partitioned between 100 mL $CH_2Cl_2$ and 25 mL $H_2O$, the aqueous phase was reextracted with 10 mL $CH_2Cl_2$, and the organic phases were combined, washed successively with 2×25 mL 5% $Na_2S_2O_3$ and 2×25 mL brine, and dried over $Na_2SO_4$. Flash column chromatography (silica gel, 2/1 ethyl acetate—petroleum ether) of the crude product obtained after concentration in vacuo gave 4.15 g material containing 92% of the title compound and traces of the starting material.

$^1$H NMR (250 MHz, $CDCl_3$) δ 1.18 (t, 3H), 1.34 (m, 1H), 1.62 (m, 1H), 2.03 (m, 1H), 2.86 (q, 2H), 3.32 (m, 1H), 6.08 (s, 2H), 6.97 (d, 1H), 7.08 (m, 1H), 7.70–7.76 (m, 2H), 8.13 (d, 1H), 8.90 (br s, 1H), 9.30 (br s, 1H).

c) (1S,2S)-N-[cis-2-(6-fluoro-2-(N-BOC-L-valyloxy)methoxycarbonyloxy-3-propionylphenyl)cyclopropyl]-N'-[2-(5-cyanopyridyl)]urea Tetrabutylammonium hydroxide (40 wt % solution in water, 6.4 mL, 9.8 mmol) was added to Boc-L-valine (2.54 g, 11.7 mmol) in 30 mL dioxane. The solution was concentrated in vacuo, coevaporating several times with dioxane, toluene, and $CH_2Cl_2$, and dried under vacuum overnight. The resulting Q salt was dissolved in 30 mL dry $CH_2Cl_2$ and (1S,2S)-N-[cis-2-(6-fluoro-2-(iodomethoxycarbonyloxy)-3-propionylphenyl)cyclopropyl]-N'-[2-(5-cyanopyridyl)]urea (7.1 mmol) in 65 mL dry $CH_2Cl_2$ was added. After stirring under $N_2$ for 18 h, the reaction mixture was washed with 3×50 mL $H_2O$, 1×50 mL 5% $Na_2S_2O_3$, and 2×50 mL $H_2O$. The organic phase was dried over $Na_2SO_4$, concentrated, and submitted to flash column chromatography (silica gel, 3/1 ethyl acetate—petroleum ether) to give 2.21 g (49%) product.

$^1$H NMR (250 MHz, $CD_3OD$) δ 0.98 (d, 3H), 1.02 (d, 3H), 1.17 (t, 3H), 1.24 (m, 1H), 1.47 (s, 9H), 1.59 (m, 1H), 2.06 (m, 1H), 2.24 (m, 1H), 2.96 (q, 2H), 3.24 (m. 1H), 4.15 (d, 1H), 5.94 and 6.02 (AB q, 2H), 7.12 (d, 1H), 7.26 (m, 1H), 7.91 (dd, 1H), 7.94 (dd, 1H), 8.23 (dd, 1H).

d) (1S,2S)-N-[cis-2-(6-fluoro-2-(L-valyloxy)methoxycarbonyloxy-3-propionylphenyl)cyclopropyl]-N'-[2-(5-cyanopyridyl)]urea Cold trifluoroacetic acid (40 mL) was added to (1S,2S)-N-[cis-2-(6-fluoro-2-(N-BOC-L-valyloxymethoxycarbonyloxy)-3-propionylphenyl)cyclopropyl]-N'-[2-(5 cyanopyridyl)]urea (1.94 g, 3.02 mmol) with cooling in an ice bath, under $N_2$. After 5 min, the solution was concentrated in vacuo, coevaporating several times with toluene, and then $CH_2Cl_2$, and dried under vacuum for several hours to give the compound as a trifluoroacetate salt in quantitative yield.

$^1$H NMR (250 MHz, $CD_3OD$) δ 1.12–1.18 (m, 9H), 1.25 (m, 1H), 1.59 (m, 1H), 2.07 (m, 1H), 2.47 (m, 1H), 2.97 (q, 2H), 3.26 (m, 1H), 4.16 (d, 1H), 6.01 and 6.37 (AB q, 2H), 7.11 (d, 1H), 7.29 (m, 1H), 7.92 (dd, 1H), 7.99 (dd, 1H), 8.22 (d, 1H).

$^{19}$F NMR (235 MHz, $CD_3OD$) δ −102.7, −74.0.

EXAMPLE P-8

(1S, 2S)-N-{cis-2 [6-fluoro-2-(3-carboxylpropionyloxy-methyloxy)-3-propionylphenyl]cyclopropyl}-N'-[2-(5-cyanopyridyl)] urea a) (1S, 2S)-N-{cis-2-[6-fluoro-2-(3-benzyloxycarbonylpropionyl-oxymethyloxy)-3-propionylphenyl]cyclopropyl}-N'-[2-(5-cyanopyridyl)]urea 3-Benzyloxycarbonylpropionic acid iodomethyl ester (522 mg, 1.5 mmole) was added to a solution of (1S, 2S)-N-{cis-2-[6-fluoro-2-hydroxy-3-propionylphenyl] cyclopropyl}-N'-[2-(5-cyanopyridyl)] urea (185 mg, 0.5 mmole) in THF (5 ml) which had been treated with sodium hydride in paraffin (60%, 20 mg, 0.5 mmole) for 30 min. After 18 hr at room temperature, the reaction mixture was poured into sodium hydrogen carbonate aqueous solution, and extracted with methylene chloride. The organic phase was dried and the product was isolated with alumina column chromatography. 115 mg.

$^1$H-NMR (CDCl$_3$): 8.20 (d, 1H) 7.72 (dd, 1H) 7.49 (dd, 1H) 7.35 (m, 5H) 6.97 (m, 2H) 5.73 (dd, 2H) 5.17 (s, 2H) 3,35 (m, 1H) 2.88 (m, 2H) 2.60 (m, 4H) 2.12 (m, 1H) 1.58 (m, 1H) 1.11 (t, 3H).

b) (1S, 2S)-N-{cis-2-[6-fluoro-2-(3-carboxylpropionyloxy-methyloxy)-3-propionylphenyl]cyclopropyl}-N'-[2-(5-cyanopyridyl)] urea (1S, 2S)-N-{cis-2-[6-fluoro-2-(3-carboxylpropionyloxy-methyloxy)-3-propionylphenyl]cyclopropyl}-N'-[2-(5cyanopyridyl)] urea (100 mg, 0.17 mmole) was dissolved in a mixed solvent of ethylacetate (3 ml) and acetic acid (1 ml). To the solution was added palladium black (30 mg). It was kept under hydrogen at atmospheric pressure for three hours. After filtration, the solution was evaporated and the product was purified by silica gel column chromatography. 81 mg.

$^1$H-NMR (CDCl$_3$): 8.21 (s, 1H) 7.75 (d, 1H) 7.49 (dd, 1H) 7.08 (d, 5H) 6.97 (t, 1H) 5.73 (dd, 2H) 5.17 (s, 2H) 3,26 (m, 1H) 2.87 (m, 2H) 2.60 (m, 4H) 2.09 (m, 1H) 1.58 (m, 1H) 1.11 (t, 3H)

EXAMPLE P-9

(1S, 2S)-N-[cis-2-(6-fluoro-2-O-(4-L-valyloxbenzoyl)-3propionylphenyl)-cyclopropyl]-N'-(5-cyanopyrid-2-yl) urea a) 4-benzyloxybenzoic acid To a solution of 4-hydroxybenzoic acid (6.9 g, 50 mmole) in 150 ml DMF was added potassium tert.-butoxide (12.34 g, 110 mmole) and the mixture was stirred at room temperature for one hour. Benzyl bromide (20.5 g, 120 mmole) was added and the mixture was stirred for two days at room temperature. The mixture was evaporated under reduced pressure and 100 ml 1,4-dioxane and a solution of sodium hydroxide (6.0 g, 150 mmole)in 50 ml water was added. The mixture was refluxed for two hours, cooled and evaporated under reduced pressure. Water was added and the mixture was acidified with acetic acid. The product was filtered, washed with cold water and dried. Yield: 10.2 g=89%.

b) 4-benzyloxybenzoyl chloride

To a mixture of 4-benzyloxybenzoic acid (2.28 g, 10 mmole) in 20 ml dried dichloromethane were added five drops of DMF and 2.5 ml thionyl chloride. The mixture was refluxed for three hours and evaporated under reduced pressure. Yield: 2.45 g=100% c) (1S, 2H)-N-[cis-2-(6-fluoro-2-O-(4-benzyloxybenzoyl)-3-propionylphenyl)cyclopropyl]-N'-[2-(5-cyanopyrid-2-yl) urea To a solution of (1S, 2S)-N-[cis-2-(6-fluoro-2-hydroxy-3-propionylphenyl) cyclopropyl]-N'-(5-cyanopyrid-2-yl) urea (184 mg, 0.5 mmole) in 3 ml DMF was added potassium tert, butoxide (78.5 mg, 0.7 mmole) and the mixture was stirred for one hour at room temperature. A solution of 4-benzyloxybenzoylchloride (185 mg, 0.75 mmole) in 1 ml DMF was added and the mixture was stirred overnight at room temperature. 40 ml ethyl acetate were added and the organic phase was washed four times with water. The solution was dried with sodium sulfate and evaporated under reduced pressure. The product was isolated by silica gel column chromatography.

Yield: 180 mg=62%.

$^1$H-NMR (DMSO δ-6) 0.92 (m, 4H) 1.31(m, 1H) 1.85 (m, 1H) 2.82 (m, 2H) 3.06 (m, 1H) 5.26 (s, 2H) 7.20 (m 2H) 7.38–8.12 (m, 1H) 8.38 (m, 1H)

d) (1S, 2S)-N-[cis-2-(6-fluoro-2-O (4-hydroxybenzoyl)-3-propionylphenyl) cyclopropyl]-N'-(5-cyanopyrid-2-yl)] urea-O-4-hydroxybenzoate A solution of the intermediate of step c) (170 mg, 0.29 mmole) in 15 ml ethyl acetate and 15 ml methanol was hydrogenated with 10% palladium on charcoal (30 mg) three times at room temperature and normal pressure. The catalyst was filtered and washed with ethyl acetate and methanol and the solution was evaporated under reduced pressure. The product was isolated by silica gel column chromatography. Yield: 100 mg=70%.

$^1$H-NMR (DMSO δ-6) 0.93 (m, 4H) 1.32 (m, 1H). 1.88 (m, 1H) 2.85 (m, 2H) 3.05 (m, 1H) 6.92 (m, 2H) 7.38 (m, 2H) 8.00 (m, 4H) 8.38 (m, 1H)

e) (1S, 2S)-N-[cis-2-(6-fluoro-2-O (4-L-valyloxybenzoyl)-3-propionylphenyl)-cyclopropyl]-N'-(5-cyanopyrid-2-yl) urea An R$_2$ group, such as N-protected L-valyl is acylated to the exposed ring hydroxy group using conventional acylation conditions as described herein and deprotected to yield a compound of the invention.

EXAMPLE P-10

(1S, 2S)-N-[cis-2-(6-fluoro-2-O ((4-isoleucyloxybenzoyloxymethyl)-3-propionylphenyl)-cyclopropyl]-N'-[2-(5-cyanopyidyl)]urea-O-methylene-4-hydroxybenzoate-O-L-isoleucyl ester a) Methyl-4-(4-methoxybenzyloxy) benzoate To a solution of methyl 4-hydoxybenzoate (6.85 g, 45 mmole) in 80 ml DMF was added potassium tert, butoxide (5.6 g, 51 mmole) and the mixture was stirred at room temperature for one hour. 4-Methoxybenzyl chloride (8.3 g, 52 mmole) was added and the mixture was stirred overnight at room temperature. The mixture was evaporated under reduced pressure and 200 ml ethyl acetate was added. The organic phase was washed four times with water, dried with sodium sulfate and evaporated under reduced pressure. Yield: 12.3 g=100%

$^1$H-NMR (CDCl$_3$) 3.82 (s, 3H) 3.88 (s, 3H) 5.03 (s, 2H) 6.96 (m, 4H) 7.36 (d, 2H) 7.98 (d, 2H)

b) 4-(4-methoxybenzyloxy) benzoic acid

To a solution of methyl 4-(4-methoxybenzyloxy) benzoate (12.2 g, 44.8 mmole) in 50 ml 1,4-dioxane was added a solution of lithium hydroxide (2.15 g, 89,6 mmole) and the mixture was stirred overnight at 60° C. The mixture was evaporated under reduced pressure and 5% acetic acid was added. The product was filtered, washed with water and dried. Yield: 10.1 g=87%

$^1$H-NMR (DMSO δ-6) 3.74 (s, 3H) 5.08 (s, 2H) 6.92 (d, 2H) 7.06 (d, 2H) 7.36 (d, 2H) 7.90 (d, 2H)

c) Chloromethyl 4-(4-methoxybenzyloxy)benzoate

To a solution of 4-(4-methoxybenzyloxy) benzoic acid (5.16 g, 20 mmole) in 100 ml 1,4-dioxane was added a 40% solution of tetrabutylammonium hydroxide (14.27 g, 22 mmole) and the mixture was stirred 2 hours at room temperature. The mixture was evaporated under reduced pressure and co-evaporated two times with 1,4-dioxane and two times with toluene. The dried product was dissolved in 60 ml dichloromethane and iodochloromethane (35.3 g 200 mmole) was added. The solution was stirred for two days at room temperature and evaporated under reduced pressure. About 100 ml ethyl actate was added and the organic phase washed twice with water, dried with sodium sulfate and evaporated under reduced pressure. The product was isolated by silica gel column chromatography. Yield: 4.48 g=73%

$^1$H-NMR (CDCl$_3$) 3.83 (s, 3H) 5.06 (s, 2H) 5.94 (s, 2H) 7.00 (m, 4H) 7.36 (d, 2H) 8.05 (d, 2H)

d) Iodomethyl 4-(4-methoxybenzyloxy) benzoate

To a solution of chloromethyl 4-(4-methoxybenzyloxy) benzoate (0.77 g, 2.5 mmole) in 15 ml dry acetone was added sodium iodide (1.87 g, 12.5 mmole) and the mixture was stirred overnight at room temperature. The mixture was evaporated under reduced pressure and extracted with ethyl actate/water. The organic phase was washed with a 5% sodium thiosulfate solution, dried with sodium sulfate and evaporated under reduced pressure. Yield 0.86 g=86%

$^1$H-NMR (CDCl$_3$) 3.84 (s, 3H) 5.05 (s, 2H) 6.14 (s, 2H) 6.98 (m, 4H) 7.36 (d, 2H) 8.00 (d, 2H)

e) (1S, 2S)-N-[cis-2-(6-fluoro-2-O-(4(4-methoxy-benzyloxy)-benzoyloxymethyl)-3-propionylphenyl (cyclopropyl]-N'-[2-(5-cyanopyridyl)urea To a solution of (1S, 2S)-N-[cis-2-(6-fluoro-2-hydroxy-3-propionylphenyl) cyclopropyl]-N'-[2-(5-cyanopyridyl)] urea (368 mg, 1 mmole) in 5 ml DMF was added a suspension of 60% sodium hydride in mineral oil (44 mg, 1.1 mmole) and the mixture was stirred for one hour at room temperature. A solution of iodomethyl-4-(4-methoxybenzyloxy) benzoate (0.84 g, 2.1 mmole) in 2 ml THF was added and the mixture was stirred overnight at room temperature. 50 ml ethyl acetate were added and the organic phase was washed four times with water, dried with sodium sulfate and evaporated under reduced pressure. The product was isolated by silica gel column chromatography. Yield: 525 mg=82%

$^1$H-NMR (CDCl$_3$) 0.91 (m, 3H) 1.32 (m, 1H) 1.60 (m, 1H) 2.04 (m, 1H) 2.90 (m, 2H) 3.20 (m, 1H) 3.82 (s, 3H) 5.04 (s, 2H) 5.84–6.06 (m, 2H) 6.91–8.18 (m, 13H)

f) (1S, 2S)-N-[cis-2-(6-fluoro-2-O (4-hydroxybenzoyloxymethyl)-3-propionylphenyl)cyclopropyl]-N'-[2-(5-cyanopyridyl)]urea-O-methylene-4-hydroxybenzoate To a solution of the intermediate of step e) (100 mg, 0.156 mmole) in 4 ml dichloromethane was added TFA (0.5 ml) and the solution was stirred for one hour at room temperature. The solution was evaporated under reduced pressure and the product was isolated by silica gel column chromatography. Yield: 45 mg=55%.

$^1$H-NMR (DMSO δ-6) 0.84 (m, 3H) 1.10 (m, 1H) 1.48 (m, 1H) 2.12 (m, 1H) 2.80 (m, 2H) 3.19 (m, 1H) 5.85–6.02 (m, 2H) 6.84 (m, 2H) 7.18 (m, 1H) 7.46 (m, 2H) 7.74 (m, 2H) 8.04 (m, 2H) 8.38 (m, 1H)

g) (1S, 2S)-N-[cis-2-(6-fluoro-2-O (4-isoleucyloxy-benzoyloxymethyl)-3-propionylphenyl)-cyclopropyl]-N'-[2-(5-cyanopyridyl)]urea-O-methylene-4 hydroxybenzoate-O-L-isoleucyl ester An R$_2$ group, such as N-protected L-isoleucine is acylated to the exposed hydroxy group using conventional acylation condtions as described herein and deprotected to yield a compound of the invention.

BIOLOGICAL EXAMPLE 1

Pharmacokinetics

Confirmation that orally administered prodrugs of the invention release FLG in vivo is obtained in a rat model which is recognized as a useful model for assessing pharmacokinetic parameters of nucleoside analogues. The oral compositions are administered in a pharmaceutical vehicle comprising propylene glycol, or in the case of the more soluble compounds such as that of Example 26 or Example 34, in water, to duplicate fasted animals in a dosage corresponding to 0.1 mmol/kg. For comparison, a set of rats is iv dosed with 0.01 mmol/kg of the metabolite 2',3'-dideoxy-3'-fluoroguanosine. Serum levels of the metabolite are then monitored in serum collected at intervals from individual animals from 0.5 to up to 12 hours following administration (5 min to 6 hours for FLG).

The metabolite is analysed with HPLC with UV detection at 254 nm, in a manner analogous to Ståhle et al 1995, J. Pharm. Biomed. Anal. 13, 369–376. An HPLC system can be based on a 0.05 M ammonium-dihydrogen-phosphate buffer, with 1.2% 2-propanol solvent, buffered to pH 4.5 or 30 mM sodium dihydrogen phosphate buffer with 2% acetonitrile solvent buffered to pH 7.0. The column may be a 100×2.1 mm BAS C18 5 μm particle size with a 7 μm C 18 guard column or Zorbax SB-CN C18 150×4.6 mm, 5 μm column. Protein binding of the compounds of the invention is neglible as is that of the metabolite and ultrafiltration through Amicon or Microcon 30 filters is useful for serum samples. Advantageously the main peak is subject to further column chromatography to better aid in resolution of FLG over low weight serum components. The iv levels are multiplied by a factor of ten in order to obtain AUC values for comparison with the oral values. Absolute oral bioavailability is determined as the ratio between $^{0-\infty}$AUC$_{iv}$ and $^{0-\infty}$AUC$_{oral}$.

TABLE 1

|  | 6 h absolute bioavail. % | 12 h absolute bioavail. % |
| --- | --- | --- |
| FLG |  | 9%** |
| Example 22 | 39% | >80%* |
| Example 13 | 37% |  |
| Example 12 | 29% |  |
| Example 25 | 81.5% |  |
| Example 28 | 47.5% |  |

TABLE 1-continued

|  | 6 h absolute bioavail. % | 12 h absolute bioavail. % |
| --- | --- | --- |
| Example 24 | 60.5% |  |
| Example 26 |  | 67.5% |
| Example 29 | 51% |  |

*estimated. **literature value

The compounds of the invention thus provide significantly enhanced oral bioavailability relative to the metabolite metabolite 2',3'-dideoxy-3'-fluoroguanosine. Notably, the compounds are released into the blood in a relatively sustained manner, rather than in an immediate peak. This means that effective amounts of the active metabolite are available in the blood for many hours assisting once daily dosage. Additionally, a sustained release avoids the problems of acute toxicity seen in compounds with a more rapid release rate.

Although the rat is well recognized as a good model for predicting human bioavailability of nuceoide analogues, species independent bioavailability of a compound of the invention (Example 34) was confirmed in =11.5 kg male and female beagle dogs administered orally with 0.05 mmol/kg (38 mg/kg) compound in water or iv 0.005 mmol/kg (1.35 mg/kg) metabolite in water. Plasma collection and analysis as above.

| Male dog | 12 hour absolute bioavailability | 51% |
| --- | --- | --- |
| Female dog | 12 hour absolute bioavailability | 74% |

BIOLOGICAL EXAMPLE 2

Antiviral Activity—Retroviruses

As can be demonstrated by the methodology of Biological Example 1, the compounds of the invention release, in vivo, the metabolite 2',3'-dideoxy, 3'-fluoroguanosine. In vitro measurement of the antiviral activity of this metabolite will thus reflect the de facto activity of the compounds of the invention.

In the XTT dye uptake assay of Koshida et al Antimicrob Agents Chemother. 33 778–780, 1989) utilising MT4 cells, the metabolite measured in Biological Example 1 above showed the following in vitro activities against retroviruses:

TABLE 2

| HIV or retroviral strain | IC$_{50}$* |
| --- | --- |
| HIV-1$_{111B}$ | 1 µg/ml |
| HIV-1$^{2441}$ AZT$^r$ | 1 µg/ml |
| HIV-1$_{111B}$ TIBO$^r$ | 1 µg/ml |
| HIV-1$^{29/9}$ | 0.7 µg/ml |
| HIV-2$_{SBL6669}$ | 2 µg/ml |
| SIV$_{SM}$ | 1 µg/ml |

*Concentration of metabolite inducing 50% inhibition of viral replication

It will thus be apparent that administration of the compounds of the invention induce powerful antiviral activities against the retroviruses HIV-1, HIV-2 and SIV. It should also be noted from the HIV-1$^{2441}$ AZT$^r$ and HIV-1$_{111B}$ TIBO$^r$ results that the antiviral activity of the compounds of the invention does not show cross resistance against strains of HIV which have become resistant to other HIV agents such as the nucleoside analogue AZT or or the non-nucleoside reverse transcriptase inhibitor TIBO.

BIOLOGICAL EXAMPLE 3

Antiviral Activity —HBV

Figure 2:
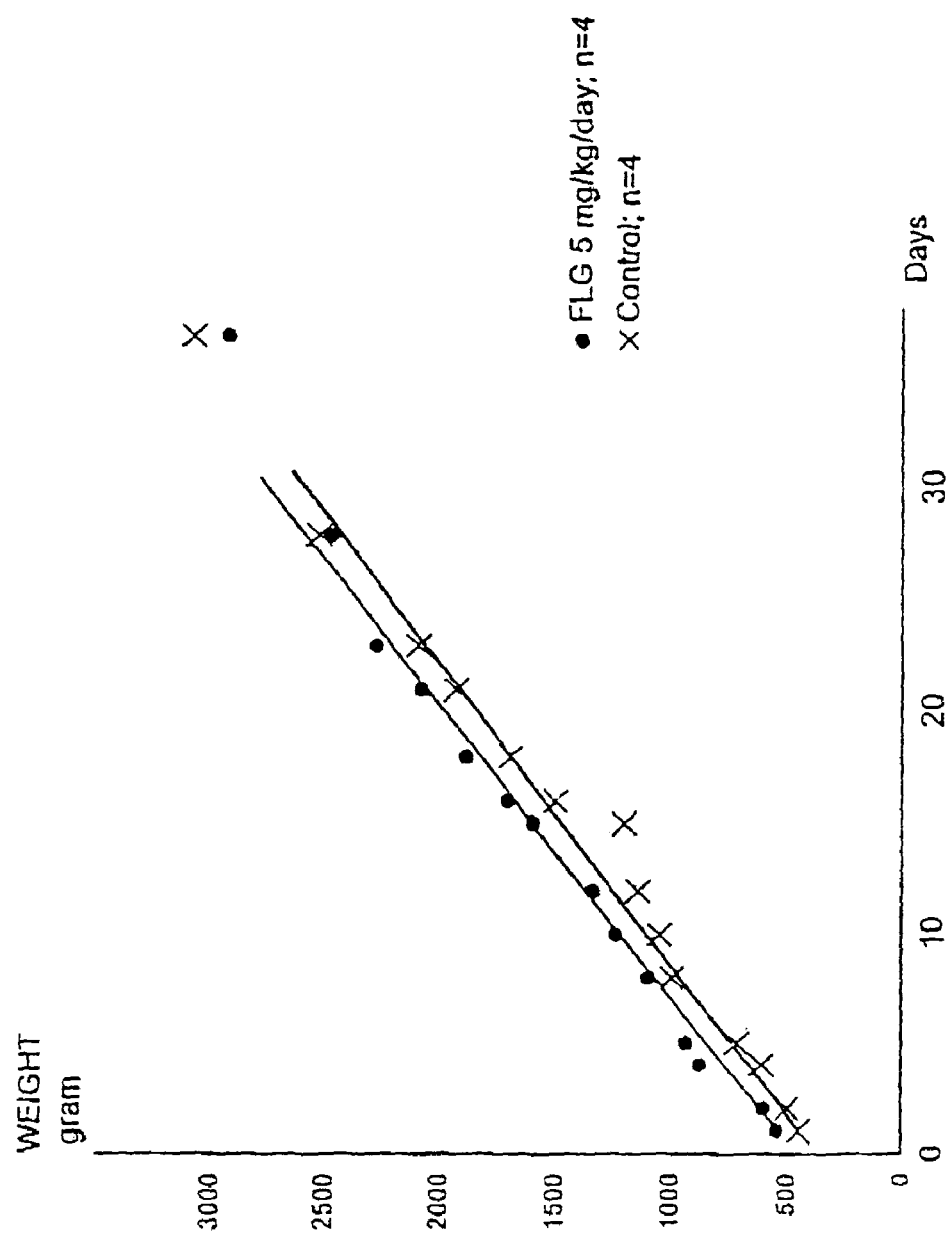
FIG. 2 depicts weight gain in treated, DHBV-infected ducks as a function of time, as described in Biological Example 3.

The activity of antivirals on duck hepatitis B virus (DHBV) in ducks is an acknowledged animal model for the validation of in vivo hepatitis B activity in humans. The activity of the in vivo metabolite measured in Biological Example 2 above has been assayed in the DHBV model described by Sherker et al (1986) Gastroenterology 91, pp 818–824. The results are depicted in FIGS. 1 and 2 In short, 4 control ducks were treated with phosphate buffered saline (PBS) and 4 ducks with 5 mg/kg/day of the active metabolite. The ducks were two days old when inoculated with DHBV and 18 days old when treatment was commenced. The metabolite and PBS (controls) were given intraperitoneally for 10 days as twice daily injections, at 8 am and 4 pm. Treatment lasted 33 days and the animals were followed 5 weeks after the end of treatment.

The efficacy of treatment was followed by dot blot-hybridisation of DHBV DNA in serum using a radioactive probe and the amount of DHBV measured as the amount of radioactivity hybridised. FIG. 1 plots the amount of DHBV DNA in serum at different timepoints before, during and after treatment.

As can be seen in FIG. 1, there is no decrease in the amount of DHBV in serum during treatment with PBS (control, solid line). The animals given the metabolite measured in Biological Example 2 (broken line) showed a dramatic decrease in the amount of DHBV in serum during the first 10 days of treatment, whereupon for the remainder of treatment the level of DHBV DNA was below the detection limit at this dose of 5 mg/kg/day. Repeat experiments at dosages of 30 and 3 mg/kg/day and with congenitally infected ducks (not shown) also produced similar results, that is a dramatic fall in serum DHBV DNA to under the detection threshold. Even at the very low dose of 0.3 mg/kg/day the metabolite caused a considerable inhibition of DHBV in vivo. After the finish of treatment, virus reappeared in the serum, as shown in FIG. 1. Reappearance of HBV after short term treatment with conventional antivirals has been observed earlier in both humans and animals with chronic hepatitis B infection.

As can be seen in FIG. 2, the weight of the ducks increased in the same way as in the control (PBS treated) animals. The weight increase from about 270 g to about 800 g which was observed during the treatement period is so large that toxic effects, had they occurred, should be easily visible as a change in growth rate. Similar growth curves were also observed for the ducks receiving the higher dosage rate of 30 mg/kg/day. This metabolite is thus clearly non-toxic. As the compounds of the invention are hydrolysed in vivo to give this metabolite, as established in Example 2 above, and a nature identical and therefore easily metabolized fatty acid, it can therefore be inferred that no long term toxicity problem can be expected from adminstration of the compounds of the invention. The absence of acute (short term) toxicity of the compounds of the invention when administered orally is established in Biological Example 2 above.

Biological Example 4

Bioavailability

The release of a compound of Formula P-2 from orally administered prodrugs of Formulae P3 to P8 were monitored in rats. The compounds of Examples P1 to P6 were made up in a propylene glycol vehicle and orally administered to paired fasted male Sprague Dawley rats at a dose corresponding to 0.027 mmol/kg. At 30, 60, 120, 240 & 360 minutes, 0.2 ml blood were collected, centrifuged and frozen for later analysis. The released drug of Formula P-2, (1S, 2S)-N-[cis-2-(6-fluoro-2-hydroxy-3-propionylphenyl) cyclopropyl]-N'-[2-(5-cyanopyridyl)] urea was assayed by HPLC. Aliquots comprising 40–100 µl of each plasma sample are mixed with an equal volume of acetonitrile (10 seconds, Vibrofex). The sample is centrifuged (2 min, 14000 RPM) and 30 µl of the supernatant is injected into an HPLC system, as follows.

| Pre column: | RP-18, 7 µm, 15 × 3.2 mm |
| --- | --- |
| Column: | YMC basic, 3 µm, 150 × 3 mm |
| Mobile phase: | 60% acetonitrile in 3 mM ammonium acetate, pH 6.4 |
| Flow rate: | 0.4 ml/min |
| Detection: | UV, 250 nm |

TABLE P-1

| Example | Bioavailability$_{0-6\ hours}$ |
| --- | --- |
| P-1 | 34% |
| P-2 | 18% |
| P-3 | 27% |
| P-4 | 18% |
| P-6 | 50% |
| P-7 | 70% |

The above bioavailabilities correspond to sustained plasma levels of the active metabolite well above the $ED_{50}$ for HIV-1.

BIOLOGICAL EXAMPLE 6

Bioavailability of the ring indanolic ring hydroxy compound of Example B-1 was assessed in rats by the procedure of Biological Example 5 also using a propylene glycol vehicle, 58 mg/kg (0.047 mmol/kg), but wherein the mother compound N1, N6-di [(1S,2R)-2-hydroxy-2,3-dihydro-1-H-1-indenyl]-(2R, 3R, 5R)-2,5-di(benzyloxy)-3,4-dihydroxy-hexanediamide was assayed by LC-MS using SiM (single ion monitoring) with M/Z ion detector 653. Plasma results are presented as µM in the table below:

| Time | Rat 1 | Rat 2 | Rat 3 |
| --- | --- | --- | --- |
| 0 | <0.02 | <0.02 | <0.02 |
| 0.5 | 0.17 | 0.46 | 0.23 |
| 1 | 0.73 | 1.4 | 1.22 |
| 2 | 0.86 | 1.7 | 1.09 |
| 4 | 0.52 | 0.67 | 0.43 |
| 6 | 0.23 | 0.24 | 0.08 |

The average bioavailability is thus 57%. This should be contrasted with the bioavailability of the mother compound (below level of detection). Interestingly, the bioavailability of the analogue bearing $R_2$ groups (depicted immediately below) but lacking the linker component of the invention was also below the level of detection in the same assay:

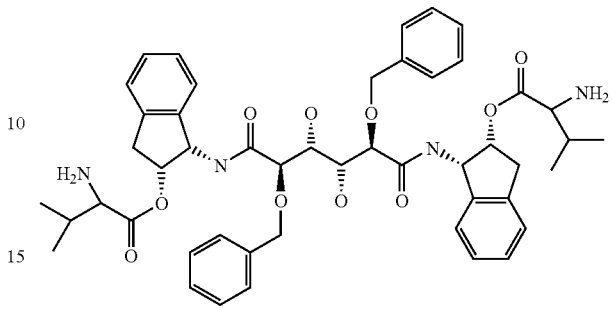

BIOLOGICAL EXAMPLE A-1

The bioavailability of a prodrug of the invention built on the bis-phosphonate alendronate was assayed in rats. 4-Amino-1-hydroxybutylidene-1,1-bisphosphonic acid, di-(2-methyl-2-(L-valyloxymethyl) propionyloxymethyl) ester and the alendronate mother compound were orally administered at a dose corresponding to 0.1 mmol/kg to respective paired rats in a propylene glycol vehicle.

Urine was collected over 24 hours in a metabolic cage and analysed as shown in Kline et al J Chromat. 534 (1990) 139–149, but modified as follows: 1 ml of urine is mixed with 50 µl or 1.25 M calcium chloride and 100 µl of 1M sodium hydroxide. After centrifugation, the urine was aspirated off and the pellet redissolved in 0.8 ml 0.2 M acetic acid, 0.4 ml of 0.01 M EDTA and 0.4 ml of 0.2 m sodium acetate. 1 ml of water was added and the solution loaded onto a preconditioned DEA cartridge. The cartridge was washed with 1 ml of water and alendronate eluted with 1 ml of 1M carbonate buffer, pH 10.4. A part of the eluent, 150 µl was mixed with 5 µl of 0.05 M potassium cyanide and 5 µl of NDA solution (1 mg/ml) in methanol. 50 µl was injected into the chromatograph.

The compound of the invention exhibited a 28–30 fold improvement relative to the bioavailabilty of alendronate itself.

We claim:
1. A compound of the formula

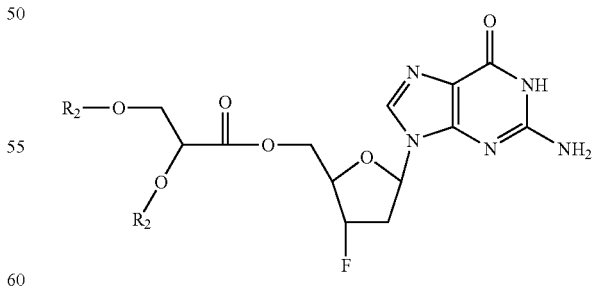

wherein $R_2$ is independently the residue of an aliphatic L-amino acid, or a pharmaceutically acceptable salt thereof.

2. A compound according to claim 1, wherein both $R_2$ are the residues of identical aliphatic L-amino acids.

3. A compound according to claim 2, wherein the L-amino acids are both L-valyl or both L-isoleucyl.

4. A compound according to claim 3, wherein the compound is denoted

5'-O-[(R) 2,3-bis-(L-(valyloxy)-propionyl]-2',3'-dideoxy-3'-fluoroguanosine;

5'-O-[(R) 2,3-bis-(L-(isleucyloxy)-propionyl]-2',3'-dideoxy -3'-fluoroguanosine;

5'-O-[(SR) 2,3-bis-(L-(valyloxy)-propionyl]-2',3'-dideoxy-3'-fluoroguanosine; or 5'-O-[(SR) 2,3-bis-(L-(valyloxy)-propionyl]-2',3'-dideoxy-3'-fluoroguanosine, or a pharmaceutically acceptable salt thereof.

5. A compound according to claim 4, denoted 5'-O-[(R) 2,3-bis-(L-(valyloxy)-propionyl]-2',3'-dideoxy -3'-fluoroguanosine, or a pharmaceutically acceptable salt thereof.

6. A pharmaceutical composition comprising a compound according to claim 1 and a pharmaceutically acceptable carrier or diluent therefor.

7. A method for the treatment of HIV comprising the administration of an effective amount of a compound as defined in claim 1 to a patient infected with HIV.

8. A method for the treatment of HIV comprising the administration of an effective amount of a compound as defined in claim 5 to a patient infected with HIV.

* * * * *